United States Patent
Lee et al.

(10) Patent No.: US 11,180,483 B2
(45) Date of Patent: Nov. 23, 2021

(54) SUBSTITUTED REVERSE PYRIMIDINE BMI-1 INHIBITORS

(71) Applicant: PTC Therapeutics, Inc., South Plainfield, NJ (US)

(72) Inventors: Chang-Sun Lee, Belle Mead, NJ (US); Ramil Baiazitov, East Brunswick, NJ (US); Liangxian Cao, East Brunswick, NJ (US); Thomas W. Davis, South Orange, NJ (US); Wu Du, Cranbury, NJ (US); Ronggang Liu, Berwyn, PA (US); Young-Choon Moon, Belle Mead, NJ (US); Steven D. Paget, Hillsborough, NJ (US); Hongyu Ren, Florence, NJ (US); Nadiya Sydorenko, Princeton, NJ (US); Richard Gerald Wilde, Somerville, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 0 days.

(21) Appl. No.: 16/583,442

(22) Filed: Sep. 26, 2019

(65) Prior Publication Data
US 2020/0024260 A1   Jan. 23, 2020

Related U.S. Application Data

(62) Division of application No. 14/443,911, filed as application No. PCT/US2013/071132 on Nov. 21, 2013, now Pat. No. 10,428,050.

(60) Provisional application No. 61/728,907, filed on Nov. 21, 2012.

(51) Int. Cl.
| | | |
|---|---|---|
| *A61K 31/506* | (2006.01) | |
| *A61K 45/06* | (2006.01) | |
| *A61N 5/10* | (2006.01) | |
| *C07D 403/04* | (2006.01) | |
| *C07D 471/04* | (2006.01) | |
| *C07D 487/04* | (2006.01) | |
| *C07D 403/12* | (2006.01) | |

(52) U.S. Cl.
CPC ......... *C07D 403/12* (2013.01); *A61K 31/506* (2013.01); *A61K 45/06* (2013.01); *A61N 5/10* (2013.01); *C07D 403/04* (2013.01); *C07D 471/04* (2013.01); *C07D 487/04* (2013.01); *Y02A 50/30* (2018.01)

(58) Field of Classification Search
None
See application file for complete search history.

(56) References Cited

FOREIGN PATENT DOCUMENTS

| CA | 2819373 A1 | 6/2012 |
|---|---|---|
| WO | 02/48148 A2 | 6/2002 |
| WO | 03/099811 A1 | 12/2003 |
| WO | 2004/007407 A2 | 1/2004 |
| WO | 2005/076854 A2 | 8/2005 |
| WO | 2010/016005 A1 | 2/2010 |
| WO | 2011/086085 A1 | 7/2011 |

OTHER PUBLICATIONS

Ohtaka et al., "Bmi1 Inhibitors Suppress Cell Growth and Notch Signalling of Acute Leukemia Cells", Experimental Hematology, 2017, vol. 53, p. S63, Abstract 3032.*

* cited by examiner

*Primary Examiner* — Savitha M Rao
*Assistant Examiner* — Gregg Polansky
(74) *Attorney, Agent, or Firm* — Hoffmann & Baron, LLP

(57) ABSTRACT

Amine substituted reverse pyrimidine compounds and forms thereof that inhibit the function and reduce the level of B-cell specific Moloney murine leukemia virus integration site 1 (Bmi-1) protein and methods for their use to inhibit Bmi-1 function and reduce the level of Bmi-1 to treat a cancer mediated by Bmi-1 are described herein.

16 Claims, 2 Drawing Sheets

SUBSTITUTED REVERSE PYRIMIDINE BMI-1 INHIBITORS

CROSS-REFERENCE TO RELATED APPLICATIONS

This application is a divisional application of U.S. application Ser. No. 14/443,911, filed May 19, 2015, which in turn is the U.S. National Stage filing under 35 U.S.C. § 371 of International Application No. PCT/US2013/071132, filed Nov. 21, 2013, which in turn claims priority to U.S. Provisional Application No. 61/728,907, filed Nov. 21, 2012, the entire contents of which are incorporated by reference herein.

INTRODUCTION

Substituted reverse pyrimidine compounds that inhibit the function of the B-cell specific Moloney murine leukemia virus integration site 1 (Bmi-1) protein and reduce the level thereof and methods of using such compounds to treat a cancer mediated by Bmi-1 are described. More particularly, amine substituted reverse pyrimidine compounds that inhibit Bmi-1 function and reduce the level of Bmi-1 are useful for treating a cancer mediated by Bmi-1.

BACKGROUND

Bmi-1 was originally identified by its over-expression in various leukemias and lymphomas. Subsequently, Bmi-1 has been shown to have oncogenic activity when overexpressed in normal cells and to play a role in the maintenance of cancer stem cell populations. Bmi-1 is elevated in many tumor types and is important in hematologic cancers and many solid tumors, including brain cancers. Reduction of Bmi-1 levels in tumor cells by siRNA causes apoptosis and/or cell senescence and increases susceptibility to cytotoxic agents. Bmi-1 serves as the key regulatory component of the PRC1 complex (polycomb repressive complex-1), but has no enzymatic activity. Therefore, targeting Bmi-1 by traditional drug discovery methods has been problematic.

Since Bmi-1 levels within cells are tightly regulated through both transcriptional and post-transcriptional mechanisms, this regulation can be exploited to target this important protein. Accordingly, there remains a need to provide compounds that inhibit Bmi-1 function and reduce the level of Bmi-1 to treat a cancer mediated by Bmi-1.

SUMMARY

Certain amine substituted reverse pyrimidine compounds that inhibit Bmi-1 function and reduce the level of Bmi-1 and methods for their use to treat a cancer mediated by Bmi-1 are described herein.

A compound of Formula (I) is described:

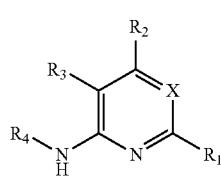

(I)

wherein X, $R_1$, $R_2$, $R_3$ and $R_4$ are as defined herein, including forms and pharmaceutical compositions thereof, and methods of using such compounds, forms or compositions thereof to treat a cancer mediated by Bmi-1 in a human subject in need thereof.

DETAILED DESCRIPTION

Figure 1:
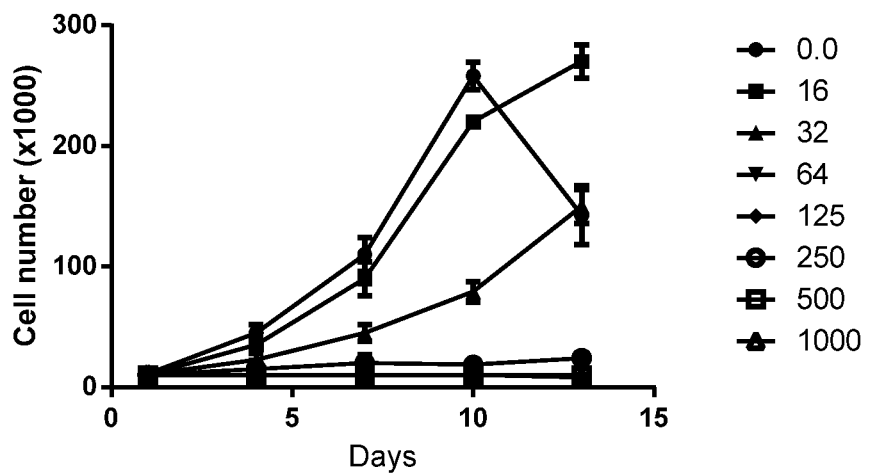
FIG. 1 demonstrates the dose dependent reduction of a CSC population in a BXD GBM model as the result of treatment with a compound of Formula (I), or a form thereof.

Amine substituted reverse pyrimidine compounds for use in inhibiting Bmi-1 function and reducing the level of Bmi-1 and in methods for treating a cancer mediated by Bmi-1 are described.

In one embodiment is a compound of Formula (I):

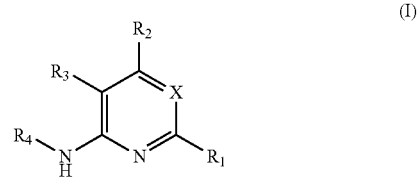

(I)

or a form thereof, wherein $R_1$ is heteroaryl or heterocyclyl optionally substituted on a carbon atom ring member with one, two, three or four $R_5$ substituents, or on a nitrogen atom ring member with an oxygen atom substituent to form an N-oxide;

X is N or N substituted with an oxygen atom substituent to form an N-oxide;

$R_2$ is hydrogen, cyano, halo, hydroxyl, nitro, $C_{1-8}$alkyl, hydroxyl-$C_{1-8}$alkyl, $C_{1-8}$alkoxy, amino, $C_{1-8}$alkyl-amino, $(C_{1-8}$alkyl$)_2$-amino, hydroxyl-amino, hydroxyl-$C_{1-8}$alkyl-amino, $C_{1-8}$alkoxy-$C_{1-8}$alkyl-amino, $C_{1-8}$alkyl-thio, $C_{1-8}$alkyl-carbonyl, $C_{1-8}$alkyl-carbonyl-amino, amino-carbonyl, $C_{1-8}$alkyl-amino-carbonyl, $(C_{1-8}$alkyl$)_2$-amino-carbonyl, amino-carbonyl-amino, $C_{1-8}$alkyl-amino-carbonyl-amino, $(C_{1-8}$alkyl$)_2$-amino-carbonyl-amino, $C_{1-8}$alkoxy-carbonyl, $C_{1-8}$alkoxy-carbonyl-amino, amino-sulfonyl, $C_{1-8}$alkyl-amino-sulfonyl, $(C_{1-8}$alkyl$)_2$-amino-sulfonyl, amino-sulfonyl-amino, $C_{1-8}$alkyl-amino-sulfonyl-amino, $(C_{1-8}$alkyl$)_2$-amino-sulfonyl-amino, P(O)$(R_7)_2$-amino or heteroaryl, wherein heteroaryl is optionally substituted with one, two, three or four $C_{1-8}$alkyl substituents;

$R_3$ is hydrogen, cyano, halo, $C_{1-8}$alkyl, amino, $C_{1-8}$alkyl-amino or $(C_{1-8}$alkyl$)_2$-amino;

$R_4$ is $C_{3-14}$cycloalkyl, aryl, heteroaryl or heterocyclyl, each optionally substituted with one, two, three or four $R_6$ substituents;

$R_5$ is independently selected from cyano, halo, hydroxyl, nitro, oxo, $C_{1-8}$alkyl, cyano-$C_{1-8}$alkyl, halo-$C_{1-8}$alkyl, hydroxyl-$C_{1-8}$alkyl, $C_{1-8}$alkoxy, $C_{1-8}$alkoxy-$C_{1-8}$alkyl, halo-$C_{1-8}$alkoxy, $C_{2-8}$alkenyl, $C_{1-8}$alkoxy-$C_{2-8}$alkenyl, $C_{2-8}$alkynyl, $C_{1-8}$alkoxy-$C_{2-8}$alkynyl, carboxyl, amino, $C_{1-8}$alkyl-amino, $(C_{1-8}$alkyl$)_2$-amino, amino-$C_{1-8}$alkyl, $C_{1-8}$alkyl-amino-$C_{1-8}$alkyl, $(C_{1-8}$alkyl$)_2$-amino-$C_{1-8}$alkyl, hydroxyl-$C_{1-8}$alkyl-amino, hydroxyl-$C_{1-8}$alkyl-amino-$C_{1-8}$alkyl, hydroxyl-$C_{1-8}$alkyl-amino-$C_{1-8}$alkyl-amino, $C_{1-8}$alkyl-thio, $C_{1-8}$alkyl-carbonyl, $C_{1-8}$alkyl-carbonyl-amino, $C_{1-8}$alkyl-carbonyl-oxy, $C_{1-8}$alkyl-carbonyl-oxy-$C_{1-8}$alkyl, $C_{1-8}$alkoxy-carbonyl, $C_{1-8}$alkoxy-carbonyl-$C_{1-8}$alkyl, $C_{1-8}$alkoxy-carbonyl-amino, $C_{1-8}$alkyl-sulfonyl, $C_{3-14}$cycloalkyl, aryl, aryl-$C_{1-8}$alkyl, aryl-amino, aryl-$C_{1-8}$alky-amino, heteroaryl, heteroaryl-$C_{1-8}$alkyl or heterocyclyl, wherein $C_{3-14}$cycloalkyl, aryl, heteroaryl or heterocyclyl and the aryl and heteroaryl portions of aryl-$C_{1-8}$alkyl, aryl-amino, aryl-$C_{1-8}$alky-amino and heteroaryl-$C_{1-8}$alkyl are each optionally substituted with one, two, three or four halo, $C_{1-8}$alkyl, halo-$C_{1-8}$alkyl, hydroxyl-$C_{1-8}$alkyl, $C_{1-8}$alkoxy, halo-$C_{1-8}$alkoxy, hydroxyl-$C_{1-8}$alkoxy or carboxyl substituents;

$R_6$ is independently selected from cyano, halo, hydroxyl, nitro, $C_{1-8}$alkyl, halo-$C_{1-8}$alkyl, hydroxyl-$C_{1-8}$alkyl, $C_{1-8}$alkoxy, halo-$C_{1-8}$alkoxy, $C_{2-8}$alkenyl, $C_{1-8}$alkoxy-$C_{2-8}$alkenyl, $C_{2-8}$alkynyl, $C_{1-8}$alkoxy-$C_{2-8}$alkynyl, carboxyl, formyl, formyl-oxy, $C_{1-8}$alkyl-carbonyl, halo-$C_{1-8}$alkyl-carbonyl, $C_{1-8}$alkyl-thio, halo-$C_{1-8}$alkyl-thio, amino, $C_{1-8}$alkyl-amino, $(C_{1-8}$alkyl$)_2$-amino, $C_{1-8}$alkyl-carbonyl, $C_{1-8}$alkyl-carbonyl-oxy, $C_{1-8}$alkyl-carbonyl-oxy-$C_{1-8}$alkyl, $C_{1-8}$alkoxy-carbonyl, halo-$C_{1-8}$alkoxy-carbonyl, $C_{1-8}$alkoxy-carbonyl-$C_{1-8}$alkyl, $C_{1-8}$alkoxy-carbonyl-amino, $C_{1-8}$alkoxy-carbonyl-amino-$C_{1-8}$alkyl, amino-carbonyl, $C_{1-8}$alkyl-amino-carbonyl, $(C_{1-8}$alkyl$)_2$-amino-carbonyl, $C_{1-8}$alkyl-carbonyl-amino, $C_{1-8}$alkyl-carbonyl-amino-$C_{1-8}$alkyl, amino-$C_{1-8}$alkyl, $C_{1-8}$alkyl-amino-$C_{1-8}$alkyl, $(C_{1-8}$alkyl$)_2$-amino-$C_{1-8}$alkyl, amino-$C_{1-8}$alkyl-amino, $C_{1-8}$alkyl-amino-$C_{1-8}$alkyl-amino, $(C_{1-8}$alkyl$)_2$-amino-$C_{1-8}$alkyl-amino, hydroxyl-$C_{1-8}$alkyl-amino, hydroxyl-$C_{1-8}$alkyl-amino-$C_{1-8}$alkyl, hydroxyl-$C_{1-8}$alkyl-amino-$C_{1-8}$alkyl-amino, imino-$C_{1-8}$alkyl, hydroxyl-imino-$C_{1-8}$alkyl, $C_{1-8}$alkoxy-imino-$C_{1-8}$alkyl, $C_{1-8}$alkyl-sulfonyl, halo-$C_{1-8}$alkyl-sulfonyl, amino-sulfonyl, $C_{1-8}$alkyl-amino-sulfonyl, $(C_{1-8}$alkyl$)_2$-amino-sulfonyl, $B(OR_8)_2$, $C_{3-14}$cycloalkyl, heterocyclyl, aryl or heteroaryl, wherein $C_{3-14}$cycloalkyl, heterocyclyl, aryl, and heteroaryl are each optionally substituted with one, two, three or four halo or $C_{1-8}$alkyl substituents;

$R_7$ is independently hydroxyl or $(C_{1-8}$alkoxy), wherein n represents an integer from 1 to 5; and, $R_8$ is independently hydrogen or $C_{1-8}$alkyl.

Another embodiment includes a compound of Formula (I), wherein $R_1$ is optionally substituted heteroaryl or heterocyclyl selected from 1H-pyrazolyl, 1H-imidazolyl, 1,2-oxazolyl, pyridinyl, 1H-indolyl, 2H-indazolyl, 4,5,6,7-tetrahydro-2H-indazolyl, 1H-benzimidazolyl, imidazo[2,1-b][1,3]thiazolyl, pyrazolo[1,5-a]pyridinyl, pyrazolo[1,5-c]pyrimidinyl, imidazo[1,2-a]pyridinyl, 5,6,7,8-tetrahydroimidazo[1,2-a]pyridinyl, 1H-imidazo[4,5-b]pyridinyl, 1H-imidazo[4,5-c]pyridinyl, 4,5,6,7-tetrahydro-3H-imidazo[4,5-c]pyridinyl, imidazo[1,2-a]pyrazinyl, imidazo[1,2-a]pyrimidinyl, 7H-purinyl or quinolinyl.

Another embodiment includes a compound of Formula (I), wherein $R_1$ is optionally substituted heteroaryl or heterocyclyl selected from 1H-pyrazolyl, 1H-imidazolyl, 1,2-oxazolyl, pyridinyl, 1H-indolyl, 2H-indazolyl, 4,5,6,7-tetrahydro-2H-indazolyl, 1H-benzimidazolyl, imidazo[2,1-b][1,3]thiazolyl, pyrazolo[1,5-a]pyridinyl, imidazo[1,2-a]pyridinyl, 5,6,7,8-tetrahydroimidazo[1,2-a]pyridinyl, 1H-imidazo[4,5-b]pyridinyl, 1H-imidazo[4,5-c]pyridinyl, 4,5,6,7-tetrahydro-3H-imidazo[4,5-c]pyridinyl, imidazo[1,2-a]pyrazinyl, imidazo[1,2-a]pyrimidinyl, 7H-purinyl or quinolinyl.

Another embodiment includes a compound of Formula (I), wherein $R_1$ is optionally substituted heteroaryl or heterocyclyl selected from 1H-pyrazol-4-yl, 1H-imidazol-1-yl, 1H-imidazol-5-yl, 1,2-oxazol-4-yl, 1,2-oxazol-5-yl, pyridin-4-yl, 1H-indol-1-yl, 1H-indol-3-yl, 1H-indol-4-yl, 2H-indazol-3-yl, 4,5,6,7-tetrahydro-2H-indazol-3-yl, 1H-benzimidazol-1-yl, imidazo[2,1-b][1,3]thiazol-5-yl, pyrazolo[1,5-a]pyridin-2-yl, pyrazolo[1,5-a]pyridin-3-yl, pyrazolo[1,5-a]pyridin-7-yl, pyrazolo[1,5-c]pyrimidin-3-yl, imidazo[1,2-a]pyridin-2-yl, imidazo[1,2-a]pyridin-3-yl, imidazo[1,2-a]pyridin-5-yl, 5,6,7,8-tetrahydroimidazo[1,2-a]pyridin-3-yl, 1H-imidazo[4,5-b]pyridin-1-yl, 1H-imidazo[4,5-c]pyridin-1-yl, 4,5,6,7-tetrahydro-3H-imidazo[4,5-c]pyridin-3-yl, imidazo[1,2-a]pyrazin-3-yl, imidazo[1,2-a]pyrimidin-3-yl, 7H-purin-7-yl or quinolin-4-yl.

Another embodiment includes a compound of Formula (I), wherein $R_1$ is optionally substituted heteroaryl or heterocyclyl selected from 1H-pyrazol-4-yl, 1H-imidazol-1-yl, 1H-imidazol-5-yl, 1,2-oxazol-4-yl, 1,2-oxazol-5-yl, pyridin-4-yl, 1H-indol-1-yl, 1H-indol-4-yl, 2H-indazol-3-yl, 4,5,6,7-tetrahydro-2H-indazol-3-yl, 1H-benzimidazol-1-yl, imidazo[2,1-b][1,3]thiazol-5-yl, pyrazolo[1,5-a]pyridin-3-yl, pyrazolo[1,5-a]pyridin-7-yl, imidazo[1,2-a]pyridin-3-yl, imidazo[1,2-a]pyridin-5-yl, 5,6,7,8-tetrahydroimidazo[1,2-a]pyridin-3-yl, 1H-imidazo[4,5-b]pyridin-1-yl, 1H-imidazo[4,5-c]pyridin-1-yl, 4,5,6,7-tetrahydro-3H-imidazo[4,5-c]pyridin-3-yl, imidazo[1,2-a]pyrazin-3-yl, imidazo[1,2-a]pyrimidin-3-yl, 7H-purin-7-yl or quinolin-4-yl.

Another embodiment includes a compound of Formula (I), wherein $R_1$ is optionally substituted heteroaryl or heterocyclyl selected from 1H-pyrazol-4-yl, 1H-imidazol-1-yl, 1H-imidazol-5-yl, 1,2-oxazol-4-yl, 1,2-oxazol-5-yl, pyridin-4-yl, 1H-indol-1-yl, 1H-indol-4-yl, 2H-indazol-3-yl, 4,5,6,7-tetrahydro-2H-indazol-3-yl, 1H-benzimidazol-1-yl, imidazo[2,1-b][1,3]thiazol-5-yl, pyrazolo[1,5-a]pyridin-3-yl, pyrazolo[1,5-a]pyridin-7-yl, imidazo[1,2-a]pyridin-3-yl, imidazo[1,2-a]pyridin-5-yl, 5,6,7,8-tetrahydroimidazo[1,2-a]pyridin-3-yl, 1H-imidazo[4,5-b]pyridin-1-yl, 1H-imidazo[4,5-c]pyridin-1-yl, 4,5,6,7-tetrahydro-3H-imidazo[4,5-c]pyridin-3-yl, 7H-purin-7-yl or quinolin-4-yl.

Another embodiment includes a compound of Formula (I), wherein $R_1$ is optionally substituted heteroaryl selected from 1H-pyrazolyl, 1H-imidazolyl, 1,2-oxazolyl, pyridinyl, 1H-indolyl, 2H-indazolyl, 1H-benzimidazolyl, imidazo[2,1-b][1,3]thiazolyl, pyrazolo[1,5-a]pyridinyl, pyrazolo[1,5-c]pyrimidinyl, imidazo[1,2-a]pyridinyl, 1H-imidazo[4,5-b]pyridinyl, 1H-imidazo[4,5-c]pyridinyl, imidazo[1,2-a]pyrazinyl, imidazo[1,2-a]pyrimidinyl, 7H-purinyl or quinolinyl.

Another embodiment includes a compound of Formula (I), wherein $R_1$ is optionally substituted heteroaryl selected from 1H-pyrazolyl, 1H-imidazolyl, 1,2-oxazolyl, pyridinyl, 1H-indolyl, 2H-indazolyl, 1H-benzimidazolyl, imidazo[2,1-b][1,3]thiazolyl, pyrazolo[1,5-a]pyridinyl, imidazo[1,2-a]pyridinyl, 1H-imidazo[4,5-b]pyridinyl, 1H-imidazo[4,5-c]pyridinyl, imidazo[1,2-a]pyrazinyl, imidazo[1,2-a]pyrimidinyl, 7H-purinyl or quinolinyl.

Another embodiment includes a compound of Formula (I), wherein $R_1$ is optionally substituted heteroaryl selected from 1H-pyrazolyl, 1H-imidazolyl, 1,2-oxazolyl, pyridinyl, 1H-indolyl, 2H-indazolyl, 1H-benzimidazolyl, imidazo[2,1- b][1,3]thiazolyl, pyrazolo[1,5-a]pyridinyl, imidazo[1,2-a]pyridinyl, 1H-imidazo[4,5-b]pyridinyl, 1H-imidazo[4,5-c]pyridinyl, 7H-purinyl or quinolinyl.

Another embodiment includes a compound of Formula (I), wherein $R_1$ is optionally substituted heteroaryl selected from 1H-pyrazolyl, 1H-indolyl, 1H-benzimidazolyl, pyrazolo[1,5-a]pyridinyl, imidazo[1,2-a]pyridinyl, 1H-imidazo[4,5-b]pyridinyl, imidazo[1,2-a]pyrazinyl or imidazo[1,2-a]pyrimidinyl.

Another embodiment includes a compound of Formula (I), wherein $R_1$ is optionally substituted heteroaryl selected from 1H-pyrazolyl, 1H-indolyl, 1H-benzimidazolyl, pyrazolo[1,5-a]pyridinyl, imidazo[1,2-a]pyridinyl or 1H-imidazo[4,5-b]pyridinyl.

Another embodiment includes a compound of Formula (I), wherein $R_1$ is optionally substituted heteroaryl selected from imidazo[1,2-a]pyrazinyl or imidazo[1,2-a]pyrimidinyl.

Another embodiment includes a compound of Formula (I), wherein $R_1$ is optionally substituted imidazo[1,2-a]pyrazinyl.

Another embodiment includes a compound of Formula (I), wherein $R_1$ is optionally substituted imidazo[1,2-a]pyrimidinyl.

Another embodiment includes a compound of Formula (I), wherein $R_1$ is optionally substituted heteroaryl selected from 1H-pyrazol-4-yl, 1H-imidazol-1-yl, 1H-imidazol-5-yl, 1,2-oxazol-4-yl, 1,2-oxazol-5-yl, pyridin-4-yl, 1H-indol-1-yl, 1H-indol-3-yl, 1H-indol-4-yl, 2H-indazol-3-yl, 1H-benzimidazol-1-yl, imidazo[2,1-b][1,3]thiazol-5-yl, pyrazolo[1,5-a]pyridin-2-yl, pyrazolo[1,5-a]pyridin-3-yl, pyrazolo[1,5-a]pyridin-7-yl, pyrazolo[1,5-c]pyrimidin-3-yl, imidazo[1,2-a]pyridin-2-yl, imidazo[1,2-a]pyridin-3-yl, imidazo[1,2-a]pyridin-5-yl, 1H-imidazo[4,5-b]pyridin-1-yl, 1H-imidazo[4,5-c]pyridin-1-yl, imidazo[1,2-a]pyrazin-3-yl, imidazo[1,2-a]pyrimidin-3-yl, 7H-purin-7-yl or quinolin-4-yl.

Another embodiment includes a compound of Formula (I), wherein $R_1$ is optionally substituted heteroaryl selected from 1H-pyrazol-4-yl, 1H-imidazol-1-yl, 1H-imidazol-5-yl, 1,2-oxazol-4-yl, 1,2-oxazol-5-yl, pyridin-4-yl, 1H-indol-1-yl, 1H-indol-4-yl, 2H-indazol-3-yl, 1H-benzimidazol-1-yl, imidazo[2,1-b][1,3]thiazol-5-yl, pyrazolo[1,5-a]pyridin-3-yl, pyrazolo[1,5-a]pyridin-7-yl, imidazo[1,2-a]pyridin-3-yl, imidazo[1,2-a]pyridin-5-yl, 1H-imidazo[4,5-b]pyridin-1-yl, 1H-imidazo[4,5-c]pyridin-1-yl, imidazo[1,2-a]pyrazin-3-yl, imidazo[1,2-a]pyrimidin-3-yl, 7H-purin-7-yl or quinolin-4-yl.

Another embodiment includes a compound of Formula (I), wherein $R_1$ is optionally substituted heteroaryl selected from 1H-pyrazol-4-yl, 1H-imidazol-1-yl, 1H-imidazol-5-yl, 1,2-oxazol-4-yl, 1,2-oxazol-5-yl, pyridin-4-yl, 1H-indol-1-yl, 1H-indol-4-yl, 2H-indazol-3-yl, 1H-benzimidazol-1-yl, imidazo[2,1-b][1,3]thiazol-5-yl, pyrazolo[1,5-a]pyridin-7-yl, imidazo[1,2-a]pyridin-5-yl, 1H-imidazo[4,5-b]pyridin-1-yl, 1H-imidazo[4,5-c]pyridin-1-yl, imidazo[1,2-a]pyrazin-3-yl, imidazo[1,2-a]pyrimidin-3-yl, 7H-purin-7-yl or quinolin-4-yl.

Another embodiment includes a compound of Formula (I), wherein $R_1$ is optionally substituted heteroaryl selected from 1H-pyrazol-4-yl, 1H-indol-1-yl, 1H-indol-3-yl, 1H-indol-4-yl, 1H-benzimidazol-1-yl, pyrazolo[1,5-a]pyridin-2-yl, pyrazolo[1,5-a]pyridin-3-yl, pyrazolo[1,5-a]pyridin-7-yl, imidazo[1,2-a]pyridin-2-yl, imidazo[1,2-a]pyridin-3-yl, imidazo[1,2-a]pyridin-5-yl, 1H-imidazo[4,5-b]pyridin-1-yl, imidazo[1,2-a]pyrazin-3-yl or imidazo[1,2-a]pyrimidin-3-yl.

Another embodiment includes a compound of Formula (I), wherein $R_1$ is optionally substituted heteroaryl selected from 1H-pyrazol-4-yl, 1H-indol-3-yl, 1H-benzimidazol-1-yl, pyrazolo[1,5-a]pyridin-2-yl, pyrazolo[1,5-a]pyridin-3-yl, imidazo[1,2-a]pyridin-2-yl, imidazo[1,2-a]pyridin-3-yl, 1H-imidazo[4,5-b]pyridin-1-yl, imidazo[1,2-a]pyrazin-3-yl or imidazo[1,2-a]pyrimidin-3-yl.

Another embodiment includes a compound of Formula (I), wherein $R_1$ is optionally substituted heteroaryl selected from 1H-pyrazol-4-yl, 1H-indol-3-yl, 1H-benzimidazol-1-yl, pyrazolo[1,5-a]pyridin-3-yl, imidazo[1,2-a]pyridin-3-yl, 1H-imidazo[4,5-b]pyridin-1-yl, imidazo[1,2-a]pyrazin-3-yl or imidazo[1,2-a]pyrimidin-3-yl.

Another embodiment includes a compound of Formula (I), wherein $R_1$ is optionally substituted imidazo[1,2-a]pyrazin-3-yl.

Another embodiment includes a compound of Formula (I), wherein $R_1$ is optionally substituted imidazo[1,2-a]pyrimidin-3-yl.

Another embodiment includes a compound of Formula (I), wherein $R_1$ is optionally substituted heterocyclyl selected from 4,5,6,7-tetrahydro-2H-indazolyl, 5,6,7,8-tetrahydroimidazo[1,2-a]pyridinyl or 4,5,6,7-tetrahydro-3H-imidazo[4,5-c]pyridinyl.

Another embodiment includes a compound of Formula (I), wherein $R_1$ is optionally substituted heterocyclyl selected from 4,5,6,7-tetrahydro-2H-indazol-3-yl, 5,6,7,8-tetrahydroimidazo[1,2-a]pyridin-3-yl or 4,5,6,7-tetrahydro-3H-imidazo[4,5-c]pyridin-3-yl.

Another embodiment includes a compound of Formula (I), wherein X is N.

Another embodiment includes a compound of Formula (I), wherein X is N substituted with an oxygen atom substituent to form an N-oxide.

Another embodiment includes a compound of Formula (I), wherein $R_2$ is cyano, halo, hydroxyl, nitro, $C_{1-8}$alkyl, hydroxyl-$C_{1-8}$alkyl, $C_{1-8}$alkoxy, amino, $C_{1-8}$alkyl-amino, $(C_{1-8}alkyl)_2$-amino, hydroxyl-amino, hydroxyl-$C_{1-8}$alkyl-amino, $C_{1-8}$alkoxy-$C_{1-8}$alkyl-amino, $C_{1-8}$alkyl-thio, $C_{1-8}$alkyl-carbonyl, $C_{1-8}$alkyl-carbonyl-amino, amino-carbonyl, $C_{1-8}$alkyl-amino-carbonyl, $(C_{1-8}alkyl)_2$-amino-carbonyl, amino-carbonyl-amino, $C_{1-8}$alkyl-amino-carbonyl-amino, $(C_{1-8}alkyl)_2$-amino-carbonyl-amino, $C_{1-8}$alkoxy-carbonyl, $C_{1-8}$alkoxy-carbonyl-amino, amino-sulfonyl, $C_{1-8}$alkyl-amino-sulfonyl, $(C_{1-8}alkyl)_2$-amino-sulfonyl, amino-sulfonyl-amino, $C_{1-8}$alkyl-amino-sulfonyl-amino, $(C_{1-8}alkyl)_2$-amino-sulfonyl-amino, $P(O)(R_7)_2$-amino or heteroaryl, wherein heteroaryl is optionally substituted with one, two, three or four $C_{1-8}$alkyl substituents.

Another embodiment includes a compound of Formula (I), wherein $R_2$ is cyano, halo, nitro, $C_{1-8}$alkyl, hydroxyl-$C_{1-8}$alkyl, $C_{1-8}$alkoxy, amino, hydroxyl-amino, hydroxyl-$C_{1-8}$alkyl-amino, $C_{1-8}$alkoxy-$C_{1-8}$alkyl-amino, $C_{1-8}$alkyl-thio, amino-carbonyl, amino-carbonyl-amino, $C_{1-8}$alkoxy-carbonyl-amino, amino-sulfonyl-amino or heteroaryl, wherein heteroaryl is optionally substituted with one, two, three or four $C_{1-8}$alkyl substituents.

Another embodiment includes a compound of Formula (I), wherein $R_2$ is cyano, halo, hydroxyl, nitro, $C_{1-8}$alkyl, hydroxyl-$C_{1-8}$alkyl, $C_{1-8}$alkoxy, amino, $C_{1-8}$alkyl-amino, $(C_{1-8}alkyl)_2$-amino, hydroxyl-amino, hydroxyl-$C_{1-8}$alkyl-amino, $C_{1-8}$alkoxy-$C_{1-8}$alkyl-amino, $C_{1-8}$alkyl-thio, $C_{1-8}$alkyl-carbonyl, $C_{1-8}$alkyl-carbonyl-amino, amino-carbonyl, $C_{1-8}$alkyl-amino-carbonyl, $(C_{1-8}alkyl)_2$-amino-carbonyl, amino-carbonyl-amino, $C_{1-8}$alkyl-amino-carbonyl-amino, $(C_{1-8}alkyl)_2$-amino-carbonyl-amino, $C_{1-8}$alkoxy-carbonyl, $C_{1-8}$alkoxy-carbonyl-amino, amino-sulfonyl, $C_{1-8}$alkyl-amino-sulfonyl, $(C_{1-8}alkyl)_2$-amino-sulfonyl, amino-sulfonyl-amino, $C_{1-8}$alkyl-amino-sulfonyl-amino, $(C_{1-8}alkyl)_2$-amino-sulfonyl-amino or $P(O)(R_7)_2$-amino.

Another embodiment includes a compound of Formula (I), wherein $R_2$ is cyano, halo, nitro, $C_{1-8}$alkyl, hydroxyl-$C_{1-8}$alkyl, $C_{1-8}$alkoxy, amino, hydroxyl-amino, hydroxyl-$C_{1-8}$alkyl-amino, $C_{1-8}$alkoxy-$C_{1-8}$alkyl-amino, $C_{1-8}$alkyl-thio, amino-carbonyl, amino-carbonyl-amino, $C_{1-8}$alkoxy-carbonyl-amino or amino-sulfonyl-amino.

Another embodiment includes a compound of Formula (I), wherein $R_2$ is heteroaryl, wherein heteroaryl is optionally substituted with one, two, three or four $C_{1-8}$alkyl substituents.

Another embodiment includes a compound of Formula (I), wherein $R_2$ heteroaryl is optionally substituted 1H-pyrrolyl.

Another embodiment includes a compound of Formula (I), wherein $R_2$ heteroaryl is optionally substituted 1H-pyrrol-1-yl.

Another embodiment includes a compound of Formula (I), wherein $R_3$ is hydrogen.

Another embodiment includes a compound of Formula (I), wherein $R_3$ is cyano, halo, $C_{1-8}$alkyl, amino, $C_{1-8}$alkyl-amino or $(C_{1-8}alkyl)_2$-amino.

Another embodiment includes a compound of Formula (I), wherein $R_3$ is cyano, halo, $C_{1-8}$alkyl or amino.

Another embodiment includes a compound of Formula (I), wherein $R_4$ is optionally substituted $C_{3-14}$cycloalkyl selected from 2,3-dihydro-1H-indenyl; or, optionally substituted aryl selected from phenyl or naphthyl; or, optionally substituted heteroaryl selected from 1,3-thiazolyl, 1,2-oxazolyl, pyridinyl, pyrimidinyl, 1H-indolyl, benzofuranyl, benzooxazolyl, 1,3-benzothiazolyl, quinolinyl or isoquinolinyl; or, optionally substituted heterocyclyl selected from 1,3-benzodioxolyl or 2,3-dihydro-1,4-benzodioxinyl.

Another embodiment includes a compound of Formula (I), wherein $R_4$ is optionally substituted $C_{3-14}$cycloalkyl selected from 2,3-dihydro-1H-indenyl.

Another embodiment includes a compound of Formula (I), wherein $R_4$ is optionally substituted $C_{3-14}$cycloalkyl selected from 2,3-dihydro-1H-inden-2-yl.

Another embodiment includes a compound of Formula (I), wherein $R_4$ is optionally substituted aryl selected from phenyl or naphthyl.

Another embodiment includes a compound of Formula (I), wherein $R_4$ is optionally substituted heteroaryl selected from 1,3-thiazolyl, 1,2-oxazolyl, pyridinyl, pyrimidinyl, 1H-indolyl, benzofuranyl, benzooxazolyl, 1,3-benzothiazolyl, quinolinyl or isoquinolinyl; or, optionally substituted heterocyclyl selected from 1,3-benzodioxolyl or 2,3-dihydro-1,4-benzodioxinyl.

Another embodiment includes a compound of Formula (I), wherein $R_4$ is optionally substituted heteroaryl selected from 1,3-thiazol-2-yl, 1,2-oxazol-5-yl, pyridin-2-yl, pyridin-3-yl, pyrimidin-5-yl, 1H-indol-5-yl, benzofuran-5-yl, benzooxazol-5-yl, 1,3-benzothiazol-2-yl, quinolin-3-yl, quinolin-6-yl or isoquinolin-3-yl; or, optionally substituted heterocyclyl selected from 1,3-benzodioxol-5-yl or 2,3-dihydro-1,4-benzodioxin-6-yl.

Another embodiment includes a compound of Formula (I), wherein $R_4$ is optionally substituted heteroaryl selected from 1,3-thiazolyl, 1,2-oxazolyl, pyridinyl, pyridinyl, pyrimidinyl, 1H-indolyl, benzofuranyl, benzooxazolyl, 1,3-benzothiazolyl, quinolinyl or isoquinolinyl.

Another embodiment includes a compound of Formula (I), wherein $R_4$ is optionally substituted heteroaryl selected from 1,3-thiazol-2-yl, 1,2-oxazol-5-yl, pyridin-2-yl, pyridin-3-yl, pyrimidin-5-yl, 1H-indol-5-yl, benzofuran-5-yl, benzooxazol-5-yl, 1,3-benzothiazol-2-yl, quinolin-3-yl, quinolin-6-yl or isoquinolin-3-yl.

Another embodiment includes a compound of Formula (I), wherein $R_4$ is optionally substituted heterocyclyl selected from 1,3-benzodioxolyl or 2,3-dihydro-1,4-benzodioxinyl.

Another embodiment includes a compound of Formula (I), wherein $R_4$ is optionally substituted heterocyclyl selected from 1,3-benzodioxol-5-yl or 2,3-dihydro-1,4-benzodioxin-6-yl.

Another embodiment includes a compound of Formula (I), wherein $R_5$ is independently selected from cyano, halo, hydroxyl, nitro, $C_{1-8}$alkyl, cyano-$C_{1-8}$alkyl, halo-$C_{1-8}$alkyl, hydroxyl-$C_{1-8}$alkyl, $C_{1-8}$alkoxy, $C_{1-8}$alkoxy-$C_{1-8}$alkyl, halo-$C_{1-8}$alkoxy, $C_{2-8}$alkenyl, $C_{1-8}$alkoxy-$C_{2-8}$alkenyl, carboxyl, amino, $C_{1-8}$alkyl-amino, $C_{1-8}$alkyl-amino-$C_{1-8}$alkyl, hydroxyl-$C_{1-8}$alkyl-amino, $C_{1-8}$alkyl-thio, $C_{1-8}$alkyl-carbonyl, $C_{1-8}$alkyl-carbonyl-oxy-$C_{1-8}$alkyl, $C_{1-8}$alkoxy-carbonyl, $C_{1-8}$alkyl-sulfonyl, $C_{3-14}$cycloalkyl, aryl-$C_{1-8}$alkyl, aryl-amino, aryl-$C_{1-8}$alky-amino, heteroaryl or heteroaryl-$C_{1-8}$alkyl, wherein heteroaryl and the aryl and heteroaryl portions of aryl-$C_{1-8}$alkyl, aryl-amino, aryl-$C_{1-8}$alky-amino and heteroaryl-$C_{1-8}$alkyl are each optionally substituted with one, two, three or four halo or halo-$C_{1-8}$alkoxy substituents.

Another embodiment includes a compound of Formula (I), wherein $R_5$ is independently selected from cyano, halo, hydroxyl, nitro, oxo, $C_{1-8}$alkyl, cyano-$C_{1-8}$alkyl, halo-$C_{1-8}$alkyl, hydroxyl-$C_{1-8}$alkyl, $C_{1-8}$alkoxy, $C_{1-8}$alkoxy-$C_{1-8}$alkyl, halo-$C_{1-8}$alkoxy, $C_{2-8}$alkenyl, $C_{1-8}$alkoxy-$C_{2-8}$alkenyl, $C_{2-8}$alkynyl, $C_{1-8}$alkoxy-$C_{2-8}$alkynyl, carboxyl, amino, $C_{1-8}$alkyl-amino, $(C_{1-8}alkyl)_2$-amino, amino-$C_{1-8}$alkyl, $C_{1-8}$alkyl-amino-$C_{1-8}$alkyl, $(C_{1-8}alkyl)_2$-amino-$C_{1-8}$alkyl, hydroxyl-$C_{1-8}$alkyl-amino, hydroxyl-$C_{1-8}$alkyl-amino-$C_{1-8}$alkyl, hydroxyl-$C_{1-8}$alkyl-amino-$C_{1-8}$alkyl-amino, $C_{1-8}$alkyl-thio, $C_{1-8}$alkyl-carbonyl, $C_{1-8}$alkyl-carbonyl-amino, $C_{1-8}$alkyl-carbonyl-oxy, $C_{1-8}$alkyl-carbonyl-oxy-$C_{1-8}$alkyl, $C_{1-8}$alkoxy-carbonyl, $C_{1-8}$alkoxy-carbonyl-$C_{1-8}$alkyl, $C_{1-8}$alkoxy-carbonyl-amino or $C_{1-8}$alkyl-sulfonyl.

Another embodiment includes a compound of Formula (I), wherein $R_5$ is independently selected from cyano, halo, hydroxyl, nitro, $C_{1-8}$alkyl, cyano-$C_{1-8}$alkyl, halo-$C_{1-8}$alkyl, hydroxyl-$C_{1-8}$alkyl, $C_{1-8}$alkoxy, $C_{1-8}$alkoxy-$C_{1-8}$alkyl, halo-$C_{1-8}$alkoxy, $C_{2-8}$alkenyl, $C_{1-8}$alkoxy-$C_{2-8}$alkenyl, carboxyl, amino, $C_{1-8}$alkyl-amino, $C_{1-8}$alkyl-amino-$C_{1-8}$alkyl, hydroxyl-$C_{1-8}$alkyl-amino, $C_{1-8}$alkyl-thio, $C_{1-8}$alkyl-carbonyl, $C_{1-8}$alkyl-carbonyl-oxy-$C_{1-8}$alkyl, $C_{1-8}$alkoxy-carbonyl or $C_{1-8}$alkyl-sulfonyl.

Another embodiment includes a compound of Formula (I), wherein $R_5$ is independently selected from optionally substituted $C_{3-14}$cycloalkyl selected from cyclopropyl or cyclobutyl; or, aryl, aryl-$C_{1-8}$alkyl, aryl-amino or aryl-$C_{1-8}$alky-amino optionally substituted on aryl and the aryl portions, wherein aryl is selected from phenyl; and, wherein the optional substituents on $C_{3-14}$cycloalkyl, aryl and the aryl portions are selected from one, two, three or four halo, $C_{1-8}$alkyl, halo-$C_{1-8}$alkyl, hydroxyl-$C_{1-8}$alkyl, $C_{1-8}$alkoxy, halo-$C_{1-8}$alkoxy, hydroxyl-$C_{1-8}$alkyl or carboxyl substituents; or, heteroaryl or heteroaryl-$C_{1-8}$alkyl optionally substituted on heteroaryl and the heteroaryl portion, wherein heteroaryl is selected from tetrazolyl or pyridinyl; and, wherein the optional substituents on heteroaryl and the heteroaryl portion are selected from one, two, three or four halo, $C_{1-8}$alkyl, halo-$C_{1-8}$alkyl, hydroxyl-$C_{1-8}$alkyl, $C_{1-8}$alkoxy, halo-$C_{1-8}$alkoxy, hydroxyl-$C_{1-8}$alkyl or carboxyl substituents.

Another embodiment includes a compound of Formula (I), wherein $R_5$ is independently selected from optionally substituted $C_{3-14}$cycloalkyl selected from cyclopropyl or cyclobutyl; or, aryl-$C_{1-8}$alkyl, aryl-amino or aryl-$C_{1-8}$alkyamino optionally substituted on the aryl portions, wherein aryl is selected from phenyl; and, wherein the optional substituents on $C_{3-14}$cycloalkyl and the aryl portions are selected from one, two, three or four halo or halo-$C_{1-8}$alkoxy substituents; or, heteroaryl or heteroaryl-$C_{1-8}$alkyl optionally substituted on heteroaryl and the heteroaryl portion, wherein heteroaryl is selected from tetrazolyl or pyridinyl; and, wherein the optional substituents on heteroaryl and the heteroaryl portion are selected from one, two, three or four halo or halo-$C_{1-8}$alkoxy substituents.

Another embodiment includes a compound of Formula (I), wherein $R_5$ is independently selected from optionally substituted $C_{3-14}$cycloalkyl selected from cyclopropyl or cyclobutyl.

Another embodiment includes a compound of Formula (I), wherein $R_5$ is independently selected from aryl, aryl-$C_{1-8}$alkyl, aryl-amino or aryl-$C_{1-8}$alky-amino optionally substituted on aryl and the aryl portions, wherein aryl is selected from phenyl; and, wherein the optional substituents are selected from one, two, three or four halo, $C_{1-8}$alkyl, halo-$C_{1-8}$alkyl, hydroxyl-$C_{1-8}$alkyl, $C_{1-8}$alkoxy, halo-$C_{1-8}$alkoxy, hydroxyl-$C_{1-8}$alkyl or carboxyl substituents.

Another embodiment includes a compound of Formula (I), wherein $R_5$ is independently selected from aryl-$C_{1-8}$alkyl, aryl-amino or aryl-$C_{1-8}$alky-amino optionally substituted on the aryl portions, wherein aryl is selected from phenyl; and, wherein the optional substituents are selected from one, two, three or four halo or halo-$C_{1-8}$alkoxy substituents.

Another embodiment includes a compound of Formula (I), wherein $R_5$ is independently selected from heteroaryl or heteroaryl-$C_{1-8}$alkyl optionally substituted on heteroaryl and the heteroaryl portion, wherein heteroaryl is selected from tetrazolyl or pyridinyl; and, wherein the optional substituents are selected from one, two, three or four halo, $C_{1-8}$alkyl, halo-$C_{1-8}$alkyl, hydroxyl-$C_{1-8}$alkyl, $C_{1-8}$alkoxy, halo-$C_{1-8}$alkoxy, hydroxyl-$C_{1-8}$alkyl or carboxyl substituents.

Another embodiment includes a compound of Formula (I), wherein $R_5$ is independently selected from heteroaryl or heteroaryl-$C_{1-8}$alkyl optionally substituted on heteroaryl and the heteroaryl portion, wherein heteroaryl is selected from tetrazolyl or pyridinyl; and, wherein the optional substituents are selected from one, two, three or four halo or halo-$C_{1-8}$alkoxy substituents.

Another embodiment includes a compound of Formula (I), wherein $R_5$ is independently selected from heteroaryl or heteroaryl-$C_{1-8}$alkyl optionally substituted on heteroaryl and the heteroaryl portion, wherein heteroaryl is selected from 2H-tetrazol-2-yl, tetrazol-1-yl, pyridin-2-yl, pyridin-3-yl or pyridin-4-yl; and, wherein the optional substituents are selected from one, two, three or four halo or halo-$C_{1-8}$alkoxy substituents.

Another embodiment includes a compound of Formula (I), wherein $R_6$ is independently selected from cyano, halo, hydroxyl, nitro, $C_{1-8}$alkyl, halo-$C_{1-8}$alkyl, hydroxyl-$C_{1-8}$alkyl, $C_{1-8}$alkoxy, halo-$C_{1-8}$alkoxy, $C_{2-8}$alkenyl, $C_{2-8}$alkynyl, formyl, formyl-oxy, $C_{1-8}$alkyl-carbonyl, halo-$C_{1-8}$alkyl-carbonyl, $C_{1-8}$alkyl-thio, halo-$C_{1-8}$alkyl-thio, amino, $C_{1-8}$alkyl-carbonyl, $C_{1-8}$alkoxy-carbonyl, amino-carbonyl, $C_{1-8}$alkyl-amino-carbonyl, amino-$C_{1-8}$alkyl, $(C_{1-8}$alkyl$)_2$-amino-$C_{1-8}$alkyl-amino, hydroxyl-$C_{1-8}$alkyl-amino, hydroxyl-imino-$C_{1-8}$alkyl, $C_{1-8}$alkyl-sulfonyl, B$(OR_8)_2$, $C_{3-14}$cycloalkyl, heterocyclyl, aryl or heteroaryl, wherein $C_{3-14}$cycloalkyl, heterocyclyl, aryl and heteroaryl are each optionally substituted with one, two, three or four halo or $C_{1-8}$alkyl substituents.

Another embodiment includes a compound of Formula (I), wherein $R_6$ is independently selected from cyano, halo, hydroxyl, nitro, $C_{1-8}$alkyl, halo-$C_{1-8}$alkyl, hydroxyl-$C_{1-8}$alkyl, $C_{1-8}$alkoxy, halo-$C_{1-8}$alkoxy, $C_{2-8}$alkenyl, $C_{1-8}$alkoxy-$C_{2-8}$alkenyl, $C_{2-8}$alkynyl, $C_{1-8}$alkoxy-$C_{2-8}$alkynyl, carboxyl, formyl, formyl-oxy, $C_{1-8}$alkyl-carbonyl, halo-$C_{1-8}$alkyl-carbonyl, $C_{1-8}$alkyl-thio, halo-$C_{1-8}$alkyl-thio, amino, $C_{1-8}$alkyl-amino, $(C_{1-8}$alkyl$)_2$-amino, $C_{1-8}$alkyl-carbonyl, $C_{1-8}$alkyl-carbonyl-oxy, $C_{1-8}$alkyl-carbonyl-oxy-$C_{1-8}$alkyl, $C_{1-8}$alkoxy-carbonyl, halo-$C_{1-8}$alkoxy-carbonyl, $C_{1-8}$alkoxy-carbonyl-$C_{1-8}$alkyl, $C_{1-8}$alkoxy-carbonyl-amino, $C_{1-8}$alkoxy-carbonyl-amino-$C_{1-8}$alkyl, amino-carbonyl, $C_{1-8}$alkyl-amino-carbonyl, $(C_{1-8}$alkyl$)_2$-amino-carbonyl, $C_{1-8}$alkyl-carbonyl-amino, $C_{1-8}$alkyl-carbonyl-amino-$C_{1-8}$alkyl, amino-$C_{1-8}$alkyl, $C_{1-8}$alkyl-amino-$C_{1-8}$alkyl, $(C_{1-8}$alkyl$)_2$-amino-$C_{1-8}$alkyl, amino-$C_{1-8}$ alkyl-amino, $C_{1-8}$alkyl-amino-$C_{1-8}$alkyl-amino, $(C_{1-8}$alkyl$)_2$-amino-$C_{1-8}$alkyl-amino, hydroxyl-$C_{1-8}$alkyl-amino, hydroxyl-$C_{1-8}$alkyl-amino-$C_{1-8}$alkyl, hydroxyl-$C_{1-8}$alkyl-amino-$C_{1-8}$alkyl-amino, imino-$C_{1-8}$alkyl, hydroxyl-imino-$C_{1-8}$alkyl, $C_{1-8}$alkoxy-imino-$C_{1-8}$alkyl, $C_{1-8}$alkyl-sulfonyl, halo-$C_{1-8}$alkyl-sulfonyl, amino-sulfonyl, $C_{1-8}$alkyl-amino-sulfonyl, $(C_{1-8}$alkyl$)_2$-amino-sulfonyl or B$(OR_8)_2$.

Another embodiment includes a compound of Formula (I), wherein $R_6$ is independently selected from cyano, halo, hydroxyl, nitro, $C_{1-8}$alkyl, halo-$C_{1-8}$alkyl, hydroxyl-$C_{1-8}$alkyl, $C_{1-8}$alkoxy, halo-$C_{1-8}$alkoxy, $C_{2-8}$alkenyl, $C_{2-8}$alkynyl, formyl, formyl-oxy, $C_{1-8}$alkyl-carbonyl, halo-$C_{1-8}$alkyl-carbonyl, $C_{1-8}$alkyl-thio, halo-$C_{1-8}$alkyl-thio, amino, $C_{1-8}$alkyl-carbonyl, $C_{1-8}$alkoxy-carbonyl, amino-carbonyl, $C_{1-8}$alkyl-amino-carbonyl, amino-$C_{1-8}$alkyl, $(C_{1-8}$alkyl$)_2$-amino-$C_{1-8}$alkyl-amino, hydroxyl-$C_{1-8}$alkyl-amino, hydroxyl-imino-$C_{1-8}$alkyl, $C_{1-8}$alkyl-sulfonyl, $C_{1-8}$alkyl-amino-sulfonyl or B$(OR_8)_2$.

Another embodiment includes a compound of Formula (I), wherein $R_6$ is independently selected from $C_{3-14}$cycloalkyl, heterocyclyl, aryl or heteroaryl, wherein $C_{3-14}$cycloalkyl, heterocyclyl, aryl and heteroaryl are each optionally substituted with one, two, three or four halo or $C_{1-8}$alkyl substituents.

Another embodiment includes a compound of Formula (I), wherein $R_6$ is independently selected from $C_{3-14}$cycloalkyl or heterocyclyl, wherein $C_{3-14}$cycloalkyl and heterocyclyl are each optionally substituted with two $C_{1-8}$alkyl substituents.

Another embodiment includes a compound of Formula (I), wherein $R_6$ optionally substituted $C_{3-14}$cycloalkyl is selected from cyclopropyl; optionally substituted heterocyclyl is selected from morpholinyl or 1,3,2-dioxaborolanyl; optionally substituted aryl is selected from phenyl; or, optionally substituted heteroaryl is selected from 1H-pyrazolyl.

Another embodiment includes a compound of Formula (I), wherein $R_6$ optionally substituted $C_{3-14}$cycloalkyl is selected from cyclopropyl.

Another embodiment includes a compound of Formula (I), wherein $R_6$ optionally substituted heterocyclyl is selected from morpholinyl or 1,3,2-dioxaborolanyl.

Another embodiment includes a compound of Formula (I), wherein $R_6$ optionally substituted heterocyclyl is selected from morpholin-4-yl or 1,3,2-dioxaborolan-2-yl.

Another embodiment includes a compound of Formula (I), wherein $R_6$ optionally substituted aryl is selected from phenyl.

Another embodiment includes a compound of Formula (I), wherein $R_6$ optionally substituted heteroaryl is selected from 1H-pyrazolyl.

Another embodiment includes a compound of Formula (I), wherein $R_6$ optionally substituted heteroaryl is selected from 1H-pyrazol-1-yl.

Another embodiment includes a compound of Formula (I), wherein $R_7$ is hydroxyl.

Another embodiment includes a compound of Formula (I), wherein $R_7$ is $(C_{1-8}alkoxy)_n$, wherein n represents an integer from 1 to 5.

Another embodiment includes a compound of Formula (I), wherein $R_8$ is hydrogen.

Another embodiment includes a compound of Formula (I), wherein $R_8$ is $C_{1-8}$alkyl.

Another embodiment includes a compound of Formula (I) or a form thereof, wherein the form of the compound of Formula (I) is selected from a free acid, free base, salt, ester, hydrate, solvate, chelate, clathrate, polymorph, isotopologue, stereoisomer, racemate, enantiomer, diastereomer or tautomer thereof.

Another embodiment includes a compound of Formula (I) or a form thereof, wherein the form of the compound of Formula (I) is selected from a free acid, free base, salt, ester, hydrate, solvate or polymorph thereof.

Another embodiment includes a compound of Formula (I) or a form thereof, wherein the form of the compound of Formula (I) is selected from a salt, ester, hydrate, solvate, chelate, clathrate, polymorph, isotopologue, stereoisomer, racemate, enantiomer, diastereomer or tautomer thereof.

Another embodiment includes a compound of Formula (I) or a form thereof, wherein the form of the compound of Formula (I) is selected from a free acid, free base, salt, hydrate or polymorph thereof.

Another embodiment includes a compound of Formula (I) or a form thereof, wherein the form of the compound of Formula (I) is selected from a free acid, free base, hydrate, solvate or polymorph thereof.

Another embodiment includes a compound of Formula (I) or a form thereof, wherein the form of the compound of Formula (I) is selected from a salt, hydrate, solvate or polymorph thereof.

Another embodiment includes a compound of Formula (I) or a form thereof, wherein the form of the compound of Formula (I) is selected from a free acid, free base or salt thereof.

Another embodiment includes a compound of Formula (I) or a form thereof, wherein the form of the compound of Formula (I) is selected from a free acid or free base thereof.

Another embodiment includes a compound of Formula (I) or a form thereof, wherein the form of the compound of Formula (I) is selected from a salt thereof.

Another embodiment includes a compound of Formula (I) or a form thereof, wherein the form of the compound of Formula (I) is selected from a polymorph thereof.

Another embodiment includes a compound of Formula (I) or a form thereof, wherein the form of the compound of Formula (I) is pharmaceutically acceptable.

Another embodiment includes a compound of Formula (I) or a form thereof, wherein the form of the compound of Formula (I) is isolated.

Another embodiment includes a compound of Formula (I) or a form thereof, wherein the compound is a compound of Formula (II), Formula (III) or Formula (IV):

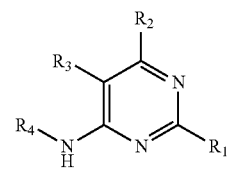

Formula (II)

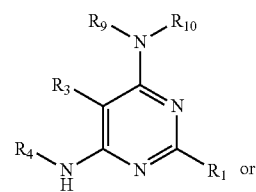

Formula (III)

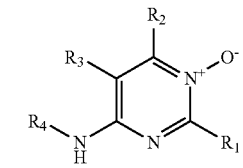

Formula (IV)

or a form thereof, wherein $R_9$ and $R_{10}$ are independently hydrogen, hydroxyl, $C_{1-8}$alkyl, hydroxyl-$C_{1-8}$alkyl, $C_{1-8}$alkoxy-$C_{1-8}$alkyl, $C_{1-8}$alkyl-carbonyl, amino-carbonyl, $C_{1-8}$alkyl-amino-carbonyl, $(C_{1-8}alky)_2$-amino-carbonyl, $C_{1-8}$alkoxy-carbonyl, amino-sulfonyl, $C_{1-8}$alkyl-amino-sulfonyl, $(C_{1-8}alkyl)_2$-amino-sulfonyl or $P(O)(R_7)_2$.

Another embodiment includes a compound of Formula (III), wherein one of $R_9$ and $R_{10}$ is hydrogen and the other is hydroxyl, $C_{1-8}$alkyl, hydroxyl-$C_{1-8}$alkyl, $C_{1-8}$alkoxy-$C_{1-8}$alkyl, $C_{1-8}$alkyl-carbonyl, amino-carbonyl, $C_{1-8}$alkyl-amino-carbonyl, $(C_{1-8}alkyl)_2$-amino-carbonyl, $C_{1-8}$alkoxy-carbonyl, amino-sulfonyl, $C_{1-8}$alkyl-amino-sulfonyl, $(C_{1-8}alkyl)_2$-amino-sulfonyl or $P(O)(R_7)_2$.

Another embodiment includes a compound of Formula (I) or a form thereof, wherein the compound is a compound of Formula (Ia), Formula (IIa), Formula (IIIa) or Formula (IVa):

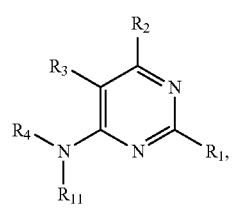

Formula (Ia)

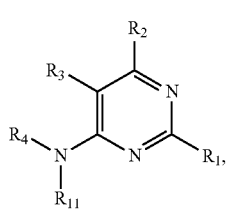

Formula (IIa)

Formula (IIIa)
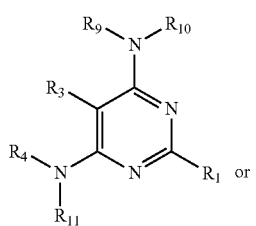
Formula (IVa)
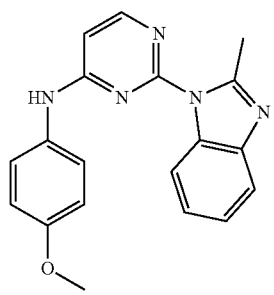
or a form thereof, wherein $R_2$, $R_3$, $R_9$, $R_{10}$ or $R_{11}$ are independently deuterium.
Another embodiment includes a compound of Formula (I) or a form thereof selected from the group consisting of:
1
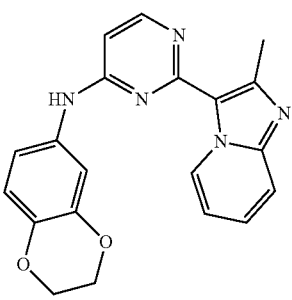
2
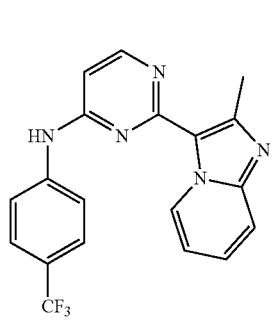
3
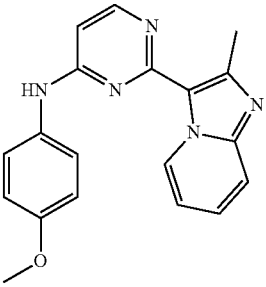
4
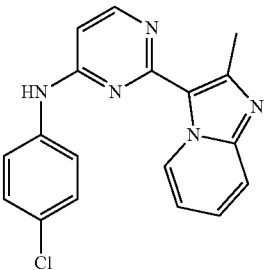
5
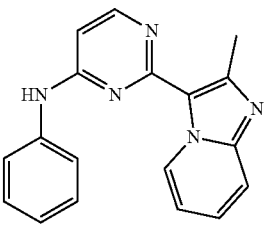
6
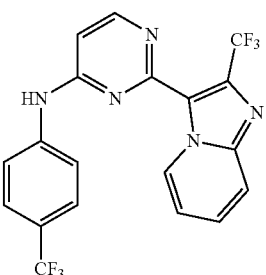
7
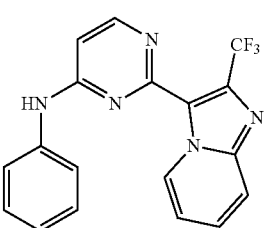
8
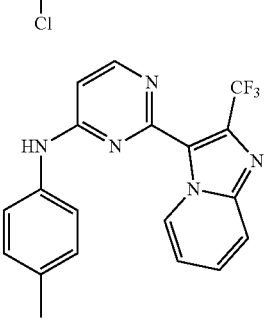
9

-continued
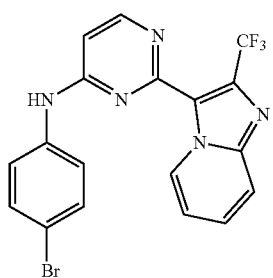
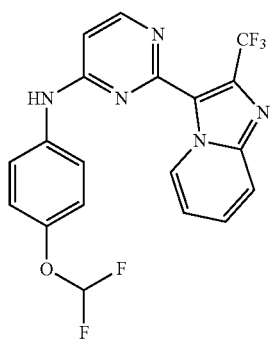
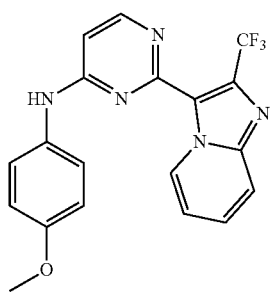
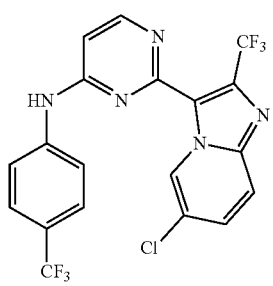
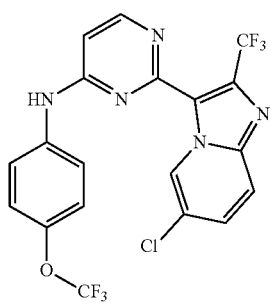
-continued
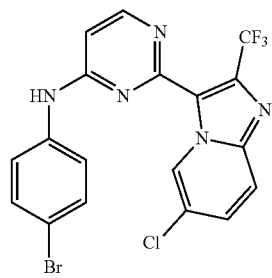
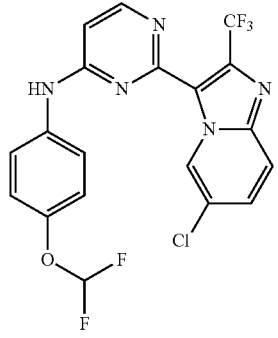
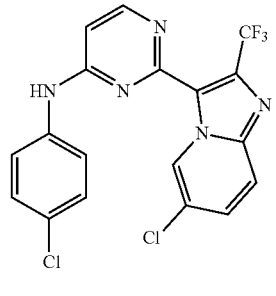
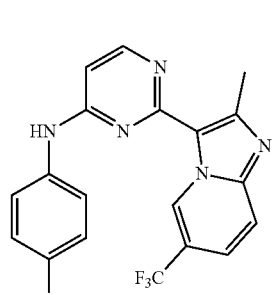
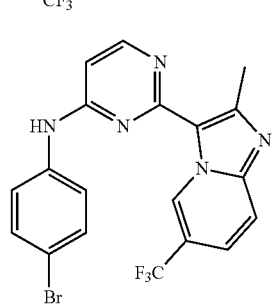

-continued
19
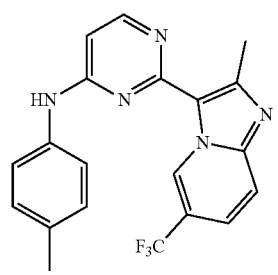
20
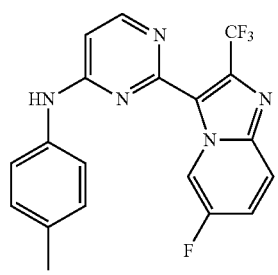
21
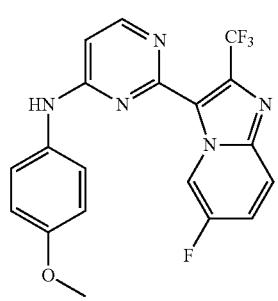
22
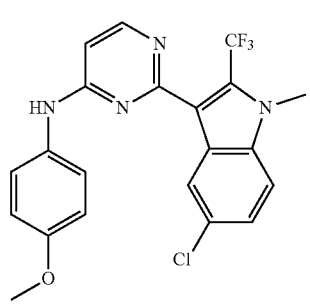
23
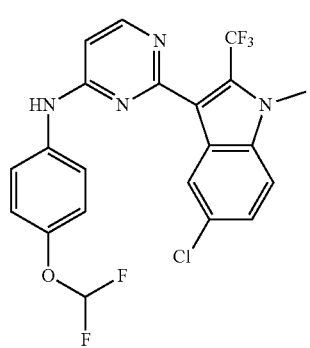
-continued
24
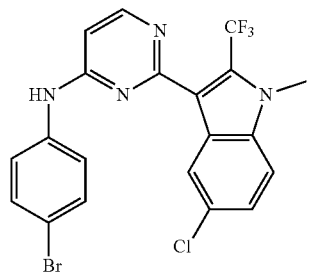
25
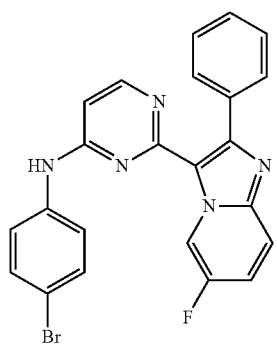
26
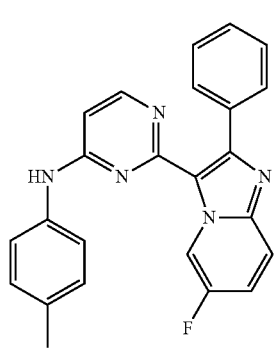
27
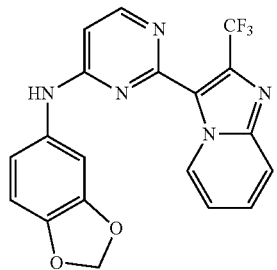
28
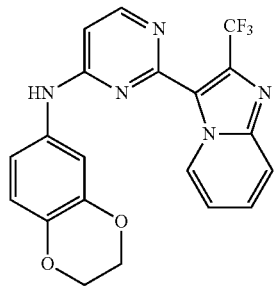

-continued
| | |
|---|---|
| 29 | 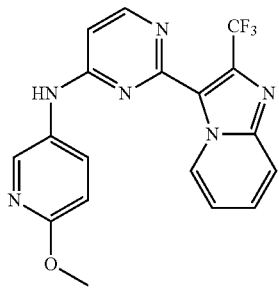 |
| 30 | 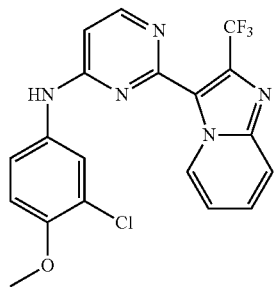 |
| 31 | 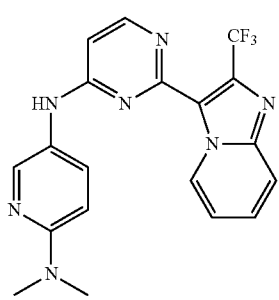 |
| 36 | 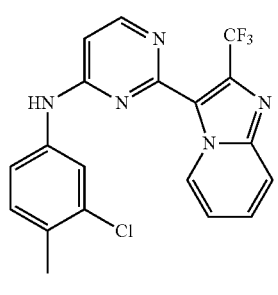 |
| 32 | 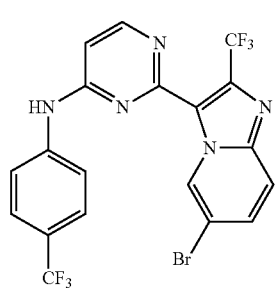 |
| 37 | 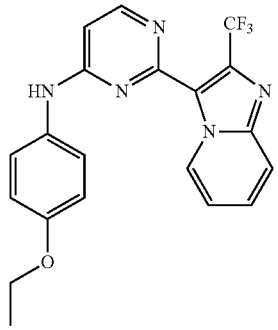 |
| 33 | 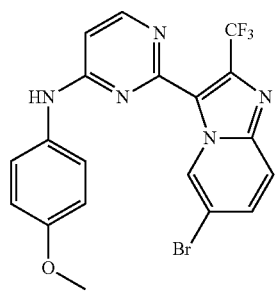 |
| 38 | 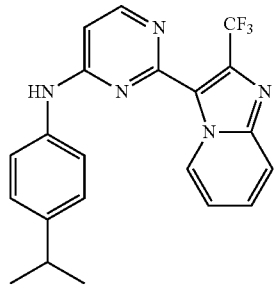 |
| 34 | 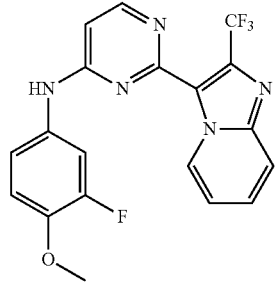 |
| 39 | 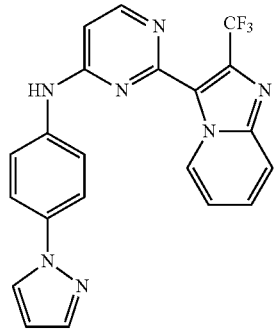 |

-continued
40
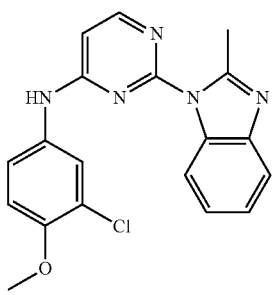
41
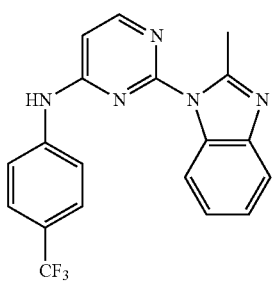
42
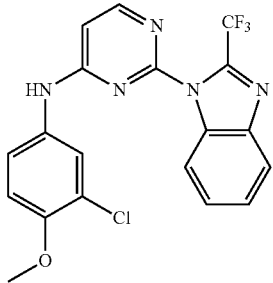
43
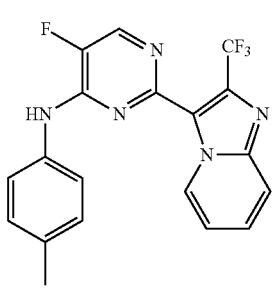
44
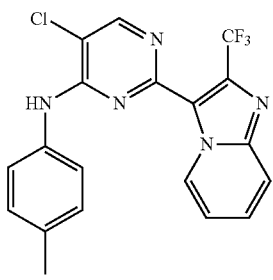
-continued
45
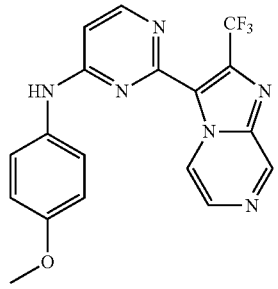
46
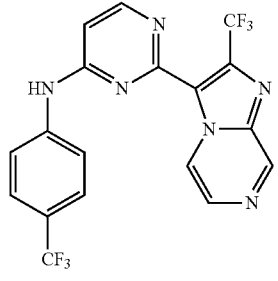
47
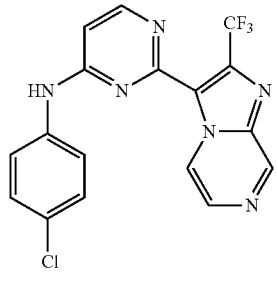
48
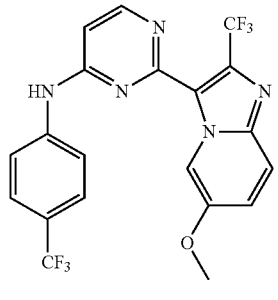
49
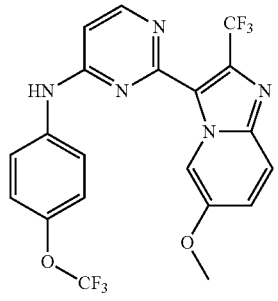

-continued
50
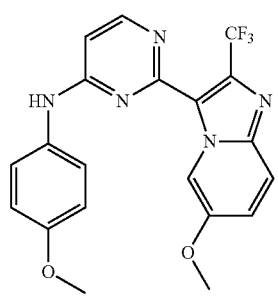
51
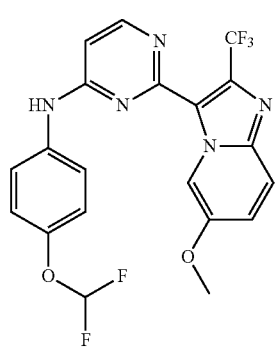
52
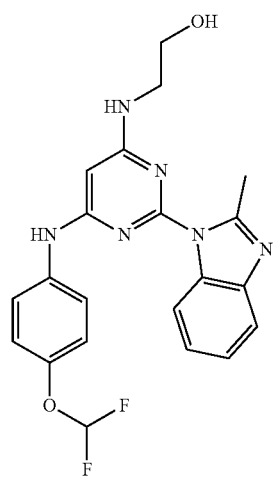
53
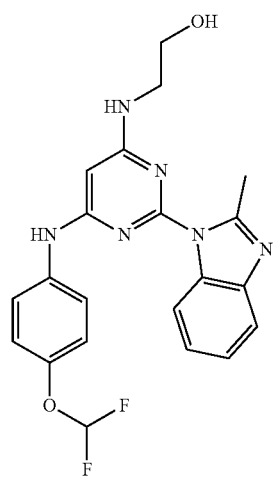
-continued
54
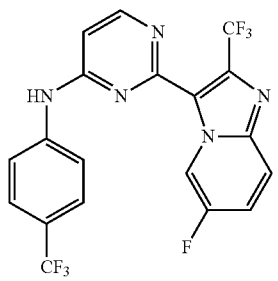
55
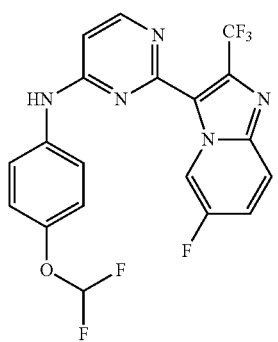
56
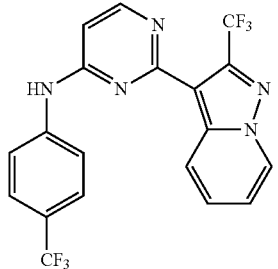
57
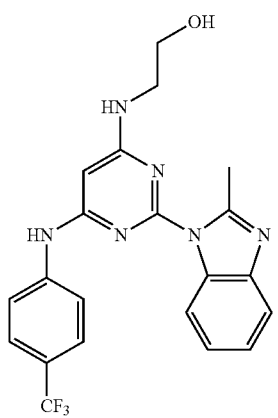

-continued
58
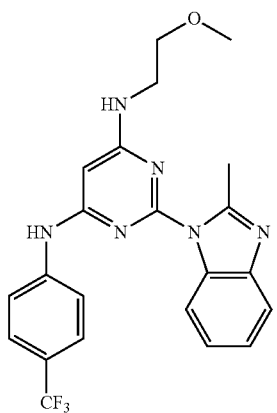
59
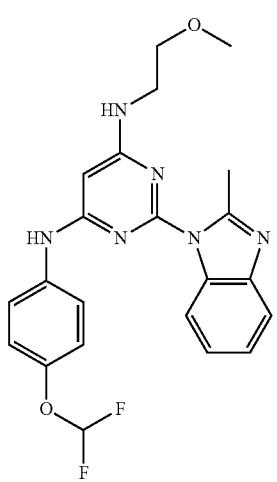
60
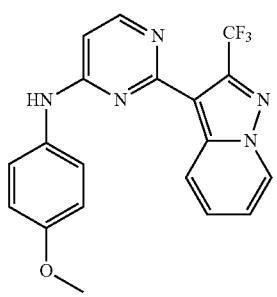
61
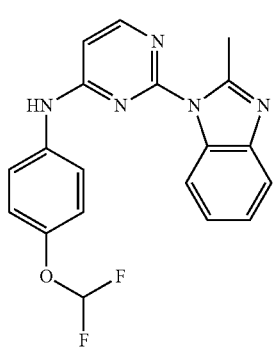
-continued
62
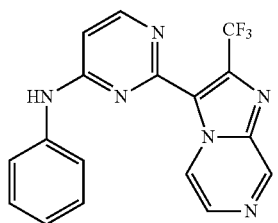
63
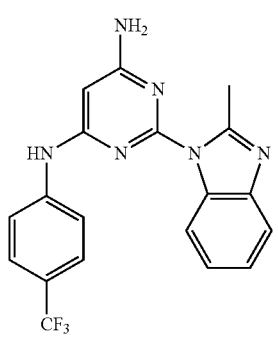
64
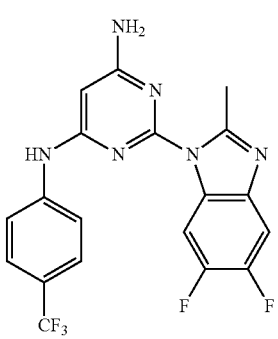
65
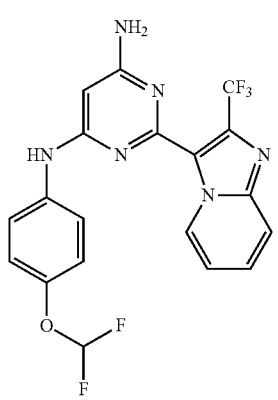
66
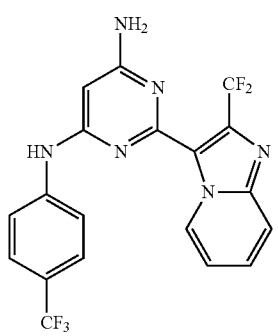

67 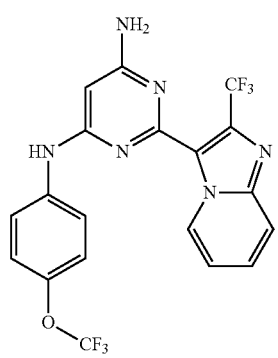
68 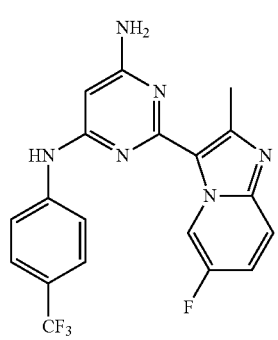
69 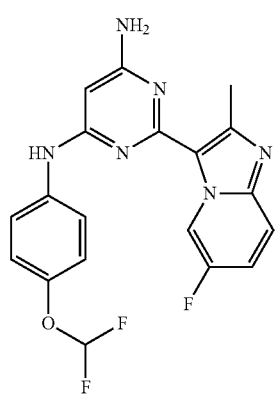
70 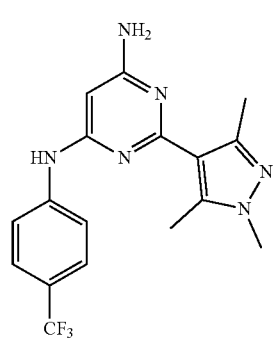
71 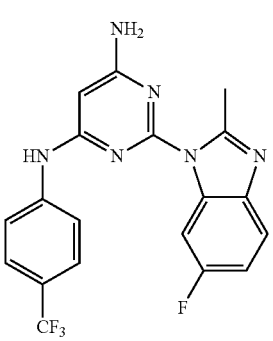
72 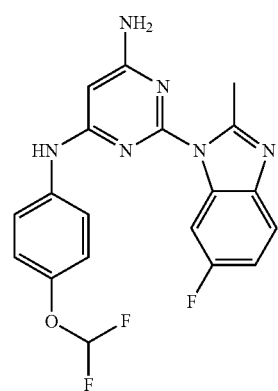
73 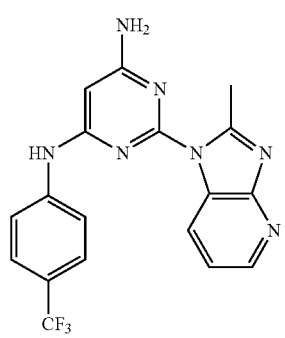
74 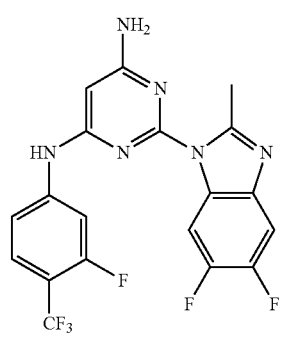

75 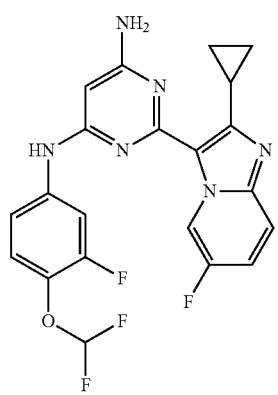
76 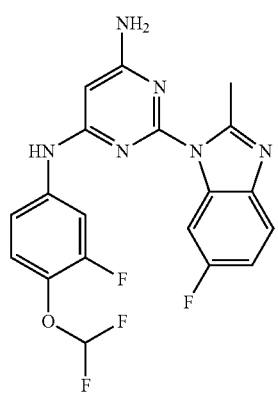
77 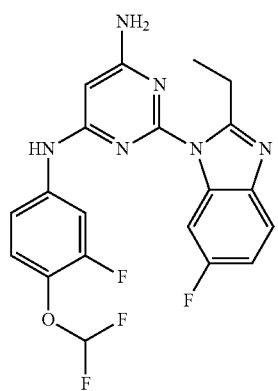
78 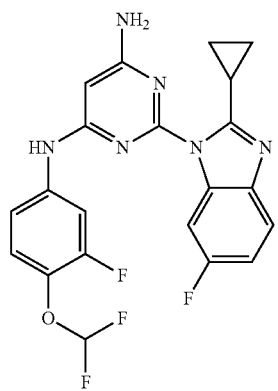
79 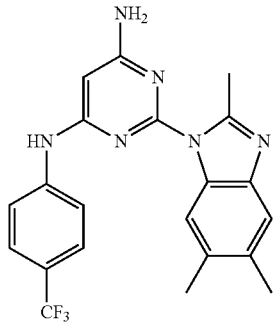
80 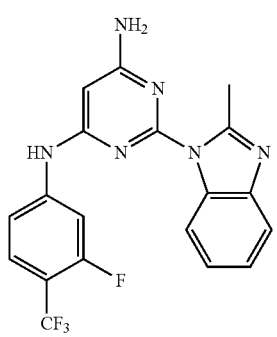
81 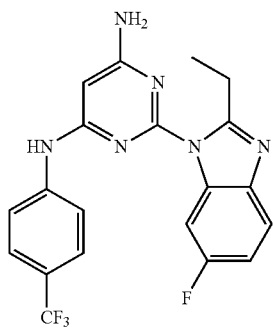
82 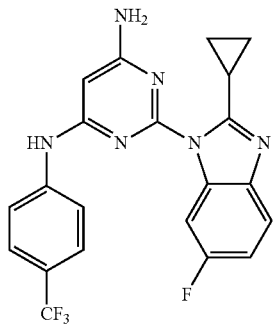
83 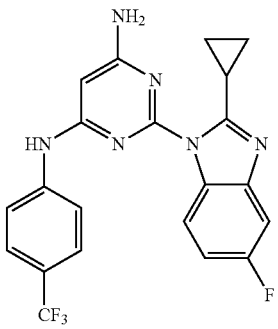

84
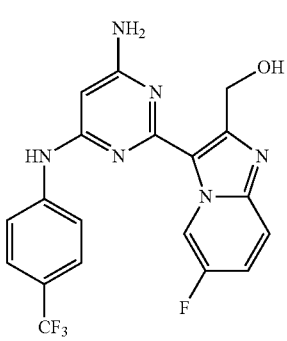
85
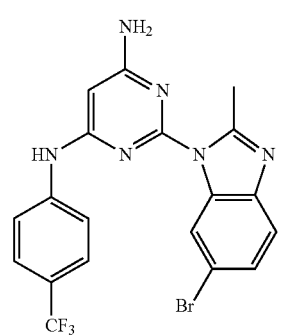
86
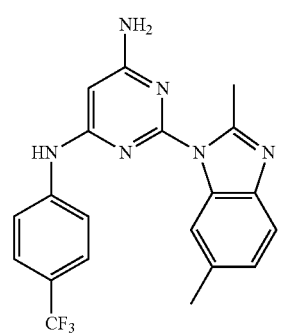
87
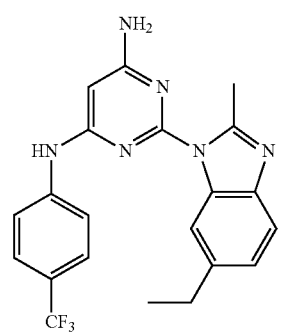
88
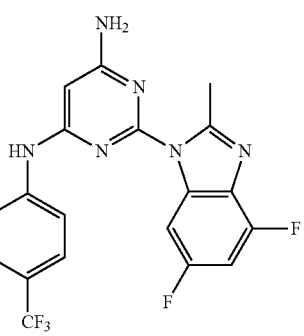
89
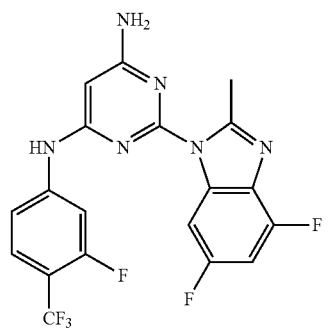
90
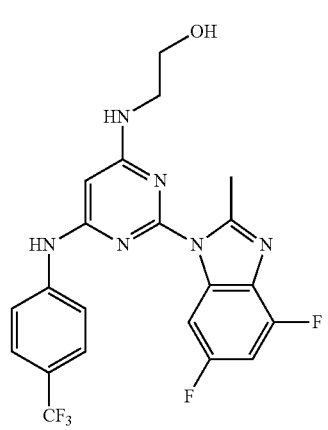
91
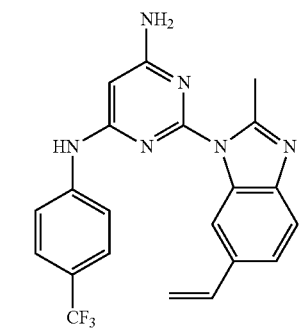
92
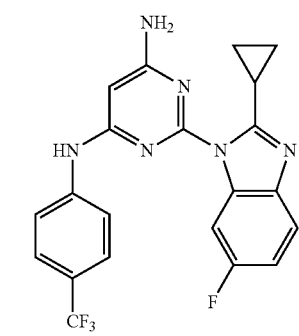

93
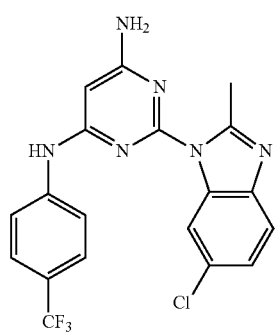
94
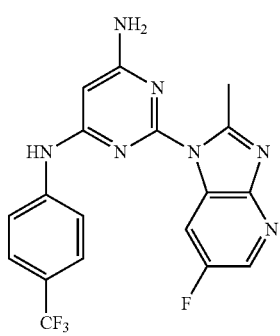
95
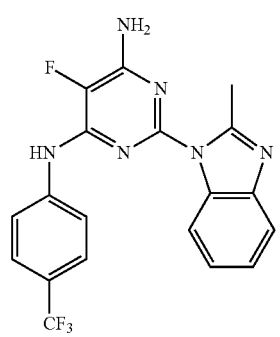
96
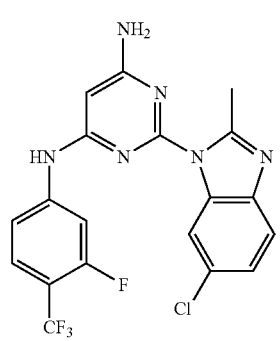
97
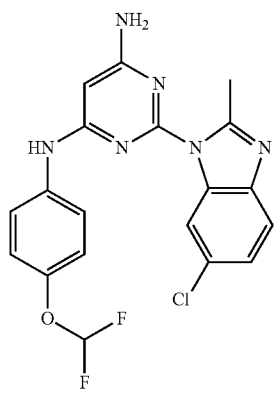
98
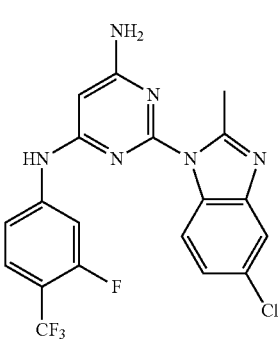
99
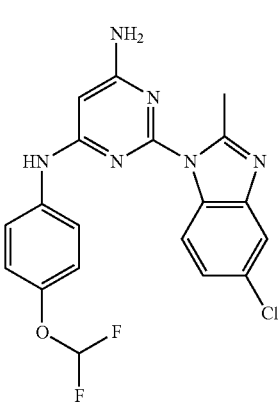
100
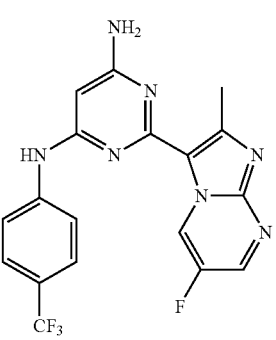

101 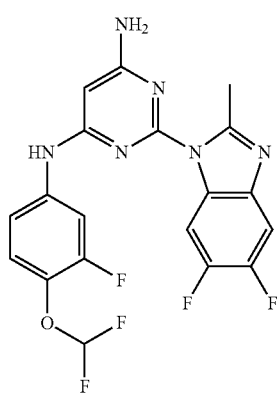
102 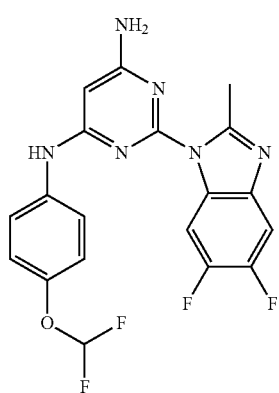
103 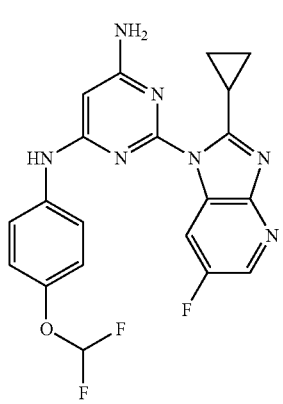
104 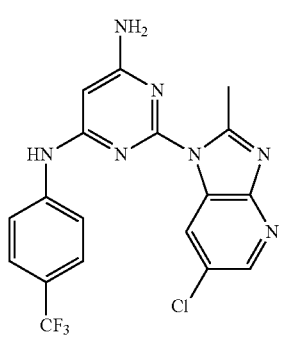
105 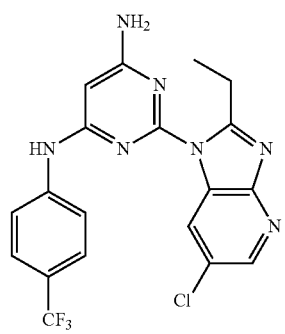
106 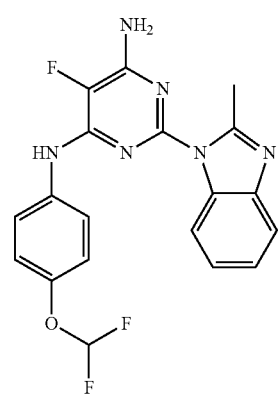
107 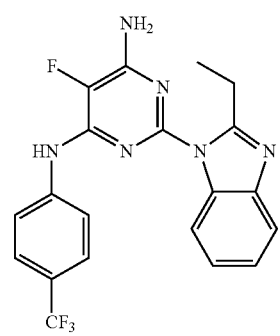
108 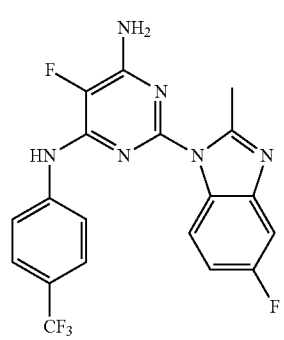

-continued
109 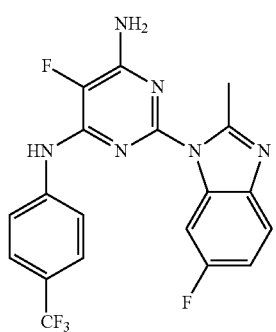
110 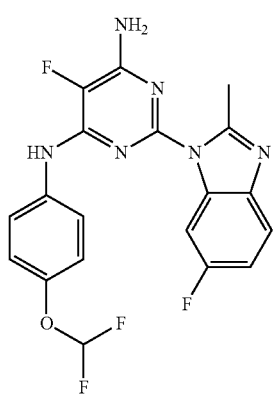
111 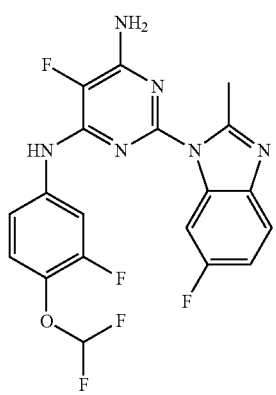
112 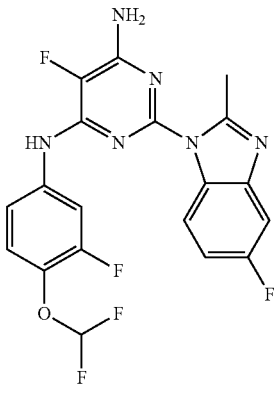
-continued
113 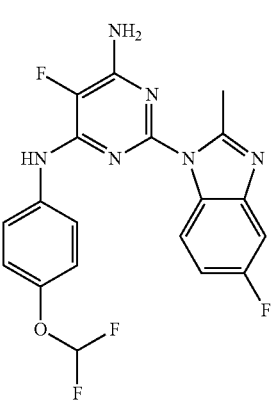
114 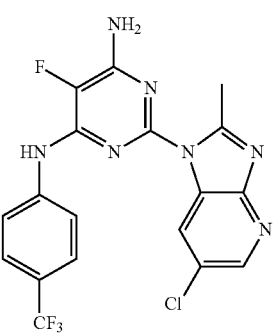
115 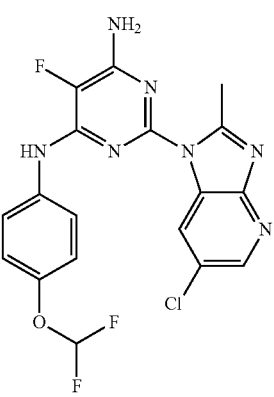
116 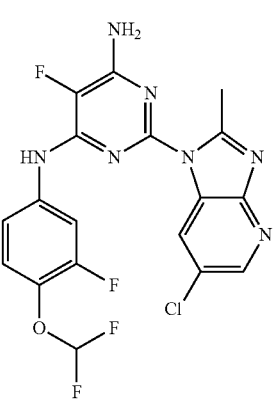

117 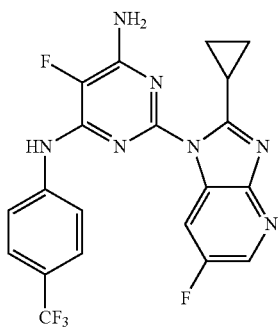
118 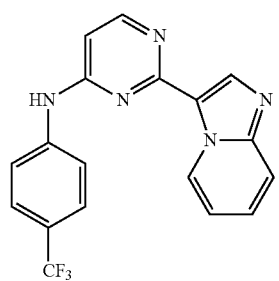
119 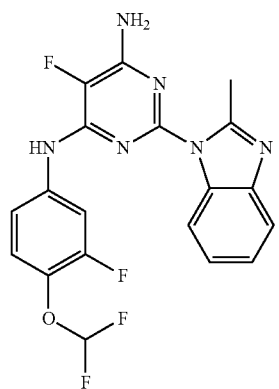
120 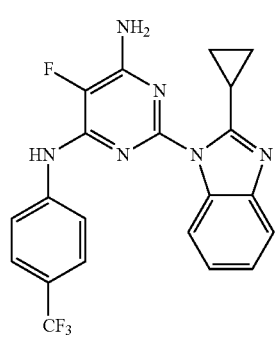
121 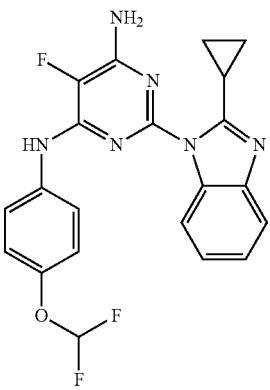
122 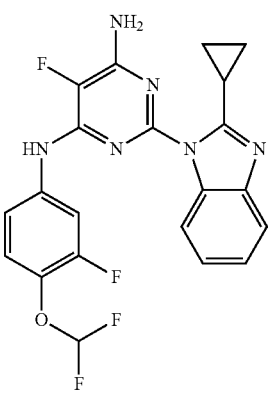
123 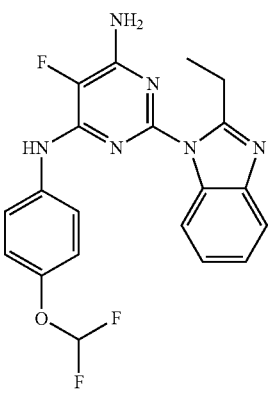
124 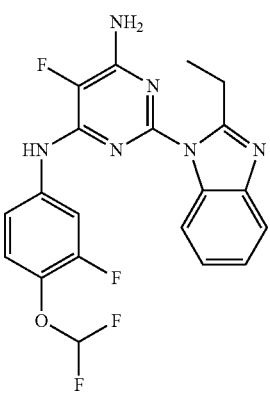

125 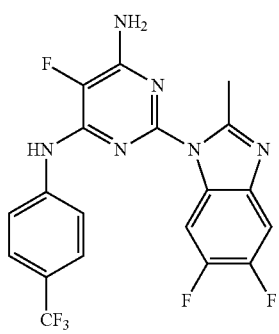
126 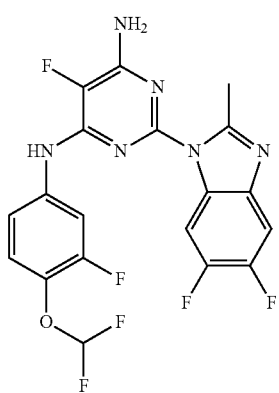
127 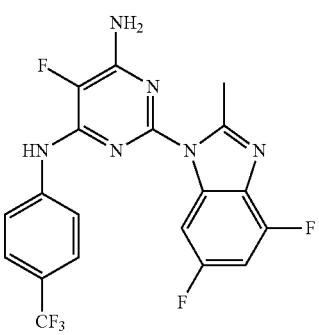
128 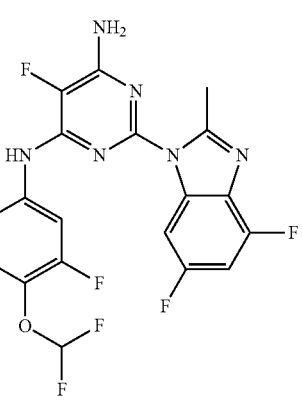
129 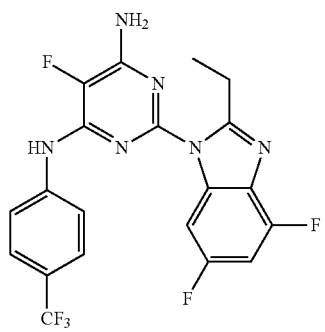
130 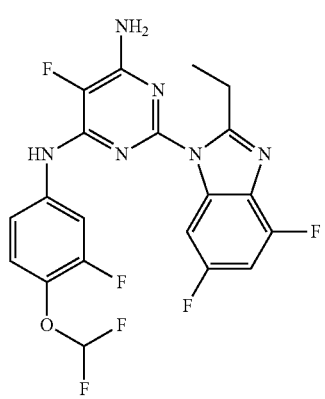
131 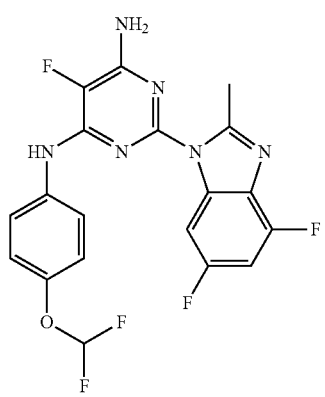
132 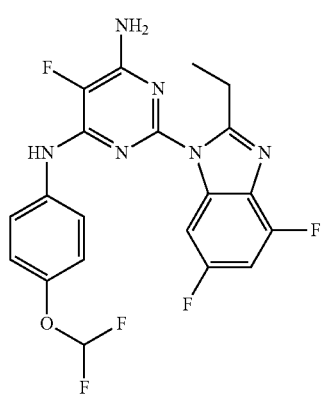

-continued
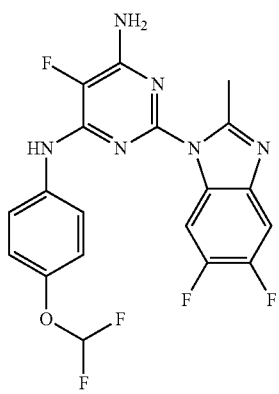
133
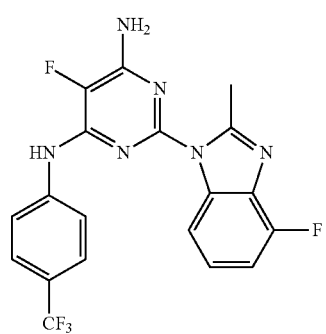
134
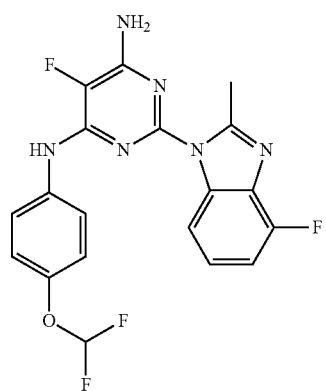
135
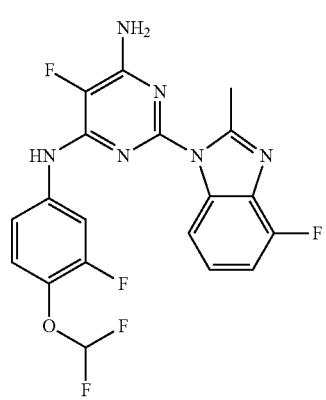
136
-continued
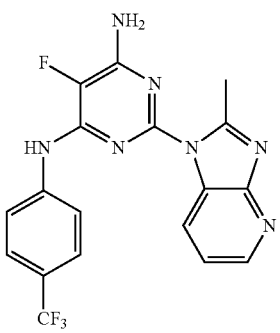
137
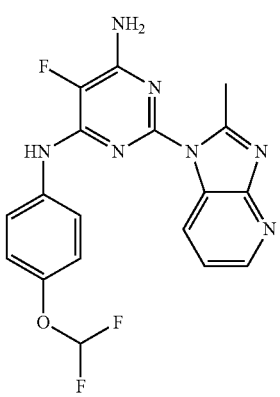
138
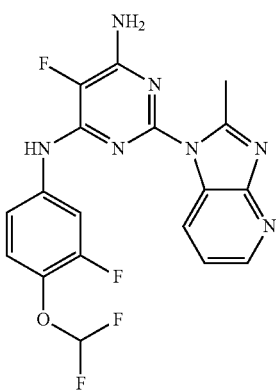
139
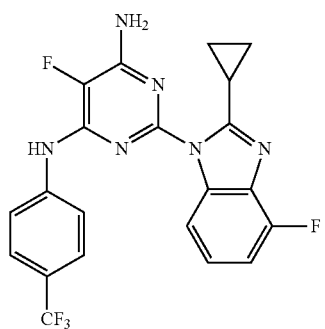
140

141 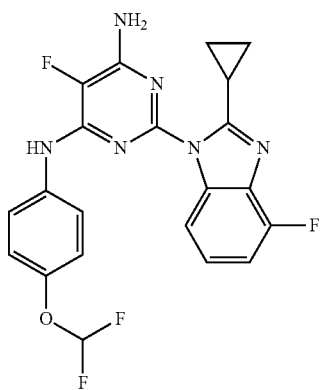
142 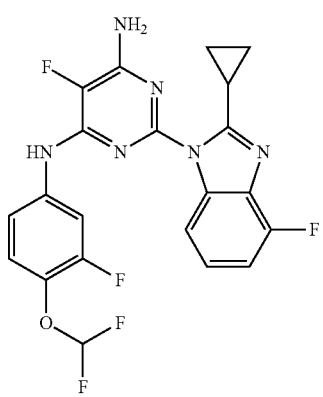
143 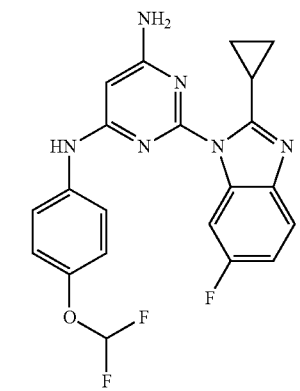
144 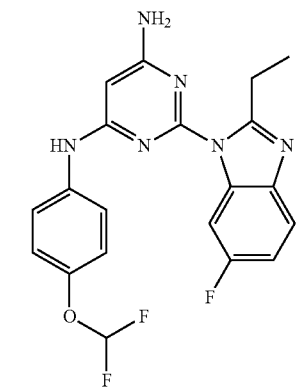
145 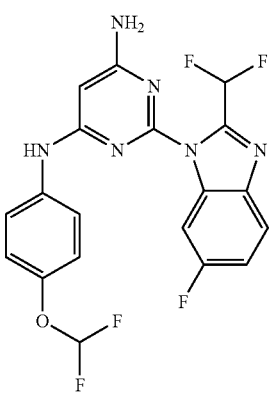
146 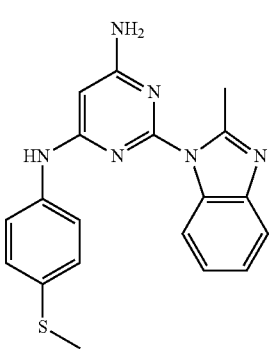
147 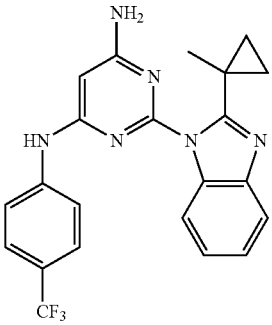
148 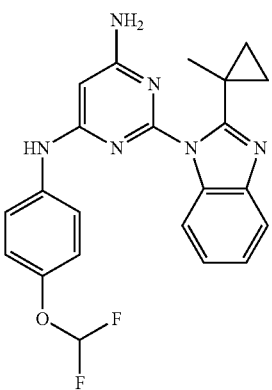

-continued
149
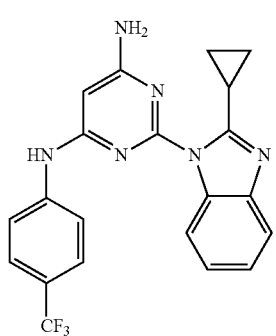
150
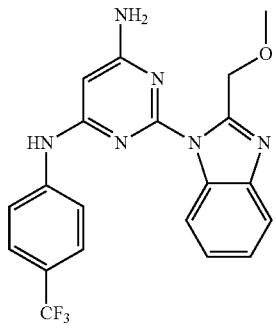
151
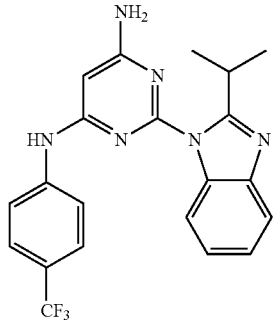
152
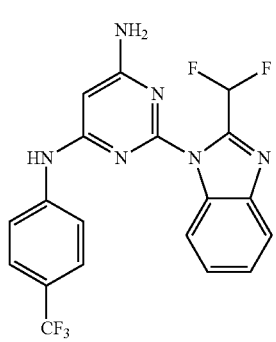
153
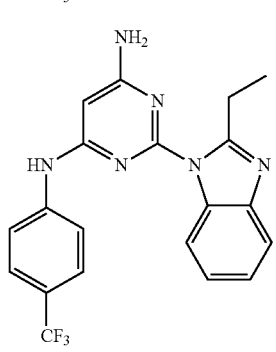
-continued
154
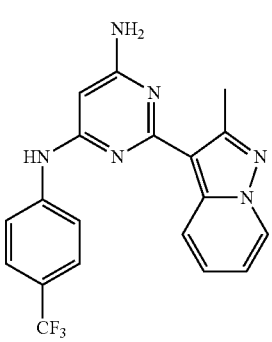
155
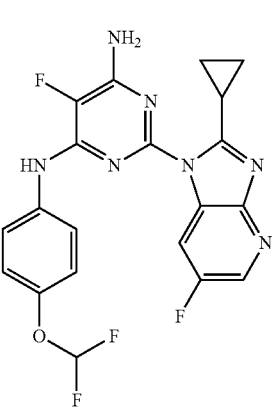
156
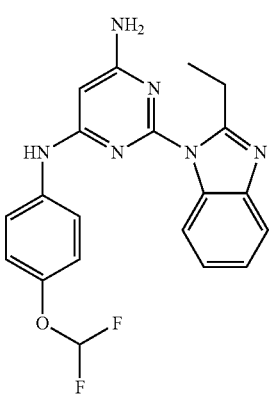
157
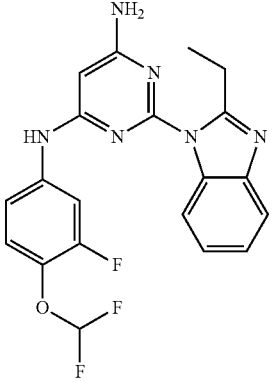

158 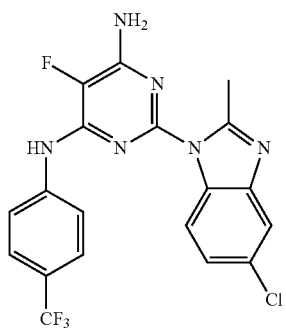
159 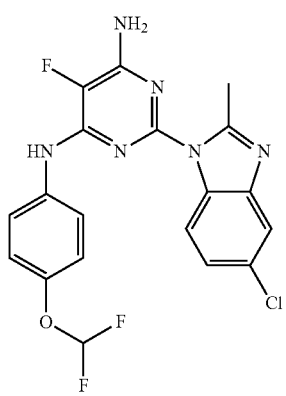
160 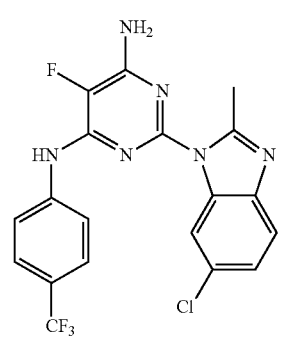
161 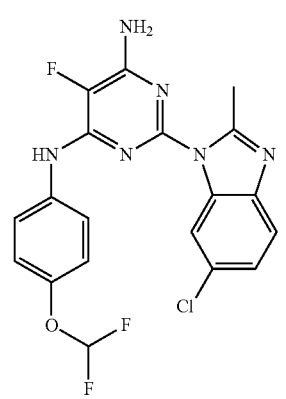
162 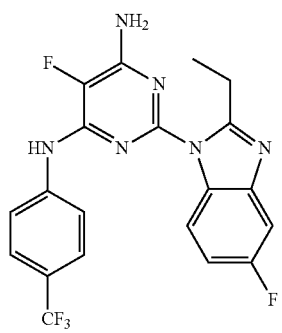
163 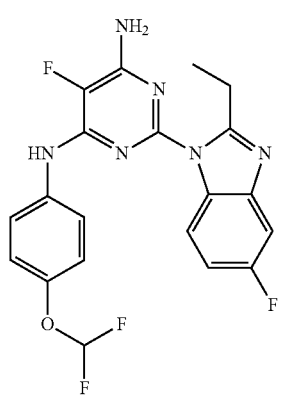
164 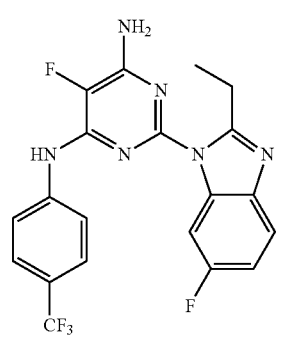
165 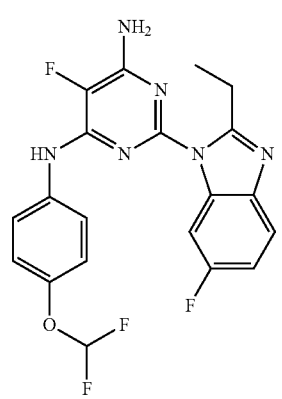

166 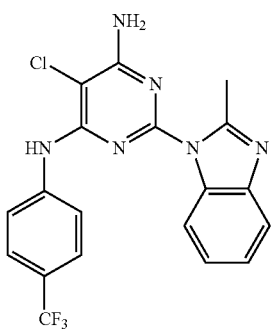
167 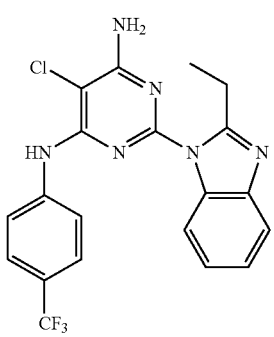
168 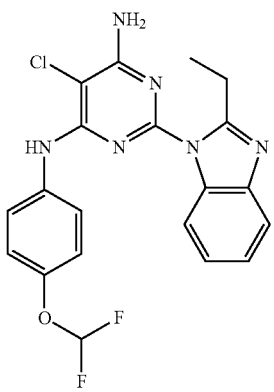
169 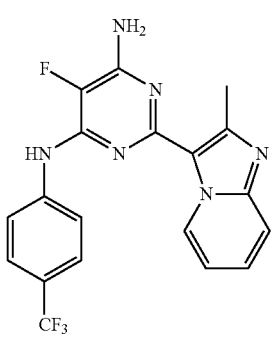
170 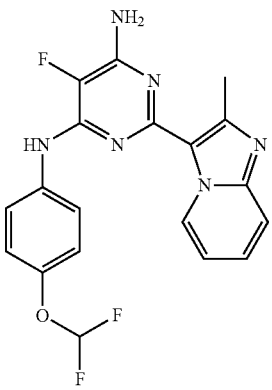
171 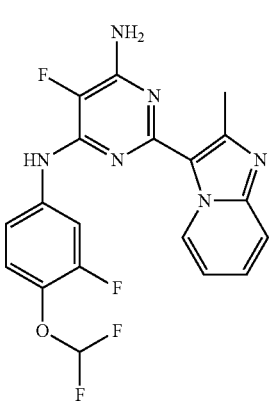
172 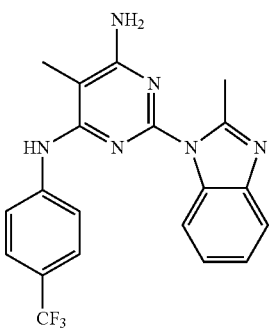
173 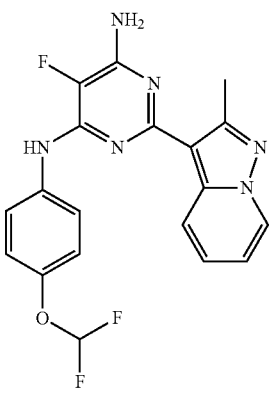

174 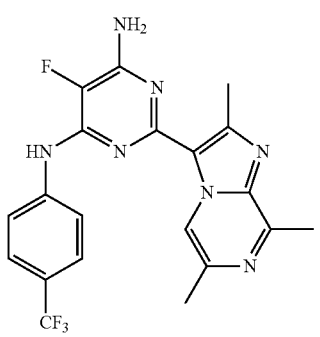
175 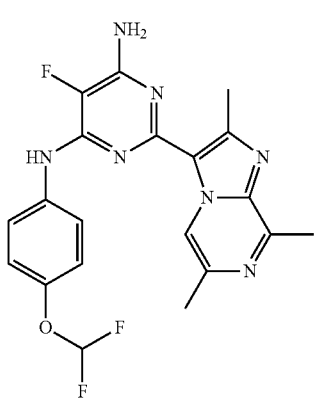
176 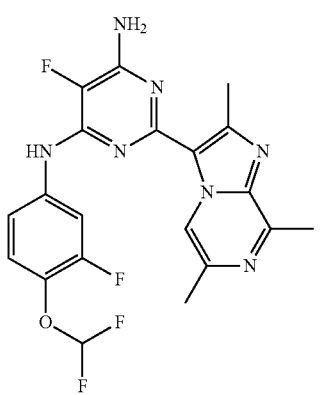
177 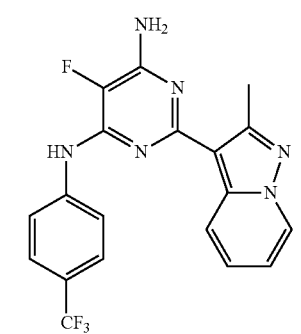
178 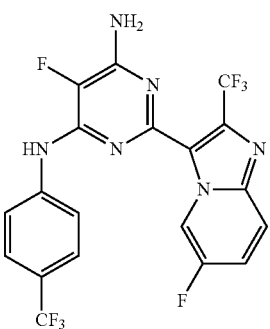
179 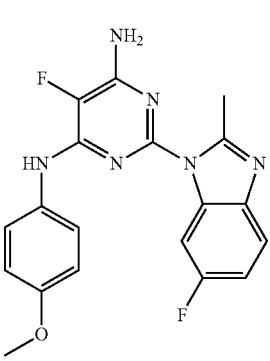
180 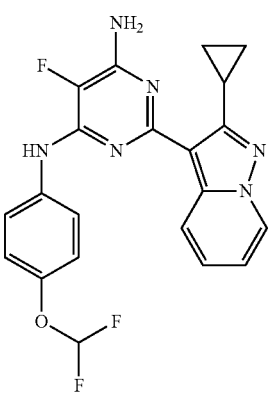
181 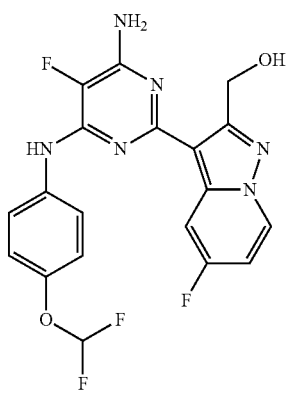

182 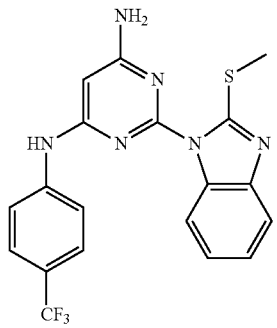
183 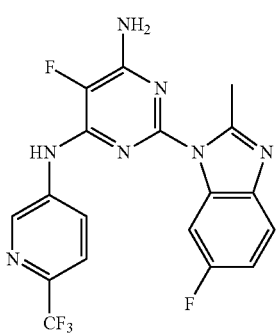
184 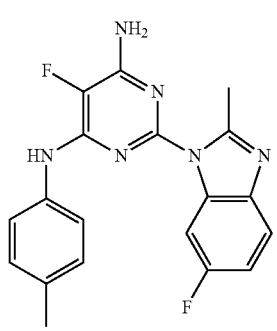
185 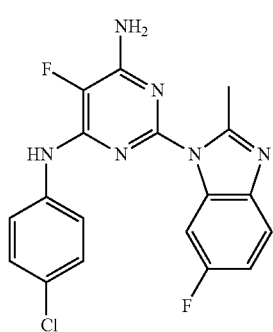
186 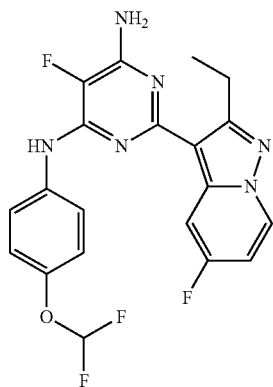
187 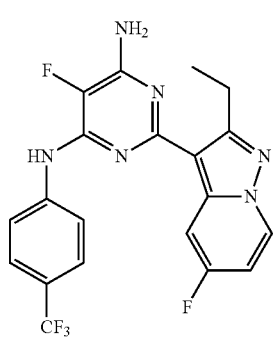
188 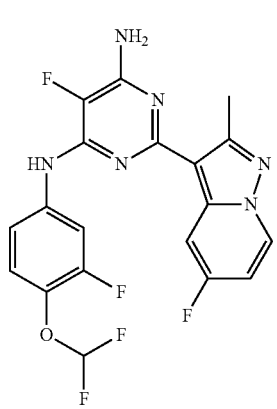
189 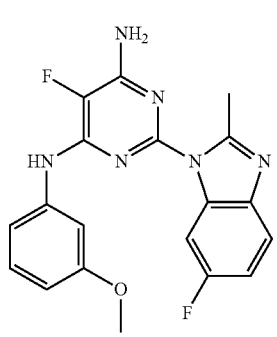

190 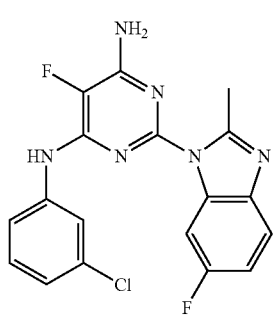
191 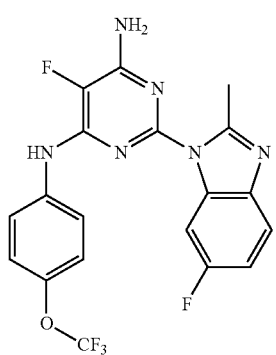
192 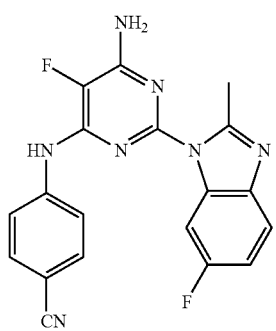
193 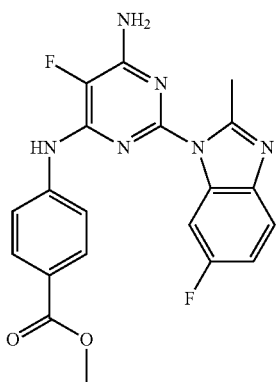
194 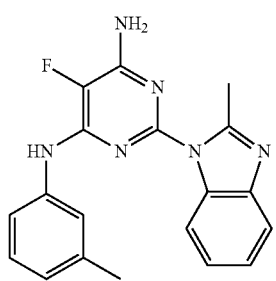
195 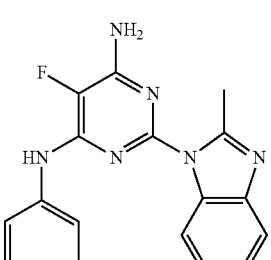
196 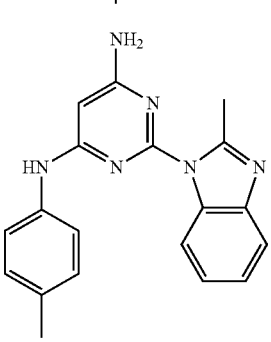
197 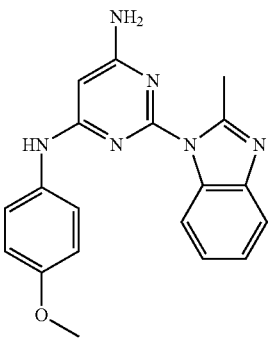
198 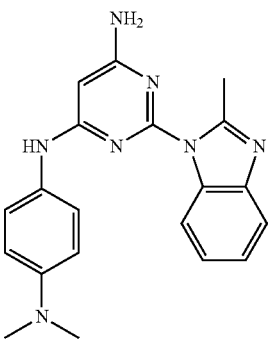
199 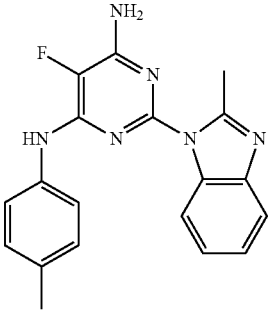

200 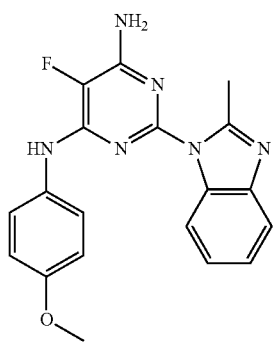
201 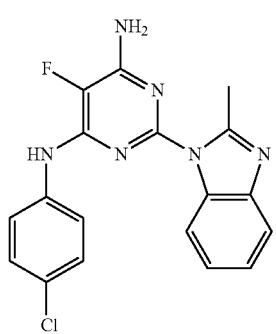
202 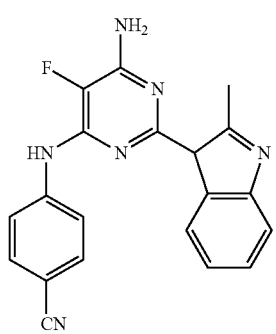
203 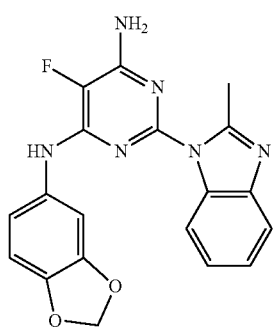
204 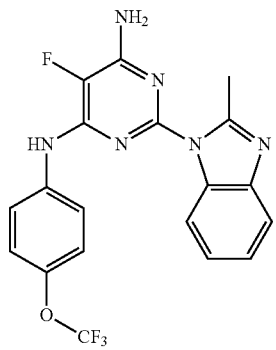
205 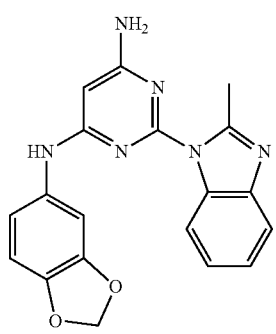
206 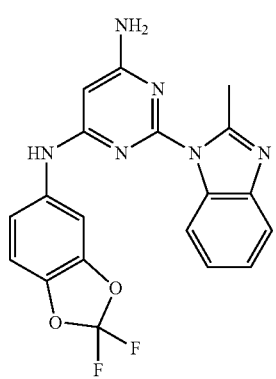
207 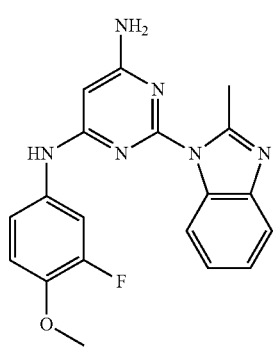

| | | | |
|---|---|---|---|
| 208 | 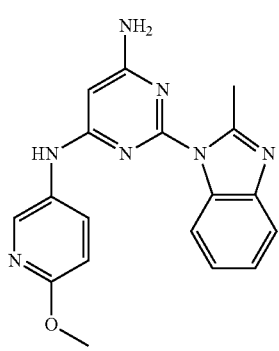 | 213 | 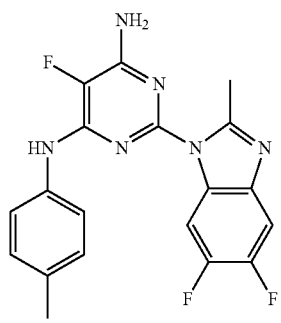 |
| 209 | 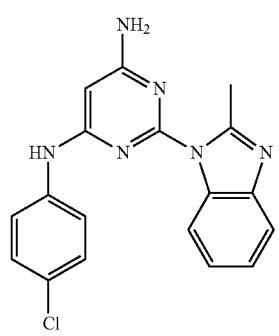 | 214 | 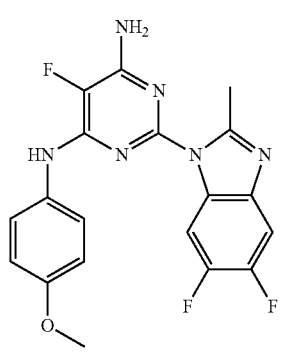 |
| 210 | 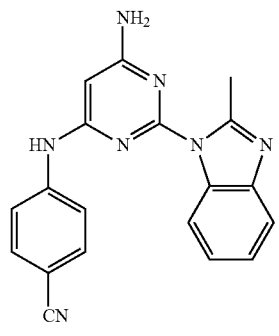 | 215 | 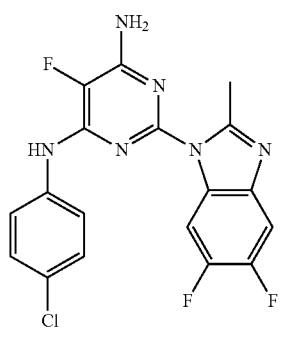 |
| 211 | 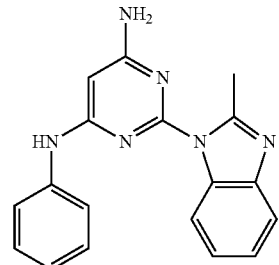 | 216 | 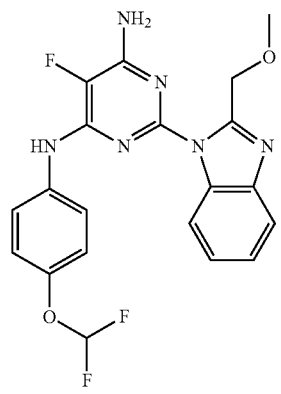 |
| 212 | 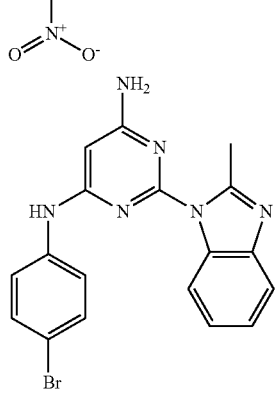 | | |

217 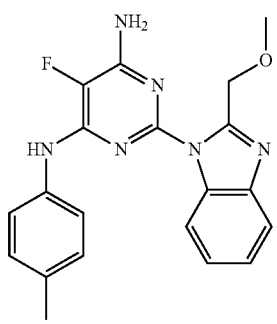
218 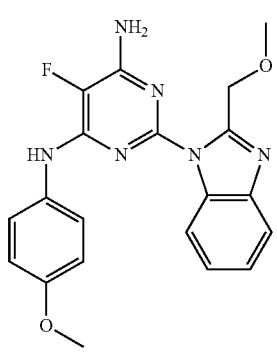
219 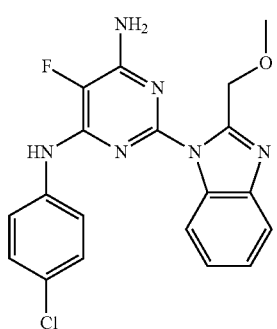
220 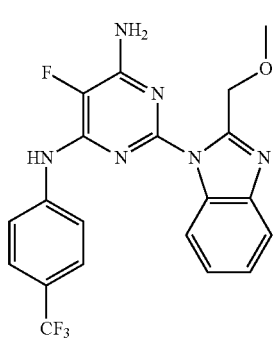
221 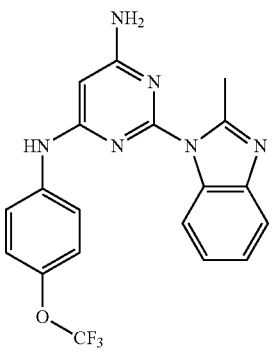
222 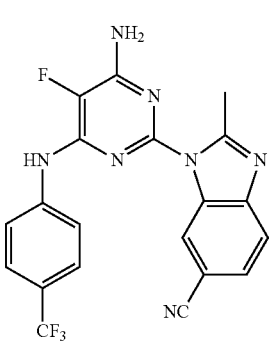
223 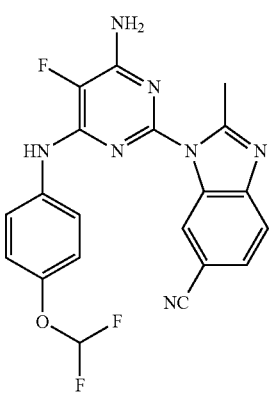
224 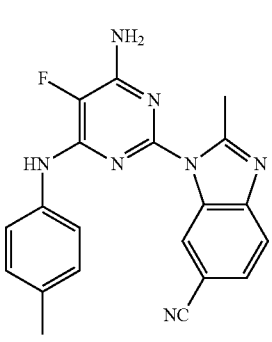

225 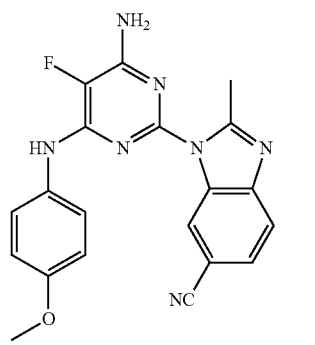
226 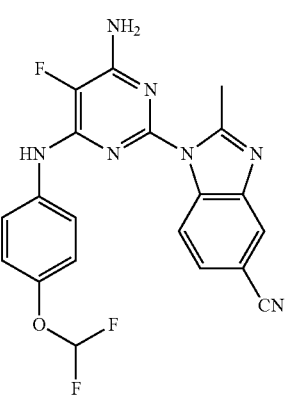
227 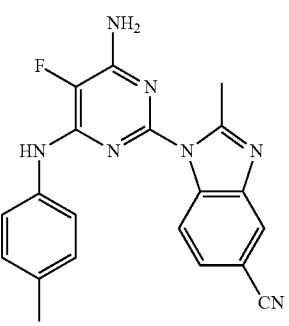
228 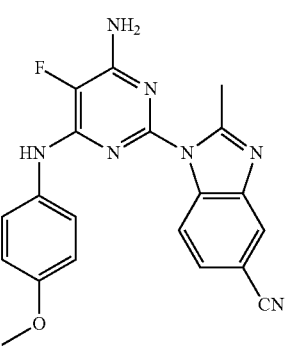
229 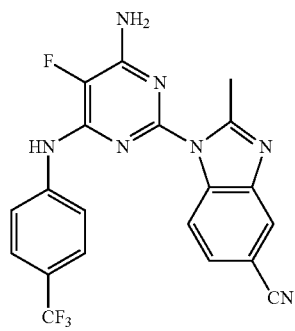
230 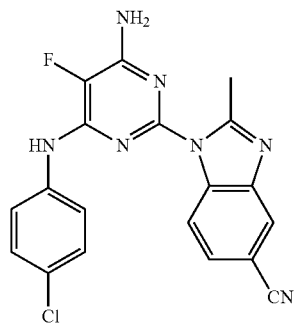
231 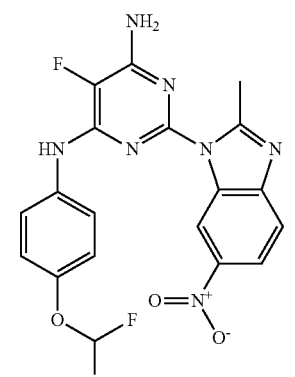
232 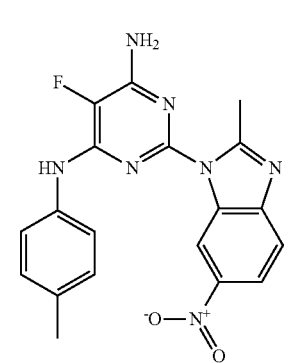

233
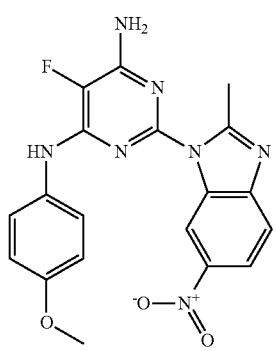
234
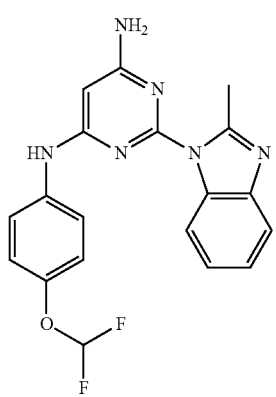
235
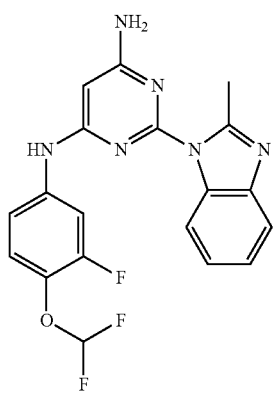
236
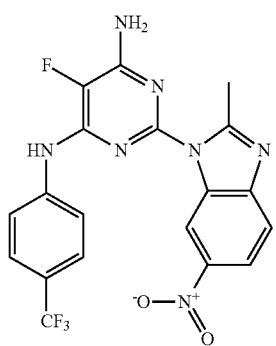
237
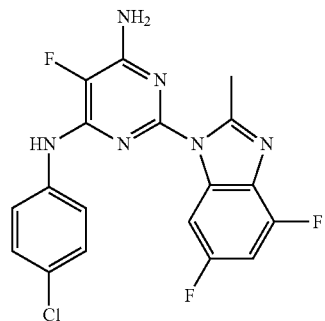
238
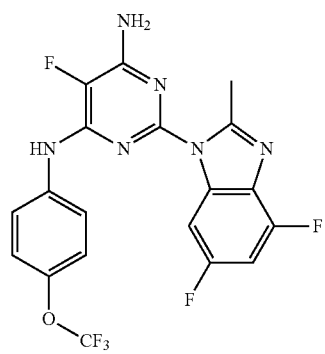
239
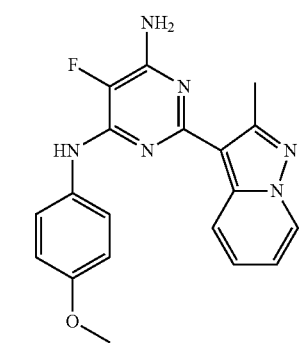
240
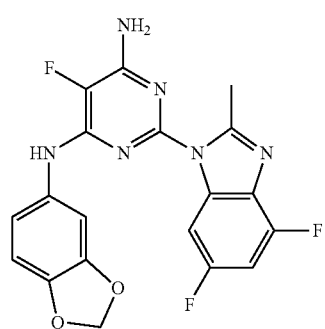

| 241 | 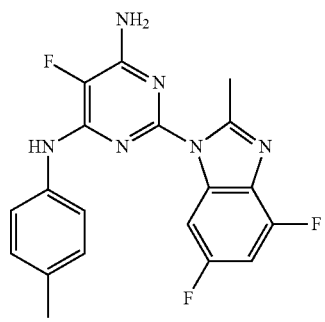 | 245 | 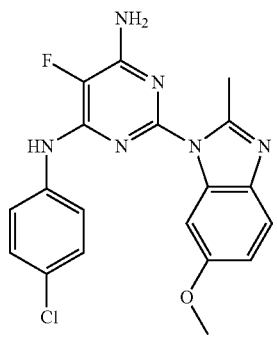 |
| 242 | 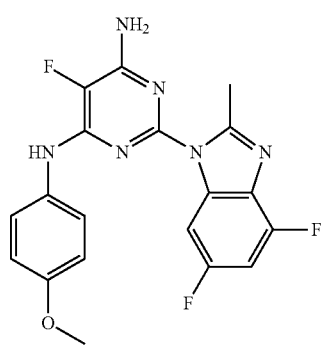 | 246 | 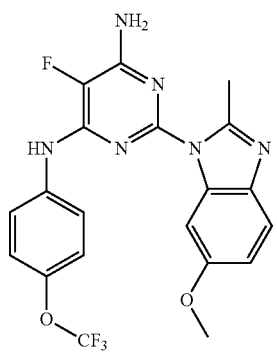 |
| 243 | 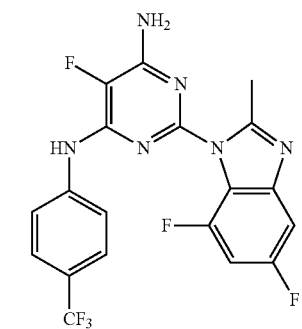 | 247 | 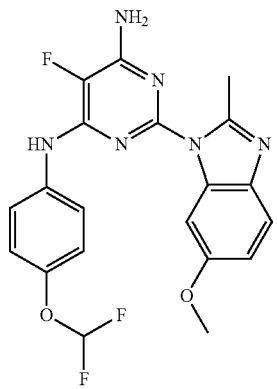 |
| 244 | 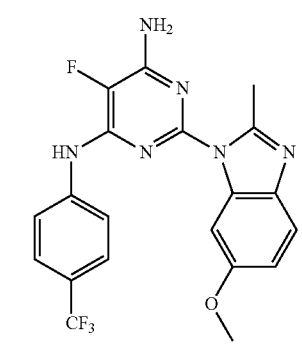 | 248 | 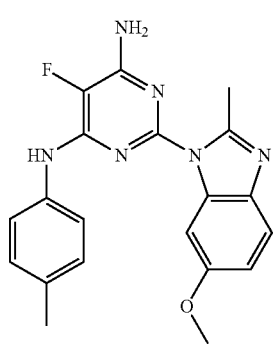 |

249 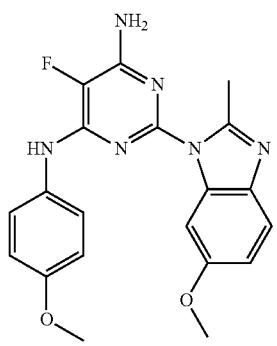
250 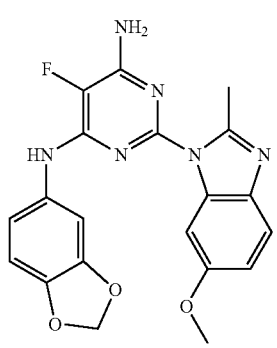
251 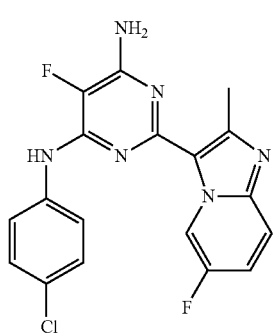
252 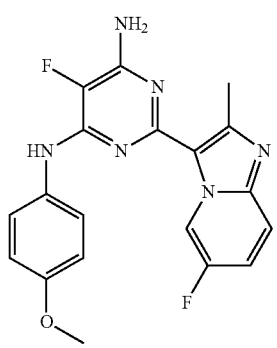
253 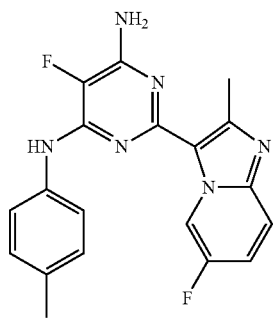
254 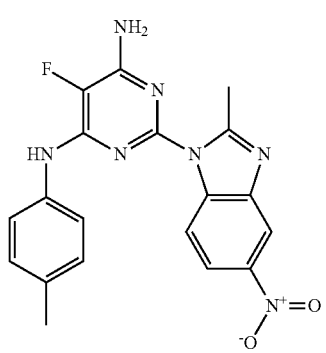
255 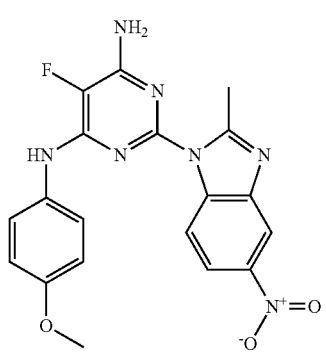
256 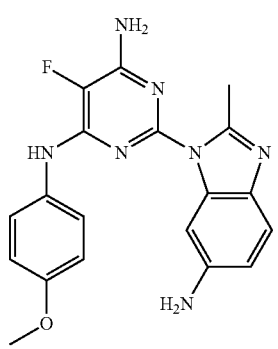

257 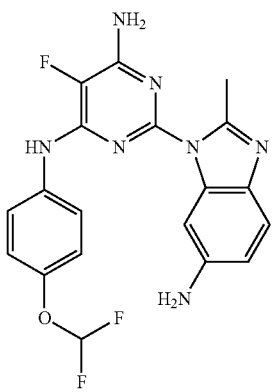
258 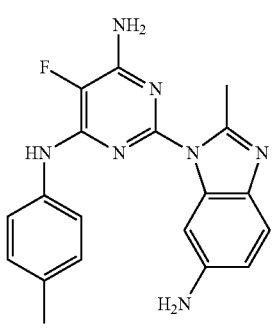
259 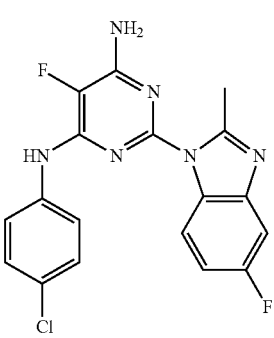
260 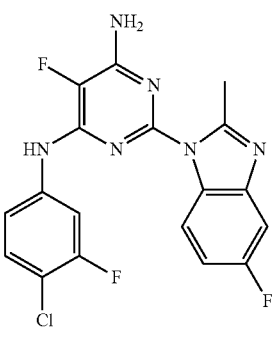
261 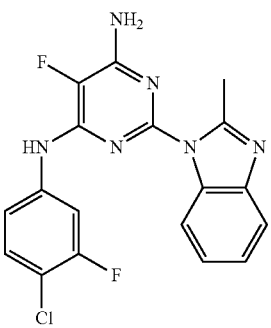
262 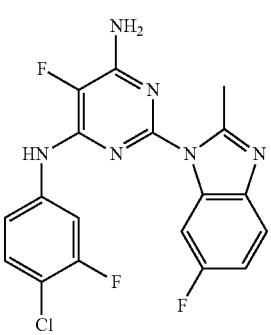
263 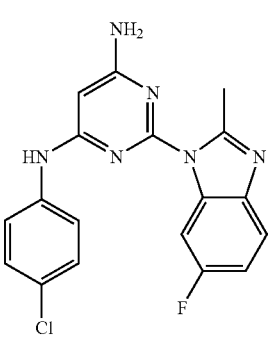
264 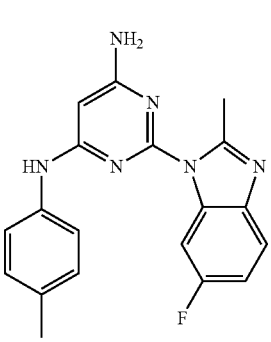
265 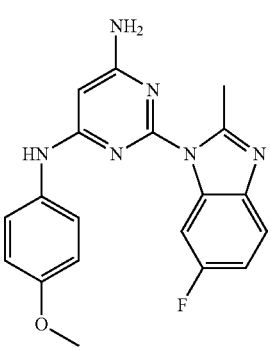

266 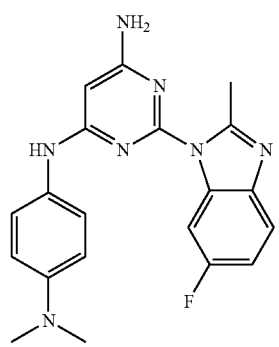
267 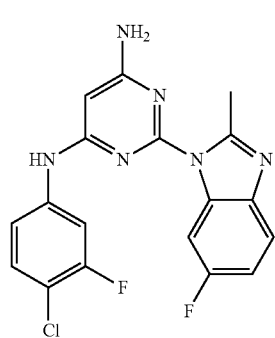
268 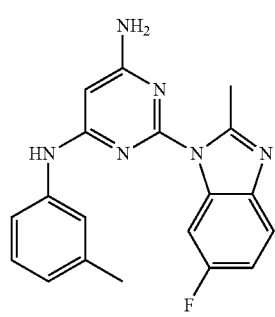
269 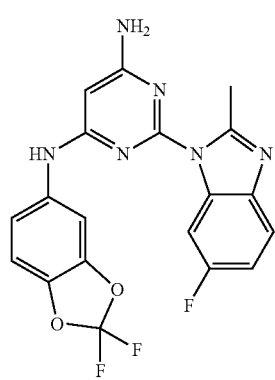
270 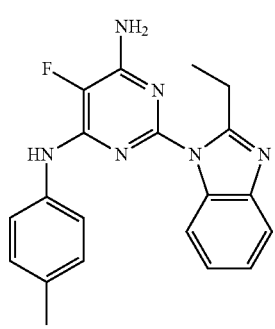
271 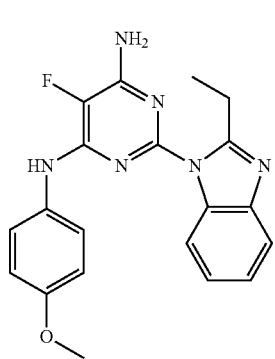
272 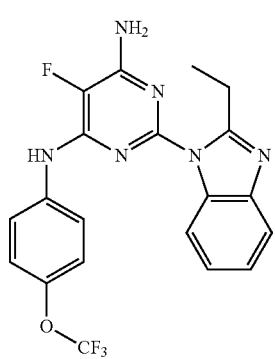
273 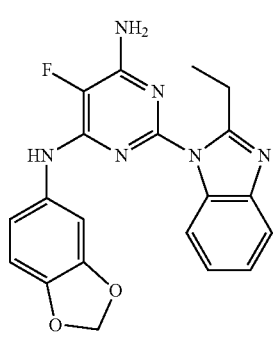

| 274 | 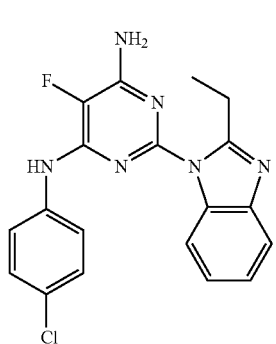 | 278 | 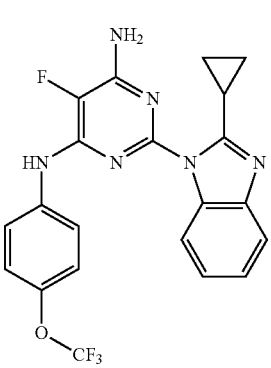 |
| 275 | 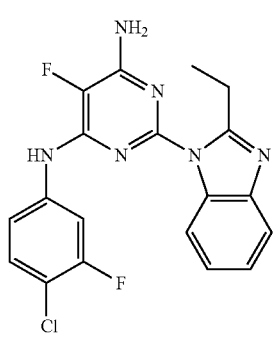 | 279 | 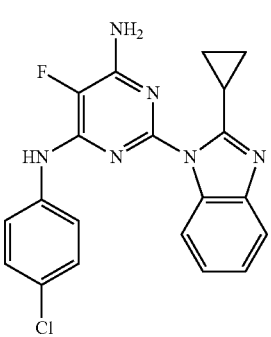 |
| 276 | 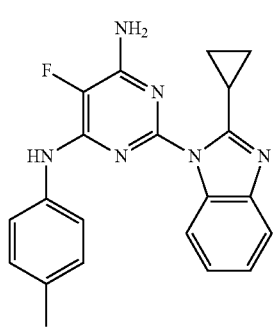 | 280 | 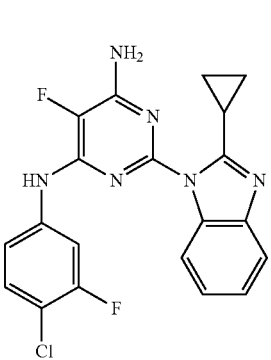 |
| 277 | 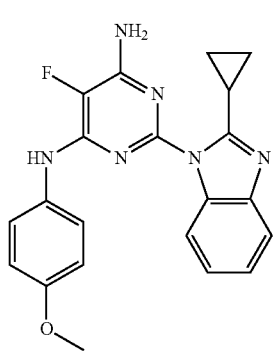 | 281 | 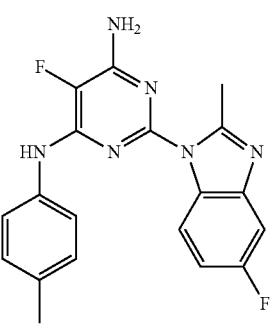 |

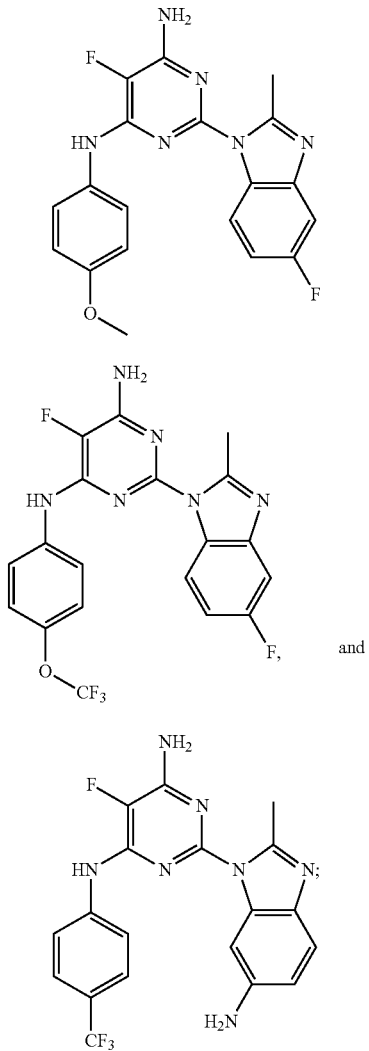

wherein the form of the compound of Formula (I) is selected from a salt, ester, hydrate, solvate, chelate, clathrate, polymorph, isotopologue, stereoisomer, racemate, enantiomer, diastereomer or tautomer thereof.

Another embodiment includes a compound of Formula (I) or a form thereof selected from the group consisting of:

| Cpd | Name |
|---|---|
| 1 | N-(4-methoxyphenyl)-2-(2-methyl-1H-benzimidazol-1-yl)pyrimidin-4-amine |
| 2 | N-(2,3-dihydro-1,4-benzodioxin-6-yl)-2-(2-methylimidazo[1,2-a]pyridin-3-yl)pyrimidin-4-amine |
| 3 | 2-(2-methylimidazo[1,2-a]pyridin-3-yl)-N-[4-(trifluoromethyl)phenyl]pyrimidin-4-amine |
| 4 | N-(4-methoxyphenyl)-2-(2-methylimidazo[1,2-a]pyridin-3-yl)pyrimidin-4-amine |
| 5 | N-(4-chlorophenyl)-2-(2-methylimidazo[1,2-a]pyridin-3-yl)pyrimidin-4-amine |
| 6 | 2-(2-methylimidazo[1,2-a]pyridin-3-yl)-N-phenylpyrimidin-4-amine |
| 7 | 2-[2-(trifluoromethyl)imidazo[1,2-a]pyridin-3-yl]-N-[4-(trifluoromethyl)phenyl]pyrimidin-4-amine |
| 8 | N-(4-chlorophenyl)-2-[2-(trifluoromethyl)imidazo[1,2-a]pyridin-3-yl]pyrimidin-4-amine |
| 9 | N-(4-methylphenyl)-2-[2-(trifluoromethyl)imidazo[1,2-a]pyridin-3-yl]pyrimidin-4-amine |
| 10 | N-(4-bromophenyl)-2-[2-(trifluoromethyl)imidazo[1,2-a]pyridin-3-yl]pyrimidin-4-amine |
| 11 | N-[4-(difluoromethoxy)phenyl]-2-[2-(trifluoromethyl)imidazo[1,2-a]pyridin-3-yl]pyrimidin-4-amine |
| 12 | N-(4-methoxyphenyl)-2-[2-(trifluoromethyl)imidazo[1,2-a]pyridin-3-yl]pyrimidin-4-amine |
| 13 | 2-[6-chloro-2-(trifluoromethyl)imidazo[1,2-a]pyridin-3-yl]-N-[4-(trifluoromethyl)phenyl]pyrimidin-4-amine |
| 14 | 2-[6-chloro-2-(trifluoromethyl)imidazo[1,2-a]pyridin-3-yl]-N-[4-(trifluoromethoxy)phenyl]pyrimidin-4-amine |
| 15 | N-(4-bromophenyl)-2-[6-chloro-2-(trifluoromethyl)imidazo[1,2-a]pyridin-3-yl]pyrimidin-4-amine |
| 16 | 2-[6-chloro-2-(trifluoromethyl)imidazo[1,2-a]pyridin-3-yl]-N-[4-(difluoromethoxy)phenyl]pyrimidin-4-amine |
| 17 | N-(4-chlorophenyl)-2-[6-chloro-2-(trifluoromethyl)imidazo[1,2-a]pyridin-3-yl]pyrimidin-4-amine |
| 18 | 2-[2-methyl-6-(trifluoromethyl)imidazo[1,2-a]pyridin-3-yl]-N-[4-(trifluoromethyl)phenyl]pyrimidin-4-amine |
| 19 | N-(4-bromophenyl)-2-[2-methyl-6-(trifluoromethyl)imidazo[1,2-a]pyridin-3-yl]pyrimidin-4-amine |
| 20 | N-(4-methylphenyl)-2-[2-methyl-6-(trifluoromethyl)imidazo[1,2-a]pyridin-3-yl]pyrimidin-4-amine |
| 21 | 2-[6-fluoro-2-(trifluoromethyl)imidazo[1,2-a]pyridin-3-yl]-N-(4-methylphenyl)pyrimidin-4-amine |
| 22 | 2-[6-fluoro-2-(trifluoromethyl)imidazo[1,2-a]pyridin-3-yl]-N-(4-methoxyphenyl)pyrimidin-4-amine |
| 23 | 2-[5-chloro-1-methyl-2-(trifluoromethyl)-1H-indol-3-yl]-N-(4-methoxyphenyl)pyrimidin-4-amine |
| 24 | 2-[5-chloro-1-methyl-2-(trifluoromethyl)-1H-indol-3-yl]-N-[4-(difluoromethoxy)phenyl]pyrimidin-4-amine |
| 25 | N-(4-bromophenyl)-2-[5-chloro-1-methyl-2-(trifluoromethyl)-1H-indol-3-yl]pyrimidin-4-amine |
| 26 | N-(4-bromophenyl)-2-(6-fluoro-2-phenylimidazo[1,2-a]pyridin-3-yl)pyrimidin-4-amine |
| 27 | 2-(6-fluoro-2-phenylimidazo[1,2-a]pyridin-3-yl)-N-(4-methylphenyl)pyrimidin-4-amine |
| 28 | N-(1,3-benzodioxol-5-yl)-2-[2-(trifluoromethyl)imidazo[1,2-a]pyridin-3-yl]pyrimidin-4-amine |
| 29 | N-(2,3-dihydro-1,4-benzodioxin-6-yl)-2-[2-(trifluoromethyl)imidazo[1,2-a]pyridin-3-yl]pyrimidin-4-amine |
| 30 | N-(6-methoxypyridin-3-yl)-2-[2-(trifluoromethyl)imidazo[1,2-a]pyridin-3-yl]pyrimidin-4-amine |
| 31 | $N^2,N^2$-dimethyl-$N^5$-{2-[2-(trifluoromethyl)imidazo[1,2-a]pyridin-3-yl]pyrimidin-4-yl}pyridine-2,5-diamine |
| 32 | 2-[6-bromo-2-(trifluoromethyl)imidazo[1,2-a]pyridin-3-yl]-N-[4-(trifluoromethyl)phenyl]pyrimidin-4-amine |
| 33 | 2-[6-bromo-2-(trifluoromethyl)imidazo[1,2-a]pyridin-3-yl]-N-(4-methoxyphenyl)pyrimidin-4-amine |
| 34 | N-(3-fluoro-4-methoxyphenyl)-2-[2-(trifluoromethyl)imidazo[1,2-a]pyridin-3-yl]pyrimidin-4-amine |
| 35 | N-(3-chloro-4-methoxyphenyl)-2-[2-(trifluoromethyl)imidazo[1,2-a]pyridin-3-yl]pyrimidin-4-amine |
| 36 | N-(3-chloro-4-methylphenyl)-2-[2-(trifluoromethyl)imidazo[1,2-a]pyridin-3-yl]pyrimidin-4-amine |
| 37 | N-(4-ethoxyphenyl)-2-[2-(trifluoromethyl)imidazo[1,2-a]pyridin-3-yl]pyrimidin-4-amine |
| 38 | N-[4-(propan-2-yl)phenyl]-2-[2-(trifluoromethyl)imidazo[1,2-a]pyridin-3-yl]pyrimidin-4-amine |
| 39 | N-[4-(1H-pyrazol-1-yl)phenyl]-2-[2-(trifluoromethyl)imidazo[1,2-a]pyridin-3-yl]pyrimidin-4-amine |
| 40 | N-(3-chloro-4-methoxyphenyl)-2-(2-methyl-1H-benzimidazol-1-yl)pyrimidin-4-amine |
| 41 | 2-(2-methyl-1H-benzimidazol-1-yl)-N-[4-(trifluoromethyl)phenyl]pyrimidin-4-amine |
| 42 | N-(3-chloro-4-methoxyphenyl)-2-[2-(trifluoromethyl)-1H-benzimidazol-1-yl]pyrimidin-4-amine |

| Cpd | Name |
|---|---|
| 43 | 5-fluoro-N-(4-methylphenyl)-2-[2-(trifluoromethyl)imidazo[1,2-a]pyridin-3-yl]pyrimidin-4-amine |
| 44 | 5-chloro-N-(4-methylphenyl)-2-[2-(trifluoromethyl)imidazo[1,2-a]pyridin-3-yl]pyrimidin-4-amine |
| 45 | N-(4-methoxyphenyl)-2-[2-(trifluoromethyl)imidazo[1,2-a]pyrazin-3-yl]pyrimidin-4-amine |
| 46 | 2-[2-(trifluoromethyl)imidazo[1,2-a]pyrazin-3-yl]-N-[4-(trifluoromethyl)phenyl]pyrimidin-4-amine |
| 47 | N-(4-chlorophenyl)-2-[2-(trifluoromethyl)imidazo[1,2-a]pyrazin-3-yl]pyrimidin-4-amine |
| 48 | 2-[6-methoxy-2-(trifluoromethyl)imidazo[1,2-a]pyridin-3-yl]-N-[4-(trifluoromethyl)phenyl]pyrimidin-4-amine |
| 49 | 2-[6-methoxy-2-(trifluoromethyl)imidazo[1,2-a]pyridin-3-yl]-N-[4-(trifluoromethoxy)phenyl]pyrimidin-4-amine |
| 50 | N-(4-methoxyphenyl)-2-[6-methoxy-2-(trifluoromethyl)imidazo[1,2-a]pyridin-3-yl]pyrimidin-4-amine |
| 51 | N-[4-(difluoromethoxy)phenyl]-2-[6-methoxy-2-(trifluoromethyl)imidazo[1,2-a]pyridin-3-yl]pyrimidin-4-amine |
| 52 | 2-{[6-{[4-(difluoromethoxy)phenyl]amino}-2-(methyl-1H-benzimidazol-1-yl)pyrimidin-4-yl]amino}ethanol |
| 53 | N-[4-(difluoromethoxy)phenyl]-2-[2-(trifluoromethyl)imidazo[1,2-a]pyrazin-3-yl]pyrimidin-4-amine |
| 54 | 2-[6-fluoro-2-(trifluoromethyl)imidazo[1,2-a]pyridin-3-yl]-N-[4-(trifluoromethyl)phenyl]pyrimidin-4-amine |
| 55 | N-[4-(difluoromethoxy)phenyl]-2-[6-fluoro-2-(trifluoromethyl)imidazo[1,2-a]pyridin-3-yl]pyrimidin-4-amine |
| 56 | N-[4-(trifluoromethyl)phenyl]-2-[2-(trifluoromethyl)pyrazolo[1,5-a]pyridin-3-yl]pyrimidin-4-amine |
| 57 | 2-{[2-(2-methyl-1H-benzimidazol-1-yl)-6-{[4-(trifluoromethyl)phenyl]amino}pyrimidin-4-yl]amino}ethanol |
| 58 | N⁴-(2-methoxyethyl)-2-(2-methyl-1H-benzimidazol-1-yl)-N⁶-[4-(trifluoromethyl)phenyl]pyrimidine-4,6-diamine |
| 59 | N⁴-[4-(difluoromethoxy)phenyl]-N⁶-(2-methoxyethyl)-2-(2-methyl-1H-benzimidazol-1-yl)pyrimidine-4,6-diamine |
| 60 | N-(4-methoxyphenyl)-2-[2-(trifluoromethyl)pyrazolo[1,5-a]pyridin-3-yl]pyrimidin-4-amine |
| 61 | N-[4-(difluoromethoxy)phenyl]-2-(2-methyl-1H-benzimidazol-1-yl)pyrimidin-4-amine |
| 62 | N-(4-methylphenyl)-2-[2-(trifluoromethyl)imidazo[1,2-a]pyrazin-3-yl]pyrimidin-4-amine |
| 63 | 2-(2-methyl-1H-benzimidazol-1-yl)-N-[4-(trifluoromethyl)phenyl]pyrimidine-4,6-diamine |
| 64 | 2-(5,6-difluoro-2-methyl-1H-benzimidazol-1-yl)-N-[4-(trifluoromethyl)phenyl]pyrimidine-4,6-diamine |
| 65 | N-[4-(difluoromethoxy)phenyl]-2-[2-(trifluoromethyl)imidazo[1,2-a]pyridin-3-yl]pyrimidine-4,6-diamine |
| 66 | 2-[2-(trifluoromethyl)imidazo[1,2-a]pyridin-3-yl]-N-[4-(trifluoromethyl)phenyl]pyrimidine-4,6-diamine |
| 67 | N-[4-(trifluoromethoxy)phenyl]-2-[2-(trifluoromethyl)imidazo[1,2-a]pyridin-3-yl]pyrimidine-4,6-diamine |
| 68 | 2-(6-fluoro-2-methylimidazo[1,2-a]pyridin-3-yl)-N-[4-(trifluoromethyl)phenyl]pyrimidine-4,6-diamine |
| 69 | N-[4-(difluoromethoxy)phenyl]-2-(6-fluoro-2-methylimidazo[1,2-a]pyridin-3-yl)pyrimidine-4,6-diamine |
| 70 | N-[4-(trifluoromethyl)phenyl]-2-(1,3,5-trimethyl-1H-pyrazol-4-yl)pyrimidine-4,6-diamine |
| 71 | 2-(6-fluoro-2-methyl-1H-benzimidazol-1-yl)-N-[4-(trifluoromethyl)phenyl]pyrimidine-4,6-diamine |
| 72 | N-[4-(difluoromethoxy)phenyl]-2-(6-fluoro-2-methyl-1H-benzimidazol-1-yl)pyrimidine-4,6-diamine |
| 73 | 2-(2-methyl-1H-imidazo[4,5-b]pyridin-1-yl)-N-[4-(trifluoromethyl)phenyl]pyrimidine-4,6-diamine |
| 74 | 2-(5,6-difluoro-2-methyl-1H-benzimidazol-1-yl)-N-[3-fluoro-4-(trifluoromethyl)phenyl]pyrimidine-4,6-diamine |
| 75 | 2-(2-cyclopropyl-6-fluoroimidazo[1,2-a]pyridin-3-yl)-N-[4-(difluoromethoxy)-3-fluorophenyl]pyrimidine-4,6-diamine |
| 76 | N-[4-(difluoromethoxy)-3-fluorophenyl]-2-(6-fluoro-2-methyl-1H-benzimidazol-1-yl)pyrimidine-4,6-diamine |
| 77 | N-[4-(difluoromethoxy)-3-fluorophenyl]-2-(2-ethyl-6-fluoro-1H-benzimidazol-1-yl)pyrimidine-4,6-diamine |
| 78 | 2-(2-cyclopropyl-6-fluoro-1H-benzimidazol-1-yl)-N-[4-(difluoromethoxy)-3-fluorophenyl]pyrimidine-4,6-diamine |
| 79 | N-[4-(trifluoromethyl)phenyl]-2-(2,5,6-trimethyl-1H-benzimidazol-1-yl)pyrimidine-4,6-diamine |
| 80 | N-[3-fluoro-4-(trifluoromethyl)phenyl]-2-(2-methyl-1H-benzimidazol-1-yl)pyrimidine-4,6-diamine |
| 81 | 2-(2-ethyl-6-fluoro-1H-benzimidazol-1-yl)-N-[4-(trifluoromethyl)phenyl]pyrimidine-4,6-diamine |
| 82 | 2-(2-cyclopropyl-6-fluoro-1H-benzimidazol-1-yl)-N-[4-(trifluoromethyl)phenyl]pyrimidine-4,6-diamine |
| 83 | 2-(2-cyclopropyl-5-fluoro-1H-benzimidazol-1-yl)-N-[4-(trifluoromethyl)phenyl]pyrimidine-4,6-diamine |
| 84 | [3-(4-amino-6-{[4-(trifluoromethyl)phenyl]amino}pyrimidin-2-yl)-6-fluoroimidazo[1,2-a]pyridin-2-yl]methanol |
| 85 | 2-(6-bromo-2-methyl-1H-benzimidazol-1-yl)-N-[4-(trifluoromethyl)phenyl]pyrimidine-4,6-diamine |
| 86 | 2-(2,6-dimethyl-1H-benzimidazol-1-yl)-N-[4-(trifluoromethyl)phenyl]pyrimidine-4,6-diamine |
| 87 | 2-(6-ethyl-2-methyl-1H-benzimidazol-1-yl)-N-[4-(trifluoromethyl)phenyl]pyrimidine-4,6-diamine |
| 88 | 2-(4,6-difluoro-2-methyl-1H-benzimidazol-1-yl)-N-[4-(trifluoromethyl)phenyl]pyrimidine-4,6-diamine |
| 89 | 2-(4,6-difluoro-2-methyl-1H-benzimidazol-1-yl)-N-[3-fluoro-4-(trifluoromethyl)phenyl]pyrimidine-4,6-diamine |
| 90 | 2-{[2-(4,6-difluoro-2-methyl-1H-benzimidazol-1-yl)-6-{[4-(trifluoromethyl)phenyl]amino}pyrimidin-4-yl]amino}ethanol |
| 91 | 2-(6-ethenyl-2-methyl-1H-benzimidazol-1-yl)-N-[4-(trifluoromethyl)phenyl]pyrimidine-4,6-diamine |
| 92 | 2-(2-cyclopropyl-6-fluoro-1H-imidazo[4,5-b]pyridin-1-yl)-N-[4-(trifluoromethyl)phenyl]pyrimidine-4,6-diamine |
| 93 | 2-(6-chloro-2-methyl-1H-benzimidazol-1-yl)-N-[4-(trifluoromethyl)phenyl]pyrimidine-4,6-diamine |
| 94 | 2-(6-fluoro-2-methyl-1H-imidazo[4,5-b]pyridin-1-yl)-N-[4-(trifluoromethyl)phenyl]pyrimidine-4,6-diamine |
| 95 | 5-fluoro-2-(2-methyl-1H-benzimidazol-1-yl)-N-[4-(trifluoromethyl)phenyl]pyrimidine-4,6-diamine |
| 96 | 2-(6-chloro-2-methyl-1H-benzimidazol-1-yl)-N-[3-fluoro-4-(trifluoromethyl)phenyl]pyrimidine-4,6-diamine |
| 97 | 2-(6-chloro-2-methyl-1H-benzimidazol-1-yl)-N-[4-(difluoromethoxy)phenyl]pyrimidine-4,6-diamine |
| 98 | 2-(5-chloro-2-methyl-1H-benzimidazol-1-yl)-N-[3-fluoro-4-(trifluoromethyl)phenyl]pyrimidine-4,6-diamine |
| 99 | 2-(5-chloro-2-methyl-1H-benzimidazol-1-yl)-N-[4-(difluoromethoxy)phenyl]pyrimidine-4,6-diamine |
| 100 | 2-(6-fluoro-2-methylimidazo[1,2-a]pyrimidin-3-yl)-N-[4-(trifluoromethyl)phenyl]pyrimidine-4,6-diamine |
| 101 | N-[4-(difluoromethoxy)-3-fluorophenyl]-2-(5,6-difluoro-2-methyl-1H-benzimidazol-1-yl)pyrimidine-4,6-diamine |
| 102 | N-[4-(difluoromethoxy)phenyl]-2-(5,6-difluoro-2-methyl-1H-benzimidazol-1-yl)pyrimidine-4,6-diamine |
| 103 | 2-(2-cyclopropyl-6-fluoro-1H-imidazo[4,5-b]pyridin-1-yl)-N-[4-(difluoromethoxy)phenyl]pyrimidine-4,6-diamine |
| 104 | 2-(6-chloro-2-methyl-1H-imidazo[4,5-b]pyridin-1-yl)-N-[4-(trifluoromethyl)phenyl]pyrimidine-4,6-diamine |
| 105 | 2-(6-chloro-2-ethyl-1H-imidazo[4,5-b]pyridin-1-yl)-N-[4-(trifluoromethyl)phenyl]pyrimidine-4,6-diamine |
| 106 | N-[4-(difluoromethoxy)phenyl]-5-fluoro-2-(2-methyl-1H-benzimidazol-1-yl)pyrimidine-4,6-diamine |
| 107 | 2-(2-ethyl-1H-benzimidazol-1-yl)-5-fluoro-N-[4-(trifluoromethyl)phenyl]pyrimidine-4,6-diamine |
| 108 | 5-fluoro-2-(5-fluoro-2-methyl-1H-benzimidazol-1-yl)-N-[4-(trifluoromethyl)phenyl]pyrimidine-4,6-diamine |
| 109 | 5-fluoro-2-(6-fluoro-2-methyl-1H-benzimidazol-1-yl)-N-[4-(trifluoromethyl)phenyl]pyrimidine-4,6-diamine |
| 110 | N-[4-(difluoromethoxy)phenyl]-5-fluoro-2-(6-fluoro-2-methyl-1H-benzimidazol-1-yl)pyrimidine-4,6-diamine |

| Cpd | Name |
|---|---|
| 111 | N-[4-(difluoromethoxy)-3-fluorophenyl]-5-fluoro-2-(6-fluoro-2-methyl-1H-benzimidazol-1-yl)pyrimidine-4,6-diamine |
| 112 | N-[4-(difluoromethoxy)-3-fluorophenyl]-5-fluoro-2-(5-fluoro-2-methyl-1H-benzimidazol-1-yl)pyrimidine-4,6-diamine |
| 113 | N-[4-(difluoromethoxy)phenyl]-5-fluoro-2-(5-fluoro-2-methyl-1H-benzimidazol-1-yl)pyrimidine-4,6-diamine |
| 114 | 2-(6-chloro-2-methyl-1H-imidazo[4,5-b]pyridin-1-yl)-5-fluoro-N-[4-(trifluoromethyl)phenyl]pyrimidine-4,6-diamine |
| 115 | 2-(6-chloro-2-methyl-1H-imidazo[4,5-b]pyridin-1-yl)-N-[4-(difluoromethoxy)phenyl]-5-fluoropyrimidine-4,6-diamine |
| 116 | 2-(6-chloro-2-methyl-1H-imidazo[4,5-b]pyridin-1-yl)-N-[4-(difluoromethoxy)-3-fluorophenyl]-5-fluoropyrimidine-4,6-diamine |
| 117 | 2-(2-cyclopropyl-6-fluoro-1H-imidazo[4,5-b]pyridin-1-yl)-5-fluoro-N-[4-(trifluoromethyl)phenyl]pyrimidine-4,6-diamine |
| 118 | 2-(imidazo[1,2-a]pyridin-3-yl)-N-[4-(trifluoromethyl)phenyl]pyrimidin-4-amine |
| 119 | N-[4-(difluoromethoxy)-3-fluorophenyl]-5-fluoro-2-(2-methyl-1H-benzimidazol-1-yl)pyrimidine-4,6-diamine |
| 120 | 2-(2-cyclopropyl-1H-benzimidazol-1-yl)-5-fluoro-N-[4-(trifluoromethyl)phenyl]pyrimidine-4,6-diamine |
| 121 | 2-(2-cyclopropyl-1H-benzimidazol-1-yl)-N-[4-(difluoromethoxy)phenyl]-5-fluoropyrimidine-4,6-diamine |
| 122 | 2-(2-cyclopropyl-1H-benzimidazol-1-yl)-N-[4-(difluoromethoxy)-3-fluorophenyl]-5-fluoropyrimidine-4,6-diamine |
| 123 | N-[4-(difluoromethoxy)phenyl]-2-(2-ethyl-1H-benzimidazol-1-yl)-5-fluoropyrimidine-4,6-diamine |
| 124 | N-[4-(difluoromethoxy)-3-fluorophenyl]-2-(2-ethyl-1H-benzimidazol-1-yl)-5-fluoropyrimidine-4,6-diamine |
| 125 | 2-(5,6-difluoro-2-methyl-1H-benzimidazol-1-yl)-5-fluoro-N-[4-(trifluoromethyl)phenyl]pyrimidine-4,6-diamine |
| 126 | N-[4-(difluoromethoxy)-3-fluorophenyl]-2-(5,6-difluoro-2-methyl-1H-benzimidazol-1-yl)-5-fluoropyrimidine-4,6-diamine |
| 127 | 2-(4,6-difluoro-2-methyl-1H-benzimidazol-1-yl)-5-fluoro-N-[4-(trifluoromethyl)phenyl]pyrimidine-4,6-diamine |
| 128 | N-[4-(difluoromethoxy)-3-fluorophenyl]-2-(4,6-difluoro-2-methyl-1H-benzimidazol-1-yl)-5-fluoropyrimidine-4,6-diamine |
| 129 | 2-(2-ethyl-4,6-difluoro-1H-benzimidazol-1-yl)-5-fluoro-N-[4-(trifluoromethyl)phenyl]pyrimidine-4,6-diamine |
| 130 | N-[4-(difluoromethoxy)-3-fluorophenyl]-2-(2-ethyl-4,6-difluoro-1H-benzimidazol-1-yl)-5-fluoropyrimidine-4,6-diamine |
| 131 | N-[4-(difluoromethoxy)phenyl]-2-(4,6-difluoro-2-methyl-1H-benzimidazol-1-yl)-5-fluoropyrimidine-4,6-diamine |
| 132 | N-[4-(difluoromethoxy)phenyl]-2-(2-ethyl-4,6-difluoro-1H-benzimidazol-1-yl)-5-fluoropyrimidine-4,6-diamine |
| 133 | N-[4-(difluoromethoxy)phenyl]-2-(5,6-difluoro-2-methyl-1H-benzimidazol-1-yl)-5-fluoropyrimidine-4,6-diamine |
| 134 | 5-fluoro-2-(4-fluoro-2-methyl-1H-benzimidazol-1-yl)-N-[4-(trifluoromethyl)phenyl]pyrimidine-4,6-diamine |
| 135 | N-[4-(difluoromethoxy)phenyl]-5-fluoro-2-(4-fluoro-2-methyl-1H-benzimidazol-1-yl)pyrimidine-4,6-diamine |
| 136 | N-[4-(difluoromethoxy)-3-fluorophenyl]-5-fluoro-2-(4-fluoro-2-methyl-1H-benzimidazol-1-yl)pyrimidine-4,6-diamine |
| 137 | 5-fluoro-2-(2-methyl-1H-imidazo[4,5-b]pyridin-1-yl)-N-[4-(trifluoromethyl)phenyl]pyrimidine-4,6-diamine |
| 138 | N-[4-(difluoromethoxy)phenyl]-5-fluoro-2-(2-methyl-1H-imidazo[4,5-b]pyridin-1-yl)pyrimidine-4,6-diamine |
| 139 | N-[4-(difluoromethoxy)-3-fluorophenyl]-5-fluoro-2-(2-methyl-1H-imidazo[4,5-b]pyridin-1-yl)pyrimidine-4,6-diamine |
| 140 | 2-(2-cyclopropyl-4-fluoro-1H-benzimidazol-1-yl)-5-fluoro-N-[4-(trifluoromethyl)phenyl]pyrimidine-4,6-diamine |
| 141 | 2-(2-cyclopropyl-4-fluoro-1H-benzimidazol-1-yl)-N-[4-(difluoromethoxy)phenyl]-5-fluoropyrimidine-4,6-diamine |
| 142 | 2-(2-cyclopropyl-4-fluoro-1H-benzimidazol-1-yl)-N-[4-(difluoromethoxy)-3-fluorophenyl]-5-fluoropyrimidine-4,6-diamine |
| 143 | 2-(2-cyclopropyl-6-fluoro-1H-benzimidazol-1-yl)-N-[4-(difluoromethoxy)phenyl]pyrimidine-4,6-diamine |
| 144 | N-[4-(difluoromethoxy)phenyl]-2-(2-ethyl-6-fluoro-1H-benzimidazol-1-yl)pyrimidine-4,6-diamine |
| 145 | N-[4-(difluoromethoxy)phenyl]-2-[2-(difluoromethyl)-6-fluoro-1H-benzimidazol-1-yl]pyrimidine-4,6-diamine |
| 146 | 2-(2-methyl-1H-benzimidazol-1-yl)-N-[4-(methylsulfanyl)phenyl]pyrimidine-4,6-diamine |
| 147 | 2-[2-(1-methylcyclopropyl)-1H-benzimidazol-1-yl]-N-[4-(trifluoromethyl)phenyl]pyrimidine-4,6-diamine |
| 148 | N-[4-(difluoromethoxy)phenyl]-2-[2-(1-methylcyclopropyl)-1H-benzimidazol-1-yl]pyrimidine-4,6-diamine |
| 149 | 2-(2-cyclopropyl-1H-benzimidazol-1-yl)-N-[4-(trifluoromethyl)phenyl]pyrimidine-4,6-diamine |
| 150 | 2-[2-(methoxymethyl)-1H-benzimidazol-1-yl]-N-[4-(trifluoromethyl)phenyl]pyrimidine-4,6-diamine |
| 151 | 2-[2-(propan-2-yl)-1H-benzimidazol-1-yl]-N-[4-(trifluoromethyl)phenyl]pyrimidine-4,6-diamine |
| 152 | 2-[2-(difluoromethyl)-1H-benzimidazol-1-yl]-N-[4-(trifluoromethyl)phenyl]pyrimidine-4,6-diamine |
| 153 | 2-(2-ethyl-1H-benzimidazol-1-yl)-N-[4-(trifluoromethyl)phenyl]pyrimidine-4,6-diamine |
| 154 | 2-(2-methylpyrazolo[1,5-a]pyridin-3-yl)-N-[4-(trifluoromethyl)phenyl]pyrimidine-4,6-diamine |
| 155 | 2-(2-cyclopropyl-6-fluoro-1H-imidazo[4,5-b]pyridin-1-yl)-N-[4-(difluoromethoxy)phenyl]-5-fluoropyrimidine-4,6-diamine |
| 156 | N-[4-(difluoromethoxy)phenyl]-2-(2-ethyl-1H-benzimidazol-1-yl)pyrimidine-4,6-diamine |
| 157 | N-[4-(difluoromethoxy)-3-fluorophenyl]-2-(2-ethyl-1H-benzimidazol-1-yl)pyrimidine-4,6-diamine |
| 158 | 2-(5-chloro-2-methyl-1H-benzimidazol-1-yl)-5-fluoro-N-[4-(trifluoromethyl)phenyl]pyrimidine-4,6-diamine |
| 159 | 2-(5-chloro-2-methyl-1H-benzimidazol-1-yl)-N-[4-(difluoromethoxy)phenyl]-5-fluoropyrimidine-4,6-diamine |
| 160 | 2-(6-chloro-2-methyl-1H-benzimidazol-1-yl)-5-fluoro-N-[4-(trifluoromethyl)phenyl]pyrimidine-4,6-diamine |
| 161 | 2-(6-chloro-2-methyl-1H-benzimidazol-1-yl)-N-[4-(difluoromethoxy)phenyl]-5-fluoropyrimidine-4,6-diamine |
| 162 | 2-(2-ethyl-5-fluoro-1H-benzimidazol-1-yl)-5-fluoro-N-[4-(trifluoromethyl)phenyl]pyrimidine-4,6-diamine |
| 163 | N-[4-(difluoromethoxy)phenyl]-2-(2-ethyl-5-fluoro-1H-benzimidazol-1-yl)-5-fluoropyrimidine-4,6-diamine |
| 164 | 2-(2-ethyl-6-fluoro-1H-benzimidazol-1-yl)-5-fluoro-N-[4-(trifluoromethyl)phenyl]pyrimidine-4,6-diamine |
| 165 | N-[4-(difluoromethoxy)phenyl]-2-(2-ethyl-6-fluoro-1H-benzimidazol-1-yl)-5-fluoropyrimidine-4,6-diamine |
| 166 | 5-chloro-2-(2-methyl-1H-benzimidazol-1-yl)-N-[4-(trifluoromethyl)phenyl]pyrimidine-4,6-diamine |
| 167 | 5-chloro-2-(2-ethyl-1H-benzimidazol-1-yl)-N-[4-(trifluoromethyl)phenyl]pyrimidine-4,6-diamine |
| 168 | 5-chloro-N-[4-(difluoromethoxy)phenyl]-2-(2-ethyl-1H-benzimidazol-1-yl)pyrimidine-4,6-diamine |
| 169 | 5-fluoro-2-(2-methylimidazo[1,2-a]pyridin-3-yl)-N-[4-(trifluoromethyl)phenyl]pyrimidine-4,6-diamine |
| 170 | N-[4-(difluoromethoxy)phenyl]-5-fluoro-2-(2-methylimidazo[1,2-a]pyridin-3-yl)pyrimidine-4,6-diamine |
| 171 | N-[4-(difluoromethoxy)-3-fluorophenyl]-5-fluoro-2-(2-methylimidazo[1,2-a]pyridin-3-yl)pyrimidine-4,6-diamine |

| Cpd | Name |
|---|---|
| 172 | 5-methyl-2-(2-methyl-1H-benzimidazol-1-yl)-N-[4-(trifluoromethyl)phenyl]pyrimidine-4,6-diamine |
| 173 | N-[4-(difluoromethoxy)phenyl]-5-fluoro-2-(2-methylpyrazolo[1,5-a]pyridin-3-yl)pyrimidine-4,6-diamine |
| 174 | 5-fluoro-N-[4-(trifluoromethyl)phenyl]-2-(2,6,8-trimethylimidazo[1,2-a]pyrazin-3-yl)pyrimidine-4,6-diamine |
| 175 | N-[4-(difluoromethoxy)phenyl]-5-fluoro-2-(2,6,8-trimethylimidazo[1,2-a]pyrazin-3-yl)pyrimidine-4,6-diamine |
| 176 | N-[4-(difluoromethoxy)-3-fluorophenyl]-5-fluoro-2-(2,6,8-trimethylimidazo[1,2-a]pyrazin-3-yl)pyrimidine-4,6-diamine |
| 177 | 5-fluoro-2-(2-methylpyrazolo[1,5-a]pyridin-3-yl)-N-[4-(trifluoromethyl)phenyl]pyrimidine-4,6-diamine |
| 178 | 5-fluoro-2-[6-fluoro-2-(trifluoromethyl)imidazo[1,2-a]pyridin-3-yl]-N-[4-(trifluoromethyl)phenyl]pyrimidine-4,6-diamine |
| 179 | 5-fluoro-2-(6-fluoro-2-methyl-1H-benzimidazol-1-yl)-N-(4-methoxyphenyl)pyrimidine-4,6-diamine |
| 180 | 2-(2-cyclopropylpyrazolo[1,5-a]pyridin-3-yl)-N-[4-(difluoromethoxy)phenyl]-5-fluoropyrimidine-4,6-diamine |
| 181 | [3-(4-amino-6-{[4-(difluoromethoxy)phenyl]amino}-5-fluoropyrimidin-2-yl)-5-fluoropyrazolo[1,5-a]pyridin-2-yl]methanol |
| 182 | 2-[2-(methylsulfanyl)-1H-benzimidazol-1-yl]-N-[4-(trifluoromethyl)phenyl]pyrimidine-4,6-diamine |
| 183 | 5-fluoro-2-(6-fluoro-2-methyl-1H-benzimidazol-1-yl)-N-[6-(trifluoromethyl)pyridin-3-yl]pyrimidine-4,6-diamine |
| 184 | 5-fluoro-2-(6-fluoro-2-methyl-1H-benzimidazol-1-yl)-N-(4-methylphenyl)pyrimidine-4,6-diamine |
| 185 | N-(4-chlorophenyl)-5-fluoro-2-(6-fluoro-2-methyl-1H-benzimidazol-1-yl)pyrimidine-4,6-diamine |
| 186 | N-[4-(difluoromethoxy)phenyl]-2-(2-ethyl-5-fluoropyrazolo[1,5-a]pyridin-3-yl)-5-fluoropyrimidine-4,6-diamine |
| 187 | 2-(2-ethyl-5-fluoropyrazolo[1,5-a]pyridin-3-yl)-5-fluoro-N-[4-(trifluoromethyl)phenyl]pyrimidine-4,6-diamine |
| 188 | N-[4-(difluoromethoxy)-3-fluorophenyl]-2-(2-ethyl-5-fluoropyrazolo[1,5-a]pyridin-3-yl)-5-fluoropyrimidine-4,6-diamine |
| 189 | 5-fluoro-2-(6-fluoro-2-methyl-1H-benzimidazol-1-yl)-N-(3-methoxyphenyl)pyrimidine-4,6-diamine |
| 190 | N-(3-chlorophenyl)-5-fluoro-2-(6-fluoro-2-methyl-1H-benzimidazol-1-yl)pyrimidine-4,6-diamine |
| 191 | 5-fluoro-2-(6-fluoro-2-methyl-1H-benzimidazol-1-yl)-N-[4-(trifluoromethoxy)phenyl]pyrimidine-4,6-diamine |
| 192 | 4-{[6-amino-5-fluoro-2-(6-fluoro-2-methyl-1H-benzimidazol-1-yl)pyrimidin-4-yl]amino}benzonitrile |
| 193 | methyl 4-{[6-amino-5-fluoro-2-(6-fluoro-2-methyl-1H-benzimidazol-1-yl)pyrimidin-4-yl]amino}benzoate |
| 194 | 5-fluoro-2-(2-methyl-1H-benzimidazol-1-yl)-N-(3-methylphenyl)pyrimidine-4,6-diamine |
| 195 | 5-fluoro-N-(3-methoxyphenyl)-2-(2-methyl-1H-benzimidazol-1-yl)pyrimidine-4,6-diamine |
| 196 | 2-(2-methyl-1H-benzimidazol-1-yl)-N-(4-methylphenyl)pyrimidine-4,6-diamine |
| 197 | N-(4-methoxyphenyl)-2-(2-methyl-1H-benzimidazol-1-yl)pyrimidine-4,6-diamine |
| 198 | N-[4-(dimethylamino)phenyl]-2-(2-methyl-1H-benzimidazol-1-yl)pyrimidine-4,6-diamine |
| 199 | 5-fluoro-2-(2-methyl-1H-benzimidazol-1-yl)-N-(4-methylphenyl)pyrimidine-4,6-diamine |
| 200 | 5-fluoro-N-(4-methoxyphenyl)-2-(2-methyl-1H-benzimidazol-1-yl)pyrimidine-4,6-diamine |
| 201 | N-(4-chlorophenyl)-5-fluoro-2-(2-methyl-1H-benzimidazol-1-yl)pyrimidine-4,6-diamine |
| 202 | 4-{[6-amino-5-fluoro-2-(2-methyl-1H-benzimidazol-1-yl)pyrimidin-4-yl]amino}benzonitrile |
| 203 | N-(1,3-benzodioxol-5-yl)-5-fluoro-2-(2-methyl-1H-benzimidazol-1-yl)pyrimidine-4,6-diamine |
| 204 | 5-fluoro-2-(2-methyl-1H-benzimidazol-1-yl)-N-[4-(trifluoromethoxy)phenyl]pyrimidine-4,6-diamine |
| 205 | N-(1,3-benzodioxol-5-yl)-2-(2-methyl-1H-benzimidazol-1-yl)pyrimidine-4,6-diamine |
| 206 | N-(2,2-difluoro-1,3-benzodioxol-5-yl)-2-(2-methyl-1H-benzimidazol-1-yl)pyrimidine-4,6-diamine |
| 207 | N-(3-fluoro-4-methoxyphenyl)-2-(2-methyl-1H-benzimidazol-1-yl)pyrimidine-4,6-diamine |
| 208 | N-(6-methoxypyridin-3-yl)-2-(2-methyl-1H-benzimidazol-1-yl)pyrimidine-4,6-diamine |
| 209 | N-(4-chlorophenyl)-2-(2-methyl-1H-benzimidazol-1-yl)pyrimidine-4,6-diamine |
| 210 | 4-{[6-amino-2-(2-methyl-1H-benzimidazol-1-yl)pyrimidin-4-yl]amino}benzonitrile |
| 211 | 2-(2-methyl-1H-benzimidazol-1-yl)-N-(4-nitrophenyl)pyrimidine-4,6-diamine |
| 212 | N-(4-bromophenyl)-2-(2-methyl-1H-benzimidazol-1-yl)pyrimidine-4,6-diamine |
| 213 | 2-(5,6-difluoro-2-methyl-1H-benzimidazol-1-yl)-5-fluoro-N-(4-methylphenyl)pyrimidine-4,6-diamine |
| 214 | 2-(5,6-difluoro-2-methyl-1H-benzimidazol-1-yl)-5-fluoro-N-(4-methoxyphenyl)pyrimidine-4,6-diamine |
| 215 | N-(4-chlorophenyl)-2-(5,6-difluoro-2-methyl-1H-benzimidazol-1-yl)-5-fluoropyrimidine-4,6-diamine |
| 216 | N-[4-(difluoromethoxy)phenyl]-5-fluoro-2-[2-(methoxymethyl)-1H-benzimidazol-1-yl]pyrimidine-4,6-diamine |
| 217 | 5-fluoro-2-[2-(methoxymethyl)-1H-benzimidazol-1-yl]-N-(4-methylphenyl)pyrimidine-4,6-diamine |
| 218 | 5-fluoro-2-[2-(methoxymethyl)-1H-benzimidazol-1-yl]-N-(4-methoxyphenyl)pyrimidine-4,6-diamine |
| 219 | N-(4-chlorophenyl)-5-fluoro-2-[2-(methoxymethyl)-1H-benzimidazol-1-yl]pyrimidine-4,6-diamine |
| 220 | 5-fluoro-2-[2-(methoxymethyl)-1H-benzimidazol-1-yl]-N-[4-(trifluoromethyl)phenyl]pyrimidine-4,6-diamine |
| 221 | 2-(2-methyl-1H-benzimidazol-1-yl)-N-[4-(trifluoromethoxy)phenyl]pyrimidine-4,6-diamine |
| 222 | 1-(4-amino-5-fluoro-6-{[4-(trifluoromethyl)phenyl]amino}pyrimidin-2-yl)-2-methyl-1H-benzimidazole-6-carbonitrile |
| 223 | 1-(4-amino-6-{[4-(difluoromethoxy)phenyl]amino}-5-fluoropyrimidin-2-yl)-2-methyl-1H-benzimidazole-6-carbonitrile |
| 224 | 1-{4-amino-5-fluoro-6-1(4-methylphenyl)amino]pyrimidin-2-yl}-2-methyl-1H-benzimidazole-6-carbonitrile |
| 225 | 1-{4-amino-5-fluoro-6-[(4-methoxyphenyl)amino]pyrimidin-2-yl}-2-methyl-1H-benzimidazole-6-carbonitrile |
| 226 | 1-(4-amino-6-{[4-(difluoromethoxy)phenyl]amino}-5-fluoropyrimidin-2-yl)-2-methyl-1H-benzimidazole-5-carbonitrile |
| 227 | 1-{4-amino-5-fluoro-6-[(4-methylphenyl)amino]pyrimidin-2-yl}-2-methyl-1H-benzimidazole-5-carbonitrile |
| 228 | 1-{4-amino-5-fluoro-6-1(4-methoxyphenyl)amino]pyrimidin-2-yl}-2-methyl-1H-benzimidazole-5-carbonitrile |
| 229 | 1-(4-amino-5-fluoro-6-{[4-(trifluoromethyl)phenyl]amino}pyrimidin-2-yl)-2-methyl-1H-benzimidazole-5-carbonitrile |
| 230 | 1-{4-amino-6-[(4-chlorophenyl)amino]-5-fluoropyrimidin-2-yl}-2-methyl-1H-benzimidazole-5-carbonitrile |
| 231 | N-[4-(difluoromethoxy)phenyl]-5-fluoro-2-(2-methyl-6-nitro-1H-benzimidazol-1-yl)pyrimidine-4,6-diamine |
| 232 | 5-fluoro-2-(2-methyl-6-nitro-1H-benzimidazol-1-yl)-N-(4-methylphenyl)pyrimidine-4,6-diamine |
| 233 | 5-fluoro-N-(4-methoxyphenyl)-2-(2-methyl-6-nitro-1H-benzimidazol-1-yl)pyrimidine-4,6-diamine |
| 234 | N-[4-(difluoromethoxy)phenyl]-2-(2-methyl-1H-benzimidazol-1-yl)pyrimidine-4,6-diamine |
| 235 | N-[4-(difluoromethoxy)-3-fluorophenyl]-2-(2-methyl-1H-benzimidazol-1-yl)pyrimidine-4,6-diamine |
| 236 | 5-fluoro-2-(2-methyl-6-nitro-1H-benzimidazol-1-yl)-N-[4-(trifluoromethyl)phenyl]pyrimidine-4,6-diamine |
| 237 | N-(4-chlorophenyl)-2-(4,6-difluoro-2-methyl-1H-benzimidazol-1-yl)-5-fluoropyrimidine-4,6-diamine |
| 238 | 2-(4,6-difluoro-2-methyl-1H-benzimidazol-1-yl)-5-fluoro-N-[4-(trifluoromethoxy)phenyl]pyrimidine-4,6-diamine |

| Cpd | Name |
|---|---|
| 239 | 5-fluoro-N-(4-methoxyphenyl)-2-(2-methylpyrazolo[1,5-a]pyridin-3-yl)pyrimidine-4,6-diamine |
| 240 | N-(1,3-benzodioxol-5-yl)-2-(4,6-difluoro-2-methyl-1H-benzimidazol-1-yl)-5-fluoropyrimidine-4,6-diamine |
| 241 | 2-(4,6-difluoro-2-methyl-1H-benzimidazol-1-yl)-5-fluoro-N-(4-methylphenyl)pyrimidine-4,6-diamine |
| 242 | 2-(4,6-difluoro-2-methyl-1H-benzimidazol-1-yl)-5-fluoro-N-(4-methoxyphenyl)pyrimidine-4,6-diamine |
| 243 | 2-(5,7-difluoro-2-methyl-1H-benzimidazol-1-yl)-5-fluoro-N-[4-(trifluoromethyl)phenyl]pyrimidine-4,6-diamine |
| 244 | 5-fluoro-2-(6-methoxy-2-methyl-1H-benzimidazol-1-yl)-N-[4-(trifluoromethyl)phenyl]pyrimidine-4,6-diamine |
| 245 | N-(4-chlorophenyl)-5-fluoro-2-(6-methoxy-2-methyl-1H-benzimidazol-1-yl)pyrimidine-4,6-diamine |
| 246 | 5-fluoro-2-(6-methoxy-2-methyl-1H-benzimidazol-1-yl)-N-[4-(trifluoromethoxy)phenyl]pyrimidine-4,6-diamine |
| 247 | N-[4-(difluoromethoxy)phenyl]-5-fluoro-2-(6-methoxy-2-methyl-1H-benzimidazol-1-yl)pyrimidine-4,6-diamine |
| 248 | 5-fluoro-2-(6-methoxy-2-methyl-1H-benzimidazol-1-yl)-N-(4-methylphenyl)pyrimidine-4,6-diamine |
| 249 | 5-fluoro-2-(6-methoxy-2-methyl-1H-benzimidazol-1-yl)-N-(4-methoxyphenyl)pyrimidine-4,6-diamine |
| 250 | N-(1,3-benzodioxol-5-yl)-5-fluoro-2-(6-methoxy-2-methyl-1H-benzimidazol-1-yl)pyrimidine-4,6-diamine |
| 251 | N-(4-chlorophenyl)-5-fluoro-2-(6-fluoro-2-methylimidazo[1,2-a]pyridin-3-yl)pyrimidine-4,6-diamine |
| 252 | 5-fluoro-2-(6-fluoro-2-methylimidazo[1,2-a]pyridin-3-yl)-N-(4-methoxyphenyl)pyrimidine-4,6-diamine |
| 253 | 5-fluoro-2-(6-fluoro-2-methylimidazo[1,2-a]pyridin-3-yl)-N-(4-methylphenyl)pyrimidine-4,6-diamine |
| 254 | 5-fluoro-2-(2-methyl-5-nitro-1H-benzimidazol-1-yl)-N-(4-methylphenyl)pyrimidine-4,6-diamine |
| 255 | 5-fluoro-N-(4-methoxyphenyl)-2-(2-methyl-5-nitro-1H-benzimidazol-1-yl)pyrimidine-4,6-diamine |
| 256 | 2-(6-amino-2-methyl-1H-benzimidazol-1-yl)-5-fluoro-N-(4-methoxyphenyl)pyrimidine-4,6-diamine |
| 257 | 2-(6-amino-2-methyl-1H-benzimidazol-1-yl)-N-[4-(difluoromethoxy)phenyl]-5-fluoropyrimidine-4,6-diamine |
| 258 | 2-(6-amino-2-methyl-1H-benzimidazol-1-yl)-5-fluoro-N-(4-methylphenyl)pyrimidine-4,6-diamine |
| 259 | N-(4-chlorophenyl)-5-fluoro-2-(5-fluoro-2-methyl-1H-benzimidazol-1-yl)pyrimidine-4,6-diamine |
| 260 | N-(4-chloro-3-fluorophenyl)-5-fluoro-2-(5-fluoro-2-methyl-1H-benzimidazol-1-yl)pyrimidine-4,6-diamine |
| 261 | N-(4-chloro-3-fluorophenyl)-5-fluoro-2-(2-methyl-1H-benzimidazol-1-yl)pyrimidine-4,6-diamine |
| 262 | N-(4-chloro-3-fluorophenyl)-5-fluoro-2-(6-fluoro-2-methyl-1H-benzimidazol-1-yl)pyrimidine-4,6-diamine |
| 263 | N-(4-chlorophenyl)-2-(6-fluoro-2-methyl-1H-benzimidazol-1-yl)pyrimidine-4,6-diamine |
| 264 | 2-(6-fluoro-2-methyl-1H-benzimidazol-1-yl)-N-(4-methylphenyl)pyrimidine-4,6-diamine |
| 265 | 2-(6-fluoro-2-methyl-1H-benzimidazol-1-yl)-N-(4-methoxyphenyl)pyrimidine-4,6-diamine |
| 266 | N-[4-(dimethylamino)phenyl]-2-(6-fluoro-2-methyl-1H-benzimidazol-1-yl)pyrimidine-4,6-diamine |
| 267 | N-(4-chloro-3-fluorophenyl)-2-(6-fluoro-2-methyl-1H-benzimidazol-1-yl)pyrimidine-4,6-diamine |
| 268 | 2-(6-fluoro-2-methyl-1H-benzimidazol-1-yl)-N-(3-methylphenyl)pyrimidine-4,6-diamine |
| 269 | N-(2,2-difluoro-1,3-benzodioxol-5-yl)-2-(6-fluoro-2-methyl-1H-benzimidazol-1-yl)pyrimidine-4,6-diamine |
| 270 | 2-(2-ethyl-1H-benzimidazol-1-yl)-5-fluoro-N-(4-methylphenyl)pyrimidine-4,6-diamine |
| 271 | 2-(2-ethyl-1H-benzimidazol-1-yl)-5-fluoro-N-(4-methoxyphenyl)pyrimidine-4,6-diamine |
| 272 | 2-(2-ethyl-1H-benzimidazol-1-yl)-5-fluoro-N-[4-(trifluoromethoxy)phenyl]pyrimidine-4,6-diamine |
| 273 | N-(1,3-benzodioxol-5-yl)-2-(2-ethyl-1H-benzimidazol-1-yl)-5-fluoropyrimidine-4,6-diamine |
| 274 | N-(4-chlorophenyl)-2-(2-ethyl-1H-benzimidazol-1-yl)-5-fluoropyrimidine-4,6-diamine |
| 275 | N-(4-chloro-3-fluorophenyl)-2-(2-ethyl-1H-benzimidazol-1-yl)-5-fluoropyrimidine-4,6-diamine |
| 276 | 2-(2-cyclopropyl-1H-benzimidazol-1-yl)-5-fluoro-N-(4-methylphenyl)pyrimidine-4,6-diamine |
| 277 | 2-(2-cyclopropyl-1H-benzimidazol-1-yl)-5-fluoro-N-(4-methoxyphenyl)pyrimidine-4,6-diamine |
| 278 | 2-(2-cyclopropyl-1H-benzimidazol-1-yl)-5-fluoro-N-[4-(trifluoromethoxy)phenyl]pyrimidine-4,6-diamine |
| 279 | N-(4-chlorophenyl)-2-(2-cyclopropyl-1H-benzimidazol-1-yl)-5-fluoropyrimidine-4,6-diamine |
| 280 | N-(4-chloro-3-fluorophenyl)-2-(2-cyclopropyl-1H-benzimidazol-1-yl)-5-fluoropyrimidine-4,6-diamine |
| 281 | 5-fluoro-2-(5-fluoro-2-methyl-1H-benzimidazol-1-yl)-N-(4-methylphenyl)pyrimidine-4,6-diamine |
| 282 | 5-fluoro-2-(5-fluoro-2-methyl-1H-benzimidazol-1-yl)-N-(4-methoxyphenyl)pyrimidine-4,6-diamine |
| 283 | 5-fluoro-2-(5-fluoro-2-methyl-1H-benzimidazol-1-yl)-N-[4-(trifluoromethoxy)phenyl]pyrimidine-4,6-diamine, and |
| 284 | 2-(6-amino-2-methyl-1H-benzimidazol-1-yl)-5-fluoro-N-[4-(trifluoromethyl)phenyl]pyrimidine-4,6-diamine; | wherein the form of the compound of Formula (I) is selected from a salt, ester, hydrate, solvate, chelate, clathrate, polymorph, isotopologue, stereoisomer, racemate, enantiomer, diastereomer or tautomer thereof.

Terminology

The chemical terms used above and throughout the description herein, unless specifically defined otherwise, shall be understood by one of ordinary skill in the art to have the following indicated meanings.

As used herein, the term "$C_{1-8}$alkyl" refers to saturated hydrocarbon radicals having from one to eight carbon atoms in a straight or branched chain configuration, including, without limitation, methyl, ethyl, n-propyl, isopropyl, n-butyl, isobutyl, sec-butyl, tert-butyl, n-pentyl, n-hexyl, n-heptyl, n-octyl and the like. In some embodiments, $C_{1-8}$alkyl includes $C_{1-6}$alkyl, $C_{1-4}$alkyl and the like. A $C_{1-8}$alkyl radical may be optionally substituted where allowed by available valences.

As used herein, the term "$C_{2-8}$alkenyl" refers to partially unsaturated hydrocarbon radicals having from two to eight carbon atoms in a straight or branched chain configuration and one or more carbon-carbon double bonds therein, including, without limitation, ethenyl, allyl, propenyl and the like. In some embodiments, $C_{2-8}$alkenyl includes $C_{2-6}$alkenyl, $C_{2-4}$alkenyl and the like. A $C_{2-8}$alkenyl radical may be optionally substituted where allowed by available valences.

As used herein, the term "$C_{2-8}$alkynyl" refers to partially unsaturated hydrocarbon radicals having from two to eight carbon atoms in a straight or branched chain configuration and one or more carbon-carbon triple bonds therein, including, without limitation, ethynyl, propynyl and the like. In some embodiments, $C_{2-8}$alkynyl includes $C_{2-6}$alkynyl, $C_{2-4}$alkynyl and the like. A $C_{2-8}$alkynyl radical may be optionally substituted where allowed by available valences.

As used herein, the term "$C_{1-8}$alkoxy" refers to saturated hydrocarbon radicals of from one to eight carbon atoms having a straight or branched chain configuration of the formula: —O—$C_{1-8}$alkyl, including, without limitation, methoxy, ethoxy, n-propoxy, isopropoxy, n-butoxy, isobutoxy, sec-butoxy, tert-butoxy, n-pentoxy, n-hexoxy and the like. In some embodiments, $C_{1-8}$alkoxy includes $C_{1-6}$alkoxy, $C_{1-4}$alkoxy and the like. A $C_{1-8}$alkoxy radical may be optionally substituted where allowed by available valences.

As used herein, the term "$C_{3-14}$cycloalkyl" refers to a saturated monocyclic, bicyclic or polycyclic hydrocarbon radical, including, without limitation, cyclopropyl, cyclobutyl, cyclopentyl, cyclohexyl, cycloheptyl, cyclooctyl, 1H-indanyl, indenyl, 2,3-dihydro-1H-indenyl, tetrahydro-naphthalenyl and the like. In some embodiments, $C_{3-14}$cycloalkyl includes $C_{3-8}$cycloalkyl, $C_{5-8}$cycloalkyl, $C_{3-10}$cycloalkyl and the like. A $C_{3-14}$cycloalkyl radical may be optionally substituted where allowed by available valences.

As used herein, the term "aryl" refers to a monocyclic, bicyclic or polycyclic aromatic carbon atom ring structure radical, including, without limitation, phenyl, naphthyl (also referred to as naphthalenyl), anthracenyl, fluorenyl, azulenyl, phenanthrenyl and the like. An aryl radical may be optionally substituted where allowed by available valences.

As used herein, the term "heteroaryl" refers to a monocyclic, bicyclic or polycyclic aromatic carbon atom ring structure radical in which one or more carbon atom ring members have been replaced, where allowed by structural stability, with one or more heteroatoms, such as an O, S or N atom, including, without limitation, furanyl, thienyl (also referred to as thiophenyl), pyrrolyl, pyrazolyl (also referred to as 1H-pyrazolyl), imidazolyl (also referred to as 1H-imidazolyl), isoxazolyl (also referred to as 1,2-oxazolyl), isothiazolyl, oxazolyl, thiazolyl, triazolyl, oxadiazolyl, thiadiazolyl, tetrazolyl, pyranyl, thiopyranyl, pyridinyl (also referred to as pyridyl), pyrimidinyl, pyrazinyl, pyridazinyl, triazinyl, indolyl (also referred to as 1H-indolyl), azaindolyl, indazolyl (also referred to as 2H-indazolyl), azaindazolyl, isoindolyl, indolizinyl, benzofuranyl, benzothienyl, benzimidazolyl (also referred to as 1H-benzimidazolyl), benzothiazolyl, benzoxazolyl, imidazo[2,1-b][1,3]thiazolyl, pyrazolo[1,5-a]pyridinyl, pyrazolo[1,5-c]pyrimidinyl, imidazo[1,2-a]pyridinyl, 1H-imidazo[4,5-b]pyridinyl, 1H-imidazo[4,5-c]pyridinyl, imidazo[1,2-a]pyrazinyl, imidazo[1,2-a]pyrimidinyl, 7H-purinyl, 9H-purinyl, quinolinyl, isoquinolinyl, quinazolinyl, quinoxalinyl, acridinyl and the like and associated homologs and regioisomers thereof. A heteroaryl radical may be optionally substituted on a carbon or nitrogen atom ring member where allowed by available valences.

As used herein, the term "heterocyclyl" refers to a saturated or partially unsaturated monocyclic, bicyclic or polycyclic carbon atom ring structure radical in which one or more carbon atom ring members have been replaced, where allowed by structural stability, with a heteroatom, such as an O, S or N atom, including, without limitation, oxiranyl, oxetanyl, azetidinyl, dihydrofuranyl, tetrahydrofuranyl, dihydrothienyl, tetrahydrothienyl, pyrrolinyl, pyrrolidinyl, dihydropyrazolyl, pyrazolinyl, pyrazolidinyl, dihydroimidazolyl, imidazolinyl, imidazolidinyl, isoxazolinyl, isoxazolidinyl, isothiazolinyl, isothiazolidinyl, oxazolinyl, oxazolidinyl, thiazolinyl, thiazolidinyl, triazolinyl, triazolidinyl, oxadiazolinyl, oxadiazolidinyl, thiadiazolinyl, thiadiazolidinyl, tetrazolinyl, tetrazolidinyl, 1,3-dioxolanyl, dihydro-2H-pyranyl, tetrahydro-2H-pyranyl, dihydro-pyridinyl, tetrahydro-pyridinyl, dihydro-pyrimidinyl, tetrahydro-pyrimidinyl, dihydro-pyrazinyl, tetrahydro-pyrazinyl, dihydro-pyridazinyl, tetrahydro-pyridazinyl, piperazinyl, piperidinyl, morpholinyl, thiomorpholinyl, dihydro-triazinyl, tetrahydro-triazinyl, hexahydro-triazinyl, 1,4-diazepanyl, dihydro-indolyl, indolinyl, tetrahydro-indolyl, dihydro-indazolyl, tetrahydro-indazolyl, dihydro-isoindolyl, dihydro-benzofuranyl, tetrahydro-benzofuranyl, dihydro-benzothienyl, tetrahydro-benzothienyl, dihydro-benzoimidazolyl, tetrahydro-benzoimidazolyl, dihydro-benzooxazolyl, tetrahydro-benzooxazolyl, dihydro-benzooxazinyl, tetrahydro-benzooxazinyl, benzo[1,3]dioxolyl (also referred to as 1,3-benzodioxolyl), benzo[1,4]dioxanyl (also referred to as 1,4-benzodioxanyl or 2,3-dihydro-1,4-benzodioxinyl), benzo[1,4]dioxinyl (also referred to as 1,4-benzodioxinyl), 4,5,6,7-tetrahydro-2H-indazolyl, 5,6,7,8-tetrahydroimidazo[1,2-a]pyridinyl, 4,5,6,7-tetrahydro-3H-imidazo[4,5-c]pyridinyl, dihydro-purinyl, tetrahydro-purinyl, dihydro-quinolinyl, tetrahydro-quinolinyl, dihydro-isoquinolinyl, tetrahydro-isoquinolinyl, dihydro-quinazolinyl, tetrahydro-quinazolinyl, dihydro-quinoxalinyl, tetrahydro-quinoxalinyl and the like and associated homologs thereof. A heterocyclyl radical may be optionally substituted on a carbon or nitrogen atom ring member where allowed by available valences.

As used herein, the term "$B(OR_8)_2$" refers to a radical of the formula: —B[(—OH)(—OH)] when $R_8$ is hydrogen; or, —B[(—OH)(—O—$C_{1-8}$alkyl)] when $R_8$ is independently hydrogen or $C_{1-8}$alkyl; or, —B[(—O—$C_{1-8}$alkyl)(—O—$C_{1-8}$alkyl)] when $R_8$ is $C_{1-8}$alkyl.

As used herein, the term "$C_{1-8}$alkoxy-$C_{1-8}$alkyl" refers to a radical of the formula: —$C_{1-8}$alkyl-O—$C_{1-8}$alkyl.

As used herein, the term "$C_{1-8}$alkoxy-$C_{1-8}$alkyl-amino" refers to a radical of the formula: —NH—$C_{1-8}$alkyl-O—$C_{1-8}$alkyl.

As used herein, the term "$C_{1-8}$alkoxy-$C_{2-8}$alkenyl" refers to a radical of the formula: —$C_{2-8}$alkenyl-O—$C_{1-8}$alkyl.

As used herein, the term "$C_{1-8}$alkoxy-$C_{2-8}$alkynyl" refers to a radical of the formula: —$C_{2-8}$alkynyl-O—$C_{1-8}$alkyl.

As used herein, the term "$C_{1-8}$alkoxy-carbonyl" refers to a radical of the formula: —C(O)—O—$C_{1-8}$alkyl.

As used herein, the term "$C_{1-8}$alkoxy-carbonyl-$C_{1-8}$alkyl" refers to a radical of the formula: —$C_{1-8}$alkyl-C(O)—O—$C_{1-8}$alkyl.

As used herein, the term "$C_{1-8}$alkoxy-carbonyl-amino" refers to a radical of the formula: —NH—C(O)—O—$C_{1-8}$alkyl.

As used herein, the term "$C_{1-8}$alkoxy-carbonyl-amino-$C_{1-8}$alkyl" refers to a radical of the formula: —$C_{1-8}$alkyl-NH—C(O)—O—$C_{1-8}$alkyl.

As used herein, the term "$C_{1-8}$alkoxy-imino-$C_{1-8}$alkyl" refers to a radical of the formula: —$C_{1-8}$alkyl(=N—O—$C_{1-8}$alkyl).

As used herein, the term "$C_{1-8}$alkyl-amino" refers to a radical of the formula: —NH—$C_{1-8}$alkyl.

As used herein, the term "($C_{1-8}$alkyl)$_2$-amino" refers to a radical of the formula: —N($C_{1-8}$alkyl)$_2$.

As used herein, the term "$C_{1-8}$alkyl-amino-$C_{1-8}$alkyl" refers to a radical of the formula: —$C_{1-8}$alkyl-NH—$C_{1-8}$alkyl.

As used herein, the term "($C_{1-8}$alkyl)$_2$-amino-$C_{1-8}$alkyl" refers to a radical of the formula: —$C_{1-8}$alkyl-N($C_{1-8}$alkyl)$_2$.

As used herein, the term "$C_{1-8}$alkyl-amino-$C_{1-8}$alkyl-amino" refers to a radical of the formula: —NH—$C_{1-8}$alkyl-NH—$C_{1-8}$alkyl.

As used herein, the term "($C_{1-8}$alkyl)$_2$-amino-$C_{1-8}$alkyl-amino" refers to a radical of the formula: —NH—$C_{1-8}$alkyl-N($C_{1-8}$alkyl)$_2$.

As used herein, the term "$C_{1-8}$alkyl-amino-carbonyl" refers to a radical of the formula: —C(O)—NH—$C_{1-8}$alkyl.

As used herein, the term "($C_{1-8}$alkyl)$_2$-amino-carbonyl" refers to a radical of the formula: —C(O)—N($C_{1-8}$alkyl)$_2$.

As used herein, the term "$C_{1-8}$alkyl-amino-carbonyl-amino" refers to a radical of the formula: —NH—C(O)—NH—$C_{1-8}$alkyl.

As used herein, the term "($C_{1-8}$alkyl)$_2$-amino-carbonyl-amino" refers to a radical of the formula: —NH—C(O)—N($C_{1-8}$ alkyl)$_2$.

As used herein, the term "$C_{1-8}$alkyl-amino-sulfonyl" refers to a radical of the formula: —SO$_2$—NH—$C_{1-8}$ alkyl.

As used herein, the term "($C_{1-8}$alkyl)$_2$-amino-sulfonyl" refers to a radical of the formula: —SO$_2$—N($C_{1-8}$ alkyl)$_2$.

As used herein, the term "$C_{1-8}$alkyl-amino-sulfonyl-amino" refers to a radical of the formula: —NH—SO$_2$—NH—$C_{1-8}$ alkyl.

As used herein, the term "($C_{1-8}$alkyl)$_2$-amino-sulfonyl-amino" refers to a radical of the formula: —NH—SO$_2$—N($C_{1-8}$ alkyl)$_2$.

As used herein, the term "$C_{1-8}$alkyl-carbonyl" refers to a radical of the formula: —C(O)—$C_{1-8}$ alkyl.

As used herein, the term "$C_{1-8}$alkyl-carbonyl-amino" refers to a radical of the formula: —NH—C(O)—$C_{1-8}$ alkyl.

As used herein, the term "$C_{1-8}$alkyl-carbonyl-amino-$C_{1-8}$alkyl" refers to a radical of the formula: —$C_{1-8}$ alkyl-NH—C(O)—$C_{1-8}$ alkyl.

As used herein, the term "$C_{1-8}$alkyl-carbonyl-oxy" refers to a radical of the formula: —O—C(O)—$C_{1-8}$ alkyl.

As used herein, the term "$C_{1-8}$alkyl-carbonyl-oxy-$C_{1-8}$alkyl" refers to a radical of the formula: —$C_{1-8}$ alkyl-O—C(O)—$C_{1-8}$ alkyl.

As used herein, the term "$C_{1-8}$alkyl-sulfonyl" refers to a radical of the formula: —SO$_2$—$C_{1-8}$ alkyl.

As used herein, the term "$C_{1-8}$alkyl-thio" refers to a radical of the formula: —S—$C_{1-8}$ alkyl.

As used herein, the term "amino" refers to a radical of the formula: —NH$_2$.

As used herein, the term "amino-$C_{1-8}$alkyl" refers to a radical of the formula: —$C_{1-8}$ alkyl-NH$_2$.

As used herein, the term "amino-$C_{1-8}$alkyl-amino" refers to a radical of the formula: —NH—$C_{1-8}$alkyl-NH$_2$.

As used herein, the term "amino-carbonyl" refers to a radical of the formula: —C(O)—NH$_2$.

As used herein, the term "amino-carbonyl-amino" refers to a radical of the formula: —NH—C(O)—NH$_2$.

As used herein, the term "amino-sulfonyl" refers to a radical of the formula: —SO$_2$—NH$_2$.

As used herein, the term "amino-sulfonyl-amino" refers to a radical of the formula: —NH—SO$_2$—NH$_2$.

As used herein, the term "aryl-$C_{1-8}$alkyl" refers to a radical of the formula: —$C_{1-8}$alkyl-aryl.

As used herein, the term "aryl-$C_{1-8}$alkyl-amino" refers to a radical of the formula: —NH—$C_{1-8}$alkyl-aryl.

As used herein, the term "aryl-amino" refers to a radical of the formula: —NH-aryl.

As used herein, the term "carboxyl" refers to a radical of the formula: —COOH, —C(O)OH or —CO$_2$H.

As used herein, the term "formyl" refers to a radical of the formula: —C(O)—H. As used herein, the term "formyl-oxyl" refers to a radical of the formula: —O—C(O)—H. As used herein, the terms "halo" or "halogen" refer to a halogen atom radical, including fluoro, chloro, bromo and iodo.

As used herein, the term "halo-$C_{1-8}$alkoxy" refers to a radical of the formula: —O—$C_{1-8}$alkyl-halo, wherein $C_{1-8}$alkyl may be partially or completely substituted where allowed by available valences with one or more halogen atoms. In some embodiments, halo-$C_{1-8}$alkoxy includes halo-$C_{1-6}$alkoxy, halo-$C_{1-4}$alkoxy and the like.

As used herein, the term "halo-$C_{1-8}$alkoxy-carbonyl" refers to a radical of the formula: —C(O)—O—$C_{1-8}$alkyl-halo.

As used herein, the term "halo-$C_{1-8}$alkyl" refers to a radical of the formula: —$C_{1-8}$alkyl-halo, wherein $C_{1-8}$alkyl may be partially or completely substituted where allowed by available valences with one or more halogen atoms. In some embodiments, halo-$C_{1-8}$alkyl includes halo-$C_{1-6}$alkyl, halo-$C_{1-4}$alkyl and the like.

As used herein, the term "halo-$C_{1-8}$alkyl-carbonyl" refers to a radical of the formula: —C(O)—$C_{1-8}$alkyl-halo.

As used herein, the term "halo-$C_{1-8}$alkyl-sulfonyl" refers to a radical of the formula: —SO$_2$—$C_{1-8}$alkyl-halo.

As used herein, the term "halo-$C_{1-8}$alkyl-thio" refers to a radical of the formula: —S—$C_{1-8}$alkyl-halo.

As used herein, the term "heteroaryl-$C_{1-8}$alkyl" refers to a radical of the formula: —$C_{1-8}$alkyl-heteroaryl.

As used herein, the term "hydroxyl-$C_{1-8}$alkoxy" refers to a radical of the formula: —O—$C_{1-8}$alkyl-OH, wherein $C_{1-8}$alkyl may be partially or completely substituted where allowed by available valences with one or more hydroxyl radicals.

As used herein, the term "hydroxyl-$C_{1-8}$alkyl" refers to a radical of the formula: —$C_{1-8}$alkyl-OH, wherein $C_{1-8}$alkyl may be partially or completely substituted where allowed by available valences with one or more hydroxyl radicals.

As used herein, the term "hydroxyl-amino" refers to a radical of the formula: —NH—OH.

As used herein, the term "hydroxyl-$C_{1-8}$alkyl-amino" refers to a radical of the formula: —NH—$C_{1-8}$alkyl-OH.

As used herein, the term "hydroxyl-$C_{1-8}$alkyl-amino-$C_{1-8}$alkyl" refers to a radical of the formula: —$C_{1-8}$alkyl-NH—$C_{1-8}$alkyl-OH.

As used herein, the term "hydroxyl-$C_{1-8}$alkyl-amino-$C_{1-8}$alkyl-amino" refers to a radical of the formula: —NH—$C_{1-8}$alkyl-NH—$C_{1-8}$alkyl-OH.

As used herein, the term "hydroxyl-imino-$C_{1-8}$alkyl" refers to a radical of the formula: —$C_{1-8}$alkyl(=N—OH).

As used herein, the term "imino" refers to a radical of the formula: =NH.

As used herein, the term "imino-$C_{1-8}$alkyl" refers to a radical of the formula: —$C_{1-8}$alkyl(=NH).

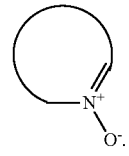

As used herein, the term "N-oxide" refers to a moiety of the formula:

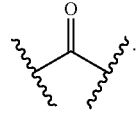

As used herein, the term "oxo" refers to a moiety of the formula:

As used herein, the term "P(O)(R$_7$)$_2$-amino" refers to a radical of the formulae: —NH—P(O)(—O—$C_{1-8}$alkyl)(OH) when R$_7$ is independently hydroxyl and ($C_{1-8}$alkoxy)$_n$, where n is 1; or, —NH—P(O)(OH)$_2$ when R$_7$ is hydroxyl; or, —NH—P(O)(—O—$C_{1-8}$alkyl)$_2$ when R$_7$ is ($C_{1-8}$alkoxy)$_n$, where n is 1.

As used herein, the term "substituent" means positional variables on the atoms of a core molecule that are attached at a designated atom position, replacing one or more hydrogen atoms on the designated atom, provided that the atom of attachment does not exceed the available valence or shared valence, such that the substitution results in a stable compound. Accordingly, combinations of substituents and/or variables are permissible only if such combinations result in stable compounds. Any carbon atom as well as heteroatom with a valence level that appears to be unsatisfied as described or shown herein is assumed to have a sufficient number of hydrogen atom(s) to satisfy the valences described or shown.

As used herein, the term "and the like," with reference to the definitions of chemical terms provided herein, means that variations in chemical structures that could be expected by one skilled in the art include, without limitation, isomers (including chain, branching or positional structural isomers), hydration of ring systems (including saturation or partial unsaturation of monocyclic, bicyclic or polycyclic ring structures) and all other variations where allowed by available valences which result in a stable compound.

For the purposes of this description, where one or more substituent variables for a compound of Formula (I) encompass functionalities incorporated into a compound of Formula (I), each functionality appearing at any location within the disclosed compound may be independently selected, and as appropriate, independently and/or optionally substituted.

As used herein, the terms "independently selected," or "each selected" refer to functional variables in a substituent list that may be attached more than once on the structure of a core molecule, where the pattern of substitution at each occurrence is independent of the pattern at any other occurrence. Further, the use of a generic substituent variable on a core structure for a compound described herein is understood to include the replacement of the generic substituent with specie substituents that are included within the particular genus, e.g., aryl may be replaced with phenyl or naphthalenyl and the like, such that the resulting compound is to be included within the scope of the compounds described herein.

As used herein, the term "optionally substituted" means that the specified substituent variables, groups, radicals or moieties represent the scope of the genus and may be independently chosen as needed to replace one or more hydrogen atoms on the designated atom of attachment of a core molecule.

As used herein, the terms "stable compound" or "stable structure" mean a compound that is sufficiently robust to be isolated to a useful degree of purity from a reaction mixture and formulations thereof into an efficacious therapeutic agent.

Compound names used herein were obtained using the ACD Labs Index Name software provided by ACD Labs and/or ChemDraw Ultra software provided by CambridgeSoft. When the compound name disclosed herein conflicts with the structure depicted, the structure shown will supercede the use of the name to define the compound intended.

Compound Forms

As used herein, the terms a "compound of Formula (Ia)," "a compound of Formula (II)," "compound of Formula (IIa)," "compound of Formula (III)," "compound of Formula (IIIa)," "compound of Formula (IV)" or "compound of Formula (IVa)" refer to subgenera of the compound of Formula (I) or a form thereof, as defined herein. Rather than repeat the various subgenera of the compound of Formula (I), in certain embodiments, the term "compound(s) of Formula (I) or a form thereof" is used inclusively to refer to compound(s) of Formula (Ia) or a form thereof, compound(s) of Formula (II) or a form thereof, compound(s) of Formula (IIa) or a form thereof, compound(s) of Formula (III) or a form thereof, compound(s) of Formula (IIIa) or a form thereof, compound(s) of Formula (IV) or a form thereof or compound(s) of Formula (IVa) or a form thereof, either separately or together. Thus, embodiments and references to "a compound of Formula (I)" are intended to be inclusive of compounds of Formula (Ia), compounds of Formula (II), compounds of Formula (IIa), compounds of Formula (III), compounds of Formula (IIIa), compounds of Formula (IV) and compounds of Formula (IVa).

As used herein, the term "form" means a compound of Formula (I) selected from a free acid, free base, salt, ester, hydrate, solvate, chelate, clathrate, polymorph, isotopologue, stereoisomer, racemate, enantiomer, diastereomer, or tautomer thereof.

In certain embodiments described herein, the form of the compound of Formula (I) is selected from a salt, isotopologue, stereoisomer, racemate, enantiomer, diastereomer or tautomer thereof.

In certain embodiments described herein, the form of the compound of Formula (I) is selected from a free acid, isotopologue, stereoisomer, racemate, enantiomer, diastereomer or tautomer thereof.

In certain embodiments described herein, the form of the compound of Formula (I) is selected from a free base, isotopologue, stereoisomer, racemate, enantiomer, diastereomer or tautomer thereof.

In certain embodiments described herein, the form of the compound of Formula (I) is a free acid, free base or salt thereof.

In certain embodiments described herein, the form of the compound of Formula (I) is an isotopologue thereof.

In certain embodiments described herein, the form of the compound of Formula (I) is a stereoisomer, racemate, enantiomer or diastereomer thereof.

In certain embodiments described herein, the form of the compound of Formula (I) is a tautomer thereof.

In certain embodiments described herein, the form of the compound of Formula (I) is a pharmaceutically acceptable form.

In certain embodiments described herein, the compound of Formula (I) or a form thereof is isolated for use.

As used herein, the term "isolated" means the physical state of a compound of Formula (I) or a form thereof after being isolated and/or separated and/or purified from a synthetic process (e.g., from a reaction mixture) or natural source or combination thereof according to an isolation, separation or purification process or processes described herein or which are well known to the skilled artisan (e.g., chromatography, recrystallization and the like) in sufficient purity to be characterizable by standard analytical techniques described herein or well known to the skilled artisan.

As used herein, the term "protected" means that a functional group on a compound of Formula (I) or a form thereof is in a form modified to preclude undesired side reactions of the functional group when the compound is subjected to a reaction. Suitable protecting groups will be recognized by those with ordinary skill in the art as well as by reference to standard textbooks such as, for example, T. W. Greene et al, *Protective Groups in Organic Synthesis* (2007), Wiley, New York.

Prodrugs and solvates of the compounds of Formula (I) or a form thereof described herein are also contemplated.

As used herein, the term "prodrug" means that a functional group on a compound of Formula (I) is in a form (e.g., acting as an active or inactive drug precursor) that is transformed in vivo to yield an active or more active compound of Formula (I) or a form thereof. The transformation may occur by various mechanisms (e.g., by metabolic and/or non-metabolic chemical processes), such as, for example, by hydrolysis and/or metabolism in blood, liver and/or other organs and tissues. A discussion of the use of prodrugs is provided by V. J. Stella, et. al., "Biotechnology: Pharmaceutical Aspects, Prodrugs: Challenges and Rewards," American Association of Pharmaceutical Scientists and Springer Press, 2007.

In one example, when a compound of Formula (I) or a form thereof contains a carboxylic acid functional group, a prodrug can comprise an ester formed by the replacement of the hydrogen atom of the acid group with a functional group such as alkyl and the like. In another example, when a compound of Formula (I) or a form thereof contains an alcohol functional group, a prodrug can be formed by the replacement of the hydrogen atom of the alcohol group with a functional group such as alkyl or carbonyloxy and the like. In another example, when a compound of Formula (I) or a form thereof contains an amine functional group, a prodrug can be formed by the replacement of one or more amine hydrogen atoms with a functional group such as alkyl or substituted carbonyl.

Pharmaceutically acceptable prodrugs of compounds of Formula (I) or a form thereof include those compounds substituted with one or more of the following groups: carboxylic acid esters, sulfonate esters, amino acid esters, phosphonate esters (e.g., a phosphoramidic acid used to derive a phosphoramidic acid) and mono-, di- or triphosphate esters further substituted with alkyl, where appropriate. As described herein, it is understood by a person of ordinary skill in the art that one or more of such substituents may be used to provide a compound of Formula (I) or a form thereof as a prodrug.

The compounds of Formula (I) or a form thereof can form salts, which are intended to be included within the scope of this description. Reference to a compound of Formula (I) or a form thereof herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula (I) or a form thereof contains both a basic moiety, such as, but not limited to a pyridine or imidazole, and an acidic moiety, such as, but not limited to a carboxylic acid, zwitterions ("inner salts") may be formed and are included within the term "salt(s)" as used herein.

The term "pharmaceutically acceptable salt(s)", as used herein, means those salts of compounds of Formula (I) or a form thereof described herein that are safe and effective (i.e., non-toxic, physiologically acceptable) for use in mammals and that possess biological activity, although other salts are also useful. Salts of the compounds of the Formula (I) may be formed, for example, by reacting a compound of Formula (I) with an amount of acid or base, such as an equivalent amount, in a medium such as one in which the salt precipitates or in an aqueous medium followed by lyophilization.

Pharmaceutically acceptable salts include one or more salts of acidic or basic groups present in compounds of Formula (I) or a form thereof described herein. Embodiments of acid addition salts include, and are not limited to, acetate, acid phosphate, ascorbate, benzoate, benzenesulfonate, bisulfate, bitartrate, borate, butyrate, chloride, citrate, camphorate, camphorsulfonate, ethanesulfonate, formate, fumarate, gentisinate, gluconate, glucaronate, glutamate, hydrobromide, hydrochloride, dihydrochloride, hydroiodide, isonicotinate, lactate, maleate, methanesulfonate, naphthalenesulfonate, nitrate, oxalate, pamoate, pantothenate, phosphate, propionate, saccharate, salicylate, succinate, sulfate, tartrate, thiocyanate, toluenesulfonate (also known as tosylate), trifluoroacetate, trifluoroacetic acid salt and the like. One or more embodiments of acid addition salts include chloride, hydrochloride, dihydrochloride, trihydrochloride, hydrobromide, acetate, diacetate, methanesulfonate, sulfate, trifluoroacetate, trifluoroacetic acid salt and the like. More particular embodiments include a chloride, hydrochloride, dihydrochloride, hydrobromide, methanesulfonate, sulfate, trifluoroacetate, trifluoroacetic acid salt and the like.

In certain embodiments of the compounds of Formula (I) or a form thereof described herein, the compound is isolated as a salt form, wherein the compound is conjugated with the salt in a ratio represented as, in a non-limiting example, "compound:salt (A:B)," wherein "A" and "B" represent the equivalents of compound to salt in the isolated form.

Additionally, acids which are considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33, 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Suitable basic salts include, but are not limited to, aluminum, ammonium, calcium, lithium, magnesium, potassium, sodium, zinc, and diethanolamine salts. Certain compounds of Formula (I) or a form thereof described herein can also form pharmaceutically acceptable salts with organic bases (for example, organic amines) such as, but not limited to, dicyclohexylamines, tert-butyl amines and the like, and with various amino acids such as, but not limited to, arginine, lysine and the like. Basic nitrogen-containing groups may be quarternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others.

All such acid salts and base salts are intended to be included within the scope of pharmaceutically acceptable salts as described herein. In addition, all such acid and base salts are considered equivalent to the free forms of the corresponding compounds for purposes of this description.

Compounds of Formula (I), and forms thereof, may further exist in a tautomeric form. All such tautomeric forms are contemplated and intended to be included within the scope of the compounds of Formula (I) or a form thereof as described herein.

The compounds of Formula (I) or a form thereof may contain asymmetric or chiral centers, and, therefore, may exist in different stereoisomeric forms. The present description is intended to include all stereoisomeric forms of the compounds of Formula (I) as well as mixtures thereof, including racemic mixtures.

The compounds of Formula (I) or a form thereof described herein may include one or more chiral centers, and as such may exist as racemic mixtures (R/S) or as substantially pure enantiomers and diastereomers. The compounds may also exist as substantially pure (R) or (S) enantiomers (when one chiral center is present). In one embodiment, the compounds of Formula (I) or a form thereof described herein are (S) isomers and may exist as enantiomerically pure compositions substantially comprising only the (S) isomer. In another embodiment, the compounds of Formula (I) or a form thereof described herein are (R) isomers and may exist as enantiomerically pure compositions substantially comprising only the (R) isomer. As one of skill in the art will recognize, when more than one chiral center is present, the compounds of Formula (I) or a form thereof described herein may also exist as a (R,R), (R,S), (S,R) or (S,S) isomer, as defined by IUPAC Nomenclature Recommendations.

As used herein, the term "substantially pure" refers to compounds of Formula (I) or a form thereof consisting substantially of a single isomer in an amount greater than or equal to 90%, in an amount greater than or equal to 92%, in an amount greater than or equal to 95%, in an amount greater than or equal to 98%, in an amount greater than or equal to 99%, or in an amount equal to 100% of the single isomer.

In one aspect of the description, a compound of Formula (I) or a form thereof is a substantially pure (S) enantiomer present in an amount greater than or equal to 90%, in an amount greater than or equal to 92%, in an amount greater than or equal to 95%, in an amount greater than or equal to 98%, in an amount greater than or equal to 99%, or in an amount equal to 100%.

In one aspect of the description, a compound of Formula (I) or a form thereof is a substantially pure (R) enantiomer present in an amount greater than or equal to 90%, in an amount greater than or equal to 92%, in an amount greater than or equal to 95%, in an amount greater than or equal to 98%, in an amount greater than or equal to 99%, or in an amount equal to 100%.

As used herein, the term "racemate" refers to any mixture of isometric forms that are not "enantiomerically pure", including mixtures such as, without limitation, in a ratio of about 50/50, about 60/40, about 70/30, or about 80/20, about 85/15 or about 90/10.

In addition, the compounds of Formula (I) or a form thereof described herein embrace all geometric and positional isomers. For example, if a compound of Formula (I) or a form thereof incorporates a double bond or a fused ring, both the cis- and trans-forms, as well as mixtures thereof, are embraced within the scope of the compounds of Formula (I) or a form thereof described herein.

Diastereomeric mixtures can be separated into their individual diastereomers on the basis of their physical chemical differences by methods well known to those skilled in the art, such as, for example, by chromatography and/or fractional crystallization. Enantiomers can be separated by use of a chiral HPLC column or other chromatographic methods known to those skilled in the art.

Enantiomers can also be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers.

All stereoisomers (for example, geometric isomers, optical isomers and the like) of the present compounds of Formula (I) or a form thereof (including salts, solvates, esters and prodrugs and transformed prodrugs thereof), which may exist due to asymmetric carbons on various substituents, including enantiomeric forms (which may exist even in the absence of asymmetric carbons), rotameric forms, atropisomers, diastereomeric and regioisomeric forms, are contemplated within the scope of the description herein. Individual stereoisomers of the compounds of Formula (I) or a form thereof described herein may, for example, be substantially free of other isomers, or may be present in a racemic mixture, as described supra.

The use of the terms "salt," "solvate," "ester," "prodrug" and the like, is intended to apply equally to the salt, solvate, ester and prodrug of enantiomers, stereoisomers, rotamers, tautomers, positional isomers, racemates, isotopologues or prodrugs of the instant compounds.

The term "isotopologue" refers to isotopically-enriched compounds of Formula (I) or a form thereof which are identical to those recited herein, but for the fact that one or more atoms are replaced by an atom having an atomic mass or mass number different from the atomic mass or mass number usually found in nature. Examples of isotopes that can be incorporated into compounds of Formula (I) or a form thereof described herein include isotopes of hydrogen, carbon, nitrogen, oxygen, phosphorus, fluorine and chlorine, such as $H^2$, $H^3$, $C^{13}$, $C^{14}$, $N^{15}$, $O^{18}$, $O^{17}$, $P^{31}$, $P^{32}$, $S^{35}$, $F^{18}$, $Cl^{35}$ and $Cl^{36}$, respectively, each of which is also within the scope of this description.

Certain isotopically-enriched forms of compounds of Formula (I) or a form thereof described herein (e.g., those labeled with $H^3$ and $C^{14}$) are useful in compound and/or substrate tissue distribution assays. Tritiated (i.e., $H^3$) and carbon-14 (i.e., $C^{14}$) isotopes are particularly preferred for their ease of preparation and detectability. Further, substitution with isotopes such as deuterium (i.e., "deuterium enriched") may afford certain therapeutic advantages resulting from greater metabolic stability (e.g., increased in vivo half-life), increased solubility, reduced dosage requirements (e.g., increased bioavailability)) or reduced toxicity (e.g., reduced inhibition of metabolic enzymes) and hence may be preferred in some circumstances.

One or more compounds of Formula (I) or a form thereof described herein may exist in unsolvated as well as solvated forms with pharmaceutically acceptable solvents such as water, ethanol, and the like, and the description herein is intended to embrace both solvated and unsolvated forms.

As used herein, the term "solvate" means a physical association of a compound of Formula (I) or a form thereof described herein with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. As used herein, "solvate" encompasses both solution-phase and isolatable solvates. Non-limiting examples of suitable solvates include ethanolates, methanolates, and the like.

One or more compounds of Formula (I) or a form thereof described herein may optionally be converted to a solvate. Preparation of solvates is generally known. A typical, non-limiting process involves dissolving a compound of Formula (I) or a form thereof in a desired amount of the desired solvent (organic or water or mixtures thereof) at a higher than ambient temperature, and cooling the solution at a rate sufficient to form crystals which are then isolated by standard methods. Analytical techniques such as, for example infrared spectroscopy, show the presence of the solvent (or water) in the crystals as a solvate (or hydrate).

As used herein, the term "hydrate" means a solvate wherein the solvent molecule is water.

Polymorphic crystalline and amorphous forms of the compounds of Formula (I) or a form thereof, and of the salts, solvates, esters and prodrugs of the compounds of Formula (I) or a form thereof, are further intended to be included in the scope of the compounds of Formula (I) or a form thereof described herein.

Compound Uses

The Bmi-1 oncogene was first identified as part of a key insertion/activation region of the Moloney murine leukemia virus in the early 1990's (1-6). Bmi-1 is a member of the Polycomb group (PcG) of transcriptional repressors and was identified as a necessary regulator of hematopoietic stem cell (HSC) self-renewal (76, 77). Park found that Bmi-1 is highly expressed in purified mouse and human HSCs and that the absence of Bmi-1, as demonstrated by Bmi-1 knockout mice, results in the progressive loss of all hematopoietic lineages (76). Furthermore, the transplantation of Bmi-1$^{-/-}$ day 14.5 fetal liver cells into lethally irradiated normal mice, demonstrated that the cells were unable to reconstitute myeloid cells, B cells, and T cells because Bmi-1$^{-/-}$ HSCs were unable to renew (76).

In addition to the role of Bmi-1 in HSC self renewal, it was found that Bmi-1 transgene expression induced lymphoma in mice (2). Bmi-1 was also found to be overexpressed in many tumor types, including acute myeloid leukemia, medulloblastoma, neuroblastoma, colorectal cancer, lung cancer, and prostate cancer, and was found to increase with malignancy (34, 78, 61, 79, 80, 65, 43). Loss of Bmi-1 in various human cancer cell lines via Bmi-1 specific RNA interference (RNAi) was shown to lead to acute cell death and growth inhibition, whereas loss of Bmi-1 in various normal cell lines was shown to lead to only moderate growth inhibition and not significant cell death (69). Thus, Bmi-1 is necessary for the survival of cancer cells but has minimal effect on the survival of normal cells.

Bmi-1 has been subsequently shown to act as an oncogene experimentally and has proven particularly potent in conjunction with c-myc to initiate lymphoma in mice (7, 8). The role of Bmi-1 in lymphomagenesis has been attributed partially to transcriptional repression of the INK4a locus (containing both the p16$^{INK4A}$ and p14$^{ARF}$ genes) leading to maintenance of cancer and tumor cell proliferation and prevention of differentiation (7, 9). Loss of expression of the INK4a locus due to promoter silencing has been extensively studied and is both important for the progression and prognosis of many types of hematologic cancers (10, 11). The INK4a locus is occasionally lost by deletion in leukemia and lymphoma (12, 13).

However, Bmi-1 has been shown to play a role in tumorigenesis in models lacking the INK4a locus, indicating that other loci important in cancer are regulated by this protein (14). Experimental results have demonstrated further that loss of Bmi-1 induces growth arrest and senescence in fibrosarcoma cells known to lack INK4a (15). There is also evidence that Bmi-1 is important for the hedgehog (Hh) pathway in breast cancer. Activation of Hh signaling increases Bmi-1 expression, while down-regulation of Bmi-1 (via siRNA) abrogates the effects of Hh signaling on mammosphere formation in vitro and inhibits ductal/alveolar development in mice (16). Recent work has demonstrated the role of Bmi-1 in the regulation of Hox gene expression. Knockdown of Bmi-1 caused a global and loci-specific loss of H2A ubiquitination, upregulation of the HoxC5 gene, and inhibition of the growth of HeLa cells (17). Another study demonstrated that E2F6 and Bmi-1 cooperate in the regulation of Hox gene expression (particularly Hox C10 and B9), and consequently affect axial skeleton development, but not in the repression of the Ink4a-Arf locus. These findings underscore the significance of the E2F6-Bmi-1 interaction and suggest that the Hox and Ink4a-Arf loci are regulated by somewhat different Bmi-1-dependent mechanisms (18). Current research suggests that Bmi-1 has different roles dependent upon cell types and/or developmental stages. Other genes regulated by Bmi-1 remain to be identified.

Bmi-1 is found to be highly expressed in malignancies, such as diffuse large B cell lymphomas (DLBCL), B cell non-Hodgkin's lymphoma, Hodgkin's lymphoma, acute myeloid leukemia, colorectal carcinoma, liver carcinoma, non-small cell lung cancer, breast carcinoma and medulloblastoma. The study of Bmi-1 knockout mice has revealed that Bmi-1 is required for the self-renewal of both leukemic and normal hematopoietic stem cells.

Additionally, evidence exists linking Bmi-1 levels to blood tumor types, particularly Burkitt's lymphoma, mantle cell lymphoma, Hodgkin's lymphoma (21-23), non-Hodgkin's lymphoma, some T cell lymphomas (2, 24-31), acute myeloid leukemia and T-ALL (32-35). Raaphorst et al observed that, in Hodgkin's lymphoma, Reed-Sternberg cells (HRS) co-express Bmi-1, EZH2, and Mib-1/Ki-67. Because HRS cells are thought to originate from germinal center lymphocytes that express Bmi-1, such lymphocytes should lose the ability to express Bmi-1 (and gain the ability to express EZH2) as they differentiate. These observations suggest that Hodgkin's lymphoma is associated with aberrant co-expression of Bmi-1 and EZH2 in these cells (22). An assessment of acute myeloid leukemia stem cell populations by van Gosliga et al (36) showed that CD34$^+$/CD38$^-$ cells capable of forming leukemic-cobblestone colonies on a bone marrow substrate through at least two rounds of expansion represented an extreme minority of the cell population. Further analysis showed that this cell population expresses high levels of Bmi-1 mRNA and can establish an aggressive leukemia in mice, while those cells that have lower levels of Bmi-1 mRNA cannot (36). Such studies implicate Bmi-1 in tumor growth and cell survival and suggest a central function in tumor initiation and maintenance of cancer and tumor stem cells.

The levels of Bmi-1 have been shown to have prognostic relevance in a number of tumor types. An example of this is found in acute myeloid leukemia based on results from a study assessing the prognostic value of high Bmi-1 levels in 64 patients (32). On the basis of the median value of Bmi-1 (54.58%), patients were divided into two groups and monitored for survival. Patients with lower Bmi-1 positivity (<55%, n=33) had significantly longer overall survival (P=0.0001), relapse-free survival (P=0.0072) and remission duration (P=0.0065) when compared to the patients with higher levels of Bmi-1 (>55%, n=31, respectively), regardless of age group (32). Similarly, Van Galen et al (37) have shown that Bmi-1 levels are highly prognostic in diffuse large B cell lymphomas (DLBCL) (37). Neoplastic cells in DLBCL cases originate from germinal centre B (GCB) cells or their descendents(38). Recent microarray analyses have shown that some DLBCL phenotypically resemble non-neoplastic GCB cells, while some show an expression profile similar to that of activated B cells (ABC) (39).

Furthermore, patients with a GCB-like phenotype have a considerably better prognosis than those with an ABC-like phenotype (40). Bmi-1 was identified as one of the genes that distinguish the ABC-like DLBCL (39),(41). Other groups have linked elevated Bmi-1 levels with poor prognosis in mantle cell lymphoma (MCL), non-Hodgkin's lymphoma and other leukemias (22, 26, 27, 29, 42-44), as well as many other tumour types including neuroblastoma, glioblastoma, hepatocellular carcinoma, and breast, colorectal, prostate, lung, gastric and salivary gland cancers (45-57). The loss of expression from the INK4A locus has also been shown to have prognostic value (12, 13). Taken together, these data strongly implicate Bmi-1 in cancer and suggest that inhibiting uncontrolled cell proliferation by inhibiting Bmi-1 function and reducing the level of Bmi-1 in a cancer cell, tumor cell, cancer stem cell or tumor stem cell will have a beneficial therapeutic effect in patients with multiple cancer types, particularly in those afflicted with hematological cancers.

For example, MCL is a rare, aggressive and incurable B cell non-Hodgkin's lymphoma that is refractory (i.e., resistant to conventional chemotherapy) and is associated with a poor prognosis. MCL is characterized by the t(11;14)(q13;q32) translocation, resulting in amplification and overexpression of the polycomb group gene Bmi-1, which normally functions for self-renewal of hematopoietic stem cells but has the capacity to induce tumors when overexpressed.

Multiple myeloma is another fatal B-cell malignancy characterized by the accumulation of abnormal plasma cells in the bone marrow. Standard therapy for multiple myeloma is similar to the course for MCL and normally consists of combination chemotherapy that often results in a 60-70% response rate. However, most patients will eventually relapse, leaving patients with limited therapeutic options. Recent gene expression profiling of multiple myeloma cells revealed elevated expression of Bmi-1 compared to that in normal plasma cells, as confirmed by immunoblotting.

Bmi-1 has been shown to be regulated transcriptionally by a number of factors including SALL4, FoxM1, c-Myc, E2F-1 and Mel18. Bmi-1 and SALL4 are putative oncogenes that modulate stem cell pluripotency and play a role in leukemigenesis (also referred to as leukemogenesis). Murine Sall4 also has been shown to play an essential role in maintaining the properties of ES (embryonic stem) cells and governing the fate of the primitive inner cell mass. Yang et al demonstrated that transcription from the Bmi-1 promoter is markedly activated by SALL4 in a dose-dependent manner (35). The Forkhead box transcription factor FoxM1 is expressed in proliferating cells and has been shown to upregulate the levels of Bmi-1 in transformed NIH 3T3 cells in response to oxidative stress through c-myc activation (58). The Bmi-1 homologue, Mel18, acts as a potent repressor on the expression of Bmi-1. The Bmi-1 promoter region contains a functional E-box through which c-Myc and Mel-18 can regulate Bmi-1 expression. Since Mel18 downregulates c-Myc expression and Bmi-1 is a c-Myc target, these data suggest that Mel18 regulates expression of Bmi-1 via repression of c-Myc during cellular senescence and, thus, link c-Myc and polycomb function (59). Similarly, a recent report suggests that E2F-1 may also regulate the levels of Bmi-1 in neuroblastoma (60). The Bmi-1 promoter contains a putative E2F binding site required for the activation of a Bmi-1 promoter-dependent reporter construct by E2F-1. Neither post-transcriptional nor post-translational control of Bmi-1 production has been reported.

Without being limited by theory, the compounds of Formula (I) or a form thereof described herein activate the apoptotic pathway as determined by annexin-V expression, as well as cleavage of poly (ADP-ribose) polymerase (PARP) and caspase-9 and caspase-7. Cell cycle analyses of cells treated with these compounds of Formula (I) or a form thereof have further demonstrated a block at the $G_2/M$ phase followed by the development of polyploidy. These findings suggest that Bmi-1 may also play a role in DNA repair and/or regulation of mitosis. The compounds of Formula (I) or a form thereof described herein are useful inhibitors of Bmi-1 function and cause a reduction in the level of Bmi-1 protein and are thus potential therapeutics for any cancer cell, tumor cell, cancer stem cell or tumor stem cell that overexpresses Bmi-1. Additionally, the compounds of Formula (I) or a form thereof described herein inhibit the function of Bmi-1 and reduce Bmi-1 levels in cancer stem cell and tumor stem cell environments and are thus useful in targeting cancer cell populations that have been shown to be resistant to current therapies (e.g., such as those using large and small molecule chemotherapeutic agents and radiation therapies, as well as targeted therapies that primarily function by indiscriminately damaging mitotic cells).

As used herein, the italicized form of "Bmi-1," unless otherwise specified or clear from the context of the specification, refers to the Bmi-1 gene. The nonitalicized form of "Bmi-1," the capitalized form of "BMI-1" or the term "Bmi-1 protein," unless otherwise specified or clear from the context of the specification, collectively refer to Bmi-1 protein.

As used herein, the term "Bmi-1 inhibitor" or the phrase (or variations thereof) "inhibit Bmi-1 function and reduce the level of Bmi-1" refer to post-translational inhibition of the function of Bmi-1 protein and subsequent degradation, resulting in decreased levels of Bmi-1 protein present in a tumor environment including, but not limited to, in vitro and in vivo environments comprising cancer stem cells or tumor stem cells or cancer stem cells and tumor stem cells.

In accordance with the present description, compounds of Formula (I) or a form thereof that inhibit Bmi-1 function and reduce the level of Bmi-1 also inhibit proliferation of tumor cells in vitro and in vivo and enhance sensitivity of intrinsically resistant populations (e.g., either "cancer stem cells," "tumor stem cells" or both) to chemotherapeutics. Elevated expression of human Bmi-1 has been reported in multiple cancer samples and cancer cell lines (2, 42, 51, 56, 61-68). Applicants have identified compounds of Formula (I) or a form thereof that inhibit Bmi-1 function and reduce the level of Bmi-1 in vitro and in vivo, with concurrent inhibition of tumor cell growth and xenograft growth in vivo.

One embodiment described herein is directed to a method of inhibiting Bmi-1 function and reducing the level of Bmi-1 to treat a cancer mediated by Bmi-1 in a subject in need thereof comprising contacting a cell having elevated Bmi-1 levels from the subject with an amount of a compound of Formula (I) or a form thereof, wherein the cell is selected from a cancer cell, tumor cell, cancer stem cell or tumor stem cell, determining an effective amount of the compound of Formula (I) or a form thereof that inhibits Bmi-1 function in the cell and subsequently administering the effective amount of the compound of Formula (I) or a form thereof to the subject.

Another embodiment described herein is directed to a method of inhibiting Bmi-1 function and reducing the level of Bmi-1 to treat a cancer mediated by Bmi-1 in a subject in need thereof comprising administering to the subject an effective amount of the compound of Formula (I) or a form thereof.

Another embodiment described herein is directed to a method for treating a cancer mediated by Bmi-1 in a subject in need thereof comprising contacting a cell having elevated Bmi-1 levels from the subject with an amount of a compound of Formula (I) or a form thereof, wherein the cell is selected from a cancer cell, tumor cell, cancer stem cell or tumor stem cell.

Another embodiment described herein is directed to a method further comprising contacting a cell having elevated Bmi-1 levels from the subject with an amount of the compound of Formula (I) or a form thereof, wherein the cell is selected from a cancer cell, tumor cell, cancer stem cell or tumor stem cell, determining an effective amount of the compound of Formula (I) or a form thereof that inhibits Bmi-1 function in the cell and subsequently administering the effective amount of the compound of Formula (I) or a form thereof to the subject.

Another embodiment described herein is directed to a method wherein the effective amount of the compound of Formula (I) or a form thereof determined to inhibit Bmi-1 function in the contacted cell reduces Bmi-1 levels in the contacted cell.

An embodiment of the method described herein comprises administering an effective amount of a compound of Formula (I) or a form thereof to inhibit the function of Bmi-1 in a cancer cell in vivo or in vitro, in a tumor cell in vivo or in vitro, in a cancer stem cell population in vivo or in vitro, or in a tumor stem population in vivo or in vitro.

An embodiment of the method described herein comprises administering an effective amount of a compound of Formula (I) or a form thereof to reduce the level of Bmi-1 in a cancer cell in vivo or in vitro, in a tumor cell in vivo or in vitro, in a cancer stem cell population in vivo or in vitro, or in a tumor stem population in vivo or in vitro.

An embodiment of the method described herein comprises administering an effective amount of a compound of Formula (I) or a form thereof to inhibit cancer cell proliferation, tumor cell proliferation, cancer stem cell proliferation or tumor stem cell proliferation.

An embodiment described herein includes the use of a compound of Formula (I) or a form thereof in the manufacture of a medicament for inhibiting Bmi-1 function and reducing the level of Bmi-1 to treat a cancer mediated by Bmi-1 in a subject in need thereof comprising administering an effective amount of the medicament to the subject.

Without being limited by theory, any type of cancer mediated by or dependent on the presence of overexpressed Bmi-1 can be treated in accordance with the intended use of the compounds of Formula (I) or a form thereof described herein.

As used herein, the term "cancer" refers to cells in which Bmi-1 is aberrantly expressed or overexpressed and the cell depends on Bmi-1 for survival or proliferation.

Without being limited by theory, the cells may be either stem-like or more differentiated, but the cell relies on Bmi-1 to enable uncontrolled cell division and develop resistance to cytotoxic, chemotherapeutic agents.

In another embodiment, the term "a cancer mediated by Bmi-1" refers to a cancer that is characterized by cells or a fraction of cells from a cancer patient that overexpress Bmi-1 compared to cells from a cancer-free patient (i.e., a patient with no detectable cancer as determined by conventional techniques, such as MRI, CAT scan, etc.). Alternatively, the term refers to cells or a fraction of cells from a cancer patient that, relative to the cancer patient's cells from surrounding normal tissues, express a level of Bmi-1 that differs by at least 2%, 4%, 8%, 10%, 15%, 20%, 25%, 30%, 35%, 40%, 45%, 50%, 55%, 60%, 65%, 70%, 75%, 80%, 85%. 90%, or 95% more, as detected by any method routinely used in the art, or described herein, e.g., in an ELISA.

Non-limiting examples of a cancer mediated by Bmi-1 that can be treated with the intended use described herein: leukemias, such as but not limited to, acute leukemia, acute lymphocytic leukemia, acute myelocytic leukemias, such as, myeloblastic, promyelocytic, myelomonocytic, monocytic, and erythroleukemia leukemias and myelodysplastic syndrome; chronic leukemias, such as but not limited to, chronic myelocytic (granulocytic) leukemia, chronic lymphocytic leukemia, hairy cell leukemia; polycythemia vera; lymphomas such as but not limited to Hodgkin's lymphoma, non-Hodgkin's lymphoma; multiple myelomas such as but not limited to smoldering multiple myeloma, nonsecretory myeloma, osteosclerotic myeloma, placancer cell leukemia, solitary placancercytoma and extramedullary placancercytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; glial brain tumors (i.e., gliomas) such as but not limited to, astrocytoma, ependymoma, oligodendroglioma, brain stem glioma, optic glioma, diffuse intrinsic pontine glioma, mixed glioma (i.e., oligoastrocytoma), glioblastoma, glioblastoma multiforme, nonglial tumor, acoustic neurinoma, craniopharyngioma, medulloblastoma, meningioma, pineocytoma, pineoblastoma, primary brain lymphoma; breast cancer including but not limited to ductal carcinoma, adenocarcinoma, lobular (cancer cell) carcinoma, intraductal carcinoma, medullary breast cancer, mucinous breast cancer, tubular breast cancer, papillary breast cancer, Paget's disease, and inflammatory breast cancer; adrenal cancer such as but not limited to pheochromocytom and adrenocortical carcinoma; thyroid cancer such as but not limited to papillary or follicular thyroid cancer, medullary thyroid cancer and anaplastic thyroid cancer; pancreatic cancer such as but not limited to, insulinoma, gastrinoma, glucagonoma, vipoma, somatostatin-secreting tumor, and carcinoid or islet cell tumor; pituitary cancers such as but limited to Cushing's disease, prolactin-secreting tumor, acromegaly, and diabetes insipius; eye cancers such as but not limited to ocular melanoma such as iris melanoma, choroidal melanoma, and cilliary body melanoma, and retinoblastoma; vaginal cancers such as squamous cell carcinoma, adenocarcinoma, and melanoma; vulvar cancer such as squamous cell carcinoma, melanoma, adenocarcinoma, basal cell carcinoma, sarcoma, and Paget's disease; cervical cancers such as but not limited to, squamous cell carcinoma, and adenocarcinoma; uterine cancers such as but not limited to endometrial carcinoma and uterine sarcoma; ovarian cancers such as but not limited to, ovarian epithelial carcinoma, borderline tumor, germ cell tumor, and stromal tumor; esophageal cancers such as but not limited to, squamous cancer, adenocarcinoma, adenoid cystic carcinoma, mucoepidermoid carcinoma, adenosquamous carcinoma, sarcoma, melanoma, placancercytoma, verrucous carcinoma, and oat cell (cancer cell) carcinoma; stomach cancers such as but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers such as but not limited to hepatocellular carcinoma and hepatoblastoma; gallbladder cancers such as adenocarcinoma; cholangiocarcinomas such as but not limited to papillary, nodular, and diffuse; lung cancers such as non-small cell lung cancer, squamous cell carcinoma (epidermoid carcinoma), adenocarcinoma, large-cell carcinoma and small-cell lung cancer; testicular cancers such as but not limited to germinal tumor, seminoma, anaplastic, classic (typical), spermatocytic, nonseminoma, embryonal carcinoma, teratoma carcinoma, choriocarcinoma (yolk-sac tumor), prostate cancers such as but not limited to, prostatic intraepithelial neoplasia, adenocarcinoma, leiomyosarcoma, and rhabdomyosarcoma; penal cancers; oral cancers such as but not limited to squamous cell carcinoma; basal cancers; salivary gland cancers such as but not limited to adenocarcinoma, mucoepidermoid carcinoma, and adenoidcystic carcinoma; pharynx cancers such as but not limited to squamous cell cancer, and verrucous; skin cancers such as but not limited to, basal cell carcinoma, squamous cell carcinoma and melanoma, superficial spreading melanoma, nodular melanoma, lentigo malignant melanoma, acral lentiginous melanoma; kidney cancers such as but not limited to renal cell carcinoma, adenocarcinoma, hypernephroma, fibrosarcoma, transitional cell cancer (renal pelvis and/or uterer); Wilms' tumor; bladder cancers such as but not limited to transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, *Medicine*, 2d Ed., J.B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

The compounds of Formula (I) or a form thereof are also useful in the treatment, prevention and/or management of a variety of cancers mediated by Bmi-1 or other abnormal proliferative diseases (where such disease is mediated by overexpressed Bmi-1 or elevated levels of Bmi-1), including (but not limited to) the following: carcinoma, including that of the bladder, breast, colon, kidney, liver, lung, ovary, pancreas, stomach, cervix, thyroid and skin; including squamous cell carcinoma; hematopoietic tumors of lymphoid lineage, including leukemia, acute lymphocytic leukemia, acute lymphoblastic leukemia, B-cell lymphoma, T cell lymphoma, Burkitt's lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma; tumors of the central and peripheral nervous system, including astrocytoma, neuroblastoma, glioma, and Schwannomas; tumors of mesenchymal origin, including fibrosarcoma, rhabdomyoscarama, and osteosarcoma; and other tumors, including melanoma, xeroderma pigmentosum, keratoactanthoma, seminoma, thyroid follicular cancer and teratocarcinoma. In some embodiments, cancers associated with aberrations in apoptosis are treated in accordance with the methods described herein. Such cancers may include, but are not limited to, follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders of the skin, lung, liver, bone, brain, stomach, colon, breast, prostate, bladder, kidney, pancreas, ovary, and/or uterus are treated in accordance with the methods described herein. In other specific embodiments, a sarcoma, or melanoma is treated as described herein.

In a specific embodiment, the cancer mediated by Bmi-1 being treated as described herein is leukemia, lymphoma or myeloma (e.g., multiple myeloma). Non-limiting examples of leukemias and other blood-borne cancers mediated by Bmi-1 that can be treated with the methods described herein include acute lymphoblastic leukemia (ALL), acute lymphoblastic B-cell leukemia, acute lymphoblastic T-cell leukemia, acute myeloblastic leukemia (AML), acute promyelocytic leukemia (APL), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia (CML), chronic lymphocytic leukemia (CLL), and hairy cell leukemia.

Non-limiting examples of lymphomas mediated by Bmi-1 that can be treated in accordance with the methods described herein include Hodgkin's lymphoma, non-Hodgkin's lymphoma, multiple myeloma, Waldenström's macroglobulinemia, heavy chain disease, and polycythemia vera.

In another embodiment, the cancer mediated by Bmi-1 being treated as described herein is a solid tumor. Examples of solid tumors that can be treated in accordance with the methods described herein include, but are not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

In certain embodiments, a cancer mediated by Bmi-1 includes, but is not limited to, brain cancer, gastric cancer, hematologic cancer, lung cancer, non-small cell lung cancer, pancreatic cancer, prostate cancer, salivary gland cancer, colorectal carcinoma, hepatocellular carcinoma, liver carcinoma, breast carcinomas or sarcomas, esophageal carcinomas or sarcomas, stomach carcinomas or sarcomas, fibrosarcoma, glioblastoma, diffuse intrinsic pontine glioma, medulloblastoma, neuroblastoma, diffuse large B cell lymphomas, B cell non-Hodgkin's lymphoma, Hodgkin's lymphoma or chronic or acute myeloid leukemia.

In certain embodiments, a cancer mediated by Bmi-1 includes, but is not limited to, tumors that relapse after therapy despite improved surgical and irradiation techniques. Tumor relapse may occur for a number of reasons, with one plausible explanation being the existence of cancer stem cells (CSC) or tumor stem cells (tumor initiating cells) in the tumor population. CSCs are defined as a population of stem cells relative to any type of blood cancer, solid tumor cancer or metastatic cancer. Tumor stem cells are those specifically found within a tumor. Both have characteristics similar to normal stem cells. Like normal stem cells, CSCs and tumor stem cells have the potential to self renew. Unlike normal stem cells, though, due to the sustained presence of high levels of Bmi-1, the CSCs and tumor stem cells fail to terminally differentiate and proliferate unchecked. Their enhanced DNA repair capacity also enables them to become resistant to cytotoxic, chemotherapeutic drugs designed to kill cancer cells and tumor cells. Therefore, targeting CSCs and tumor stem cells that overexpress Bmi-1 could be an approach for effective cancer treatment. One further approach is to target various transcription factors responsible for maintenance of the self renewal capacity of CSCs and tumor stem cells.

As used herein, the term "treat," "treatment" or "treating" refers to: (i) preventing a disease, disorder and/or condition from occurring in a subject that may be predisposed to the disease, disorder and/or condition but has not yet been diagnosed as having said disease, disorder and/or condition; (ii) inhibiting a disease, disorder and/or condition, i.e., arresting its development; and/or (iii) relieving a disease, disorder and/or condition, i.e., causing regression of the disease, disorder and/or condition.

As used herein, the term "subject" refers to members of the human, equine, porcine, bovine, murine, rattus, canine and feline species. In some embodiments, the subject is a mammal or a warm-blooded vertebrate animal. In other embodiments, the subject is a human. As used herein, the term "patient" may be used interchangeably with "subject" and "human".

In certain embodiments, the subject is a human that is 0 to 6 months old, 6 to 12 months old, 6 to 18 months old, 18 to 36 months old, 1 to 5 years old, 5 to 10 years old, 10 to 15 years old, 15 to 20 years old, 20 to 25 years old, 25 to 30 years old, 30 to 35 years old, 35 to 40 years old, 40 to 45 years old, 45 to 50 years old, 50 to 55 years old, 55 to 60 years old, 60 to 65 years old, 65 to 70 years old, 70 to 75 years old, 75 to 80 years old, 80 to 85 years old, 85 to 90 years old, 90 to 95 years old or 95 to 100 years old. In some embodiments, the subject is a human infant. In other embodiments, the subject is a human toddler. In other embodiments, the subject is a human child. In other embodiments, the subject is human adult. In yet other embodiments, the subject is an elderly human.

As used herein, the term "elderly human" refers to a human 65 years or older; the term "human adult" refers to a human that is 18 years or older; the term "human child" refers to a human that is 1 year to 18 years old; the term "human infant" refers to a newborn to 1 year old year human; and, the term "human toddler" refers to a human that is 1 year to 3 years old.

In certain embodiments, the subject is in an immunocompromised state or immunosuppressed state or at risk for becoming immunocompromised or immunosuppressed.

In certain embodiments, the subject is receiving or recovering from an immunosuppressive therapy. In certain embodiments, the subject has or is at risk of getting cancer, AIDS, or a bacterial infection. In certain embodiments, the subject is, will or has undergone surgery, chemotherapy and/or radiation therapy. In certain embodiments, the subject has cystic fibrosis, pulmonary fibrosis or another condition affecting the lungs. In certain embodiments, the subject has, will have or had a tissue transplant.

In some embodiments, the subject's cancer, due to the overexpression of Bmi-1 in cancer cells, tumor cells, cancer stem cells or tumor stem cells thereof, has proven refractory to conventional "standard of care" therapies (excluding treatment with a compound of Formula (I) or a form thereof), such that the patient has discontinued the conventional therapy. In one embodiment, without being limited by theory, the term "refractory" means that at least some significant portion of the cancer cells, tumor cells, cancer stem cells or tumor stem cells continue to proliferate due to the overexpression of Bmi-1, despite therapy. The determination of whether the cancer is refractory to a particular therapy can be made either in vivo or in vitro by any method known in the art for assaying the effect of a therapy on the cancer cells, tumor cells, cancer stem cells or tumor stem cells, using the art-accepted meanings of "refractory" in such a context. In certain embodiments, a patient having a refractory cancer due to the overexpression of Bmi-1 is a patient in which the cancer is non-responsive or resistant to a conventional or "standard of care" therapy. In certain embodiments, a patient with refractory cancer has a cancer mediated by Bmi-1 that progresses. Disease progression, as a lack of clinical response to a therapy, is demonstrated when the tumor or neoplasm has not been significantly eradicated and/or the symptoms have not been significantly alleviated. The determination of whether a patient has a refractory cancer mediated by Bmi-1 can be made either in vivo or in vitro by any method known in the art for assaying the effectiveness of the therapy for the treatment of the cancer, using art-accepted meanings of "refractory" in such a context.

In certain embodiments, the patient to be treated in accordance with the methods described herein is a patient already being treated with antibiotics, anti-virals, anti-fungals, or other biological therapy, immunotherapy or anticancer therapy. Among these patients are patients with a refractory cancer mediated by Bmi-1 or patients too young for conventional therapies. In some embodiments, the patient being treated is treatment naive, not having received any prior therapy. In any of the foregoing embodiments, a patient to be treated may receive a small molecule therapy.

In some embodiments, a compound of Formula (I) or a form thereof may be prophylactically administered to a patient to prevent the onset of cancer mediated by Bmi-1 in a patient at risk of developing cancer. In some embodiments, a compound of Formula (I) or a form thereof may be therapeutically administered to a patient that is susceptible to adverse reactions to conventional therapies. In some embodiments, the subject being administered one or more compounds of Formula (I) or a form thereof has not received prior therapy. In other embodiments, one or more compounds of Formula (I) or a form thereof are administered to a subject who has received a prior therapy. In some embodiments, the subject administered a compound of Formula (I) or a form thereof has discontinued a prior therapy due to lack of benefit from the therapy, adverse effects from the therapy or unacceptable levels of toxicity.

In some embodiments, the subject being administered one or more compounds of Formula (I) or a form thereof, will or has undergone surgery, chemotherapy, antibody therapy, hormonal therapy and/or radiation therapy. In certain embodiments, the patient has undergone surgery to remove the tumor or neoplasm. In certain embodiments, the subject will have, or has had, or is undergoing a tissue or organ transplant.

As used herein, the terms "effective amount," "prophylactically effective amount" or "therapeutically effective amount" mean an amount of a compound of Formula (I) or a form thereof that is effective in inhibiting Bmi-1 protein function and reducing the level of Bmi-1 protein, as described herein, and thus producing the desired prophylactic, therapeutic, ameliorative, inhibitory or preventative effect in a cancer mediated by Bmi-1 in a patient in need thereof.

As used herein, the term "effective amount," in the context of administering a compound of Formula (I) or a form thereof to a patient, refers to the amount of a compound of Formula (I) or a form thereof which is sufficient to achieve at least one or more of the following effects, as applicable, in a patient or in patient cell(s): (i) inhibition of Bmi-1 protein function; (ii) reduction in the level or quantity of Bmi-1 protein; (iii) reduction or amelioration in the severity of a cancer mediated by Bmi-1 or a symptom associated therewith; (iv) prevention of the progression of a cancer mediated by Bmi-1 or a symptom associated therewith; (v) regression of a cancer mediated by Bmi-1 or a symptom associated therewith; (vi) prevention of the development or onset of a cancer mediated by Bmi-1 or a symptom associated therewith; (vii) prevention of the recurrence of a cancer mediated by Bmi-1 or a symptom associated with a cancer mediated by Bmi-1; (viii) reduction of the duration of a symptom associated with a cancer mediated by Bmi-1; (ix) reduction or elimination of the cancer stem cell or tumor stem cell population; (x) reduction or elimination of the growth of a tumor or neoplasm overexpressing Bmi-1; (xi) reduction or elimination of the proliferation of cancer cells or tumor cells; (xii) reduction or elimination of the formation of a tumor or neoplasm overexpressing Bmi-1; (xiii) eradication or control of a primary, regional and/or metastatic cancer mediated by Bmi-1; (xiv) reduction in patient mortality; (xv) increased number of patients in remission; (xvi) increased length of remission in patients; (xvii) the size of a tumor or neoplasm overexpressing Bmi-1 is maintained or controlled such that the size does not increase or increases less than the size of the tumor after administration of a standard therapy as measured by conventional methods available to one of skill in the art, such as MRI, X-ray and CAT scan; (xviii) increased delay in disease progression; (xix) increased patient survival; (xx) reduction in incidences of patient hospitalization; (xxi) reduction in the length of patient hospitalization; (xxii) enhancement or improvement in the prophylactic or therapeutic effect(s) of another therapy; (xxiii) reduction in the number of symptoms associated with a cancer mediated by Bmi-1; (xxiv) increased cancer-free survival of patients; and/or (xxv) increased symptom-free survival of cancer patients.

In general, the term "effective amount" also includes that amount of a compound of Formula (I) or a form thereof administered to a patient which is in a range of from about 0.001 mg/Kg/day to about 500 mg/Kg/day, or about 0.01 mg/Kg/day to about 500 mg/Kg/day, or about 0.1 mg to about 500 mg/Kg/day, or about 1.0 mg/day to about 500 mg/Kg/day, in single, divided, or a continuous dose for a patient or subject having a weight in a range of between about 40 to about 200 Kg (which dose may be adjusted for patients or subjects above or below this range, particularly children under 40 Kg). The typical adult subject is expected to have a median weight in a range of between about 60 to about 100 Kg. The effective amount for the subject will also depend upon various factors, including the body weight, size and health of the subject. An effective amount for a given patient can be determined according to the skill and judgment of the clinician.

In another embodiment, where daily doses are adjusted based upon the weight of the subject or patient, compounds of Formula (I) or a form thereof described herein may be formulated for delivery at about 0.02, 0.025, 0.03, 0.05, 0.06, 0.075, 0.08, 0.09, 0.10, 0.20, 0.25, 0.30, 0.50, 0.60, 0.75, 0.80, 0.90, 1.0, 1.10, 1.20, 1.25, 1.50, 1.75, 2.0, 5.0, 10, 20 or 50 mg/Kg/day. Daily doses adjusted based upon the weight of the subject or patient may be administered as a single, divided, or continuous dose. In embodiments where a dose of a compound of Formula (I) or a form thereof is given more than once per day, the dose may be administered once, twice, three times, or more per day. In another embodiment, a subject is administered one or more doses of an effective amount of a compound of Formula (I) or a form thereof, wherein the effective amount may not be the same for each dose.

Another embodiment described herein includes an effective amount of the compound of Formula (I) or a form thereof in a range of from about 0.001 mg/Kg/day to about 500 mg/Kg/day.

Within the scope described herein, the "effective amount" of a compound of Formula (I) or a form thereof for use in the manufacture of a medicament or in a method for treating a cancer mediated by Bmi-1 in a subject in need thereof, is intended to include an amount in a range of from about 0.1 ng to about 3500 mg administered daily; from about 0.1 µg to about 3500 mg administered daily; from about 0.1 mg to about 3500 mg administered daily; from about 1 mg to about 3500 mg administered daily; from about 1 mg to about 3000 mg administered daily; from about 0.05 mg to about 1500 mg administered daily; from about 0.5 mg to about 1500 mg administered daily; from about 1 mg to about 1500 mg administered daily; from about 5 mg to about 1500 mg administered daily; from about 10 mg to about 600 mg administered daily; from about 0.5 mg to about 2000 mg administered daily; or, an amount in a range of from about 5.0 mg to about 1500 mg administered daily.

Another embodiment described herein includes an effective amount of the compound of Formula (I) or a form thereof in a range of from about 0.1 ng to about 3500 mg. For any compound of Formula (I) or a form thereof, the effective amount can be estimated initially by results from cell culture assays or from relevant animal models, such as the mouse, chimpanzee, marmoset or tamarin animal model. Relevant animal models may also be used to determine the appropriate concentration range and route of administration. Such information can then be used to determine useful doses and routes for administration in humans. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between the toxic and therapeutic effect is referred to as the therapeutic index, and can be expressed as the ratio, $LD_{50}/ED_{50}$. In some embodiments, the effective amount is such that a large therapeutic index is achieved. In further embodiments, the dosage is within a range of plasma concentrations that include an $ED_{50}$ with little or no toxicity. The dosage may vary within this range depending upon the dosage form employed, sensitivity of the patient, and the route of administration.

More specifically, the concentration-biological effect (pharmacodynamic) relationship observed with regard to a compound of Formula (I) or a form thereof suggests a target plasma concentration ranging from about 0.001 µg/mL to about 50 µg/mL, from about 0.01 µg/mL to about 20 µg/mL, from about 0.05 µg/mL to about 10 µg/mL, or from about 0.1 µg/mL to about 5 µg/mL. To achieve such plasma concentrations, the compounds of Formula (I) or a form thereof described herein may be administered at doses that vary from 0.001 µg to 100,000 mg, depending upon the route of administration in single, divided, or continuous doses for a patient weighing between about 40 to about 100 kg (which dose may be adjusted for patients above or below this weight range, particularly for children under 40 kg).

The exact dosage will be determined by the practitioner, in light of factors related to the subject. Dosage and administration may be adjusted to provide sufficient levels of the active agent(s) or to maintain the desired effect. Administration factors that may be taken into account include the severity of the disease state, general health of the subject, ethnicity, age, weight, and gender of the subject, diet, time and frequency of administration, drug combination(s), reaction sensitivities, tolerance for toxicity related to drug metabolites, experience with other cancer therapies and regimens, and tolerance/response to such therapies and regimens. Long-acting pharmaceutical compositions may be administered every 2, 3 or 4 days, once every week, or once every two weeks depending on half-life and clearance rate of the particular formulation.

The compounds of Formula (I) or a form thereof described herein may be administered to the subject via any drug delivery route known in the art. Nonlimiting examples include oral, ocular, rectal, buccal, topical, nasal, ophthalmic, subcutaneous, intramuscular, intraveneous (bolus and infusion), intracerebral, transdermal, and pulmonary routes of administration.

Compound Metabolites

Also falling within the scope described herein are the in vivo metabolic products of the compounds of Formula (I) or a form thereof. Such products may result, for example, from the oxidation, reduction, hydrolysis, amidation, glucuronidation, esterification and the like of the administered compound of Formula (I) or a form thereof, primarily due to enzymatic processes. Accordingly, the compounds of Formula (I) or a form thereof described herein include those produced by a process comprising contacting a compound of Formula (I) or a form thereof described herein with a mammalian tissue or a mammal for a period of time sufficient to yield a metabolic product thereof.

Such products typically are identified by preparing a radio-labeled (e.g. $C^{14}$ or $H^3$) compound of Formula (I) or a form thereof described herein, administering it in a detectable dose (e.g., greater than about 0.5 mg/kg) to a mammal such as rat, mouse, guinea pig, monkey, or to man, allowing sufficient time for metabolism to occur (typically about 30 seconds to 30 hours), and isolating its conversion products from urine, blood or other biological samples. These products are easily isolated since they are labeled (others are isolated by the use of antibodies capable of binding epitopes surviving in the metabolite). The metabolite structures are determined in conventional fashion, e.g., by MS or NMR analysis. In general, analysis of metabolites may be done in the same way as conventional drug metabolism studies well-known to those skilled in the art. The conversion products, so long as they are not otherwise found in vivo, are useful in diagnostic assays for therapeutic dosing of the compounds of Formula (I) or a form thereof described herein even if they possess no biological activity of their own.

Combination Therapies

The methods of treating a cancer mediated by Bmi-1 in a subject in need thereof, in addition to those previously described herein, further comprise administering to the subject in need thereof an effective amount of one or more of the compounds of Formula (I) or a form thereof alone or in combination with one or more additional agents selected from anti-cancer agents, anti-proliferative agents, chemotherapeutic agents, immunomodulatory agents, anti-angiogenic agents, anti-inflammatory agents, an alkylating agents, steroidal and non-steriodal anti-inflammatory agents, pain relievers, leukotriene antagonists, β2-agonists, anticholinergic agents, hormonal agents, biological agents, tubulin binding agents, glucocorticoids, corticosteroid agents, antibacterial agents, antihistamines, anti-malarial agents, antiviral agents, antibiotics and the like; and, optionally with radiation therapy.

In another embodiment, one or more compounds of Formula (I) or a form thereof alone or in combination with one or more additional agents may be administered to the subject in combination with a supportive therapy, a pain relief therapy, or other therapy that does not have an effect on a cancer mediated by Bmi-1.

In some embodiments, one or more compounds of Formula (I) or a form thereof described herein and one or more additional agents described herein are administered as the same pharmaceutical composition. In certain embodiments, one or more compounds of Formula (I) or a form thereof described herein and one or more additional agents described herein are administered in different pharmaceutical compositions. In certain embodiments, one or more compounds of Formula (I) or a form thereof described herein and one or more additional agents described herein are administered by the same route of administration. In certain embodiments, one or more compounds of Formula (I) or a form thereof described herein and one or more additional agents described herein are administered by different routes of administration.

In other embodiments are pharmaceutical compositions wherein one or more compounds of Formula (I) or a form thereof are administered in a combination product with one or more additional agents useful in the treatment of a cancer mediated by Bmi-1. The skilled artisan will recognize that a variety of active ingredients may be administered in a combination with the compounds of Formula (I) or a form thereof described herein whereby the product may act to augment or synergistically enhance the anticancer activity of either or both the additional agent(s) and the compound(s) of Formula (I) or a form thereof described herein.

As used herein, the term "synergistic," refers to the effect of the administration of a combination product as described herein which is more effective than the additive effects of any two or more single agents. In a specific embodiment, a synergistic effect of a combination product permits the use of lower dosages of one or more agents and/or less frequent administration of said agents to a subject with a cancer mediated by Bmi-1. In certain embodiments, the ability to utilize lower dosages of an agent and/or to administer said agents less frequently reduces the toxicity associated with the administration of said agents to a subject without reducing the efficacy of said agents in the prevention or treatment of a cancer mediated by Bmi-1. In some embodiments, a synergistic effect results in improved efficacy of each of the agents in treating a cancer mediated by Bmi-1. In some embodiments, a synergistic effect of a combination of agents avoids or reduces adverse or unwanted side effects associated with the use of any single agent. The combination of agents in such a product can be administered to a subject in the same pharmaceutical composition. Alternatively, the agents can be administered concurrently to a subject in separate pharmaceutical compositions. The agents may also be administered to a subject by the same or different routes of administration. In a specific embodiment, at least one of the agents is a compound of Formula (I) or a form thereof described herein.

It is also possible to combine any compound of Formula (I) or a form thereof described herein with such additional agents useful in the treatment of a cancer mediated by Bmi-1, including compounds of Formula (I) or a form thereof as described herein, in a unitary dosage form, or in separate dosage forms intended for simultaneous or sequential administration to a patient in need of treatment. When administered sequentially, the combination may be administered in two or more administrations. In an alternative embodiment, it is possible to administer one or more compounds of Formula (I) or a form thereof described herein and one or more additional agents described herein by different routes.

According to the methods described herein, a combination product may include a combination of active ingredients that may be: (1) co-formulated and administered or delivered simultaneously in a combined formulation; (2) delivered sequentially or in parallel as separate formulations; or (3) by any other combination regimen known in the art. When delivered as separate formulations in alternation therapy, the methods described herein may comprise administration or delivery, for example, without limitation, in separate solutions, emulsions, suspensions, tablets, pills or capsules, or by different injections in separate syringes. In general, when administered in alternation, an effective dosage of each active ingredient is administered serially, one dose following another. In contrast, in parallel or simultaneous administration, effective dosages of two or more active ingredients are administered together. Various alternative combinations of intermittent sequential or in parallel combination administration may also be used.

Specific examples of such agents include, but are not limited to, immunomodulatory agents (e.g., interferon, penicillamine and the like), anti-angiogenic agent, anti-inflammatory agents (e.g., adrenocorticoids, corticosteroids (e.g., beclomethasone, budesonide, flunisolide, fluticasone, triamcinolone, methylprednisolone, prednisolone, prednisone, hydrocortisone), glucocorticoids, steroidal and non-steriodal anti-inflammatory drugs (e.g., aspirin, ibuprofen, diclofenac, and COX-2 inhibitors)), pain relievers, leukotriene antagonists (e.g., montelukast, methyl xanthines, zafirlukast, and zileuton), β2-agonists (e.g., albuterol, biterol, fenoterol, isoetharie, metaproterenol, pirbuterol, salbutamol, terbutalin formoterol, salmeterol, and salbutamol terbutaline), anticholinergic agents (e.g., ipratropium bromide and oxitropium bromide), antibacterial agents (e.g., sulphasalazine, dapsone and the like), antihistamines, anti-malarial agents (e.g., hydroxychloroquine), anti-viral agents (e.g., nucleoside analogs (e.g., zidovudine, acyclovir, gangcyclovir, vidarabine, idoxuridine, trifluridine, ribavirin, foscarnet, amantadine, rimantadine, saquinavir, indinavir, ritonavir, and AZT) and antibiotics (e.g., dactinomycin (formerly actinomycin), bleomycin, erythomycin, penicillin, mithramycin, and anthramycin (AMC)).

Specific examples of additional agents that may be used in combination with a compound of Formula (I) or a form thereof described herein include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthracyclin; anthramycin; asparaginase; asperlin; azacitidine; azetepa; azotomycin; batimastat; benzodepa; bicalutamide; bisantrene hydrochloride; bisnafide dimesylate; bisphosphonates (e.g., pamidronate (Aredria®), sodium clondronate (Bonefos®), zoledronic acid (Zometa®), alendronate (Fosamax®), etidronate, ibandornate, cimadronate, risedromate, and tiludromate); bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; demethylation agents; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; EphA2 inhibitors; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; 5-fluorouracil; fluorocitabine; fosquidone; fostriecin sodium; gemcitabine; gemcitabine hydrochloride; histone deacetylase inhibitors; hydroxyurea; idarubicin hydrochloride; ifosfamide; ilmofosine; imatinib mesylate; interleukin II (including recombinant interleukin II, or rIL2), interferon alpha-2a; interferon alpha-2b; interferon alpha-n1; interferon alpha-n3; interferon beta-I a; interferon gamma-I b; iproplatin; irinotecan hydrochloride; lanreotide acetate; lenalidomide; letrozole; leuprolide acetate; liarozole hydrochloride; lometrexol sodium; lomustine; losoxantrone hydrochloride; masoprocol; maytansine; mechlorethamine hydrochloride; anti-CD2 antibodies; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; volitinib; vorozole; zeniplatin; zinostatin; zorubicin hydrochloride and the like.

Other examples of treating a cancer mediated by Bmi-1 include treatment with an anti-cancer or anti-proliferative agent wherein the anti-cancer or anti-proliferative agent is selected from, but not limited to: 20-Epi-1,25-dihydroxyvitamin D3 (MC 1288, MC 1301, KH 1060); 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, antiestrogen; antineoplaston; antisense oligonucleotides; aphidicolin glycinate; apoptosis gene modulators; apoptosis regulators; apurinic acid; ara-CDP-DL-PTBA (0-palmitoyl-1-thioglycerol); arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole (CaRest M3); CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate (YNK01 or Starasid®); cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; HMG CoA reductase inhibitors (e.g., atorvastatin, cerivastatin, fluvastatin, lescol, lupitor, lovastatin, rosuvastatin, and simvastatin); hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide/estrogen/progesterone combinations; leuprorelin; levamisole; LFA-3TIP (see, International Publication No. WO93/0686 and U.S. Pat. No. 6,162,432); liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF tautomerase inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A/myobacterium cell wall skeleton (CWS/MPL); mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone/pentazocine combinations; napavin; naphterpin; nartograstim; nedaplatin; nemorubicin; neridronic acid; neutral endopeptidase; nilutamide; nisamycin; nitric oxide modulators; nitroxide antioxidant; nitrullyn; 06-benzylguanine; octreotide; okicenone; oligonucleotides; onapristone; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine (BCX-34); pentosan polysulfate sodium; pentostatin; pentrozole; perflubron; perfosfamide; perillyl alcohol dehydrogenase; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RH retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem cell division inhibitors; stipiamide; stromelysin inhibitors; sulfinosine; superactive vasoactive intestinal peptide antagonist; suradista; suramin; swainsonine; synthetic glycosaminoglycans; tallimustine; 5-fluorouracil; leucovorin; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; thalidomide; velaresol; veramine; verdins; verteporfin; vinorelbine; vinxaltine; volitinib; vorozole; zanoterone; zeniplatin; zilascorb; zinostatin stimalamer and the like.

In some embodiments, the additional agent used in combination with a compound of Formula (I) or a form thereof described herein is one or more immunomodulatory agent(s). Non-limiting examples of immunomodulatory agents include proteinaceous agents such as cytokines, peptide mimetics, and antibodies (e.g., human, humanized, chimeric, monoclonal, polyclonal, Fvs, ScFvs, Fab or F(ab)$_2$ fragments or epitope binding fragments), nucleic acid molecules (e.g., antisense nucleic acid molecules and triple helices), cancer molecules, organic compounds, and inorganic compounds.

In particular, one or more immunomodulatory agents that may be used in combination with a compound of Formula (I) or a form thereof described herein include, but are not limited to, methotrexate, leflunomide, cyclophosphamide, cytoxan, cyclosporine A, minocycline, azathioprine (Imuran®), antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloamindes (e.g., leflunamide), T cell receptor modulators, cytokine receptor modulators, and modulators mast cell modulators.

In one embodiment, the immunomodulatory agent is a chemotherapeutic agent. In an alternative embodiment, the immunomodulatory agent is an immunomodulatory agent other than a chemotherapeutic agent. In some embodiments, the additional agent used described herein is not an immunomodulatory agent.

In some embodiments, the additional agent that may be used in combination with a compound of Formula (I) or a form thereof described herein is one or more anti-angiogenic agent(s). Non-limiting examples of anti-angiogenic agents include proteins, polypeptides, peptides, fusion proteins, antibodies (e.g., human, humanized, chimeric, monoclonal, polyclonal, Fvs, ScFvs, Fab fragments, F(ab)$_2$ fragments, and antigen-binding fragments thereof) such as antibodies that immunospecifically bind to TNF-$\alpha$, nucleic acid molecules (e.g., antisense molecules or triple helices), organic molecules, inorganic molecules, and cancer molecules that reduce or inhibit angiogenesis. In other embodiments, the additional agent described herein is not an anti-angiogenic agent.

In some embodiments, the additional agent that may be used in combination with a compound of Formula (I) or a form thereof described herein is one or more anti-inflammatory agent(s). Non-limiting examples of anti-inflammatory agents include any anti-inflammatory agent useful in treating inflammatory disorders. Non-limiting examples of anti-inflammatory agents include non-steroidal anti-inflammatory drugs (NSAIDs), steroidal anti-inflammatory drugs, anticholinergics (e.g., atropine sulfate, atropine methylnitrate, and ipratropium bromide (ATROVENT®), $\beta$2-agonists (e.g., albuterol (VENTOLIN® and PROVENTIL®), bitolterol (TORNALATE®), levalbuterol (XOPONEX®), metaproterenol (ALUPENT®), pirbuterol (MAXAIR®), terbutlaine (BRETHAIRE® and BRETHINE®), albuterol (PROVENTIL®, REPETABS®, and VOLMAX®), formoterol (FORADIL AEROLIZER®), salmeterol (SEREVENT® and SEREVENT DISKUS®)), methylxanthines (e.g., theophylline (UNIPHYL®, THEO-DUR®, SLO-BID®, AND TEHO-42®)) and the like. Examples of NSAIDs include, but are not limited to, aspirin, ibuprofen, celecoxib (CELEBREX®), diclofenac (VOLTAREN®), etodolac (LODINE®), fenoprofen (NALFON®), indomethacin (INDOCIN®), ketorolac (TORADOL®), oxaprozin (DAYPRO®), nabumentone (RELAFEN®), sulindac (CLINORIL®), tolmentin (TOLECTIN®), rofecoxib (VIOXX®), naproxen (ALEVE®, NAPROSYN®), ketoprofen (ACTRON®), nabumetone (RELAFEN®) and the like. Such NSAIDs function by inhibiting a cyclooxgenase enzyme (e.g., COX-1 and/or COX-2). Examples of steroidal anti-inflammatory drugs include, but are not limited to, glucocorticoids, dexamethasone (DECADRON®), corticosteroids (e.g., methylprednisolone (MEDROL®), cortisone, hydrocortisone, prednisone (PREDNISONE® and DELTASONE®), prednisolone (PRELONE® and PEDIAPRED®), triamcinolone, azulfidine, inhibitors of eicosanoids (e.g., prostaglandins, thromboxanes, and leukotrienes) and the like.

In certain embodiments, the additional agent that may be used in combination with a compound of Formula (I) or a form thereof described herein is an alkylating agent, a nitrosourea, an antimetabolite, an anthracyclin, a topoisomerase II inhibitor, a mitotic inhibitor and the like. Alkylating agents include, but are not limited to, busulfan, cisplatin, carboplatin, cholormbucil, cyclophosphamide, ifosfamide, decarbazine, mechlorethamine, mephalen, themozolomide and the like. Nitrosoureas include, but are not limited to carmustine (BiCNU®), lomustine (CeeNU®) and the like. Antimetabolites include, but are not limited to, 5-fluorouracil, capecitabine, methotrexate, gemcitabine, cytarabine, fludarabine and the like. Anthracyclins include but are not limited to daunorubicin, doxorubicin, epirubicin, idarubicin, mitoxantrone and the like. Topoisomerase II inhibitors include, but are not limited to, topotecan, irinotecan, etopiside (VP-16), teniposide and the like. Mitotic inhibitors include, but are not limited to taxanes (paclitaxel, docetaxel), and the vinca alkaloids (vinblastine, vincristine, and vinorelbine) and the like.

In more specific embodiments, the additional anti-cancer agent, anti-proliferative agent or chemotherapeutic agent that may be used in combination with a compound of Formula (I) or a form thereof described herein includes, and is not limited to aflibercept, amsacrine, bleomycin, busulfan, capecitabine, carboplatin, carmustine, chlorambucil, cisplatin, cladribine, clofarabine, crisantaspase, cyclophosphamide, cytarabine, dacarbazine, dactinomycin, daunorubicin (IV and liposomal), docetaxel, doxorubicin (IV and liposomal), enzastaurin, epirubicin, etoposide, fludarabine, 5-fluorouracil (5-FU), gemcitabine, gliadel implants, hydroxycarbamide, idarubicin, ifosfamide, imatinib mesylate, irinotecan, lanreotide, lenalidomide, leucovorin, lomustine, melphalan, mercaptopurine, mesna, methotrexate, mitomycin, mitoxantrone, octreotide, oxaliplatin, paclitaxel, pemetrexed, pentostatin, procarbazine, raltitrexed, satraplatin, sorafenib, streptozocin, sunitinib, tegafur-uracil, temozolomide, teniposide, thalidomide, thiotepa, tioguanine, topotecan, treosulfan, vatalanib, vinblastine, vincristine, vindesine, vinorelbine, volitinib, ZD6474, monoclonal antibodies (such as bevacizumab, cetuximab, IMC-A12, IMC-1121B, medi-522, rituximab and the like), hormonal agents (such as anastrozole, bicalutamide, buserelin, cyproterone, diethylstilbestrol, exemestane, flutamide, goserelin (breast and prostrate), letrozole, leuprorelin, medroxyprogesterone, megestrol acetate, tamoxifen, toremifene, triptorelin and the like), biological agents (such as interferon, interleukin-12 and the like), angiogenesis receptor tyrosine kinase (RTK) inhibitors (such as AE-941, angiostatin, carboxyamidotriazole, cilengitide, endostatin, halofuginone hydrobromide, 2-methoxyestradiol, squalamine lactate, SU6668 and the like), tubulin binding agents (such as combretastatin A4 phosphate and the like), matrix metalloproteinase inhibitors (such as BMS-275291 and the like) and/or serine/threonine/tyrosine kinase inhibitors and an optional nonsteroidal or COX-2 anti-inflammatory agents (such as celecoxib and the like) or corticosteroid (such as prednisone and the like).

In more particular embodiments, one or more additional anti-cancer, anti-proliferative or chemotherapeutic agents that may be used in combination with a compound of Formula (I) or a form thereof described herein is selected from bevacizumab, carboplatin, cisplatin, docetaxel, doxorubicin, exemestane, gemcitabine, 5-fluorouracil, imatinib, irinotecan, sorafenib, sunitinib, temozolomide, volitinib or combinations thereof.

In some embodiments, a compound of Formula (I) or a form thereof described herein and one or more additional anti-cancer, anti-proliferative or chemotherapeutic agents is used in combination with radiation therapy comprising the use of x-rays, gamma rays and other sources of radiation to destroy cancer cells or tumor cells. In specific embodiments, the radiation therapy is administered as external beam radiation or teletherapy, wherein the radiation is directed from a remote source. In other embodiments, the radiation therapy is administered as internal therapy or brachytherapy wherein a radioactive source is placed close to cancer cells, tumor cells and/or a tumor mass.

Currently available anti-cancer, anti-proliferative or chemotherapeutic agents, their dosage regimens, routes of administration and recommended usage alone or in combination are known in the art and have been described in literature such as the *Physician's Desk Reference*.

Any anti-cancer, anti-proliferative or chemotherapeutic agent or anti-cancer therapy which is known to be useful, or which has been used or is currently being used for the treatment of a cancer mediated by Bmi-1, can be used in combination with compounds of Formula (I) or a form thereof described herein. See, e.g., Gilman et al., Goodman and Gilman's: The Pharmacological Basis of Therapeutics, 10th ed., McGraw-Hill, New York, 2001; The Merck Manual of Diagnosis and Therapy, Berkow, M. D. et al. (eds.), 17th Ed., Merck Sharp & Dohme Research Laboratories, Rahway, N J, 1999; Cecil Textbook of Medicine, 20th Ed., Bennett and Plum (eds.), W.B. Saunders, Philadelphia, 1996, and Physician's Desk Reference for information regarding cancer therapies (e.g., using prophylactic or therapeutic agents) which have been or are currently being used for preventing, treating and/or managing a cancer mediated by Bmi-1.

Pharmaceutical Compositions

The present description is also directed to a pharmaceutical composition comprising an effective amount of a compound of Formula (I) or a form thereof in admixture with a pharmaceutically acceptable excipient.

An embodiment described herein includes a pharmaceutical composition made by the process of admixing a compound of Formula (I) or a form thereof with a pharmaceutically acceptable excipient. The pharmaceutical composition may also be formulated to achieve a physiologically compatible pH of about pH 7, ranging from about pH 3 to about pH 11.

Another embodiment of the present includes the use of a compound of Formula (I) or a form thereof in a pharmaceutical composition for use in treating a cancer mediated by Bmi-1 comprising an effective amount of a compound of Formula (I) or a form thereof in admixture with a pharmaceutically acceptable excipient.

As used herein, the term "composition" means a product comprising the specified ingredients in the specified amounts, as well as any product which results, directly or indirectly, from combination of the specified ingredients in the specified amounts.

In another embodiment, the pharmaceutical composition may comprise a combination product of one or more compounds of Formula (I) or a form thereof described herein and one or more additional agents useful in the treatment of a cancer mediated by Bmi-1, such as an anti-cancer, anti-proliferative, chemotherapeutic or biochemotherapeutic agent.

The term "pharmaceutically acceptable excipient" refers to a pharmacologically inactive substance formulated for administration with an active pharmaceutical agent, such as the compounds of Formula (I) or a form thereof described herein. The term refers to any pharmaceutical excipient that may be administered without undue toxicity. Pharmaceutically acceptable excipients may be determined in part by the particular composition being administered, as well as by the particular mode of administration and/or dosage form. Non-limiting examples of pharmaceutically acceptable excipients include carriers, solvents, stabilizers, adjuvants, diluents, etc. Accordingly, there exists a wide variety of suitable formulations of pharmaceutical compositions as described herein (see, e.g., Remington's Pharmaceutical Sciences).

Suitable excipients may be carrier molecules that include large, slowly metabolized macromolecules such as proteins, polysaccharides, polylactic acids, polyglycolic acids, polymeric amino acids, amino acid copolymers, and inactive virus particles. Other exemplary excipients include antioxidants such as ascorbic acid; chelating agents such as EDTA; carbohydrates such as dextrin, hydroxyalkylcellulose, hydroxyalkylmethylcellulose, stearic acid; liquids such as oils, water, saline, glycerol and ethanol; wetting or emulsifying agents; pH buffering substances; and the like. Liposomes are also included within the definition of pharmaceutically acceptable excipients.

The pharmaceutical compositions described herein may be formulated in any form suitable for the intended method of administration. Suitable formulations for oral administration include solids, liquid solutions, emulsions and suspensions, while suitable inhalable formulations for pulmonary administration include liquids and powders. Alternative formulations include syrups, creams, ointments, tablets, and lyophilized solids which can be reconstituted with a physiologically compatible solvent prior to administration.

When intended for oral use for example, tablets, troches, lozenges, aqueous or oil suspensions, non-aqueous solutions, dispersible powders or granules (including micronized particles or nanoparticles), emulsions, hard or soft capsules, syrups or elixirs may be prepared. Compositions intended for oral use may be prepared according to any method known to the art for the manufacture of pharmaceutical compositions, and such compositions may contain one or more agents including sweetening agents, flavoring agents, coloring agents and preserving agents, in order to provide a palatable preparation.

Pharmaceutically acceptable excipients suitable for use in conjunction with tablets include, for example, inert fillers, such as celluloses, calcium or sodium carbonate, lactose, calcium or sodium phosphate; disintegrating agents, such as croscarmellose sodium, cross-linked povidone, maize starch, or alginic acid; binding agents, such as povidone, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period.

Formulations for oral use may be also presented as hard gelatin capsules where the active ingredient is mixed with an inert solid diluent, for example celluloses, lactose, calcium phosphate or kaolin, or as soft gelatin capsules wherein the active ingredient is mixed with non-aqueous or oil medium, such as glycerin, propylene glycol, polyethylene glycol, peanut oil, liquid paraffin or olive oil.

In other embodiments, pharmaceutical compositions described herein may be formulated as suspensions comprising a compound of Formula (I) or a form thereof described herein in admixture with at least one pharmaceutically acceptable excipient suitable for the manufacture of a suspension. In yet other embodiments, pharmaceutical compositions described herein may be formulated as dispersible powders and granules suitable for preparation of a suspension by the addition of one or more excipient(s).

Excipients suitable for use in connection with suspensions include suspending agents, such as sodium carboxymethylcellulose, methylcellulose, hydroxypropyl methylcelluose, sodium alginate, polyvinylpyrrolidone, gum tragacanth, gum acacia, dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate); and thickening agents, such as carbomer, beeswax, hard paraffin or cetyl alcohol. The suspensions may also contain one or more preservatives such as acetic acid, methyl and/or n-propyl p-hydroxy-benzoate; one or more coloring agents; one or more flavoring agents; and one or more sweetening agents such as sucrose or saccharin.

The pharmaceutical compositions described herein may also be in the form of oil-in-water emulsions. The oily phase may be a vegetable oil, such as olive oil or *arachis* oil, a mineral oil, such as liquid paraffin, or a mixture of these. Suitable emulsifying agents include naturally-occurring gums, such as gum acacia and gum tragacanth; naturally occurring phosphatides, such as soybean lecithin, esters or partial esters derived from fatty acids; hexitol anhydrides, such as sorbitan monooleate; and condensation products of these partial esters with ethylene oxide, such as polyoxyethylene sorbitan monooleate. The emulsion may also contain sweetening and flavoring agents. Syrups and elixirs may be formulated with sweetening agents, such as glycerol, sorbitol or sucrose. Such formulations may also contain a demulcent, a preservative, a flavoring or a coloring agent.

Additionally, the pharmaceutical compositions described herein may be in the form of a sterile injectable preparation, such as a sterile injectable aqueous emulsion or oleaginous suspension. Such emulsion or suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,2-propane-diol. The sterile injectable preparation may also be prepared as a lyophilized powder. Among the acceptable vehicles and solvents that may be employed are water, Ringer's solution, isotonic sodium chloride solution and the like. In addition, sterile fixed oils may be employed as a solvent or suspending medium. For this purpose any bland fixed oil may be employed including synthetic mono- or di-glycerides. In addition, fatty acids such as oleic acid may likewise be used in the preparation of injectables.

The compounds of Formula (I) or a form thereof described herein may be substantially modified by substitutions or additions of chemical or biochemical moieties which make them more suitable for delivery (e.g., increase solubility, bioactivity, palatability, decrease adverse reactions, etc.), for example by esterification, glycosylation, PEGylation and the like.

In some embodiments, the compound of Formula (I) or a form thereof described herein is formulated for oral administration in formulations that enhance the oral bioavailability of such compounds of Formula (I) or a form thereof. As such, pharmaceutical compositions described herein may comprise a effective amount of a compound of Formula (I) or a form thereof, together with at least one pharmaceutically acceptable excipient selected from medium chain fatty acids or propylene glycol esters thereof (e.g., propylene glycol esters of edible fatty acids such as caprylic and capric fatty acids) and pharmaceutically acceptable surfactants, such as polyoxyl 40 hydrogenated castor oil and the like.

In other embodiments, the bioavailability of a compound of Formula (I) or a form thereof may be enhanced by using particle size optimization techniques including, but not limited to, the preparation of nanoparticles or nanosuspensions using techniques known to those skilled in art. The compound forms present in such preparations include amorphous, partially amorphous, partially crystalline or crystalline forms.

In alternative embodiments, the pharmaceutical composition may further comprise one or more aqueous solubility enhancer(s), such as a cyclodextrin. Nonlimiting examples of cyclodextrin include hydroxypropyl, hydroxyethyl, glucosyl, maltosyl and maltotriosyl derivatives of α-, β-, and γ-cyclodextrin, and hydroxypropyl-β-cyclodextrin (HPBC). In some embodiments, the pharmaceutical composition further comprises HPBC in a range of from about 0.1% to about 20%, from about 1% to about 15%, or from about 2.5% to about 10%. The amount of solubility enhancer employed may depend on the amount of the active pharmaceutical ingredient in the composition.

GENERAL SYNTHETIC EXAMPLES

As disclosed herein, the methods for preparing the compounds of Formula (I) or a form thereof described herein commonly use standard, well-known synthetic methodology. Many of the starting materials are commercially available or can be prepared in the Specific Synthetic Examples that follow using techniques known to those skilled in the art. Functional transformations to modify substituents may also be undertaken where chemically feasible and are considered to be included within the scope of the General Schemes and the knowledge of a person of ordinary skill in the art. Compounds of Formula (I) or a form thereof can be prepared as described in the Schemes below.

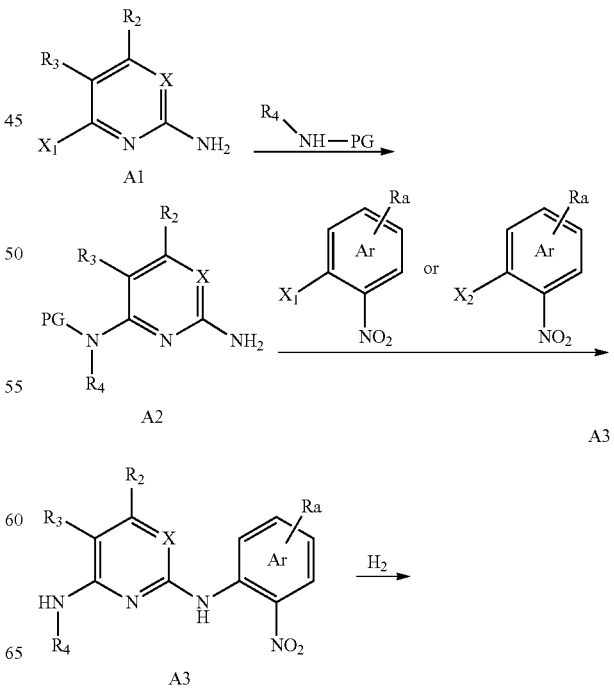

Scheme A Benzimidazole Substituted Pyrimidine Compounds

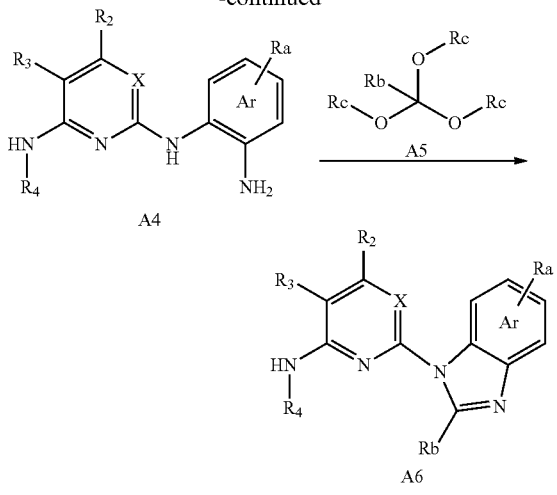

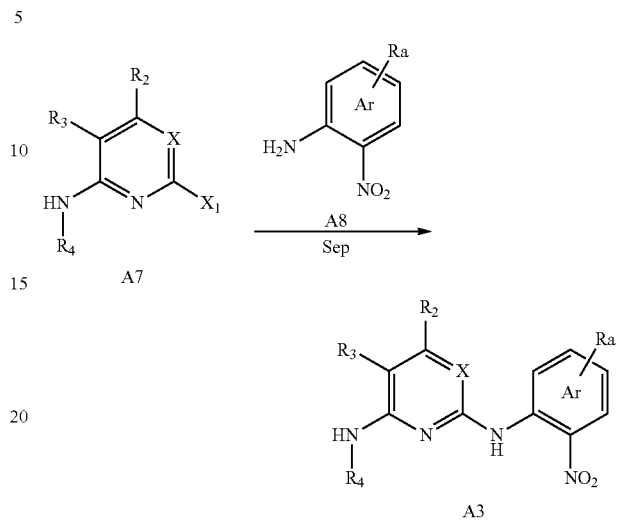

An amine substituted Compound A1 (wherein $X_1$ represents a halogen atom selected from bromo, chloro or iodo) is coupled with various substituted aryl, heteroaryl or heterocyclyl amines (wherein PG represents an optionally present protecting group monosubstituted on the amine) in the presence of a strong base (such as KOtBu, NaOtBu, NaO$^t$Am, NaH, NaHMDS and the like) in a solvent (such as THF, DMF and the like) to provide a Compound A2.

When one or both of $R_2$ and $R_3$ are optionally halogen, the product Compound A2 is obtained as a mixture of regioisomers, wherein the term "Sep" refers to isolating the desired Compound A2 isomer to be carried forward from the mixture using separation techniques known to those of ordinary skill in the art, followed by deprotection.

Alternatively, Compound A2 may be prepared by reacting Compound A1 with various substituted aryl, heteroaryl or heterocyclyl amines (wherein the protecting group is absent) in the presence of a mixture of a phosphino ligand:palladium source (wherein the palladium source is selected from Pd$_2$(dba)$_3$, PdCl$_2$(allyl), PdCl$_2$(ACN), [Pd(OAc)$_2$]$_3$ and the like and the phosphino ligand is selected from PCy$_3$, Q-Phos, XPhos and the like; alternatively, a commercially available catalyst such as Pd(dppf)Cl$_2$, Pd(PPh$_3$)$_4$ and the like may be used), followed by separation as needed.

Compound A3 may be prepared by reacting Compound A2 with a substituted ortho-halo-nitro benzene (wherein $X_1$ represents a halogen atom selected from bromo, chloro or iodo) in the presence of a transition metal catalyst (such as a catalyst containing a metal selected from copper, palladium and the like).

Alternatively, Compound A3 may be prepared by reacting Compound A2 with the substituted ortho-halo-nitro benzene (wherein $X_2$ represents a halogen atom selected from bromo, chloro, fluoro or iodo) in the presence of a strong base (such as KOtBu, NaOtBu, NaO$^t$Am, NaH, NaHMDS and the like) in a solvent (such as THF, DMF and the like).

Compound A4 is prepared by reacting Compound A3 in the presence of hydrogen and a catalyst (such as nickel, platinum, palladium on carbon and the like).

Compound A6 is prepared by condensation of Compound A4 with an orthoester Compound A5 (wherein Rb represents an additional optional $R_5$ substituent and Rc represents $C_{1-3}$alkyl). Compound A6 may also be prepared by cyclizing Compound A4 with a variety of reactants to obtain the addition of the optional $R_5$ substituent. For example, the reactant may be TCDI, wherein the additional optional $R_5$ substituent is a thio-carbonyl which may be further substituted.

Alternatively, Compound A3 is prepared by cross-coupling of Compound A7 (wherein $X_1$ represents a halogen atom selected from bromo, chloro or iodo) with a nitro substituted amine Compound A8 (wherein Ar represents an aromatic or heteroaromatic ring; and, wherein Ra represents one, two or three optional $R_5$ substituents) via a palladium catalyzed cross-coupling reaction using a mixture of a phosphino ligand:palladium source (wherein the palladium source is selected from Pd$_2$(dba)$_3$, PdCl$_2$(allyl), PdCl$_2$(ACN), [Pd(OAc)$_2$]$_3$ and the like and the phosphino ligand is selected from PCy$_3$, Q-Phos, XPhos and the like; alternatively, a commercially available catalyst such as Pd(dppf)Cl$_2$, Pd(PPh$_3$)$_4$ and the like may be used).

When one or both of $R_2$ and $R_3$ are optionally halogen, the product Compound A3 is obtained as a mixture of regioisomers, wherein the term "Sep" refers to isolating the desired Compound A3 isomer to be carried forward from the mixture using separation techniques known to those of ordinary skill in the art.

Scheme B Imidazo[1,2-a]pyridine Substituted Pyrimidine Compounds

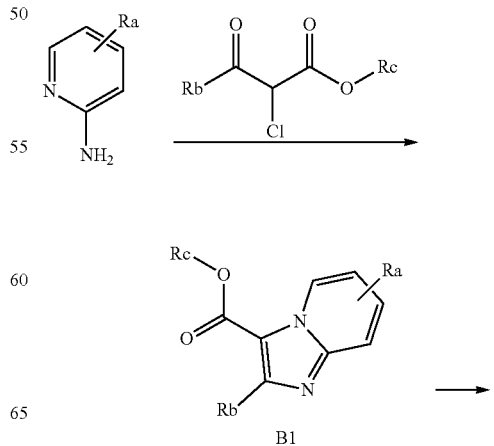

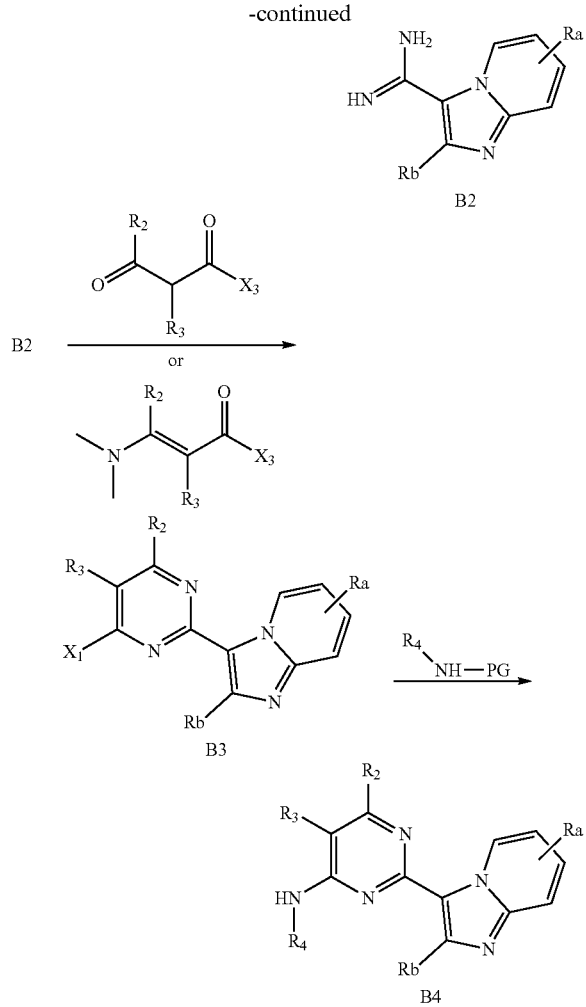

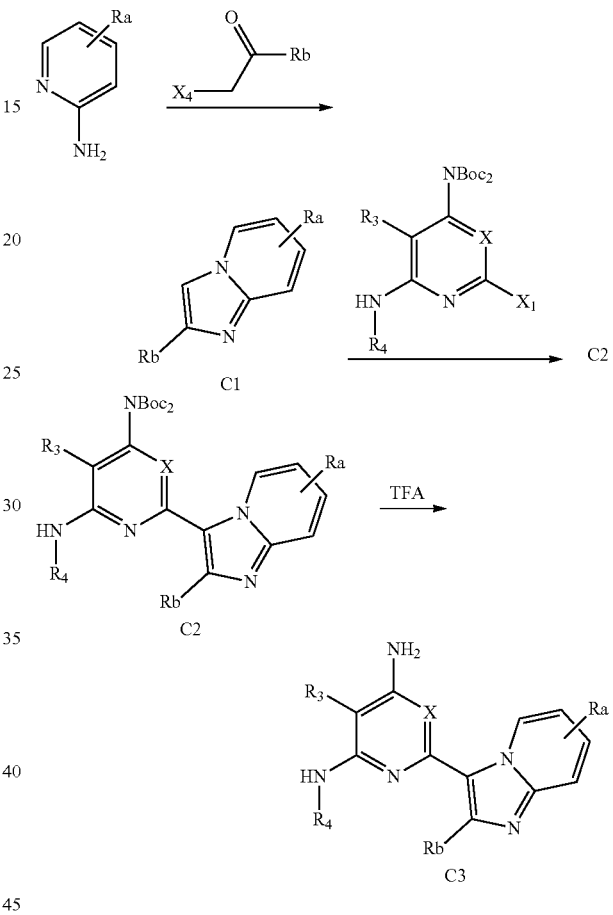

Compound B1 is prepared by condensation of a substituted 2-amino-pyridine (wherein Ra represents one, two or three optional $R_5$ substituents) with an α-halogenated ketoester (wherein Rb represents an additional optional $R_5$ substituent and Rc represents $C_{1-3}$alkyl).

Compound B2 is prepared by treating Compound B1 with an ammonia source (such as $NH_4Cl$, $NH_3$ and the like) in the presence of an organoaluminum reagent (such $AlMe_3$ in toluene and the like).

Compound B3 (wherein $X_1$ represents a halogen atom selected from bromo, chloro or iodo) is prepared by condensation of Compound B2 with a substituted alkyl ester (such as a β-keto ester or a substituted acrylate in a solvent such as phenyl ether and the like; wherein $X_3$ represents a leaving group such as $C_{1-3}$alkoxy, benzoxy or halogen) followed by reflux in the presence of a halogenation reagent (such as $POCl_3$, $POBr_3$ and the like).

Compound B4 is prepared by coupling Compound B3 with various substituted aryl, heteroaryl or heterocyclyl amines (wherein PG represents an optionally present protecting group monosubstituted on the amine) in the presence of a strong base (such as KOtBu, NaOtBu, $NaO^tAm$, NaH, NaHMDS and the like) in a solvent (such as THF, DMF and the like).

Alternatively, Compound B4 may be prepared by reacting Compound B3 with a substituted aryl, heteroaryl or heterocyclyl amine (wherein the protecting group is absent) via a palladium catalyzed cross-coupling reaction using a mixture of a phosphino ligand:palladium source (wherein the palladium source is selected from $Pd_2(dba)_3$, $PdCl_2$(allyl), $PdCl_2$(ACN), $[Pd(OAc)_2]_3$ and the like and the phosphino ligand is selected from $PCy_3$, Q-Phos, XPhos and the like; alternatively, a commercially available catalyst such as Pd(dppf)$Cl_2$, $Pd(PPh_3)_4$ and the like may be used).

Scheme C 4,6-Diamino Substituted Pyrimidine Compounds

Compound C1 is prepared by condensation of a substituted 2-amino-pyridine (wherein Ra represents one, two or three optional $R_5$ substituents) and an α-halogenated ketone (wherein $X_4$ represents a leaving group such as chloro or bromo and Rb represents an additional optional $R_5$ substituent) at reflux in an organic solvent (such as acetonitrile and the like).

Compound C2 is prepared by reacting Compound C1 with a substituted pyrimidine compound (wherein $X_1$ represents a halogen atom selected from bromo, chloro or iodo) via a palladium catalyzed cross-coupling reaction using a mixture of a phosphino ligand:palladium source (wherein the palladium source is selected from $Pd_2(dba)_3$, $PdCl_2$(allyl), $PdCl_2$(ACN), $[Pd(OAc)_2]_3$ and the like and the phosphino ligand is selected from $PCy_3$, Q-Phos, XPhos and the like; alternatively, a commercially available catalyst such as Pd(dppf)$Cl_2$, $Pd(PPh_3)_4$ and the like may be used) and at least 2 equivalents of a base (such as cesium acetate and the like) in an organic solvent (such as dimethylacetamide and the like), undergoing Heck coupling. The reaction may be carried out at elevated temperatures up to 100° C.

Compound C3 is prepared by treating Compound C2 with a deprotection reagent (such as 20-40% TFA in DCM and the like) at ambient or elevated temperature.

Scheme D 4,6-Diamino Substituted Pyrimidine Compounds

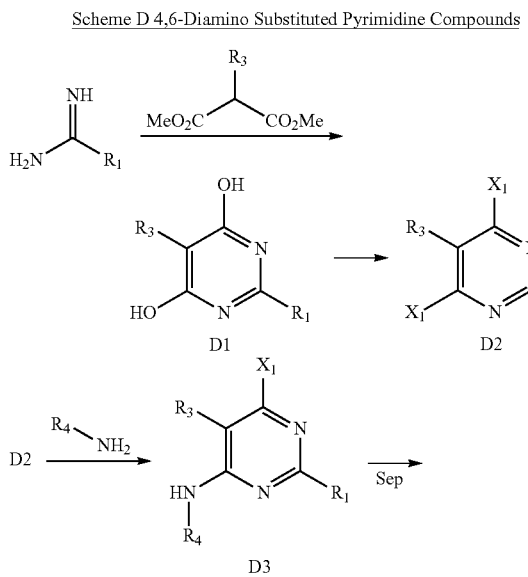

Compound D1 is prepared by a condensation reaction with a substituted malonate compound and an amidated $R_1$ group in solution with a sodium alkoxide-solvent mixture (such as NaOMe in MeOH or NaOEt in EtOH and the like).

Compound D2 (wherein $X_1$ represents a halogen atom selected from bromo, chloro or iodo) is prepared by refluxing Compound D1 in the presence of a halogenation reagent (such as $POCl_3$, $POBr_3$ and the like).

Compound D3 is prepared by mono-amination of Compound D2 with various substituted aryl, heteroaryl or heterocyclyl amines in a solvent (wherein the solvent is selected from EtOH, THF, DMF, mixtures thereof and the like).

Compound D4 is prepared by treating Compound D3 with an aqueous ammonia source in a mixture with a solvent (wherein the solvent is selected from $CH_3CN$, DMSO, mixtures thereof and the like).

Scheme E Benzimidazole Substituted Pyrimidine Compounds

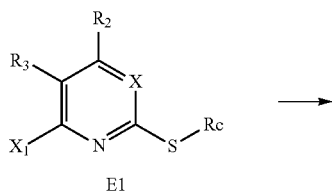

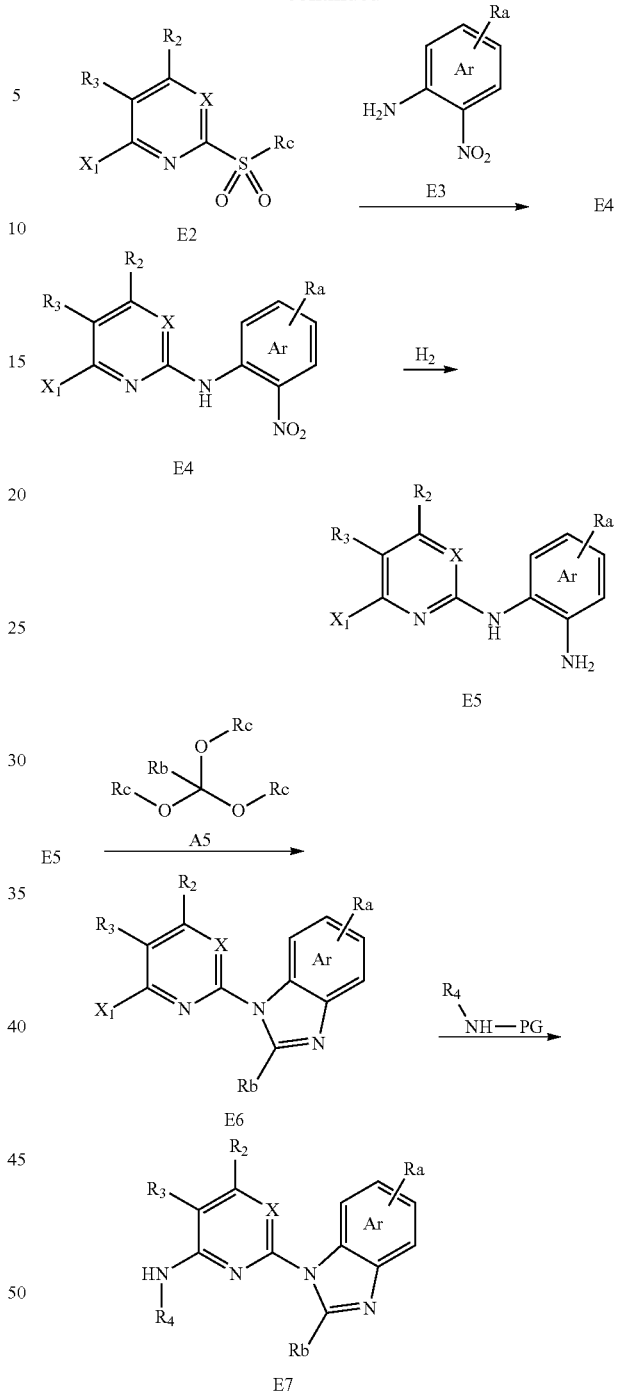

A 2-methylsulfonyl substituted Compound E2 is prepared by reacting a 2-methylthio substituted pyrimidine Compound E1 (wherein $X_1$ represents a halogen atom selected from bromo, chloro or iodo and Rc represents $C_{1-3}$alkyl) with an oxidizing agent (such as mCPBA, MPS and the like) in a solvent (such as $CH_2Cl_2$ and the like) at a suitable temperature.

Compound E4 is prepared by reacting Compound E2 with a nitro substituted amine Compound E3 (wherein Ar represents an aromatic or heteroaromatic ring; and, wherein Ra represents one, two or three optional $R_5$ substituents) in the presence of a strong base (such as KOtBu, NaOtBu, NaOʳAm, NaH, NaHMDS and the like) in a solvent (such as THF, DMF and the like). The amine substituent on Compound E3 may be optionally monosubstituted on the amine with a protecting group.

Compound E5 is prepared by reacting Compound E4 in the presence of hydrogen and a catalyst (such as nickel, platinum, palladium on carbon and the like).

Compound E6 is prepared by condensation of Compound E5 with an orthoester Compound A5 (wherein Rb represents an additional optional $R_5$ substituent and Rc represents $C_{1-3}$alkyl). Compound E6 may also be prepared by cyclizing Compound E5 with a variety of reactants to obtain the addition of an optional $R_5$ substituent. For example, the reactant may be TCDI, wherein the additional optional $R_5$ substituent is a thio-carbonyl which may be further substituted.

Compound E7 may be prepared by reacting Compound E6 with various substituted aryl, heteroaryl or heterocyclyl amines in a solvent (wherein the solvent is selected from EtOH, THF, DMF, mixtures thereof and the like).

When $R_3$ is optionally halogen, the product Compound E7 is obtained as a mixture of regioisomers, wherein the term "Sep" refers to isolating the desired Compound E7 isomer to be carried forward from the mixture using separation techniques known to those of ordinary skill in the art, followed by deprotection.

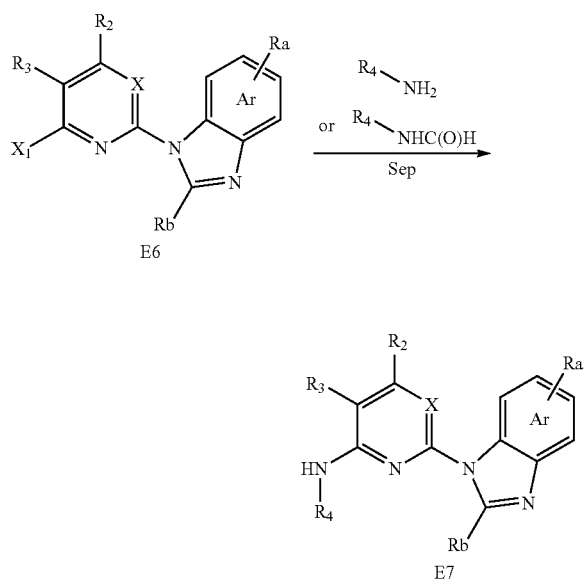

Alternatively, Compound E7 may be prepared by reacting Compound E6 with a substituted aryl, heteroaryl or heterocyclyl amine or amide (wherein the protecting group is absent) via a palladium catalyzed cross-coupling reaction using a mixture of a phosphino ligand:palladium source (wherein the palladium source is selected from $Pd_2(dba)_3$, $PdCl_2$(allyl), $PdCl_2$(ACN), $[Pd(OAc)_2]_3$ and the like and the phosphino ligand is selected from $PCy_3$, Q-Phos, XPhos and the like; alternatively, a commercially available catalyst such as Pd(dppf)$Cl_2$, Pd(PPh$_3$)$_4$ and the like may be used).

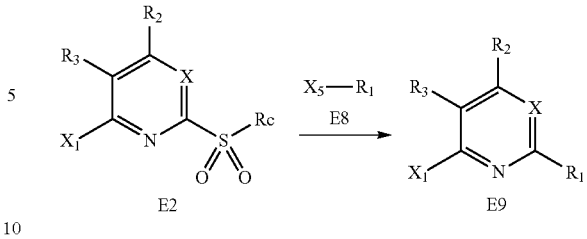

Compound E9 may be prepared directly by reacting Compound E2 with a Compound E8 (such as an $R_1$ substituent having an acidic proton group, wherein $X_5$ represents a reactive hydrogen atom) in the presence of a strong base (such as KOtBu, NaOtBu, NaOʳAm, NaH, NaHMDS and the like). Compound E9 may be carried forward in place to Compound E6 to provide a Compound of Formula (I).

Scheme F Substituted Pyrimidine Compounds

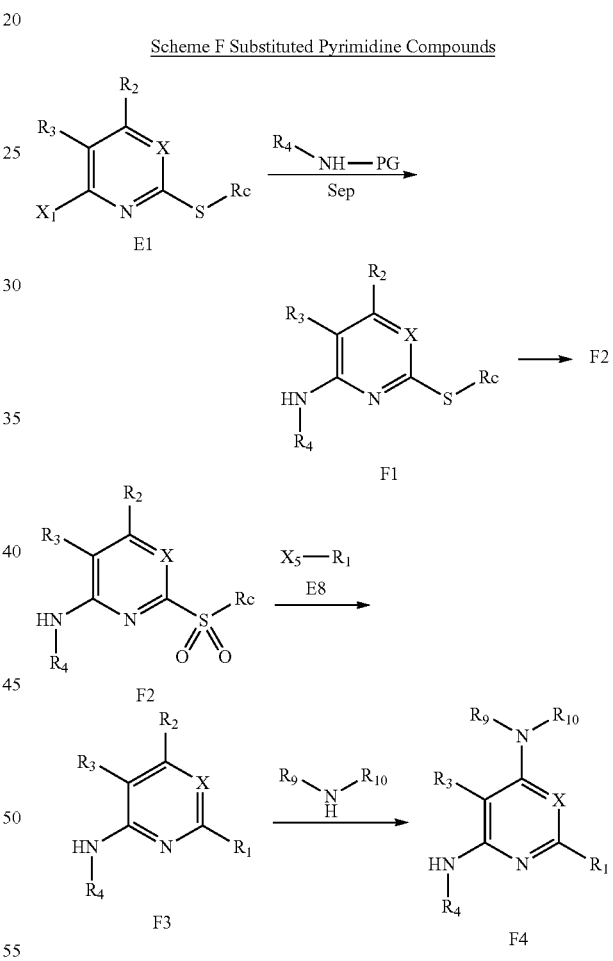

Compound F1 is prepared by reacting Compound E1 (wherein $X_1$ represents a halogen atom selected from bromo, chloro or iodo and Rc represents $C_{1-3}$alkyl) with a substituted aryl, heteroaryl or heterocyclyl amine (wherein PG represents an optionally present protecting group monosubstituted on the amine) in the presence of a strong base (such as KOtBu, NaOtBu, NaOʳAm, NaH, NaHMDS and the like) in a solvent (such as THF, DMF and the like) at a suitable temperature.

When $R_3$ is optionally halogen, the product Compound F1 is obtained as a mixture of regioisomers, wherein the term "Sep" refers to isolating the desired Compound F1 isomer to be carried forward from the mixture using separation techniques known to those of ordinary skill in the art.

Alternatively, Compound F1 is prepared by reacting Compound E1 with a substituted aryl, heteroaryl or heterocyclyl amine or amide (wherein the protecting group is absent) via a palladium catalyzed cross-coupling reaction using a mixture of a phosphino ligand:palladium source (wherein the palladium source is selected from $Pd_2(dba)_3$, $PdCl_2(allyl)$, $PdCl_2(ACN)$, $[Pd(OAc)_2]_3$ and the like and the phosphino ligand is selected from $PCy_3$, Q-Phos, XPhos and the like; alternatively, a commercially available catalyst such as $Pd(dppf)Cl_2$, $Pd(PPh_3)_4$ and the like may be used).

Compound F2 is prepared by reacting Compound F1 with an oxidizing agent (such as mCPBA, MPS and the like) in a solvent (such as $CH_2Cl_2$ and the like).

Compound F2 may be reacted with a Compound E8 (such as an $R_1$ substituent having an acidic proton group, wherein $X_5$ represents a reactive hydrogen atom) in the presence of a strong base (such as KOtBu, NaOtBu, NaO$^t$Am, NaH, NaHMDS and the like) to provide a Compound F3, representative of a Compound of Formula (I).

When $R_2$ is halogen, Compound F3 may be treated with a substituted amine in a mixture with a solvent (wherein the solvent is selected from $CH_3CN$, DMSO, mixtures thereof and the like) to provide a Compound F4, representative of a Compound of Formula (III).

Scheme G Oxide Substituted Pyrimidine Compounds

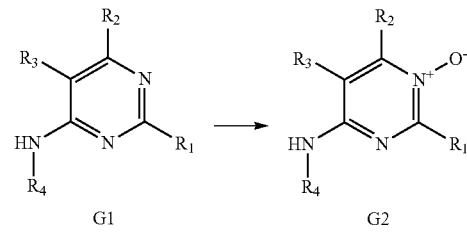

Compound G1 may be reacted with an oxidizing agent (such as mCPBA, MPS and the like) to provide a Compound G2, representative of a Compound of Formula (IV).

Scheme H Substituted Pyrimidine Compounds

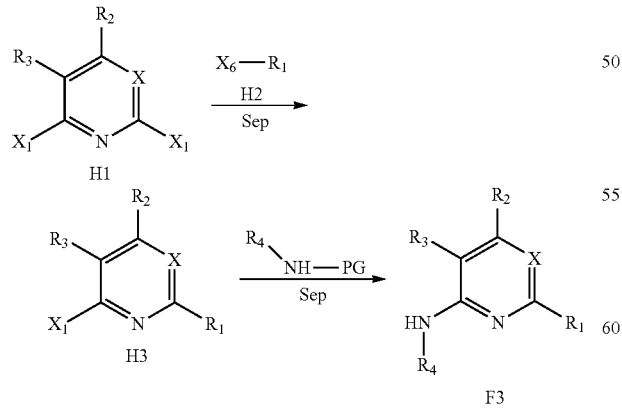

A Compound H3 is prepared by reacting a Compound 111 (wherein $X_1$ represents a halogen atom selected from bromo, chloro or iodo) with a Compound 112 (wherein $R_1$ is a substituted heteroaromatic or heterocyclic monocyclic or bicyclic ring system and $X_6$ represents a reactive group such as a boronic acid, boronate ester, trialkyltin, zinc chloride and the like attached to a carbon atom of $R_1$), in the presence of a mixture of a phosphino ligand:palladium source (wherein the palladium source is selected from $Pd_2(dba)_3$, $PdCl_2(allyl)$, $PdCl_2(ACN)$, $[Pd(OAc)_2]_3$ and the like and the phosphino ligand is selected from $PCy_3$, Q-Phos, XPhos and the like; alternatively, a commercially available catalyst such as $Pd(dppf)Cl_2$, $Pd(PPh_3)_4$ and the like may be used).

When one or both of $R_2$ and $R_3$ are optionally halogen, the product Compound H3 may be obtained as a mixture of regioisomers, wherein the term "Sep" refers to isolating the desired Compound H3 isomer to be carried forward from the mixture using separation techniques known to those of ordinary skill in the art.

Compound F3 is prepared by reacting Compound H3 with various substituted aryl, heteroaryl or heterocyclyl amines in a solvent (wherein PG represents an optionally present protecting group monosubstituted on the amine; and, wherein the solvent is selected from EtOH, THF, DMF, mixtures thereof and the like), followed by separation and deprotection as needed.

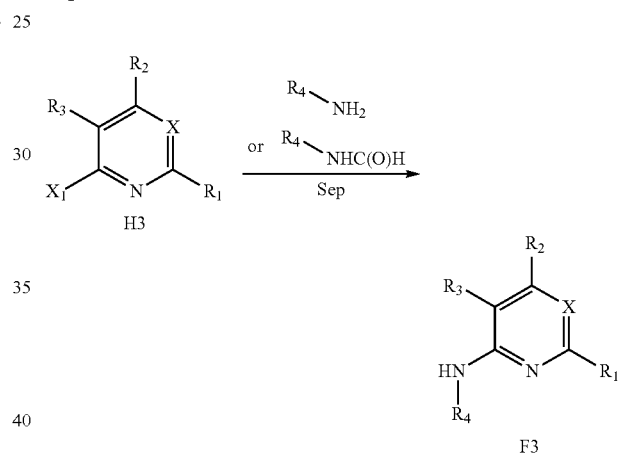

Alternatively, Compound F3 is prepared by reacting a Compound H3 with various substituted aryl, heteroaryl or heterocyclyl amines or amides in the presence of a mixture of a phosphino ligand:palladium source (wherein the palladium source is selected from $Pd_2(dba)_3$, $PdCl_2(allyl)$, $PdCl_2$ (ACN), $[Pd(OAc)_2]_3$ and the like and the phosphino ligand is selected from $PCy_3$, Q-Phos, XPhos and the like; alternatively, a commercially available catalyst such as $Pd(dppf)Cl_2$, $Pd(PPh_3)_4$ and the like may be used). When a Compound H3 is reacted with an amide, the resulting intermediate product is hydrolyzed under basic conditions with a reagent (such as NaOH, KOH, LiOH and the like) at a suitable temperature, followed by separation as needed to obtain product Compound F3.

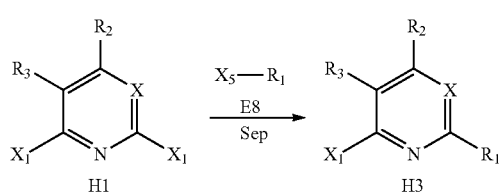

Alternatively, Compound H3 may be prepared via a Heck reaction of Compound 111 with Compound E8, followed by separation as needed.

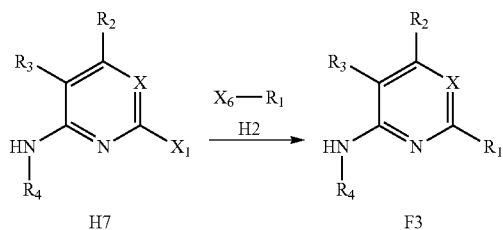

Alternatively, Compound F3 is prepared by reacting Compound 117 with a substituted Compound 112 (wherein $R_1$ is a substituted heteroaromatic or heterocyclic monocyclic or bicyclic ring system and $X_6$ represents a reactive group such as a boronic acid, boronate ester, trialkyltin, zinc chloride and the like attached to a carbon atom of $R_1$).

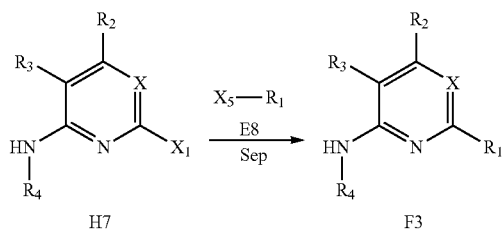

Alternatively, Compound F3 may be prepared via a Heck reaction of Compound 117 with Compound E8 (wherein $X_5$ represents a reactive hydrogen group), followed by separation as needed.

Scheme I Substituted Pyrimidine Compounds

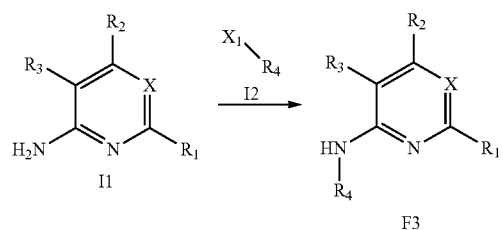

Compound F3 is prepared by reacting a substituted Compound I1 with a Compound 12 (such as various substituted aryl, heteroaryl or heterocyclyl ring systems, wherein $X_1$ represents a halogen atom selected from bromo, chloro or iodo) in the presence of a transition metal catalyst (such as a catalyst containing a metal selected from copper, palladium and the like).

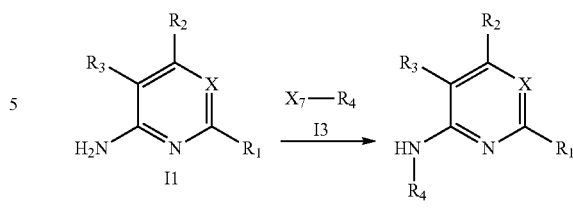

Compound F3 is prepared by reacting a substituted Compound I1 with a Compound 13 (such as various substituted aryl, heteroaryl or heterocyclyl ring systems, wherein $X_7$ represents a ketone or aldehyde leaving group) in the presence of a borohydride (such as $NaCNBH_3$ or $NaBH(OAc)_3$ and the like).

SPECIFIC SYNTHETIC EXAMPLES

To assist in understanding the scope of the compounds of Formula (I) or a form thereof described herein, the following Specific Examples are included. The experiments relating to the compounds of Formula (I) or a form thereof described herein should not, of course, be construed as specifically limiting the scope of the compounds of Formula (I) or a form thereof described herein and such variations of the compounds of Formula (I) or a form thereof as described herein, now known or later developed, which would be within the purview of one skilled in the art are considered to fall within the scope as described herein and hereinafter claimed.

Other than in the working examples, unless indicated to the contrary, all numbers expressing quantities of ingredients, reaction conditions, experimental data, and so forth used in the specification and claims are to be understood as being modified by the term "about". Accordingly, all such numbers represent approximations that may vary depending upon the desired properties sought to be obtained by a reaction or as a result of variable experimental conditions. Therefore, within an expected range of experimental reproducibility, the term "about" in the context of the resulting data, refers to a range for data provided that may vary according to a standard deviation from the mean. As well, for experimental results provided, the resulting data may be rounded up or down to present data consistently, without loss of significant figures. At the very least, and not as an attempt to limit the application of the doctrine of equivalents to the scope of the claims, each numerical parameter should be construed in light of the number of significant digits and ordinary rounding techniques.

While the numerical ranges and parameters setting forth the characterization of the compounds of Formula (I) or a form thereof described herein are approximations, the numerical values set forth in the working examples are reported as precisely as possible. Any numerical value, however, inherently contains certain errors necessarily resulting from the standard deviation found in their respective testing measurements.

The compounds of Formula (I) or a form thereof provided herein are described in more detail with reference to the following non-limiting examples, which are offered to more fully illustrate the scope of the compounds of Formula (I) or a form thereof described herein, but are not to be construed as limiting the scope thereof. The examples illustrate the preparation of compounds of Formula (I) or a form thereof described herein, and the testing of these compounds of Formula (I) or a form thereof in vitro and/or in vivo. Those of skill in the art will understand that the synthesis techniques described in these examples represent techniques that fall within the practice of those having ordinary skill in the chemical arts, and as such constitute preferred modes for the practice thereof. However, it should be appreciated that those having skill in the art should, in light of the present disclosure, appreciate that many changes can be made in the specific methods that are disclosed herein while still obtaining a like or similar result without departing from the spirit and scope described herein.

The reagents and solvents were used as purchased (from a variety of vendors), except where noted. Where applicable, the term "Celite" is used as shown in the following examples to represent the tradename CELITE® (brand of diatomaceous earth). Where applicable, chromatographic separations were performed using techniques and equipment commonly available such as, for example, by using an ISCO CombiFlash® Rf system. Where applicable, NMR spectra were obtained using techniques and equipment commonly available such as, for example, by using a Bruker Avance III$^{500}$ spectrometer with deuterated solvents such as, for example, DMSO-d$_6$ or residual solvent as standard. Where applicable, melting points were determined using techniques and equipment commonly available such as, for example, by using a SRS OptiMelt® MPA100 (values as obtained without correction/calibration). Where applicable, TLC analysis was performed using techniques and equipment commonly available such as, for example, by using Aldrich 254 nm glass-backed plates (60 Å, 250 um), visualized using UV and I$_2$ stains. Where applicable, ESI mass spectra were obtained using techniques and equipment commonly available such as, for example, by using an ACQUITY UPLC® System, with values shown as [M+H]$^+$ or [M−H]$^-$, unless otherwise indicated. Where applicable, the structure of the product was obtained via a 2D NOESY (Nuclear Overhauser Spectroscopy) experiment.

The following abbreviations are provided to ensure the terms used herein are unambiguous to one skilled in the art:

| Abbreviation | Meaning |
| --- | --- |
| AcOH or HOAc | acetic acid |
| ACN or MeCN | acetonitrile |
| AlMe$_3$ | trimethylaluminum |
| APC | allylpalladium (II) chloride dimer |
| Boc | tert-butoxycarbonyl |
| CsOAc | cesium acetate |
| DCM or CH$_2$Cl$_2$ | dichloromethane |
| DME | dimethyl ether |
| DMF | dimethyl formamide |
| DMA | dimethylacetamide |
| DMAP | 4-dimethylaminopyridine |
| DMSO | dimethylsulfoxide |
| EtOAc | ethyl acetate |
| EtOH | ethanol |
| HPLC | high performance liquid chromatography |
| h, hr, min, s | hour (h or hr), minute (min), second (s) |
| iPrMgCl * LiCl | isopropylmagnesium chloride lithium chloride complex |
| iPrOAc | isopropyl acetate |
| K$_2$CO$_3$ | potassium carbonate |
| K$_3$PO$_4$ | potassium phosphate |
| KOtBu or t-BuOK | potassium tert-butoxide |
| LC/MS, LCMS or LC-MS | liquid chromatographic mass spectroscopy |
| MeOH | methanol |
| MeNH$_2$ × HCl | methanamine hydrochloride |
| MS | mass spectroscopy |
| m.p. | melting point (shown in ° Centigrade) |
| MPS | potassium peroxymonosulfate (2KHSO$_5$•KHSO$_4$•K$_2$SO$_4$) |
| NaH | sodium hydride |
| NaHCO$_3$ | sodium bicarbonate |
| NaHMDS | sodium hexamethyldisilazide |
| NaIO$_4$ | sodium periodate |
| NaOH | sodium hydroxide |
| NaOtAm | sodium tert-pentoxide |
| NaOMe | sodium methoxide |
| NaOEt | sodium ethoxide |
| NaOtBu | sodium tert-butoxide |
| NCS | N-chlorosuccinimide |
| NH$_4$Cl | ammonium chloride |
| NH$_4$OH | ammonium hydroxide |
| NIS | N-iodosuccinimide |
| NMP | N-methylpyrrolidone |
| NMR | nuclear magnetic resonance |
| Oxone | potassium peroxymonosulfate |
| PCl$_5$ | phosphorus perchloride or phosphorus pentachloride |
| PCy$_3$ | tricyclohexylphosphine |
| [Pd] | palladium |
| Pd/C° | palladium on carbon |
| Pd$_2$(dba)$_3$ or Pd$_2$dba$_3$ | tris(dibenzylideneacetone)dipalladium(0) |
| Pd(dppf)Cl$_2$ | [1,1'-bis(diphenylphosphino)ferrocene] dichloropalladium(II) |
| PdCl$_2$(ACN) | bis(acetonitrile)dichloropalladium(II) |
| PdCl$_2$(allyl) | chloroallylpalladium(II) dimer |
| [Pd(OAc)$_2$]$_3$ | palladium (II) acetate |
| Pd(PPh$_3$)$_4$ | tetrakis(triphenylphosphine)palladium |
| POCl$_3$ | phosphorus oxychloride |
| PPh$_3$ | triphenylphosphine |
| psi | pounds per square inch pressure |
| Pt/C | platinum on carbon |
| PTSA | p-toluenesulfonic acid |
| Q-Phos or QPhos | 1,2,3,4,5-pentaphenyl-1-1'-(di-tert-butylphosphino)ferrocene |
| RT | room temperature |
| TBSO or OTBS | tert-butyldimethylsilyloxy |
| TCDI | 1,1'-thiocarbonyldiimidazole |
| t-Bu | tert-butyl |
| TEA, NEt$_3$, Et$_3$N | triethylamine |
| TFA | trifluoroacetic acid |
| TFAA | trifluoroacetic anhydride |
| THF | tetrahydrofuran |
| TsOH × H$_2$O | p-toluenesulfonic acid monohydrate |
| UPLC | Ultra Performance Liquid Chromatography |
| Xphos or XPhos | 2-dicyclohexylphosphino-2',4',6'-triisopropylbiphenyl |

Example 1

N-(1,3-benzodioxol-5-yl)-2-[2-(trifluoromethyl)imidazo[1,2-a]pyridin-3-yl]pyrimidin-4-amine (Cpd 28)

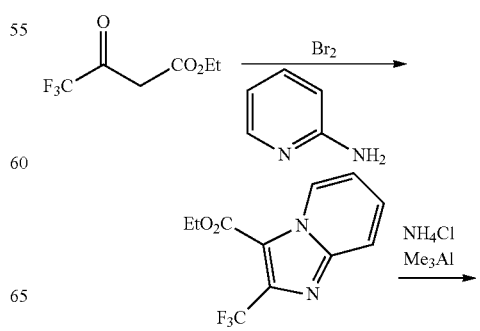

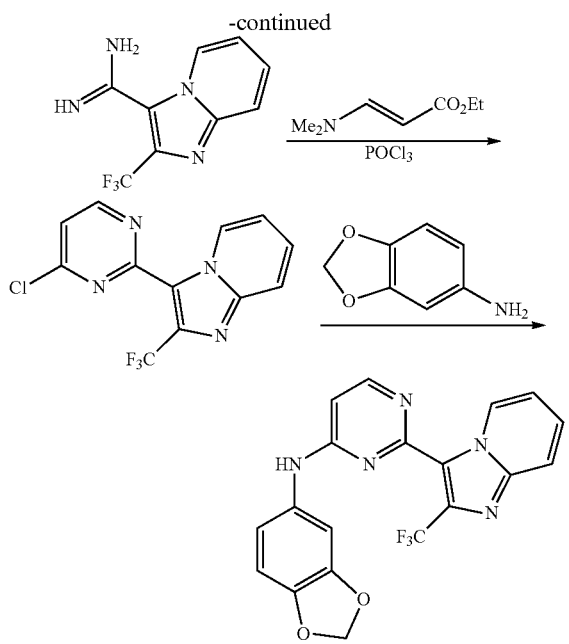

Step 1. To a solution of ethyl 4,4,4-trifluoro-3-oxobutanoate (9.0 g, 48.9 mmol) in CH$_2$Cl$_2$ (50 mL) was added bromine (2.5 mL, 49 mmol). The reaction mixture was stirred for 15 hours at room temperature, and then concentrated under dry nitrogen. To the crude material in ethanol (30 mL) was added pyridin-2-amine (5.2 g, 55 mmol). The reaction mixture was heated at 60° C. for 3 hours. The ethanol was evaporated, and the remainder was partitioned between EtOAc and water. The organic layer was dried, filtered through a short plug of silica gel, then concentrated under reduced pressure, and purified by silica gel chromatography to provide ethyl 2-(trifluoromethyl)imidazo[1,2-a]pyridine-3-carboxylate as a white solid (5.3 g, 42%).

Step 2. To a suspension of NH$_4$Cl (2.67 g, 50 mmol) in toluene (20 mL) at 0° C. was added AlMe$_3$ (2M solution in toluene, 25 mL, 50 mmol) over about a 5 minute period followed by gas evolution. The suspension was stirred at 0° C. for 5 minutes, then warmed to room temperature. A solution of ethyl 2-(trifluoromethyl)imidazo[1,2-a]pyridine-3-carboxylate (2.58 g, 10 mmol) in toluene (50 mL) was added to the suspension. The reaction mixture was heated at 80° C. for 72 hours and then cooled in an ice-bath, quenched with MeOH (100 mL) and NaOH (2 g, 50 mmol). The mixture was filtered through Celite, and concentrated to provide crude 2-(trifluoromethyl)imidazo[1,2-a]pyridine-3-carboximidamide as a brownish solid (2.3 g).

Step 3. A mixture of 2-(trifluoromethyl)imidazo[1,2-a]pyridine-3-carboximidamide (2.3 g, 10 mmol) and ethyl 3-(dimethylamino)acrylate (7.2 g, 50 mmol) in diphenyl ether (10 mL) was heated at 160° C. for 1 hour. The mixture was cooled to room temperature and diluted with hexane (200 mL). The precipitate was filtered and washed with hexanes to provide 2-(2-(trifluoromethyl)imidazo[1,2-a]pyridin-3-yl)pyrimidin-4(3H)-one as a light brown solid. The solid was dissolved in acetonitrile (10 mL) and to the mixture was added POCl$_3$ (1.9 mL, 20 mmol). The reaction mixture was heated to 100° C. for 30 minutes, cooled in an ice-water bath, then diluted with dichloromethane (100 mL), and washed with an aqueous NaHCO$_3$ solution. The organic layer was dried, then filtered through Celite and purified by silica gel chromatography to provide 3-(4-chloropyrimidin-2-yl)-2-(trifluoromethyl)imidazo[1,2-a]pyridine as a light yellow solid material (1.09 g, 37% over 3 steps).

$^1$H NMR (500 MHz, DMSO-d$_6$) δ ppm 9.61 (d, J=6.9 Hz, 1H), 9.00 (d, J=5.0 Hz, 1H), 7.94 (d, J=8.8 Hz, 1H), 7.73 (d, J=5.4 Hz, 1H), 7.69 (ddd, J=8.7, 7.1, 1.3 Hz, 1H), 7.37 (td, J=7.0, 1.1 Hz, 1H).

Step 4. To a solution of 3-(4-chloropyrimidin-2-yl)-2-(trifluoromethyl)imidazo[1,2-a]pyridine (75 mg, 0.25 mmol) and benzo[d][1,3]dioxol-5-amine (69 mg, 0.5 mmol) in THF (1 mL) at 0° C. was added KOtBu (1M solution in THF, 1 mL, 1 mmol). After 10 minutes, the reaction mixture was quenched with HOAc, then partitioned between EtOAc and water. The organic portion was dried, then concentrated, and the remainder was purified by silica gel chromatography to provide the title compound as a tan solid (58 mg, 58%).

$^1$H NMR (500 MHz, DMSO-d$_6$) δ ppm 9.70 (s, 1H), 9.43 (d, J=6.6 Hz, 1H), 8.43 (d, J=5.7 Hz, 1H), 7.84 (d, J=9.1 Hz, 1H), 7.58 (ddd, J=9.1, 6.9, 1.1 Hz, 1H), 7.37 (br. s., 1H), 7.17 (td, J=6.9, 0.9 Hz, 1H), 6.95 (dd, J=8.2, 1.9 Hz, 1H), 6.91 (d, J=8.5 Hz, 1H), 6.72 (d, J=6.0 Hz, 1H), 6.03 (s, 2H); MS m/z 400 [M+H]$^+$.

Additional compounds of Formula (I) or a form thereof described herein may be prepared according to the procedure of Example 1 by substituting the appropriate starting materials, reagents and reaction conditions.

| Cpd | Name & Data |
|---|---|
| 2 | N-(2,3-dihydro-1,4-benzodioxin-6-yl)-2-(2-methylimidazo[1,2-a]pyridin-3-yl)pyrimidin-4-amine<br>$^1$H NMR (500 MHz, DMSO-d$_6$) δ ppm 9.85 (dt, J = 6.9, 0.9 Hz, 1H), 9.45 (br. s, 1H), 8.36 (d, J = 5.7 Hz, 1H), 7.60 (dt, J = 8.8, 0.9 Hz, 1H), 7.38 (ddd, J = 8.8, 6.6, 1.3 Hz, 1H), 7.06 (d, J = 2.2 Hz, 1H), 6.95-6.98 (m, 2H), 6.87 (dd, J = 4.4, 3.5 Hz, 1H), 6.54 (d, J = 6.0 Hz, 1H), 4.25-4.30 (m, 4H), 2.75 (s, 3H); MS m/z 360 [M + H]$^+$ |
| 3 | 2-(2-methylimidazo[1,2-a]pyridin-3-yl)-N-[4-(trifluoromethyl)phenyl]pyrimidin-4-amine<br>$^1$H NMR (500 MHz, DMSO-d$_6$) δ ppm 10.06 (br. s, 1H), 9.81 (dt, J = 6.9, 1.1 Hz, 1H), 8.53 (d, J = 5.7 Hz, 1H), 7.90 (d, J = 8.5 Hz, 2H), 7.74 (d, J = 8.5 Hz, 2H), 7.63 (dt, J = 8.8, 1.1 Hz, 1H), 7.42 (ddd, J = 8.8, 6.6, 1.3 Hz, 1H), 7.03 (td, J = 6.9, 1.3 Hz, 1H), 6.74 (d, J = 5.7 Hz, 1H), 2.78 (s, 3H); MS m/z 370 [M + H]$^+$ |
| 4 | N-(4-methoxyphenyl)-2-(2-methylimidazo[1,2-a]pyridin-3-yl)pyrimidin-4-amine<br>$^1$H NMR (500 MHz, DMSO-d$_6$) δ ppm 9.84 (d, J = 6.6 Hz, 1H), 9.44 (br. s, 1H), 8.35 (d, J = 6.0 Hz, 1H), 7.59 (dt, J = 8.8, 0.9 Hz, 1H), 7.47 (d, J = 8.5 Hz, 2H), 7.37 (ddd, J = 8.9, 6.9, 1.3 Hz, 1H), 6.97-7.00 (m, 2H), 6.95 (td, J = 6.9, 0.9 Hz, 1H), 6.52 (d, J = 5.7 Hz, 1H), 3.78 (s, 3H), 2.73 (s, 3H); MS m/z 332 [M + H]$^+$ |
| 5 | N-(4-chlorophenyl)-2-(2-methylimidazo[1,2-a]pyridin-3-yl)pyrimidin-4-amine<br>$^1$H NMR (500 MHz, DMSO-d$_6$) δ ppm 9.81 (d, J = 6.9 Hz, 1H), 9.78 (br. s, 1H), 8.45 (d, J = 5.7 Hz, 1H), 7.67 (d, J = 8.8 Hz, 2H), 7.61 (d, J = 8.8 Hz, 1H), 7.44 (s, 2H), 7.40 (ddd, J = 8.2, 6.9, 1.3 Hz, 1H), 7.01 (td, J = 6.9, 1.3 Hz, 1H), 6.64 (d, J = 6.0 Hz, 1H), 2.74 (s, 3H); MS m/z 336 [M + H]$^+$ |

| Cpd | Name & Data |
|---|---|
| 6 | 2-(2-methylimidazo[1,2-a]pyridin-3-yl)-N-phenylpyrimidin-4-amine<br>$^1$H NMR (500 MHz, DMSO-d$_6$) δ ppm 9.85 (dt, J = 6.9, 0.9 Hz, 1H), 9.65 (br. s, 1H), 8.42 (d, J = 5.7 Hz, 1H), 7.59-7.64 (m, 3H), 7.36-7.43 (m, 3H), 7.11 (tt, J = 7.4, 0.9 Hz, 1H), 6.98 (ddd, J = 7.5, 5.5, 0.9 Hz, 1H), 6.63 (d, J = 6.0 Hz, 1H), 2.75 (s, 3H); MS m/z 302 [M + H]$^+$ |
| 7 | 2-[2-(trifluoromethyl)imidazo[1,2-a]pyridin-3-yl]-N-[4-(trifluoromethyl)phenyl]pyrimidin-4-amine<br>$^1$H NMR (500 MHz, DMSO-d$_6$) δ ppm 10.25 (br. s, 1H), 9.36 (d, J = 6.9 Hz, 1H), 8.59 (d, J = 5.7 Hz, 1H), 7.92 (d, J = 8.5 Hz, 2H), 7.86 (d, J = 9.1 Hz, 1H), 7.67 (d, J = 8.5 Hz, 2H), 7.60 (ddd, J = 9.1, 6.9, 1.1 Hz, 1H), 7.21 (td, J = 6.9, 1.3 Hz, 1H), 6.92 (d, J = 5.7 Hz, 1H); MS m/z 424 [M + H]$^+$ |
| 8 | N-(4-chlorophenyl)-2-[2-(trifluoromethyl)imidazo[1,2-a]pyridin-3-yl]pyrimidin-4-amine<br>$^1$H NMR (500 MHz, DMSO-d$_6$) δ ppm 9.95 (br. s., 1H), 9.37 (d, J = 6.9 Hz, 1H), 8.52 (d, J = 5.7 Hz, 1H), 7.85 (d, J = 8.8 Hz, 1H), 7.71 (d, J = 8.5 Hz, 2H), 7.59 (t, J = 7.6 Hz, 1H), 7.39 (d, J = 8.5 Hz, 2H), 7.20 (t, J = 6.8 Hz, 1H), 6.83 (d, J = 6.0 Hz, 1H); MS m/z 390 [M + H]$^+$ |
| 9 | N-(4-methylphenyl)-2-[2-(trifluoromethyl)imidazo[1,2-a]pyridin-3-yl]pyrimidin-4-amine<br>$^1$H NMR (500 MHz, DMSO-d$_6$) δ ppm 9.75 (br. s, 1H), 9.41 (d, J = 6.6 Hz, 1H), 8.45 (d, J = 6.0 Hz, 1H), 7.84 (d, J = 9.1 Hz, 1H), 7.58 (t, J = 6.9 Hz, 1H), 7.53 (d, J = 7.6 Hz, 2H), 7.26 (d, J = 7.6 Hz, 1H), 7.17 (d, J = 6.9 Hz, 2H), 6.77 (d, J = 5.7 Hz, 1H), 2.31 (s, 3H); MS m/z 370 [M + H]$^+$ |
| 10 | N-(4-bromophenyl)-2-[2-(trifluoromethyl)imidazo[1,2-a]pyridin-3-yl]pyrimidin-4-amine<br>$^1$H NMR (500 MHz, DMSO-d$_6$) δ ppm 9.97 (br. s, 1H), 9.37 (d, J = 6.9 Hz, 1H), 8.52 (d, J = 6.0 Hz, 1H), 7.85 (d, J = 8.8 Hz, 1H), 7.66 (d, J = 8.5 Hz, 2H), 7.59 (dd, J = 8.0, 6.9 Hz, 1H), 7.51 (d, J = 8.5 Hz, 2H), 7.20 (t, J = 6.9 Hz, 1H), 6.83 (d, J = 6.0 Hz, 1H); MS m/z 435 [M + H]$^+$ |
| 11 | N-[4-(difluoromethoxy)phenyl]-2-[2-(trifluoromethyl)imidazo[1,2-a]pyridin-3-yl]pyrimidin-4-amine<br>$^1$H NMR (500 MHz, CHLOROFORM-d) δ ppm 9.52 (dt, J = 7.3, 0.9 Hz, 1H), 8.38 (d, J = 6.0 Hz, 1H), 7.72 (dt, J = 9.1, 0.9 Hz, 1H), 7.30-7.37 (m, 3H), 7.11 (d, J = 8.8 Hz, 2H), 6.93 (td, J = 6.9, 1.3 Hz, 1H), 6.87 (br. s., 1H), 6.54 (d, J = 6.0 Hz, 1H), 6.46 (t, J = 73.8 Hz, 1H); MS m/z 422 [M + H]$^+$ |
| 12 | N-(4-methoxyphenyl)-2-[2-(trifluoromethyl)imidazo[1,2-a]pyridin-3-yl]pyrimidin-4-amine<br>$^1$H NMR (500 MHz, CHLOROFORM-d) δ ppm 9.63 (dt, J = 7.3, 0.9 Hz, 1H), 8.40 (d, J = 6.0 Hz, 1H), 7.79 (dt, J = 9.1, 0.9 Hz, 1H), 7.41 (ddd, J = 9.0, 6.8, 1.3 Hz, 1H), 7.24-7.33 (m, 2H), 7.00 (td, J = 6.9, 0.9 Hz, 1H), 6.94-6.98 (m, 2H), 6.91 (br. s, 1H), 6.50 (d, J = 6.0 Hz, 1H), 3.87 (s, 3H); MS m/z 386 [M + H]$^+$ |
| 13 | 2-[6-chloro-2-(trifluoromethyl)imidazo[1,2-a]pyridin-3-yl]-N-[4-(trifluoromethyl)phenyl]pyrimidin-4-amine<br>$^1$H NMR (500 MHz, DMSO-d$_6$) δ ppm 10.24 (br. s., 1H), 9.56-9.72 (m, 1H), 8.60 (d, J = 5.4 Hz, 1H), 7.83-7.98 (m, 3H), 7.63-7.74 (m, 3H), 6.90 (d, J = 5.4 Hz, 1H); MS m/z 458 [M + H]$^+$ |
| 14 | 2-[6-chloro-2-(trifluoromethyl)imidazo[1,2-a]pyridin-3-yl]-N-[4-(trifluoromethoxy)phenyl]pyrimidin-4-amine<br>$^1$H NMR (500 MHz, CHLOROFORM-d) δ ppm 9.72-9.82 (m, 1H), 8.49 (d, J = 6.0 Hz, 1H), 7.65-7.77 (m, 1H), 7.46 (dd, J = 9.0, 2.7 Hz, 2H), 7.39 (dd, J = 9.6, 2.0 Hz, 1H), 7.29 (d, J = 8.5 Hz, 2H), 6.84 (br. s, 1H), 6.64 (d, J = 6.0 Hz, 1H); MS m/z 474 [M + H]$^+$ |
| 15 | N-(4-bromophenyl)-2-[6-chloro-2-(trifluoromethyl)imidazo[1,2-a]pyridin-3-yl]pyrimidin-4-amine<br>$^1$H NMR (500 MHz, DMSO-d$_6$) δ ppm 9.96 (br. s, 1H), 9.60 (dd, J = 2.0, 0.8 Hz, 1H), 8.52 (d, J = 6.0 Hz, 1H), 7.92 (dd, J = 9.6, 0.8 Hz, 1H), 7.66 (dd, J = 9.6, 2.0 Hz, 1H), 7.61-7.64 (m, 2H), 7.50-7.55 (m, 2H), 6.81 (d, J = 6.0 Hz, 1H); MS m/z 469 [M + H]$^+$ |
| 16 | 2-[6-chloro-2-(trifluoromethyl)imidazo[1,2-a]pyridin-3-yl]-N-[4-(difluoromethoxy)phenyl]pyrimidin-4-amine<br>$^1$H NMR (500 MHz, CHLOROFORM-d) δ ppm 9.60-9.78 (m, 1H), 8.40 (dd, J = 6.0, 0.9 Hz, 1H), 7.66 (dd, J = 9.5, 0.6 Hz, 1H), 7.34 (dd, J = 8.8, 2.5 Hz, 2H), 7.31 (dd, J = 9.6, 2.0 Hz, 1H), 7.13 (d, J = 8.8 Hz, 2H), 6.76 (br. s, 1H), 6.54 (d, J = 6.0 Hz, 1H), 6.46 (t, J = 74.4 Hz, 1H); MS m/z 456 [M + H]$^+$ |
| 17 | N-(4-chlorophenyl)-2-[6-chloro-2-(trifluoromethyl)imidazo[1,2-a]pyridin-3-yl]pyrimidin-4-amine<br>$^1$H NMR (500 MHz, CHLOROFORM-d) δ ppm 9.59-9.75 (m, 1H), 8.41 (dd, J = 6.0, 0.9 Hz, 1H), 7.66 (dd, J = 9.6, 0.8 Hz, 1H), 7.23-7.36 (m, 5H), 6.74 (br. s, 1H), 6.55 (dd, J = 6.0, 1.3 Hz, 1H); MS m/z 425 [M + H]$^+$ |
| 18 | 2-[2-methyl-6-(trifluoromethyl)imidazo[1,2-a]pyridin-3-yl]-N-[4-(trifluoromethyl)phenyl]pyrimidin-4-amine<br>$^1$H NMR (500 MHz, DMSO-d$_6$) δ ppm 10.33 (br. s, 1H), 10.26 (s, 1H), 8.59 (d, J = 6.0 Hz, 1H), 7.98 (d, J = 9.1 Hz, 1H), 7.88 (d, J = 11.0 Hz, 1H), 7.86 (d, J = 8.5 Hz, 2H), 7.70 (d, J = 8.5 Hz, 2H), 6.85 (d, J = 6.0 Hz, 1H), 2.86 (s, 3H); MS m/z 438 [M + H]$^+$ |
| 19 | N-(4-bromophenyl)-2-[2-methyl-6-(trifluoromethyl)imidazo[1,2-a]pyridin-3-yl]pyrimidin-4-amine<br>$^1$H NMR (500 MHz, DMSO-d$_6$) δ ppm 10.30 (s, 1H), 10.07 (br. s, 1H), 8.52 (d, J = 6.0 Hz, 1H), 7.99 (d, J = 8.8 Hz, 1H), 7.87-7.96 (m, 1H), 7.60 (d, J = 8.8 Hz, 2H), 7.53 (d, J = 8.8 Hz, 2H), 6.78 (d, J = 6.0 Hz, 1H), 2.83 (s, 3H); MS m/z 449 [M + H]$^+$ |

-continued

| Cpd | Name & Data |
|---|---|
| 20 | N-(4-methylphenyl)-2-[2-methyl-6-(trifluoromethyl)imidazo[1,2-a]pyridin-3-yl]pyrimidin-4-amine<br>$^1$H NMR (500 MHz, DMSO-$d_6$) δ ppm 10.28 (s, 1H), 9.83 (br. s, 1H), 8.44 (d, J = 6.0 Hz, 1H), 7.92 (d, J = 9.3 Hz, 1H), 7.80 (d, J = 9.3 Hz, 1H), 7.47 (d, J = 8.2 Hz, 2H), 7.17 (d, J = 8.2 Hz, 2H), 6.70 (d, J = 6.0 Hz, 1H), 2.81 (s, 3H), 2.30 (s, 3H); MS m/z 384 [M + H]$^+$ |
| 21 | 2-[6-fluoro-2-(trifluoromethyl)imidazo[1,2-a]pyridin-3-yl]-N-(4-methylphenyl)pyrimidin-4-amine<br>$^1$H NMR (500 MHz, DMSO-$d_6$) δ ppm 9.78 (s, 1H), 9.63 (br. s, 1H), 8.44 (d, J = 6.0 Hz, 1H), 7.94 (dd, J = 10.1, 5.4 Hz, 1H), 7.70 (ddd, J = 10.7, 7.9, 2.5 Hz, 1H), 7.49 (d, J = 8.0 Hz, 2H), 7.18 (d, J = 8.0 Hz, 2H), 6.74 (d, J = 8.8 Hz, 1H), 2.30 (s, 3H); MS m/z 388 [M + H]$^+$ |
| 22 | 2-[6-fluoro-2-(trifluoromethyl)imidazo[1,2-a]pyridin-3-yl]-N-(4-methoxyphenyl)pyrimidin-4-amine<br>$^1$H NMR (500 MHz, DMSO-$d_6$) δ ppm 9.63 (br. s, 1H), 8.41 (d, J = 5.7 Hz, 1H), 7.94 (dd, J = 9.9, 5.2 Hz, 1H), 7.69 (ddd, J = 10.0, 7.8, 2.4 Hz, 1H), 7.48 (d, J = 8.2 Hz, 2H), 6.96 (d, J = 8.8 Hz, 2H), 6.75-6.82 (m, 1H), 6.68 (d, J = 6.0 Hz, 1H), 3.77 (s, 3H); MS m/z 404 [M + H]$^+$ |
| 23 | 2-[5chloro-1-methyl-2-(trifluoromethyl)-1H-indol-3-yl]-N-(4-methoxyphenyl)pyrimidin-4-amine<br>$^1$H NMR (500 MHz, CHLOROFORM-d) δ ppm 8.27 (d, J = 6.3 Hz, 1H), 7.87 (d, J = 1.9 Hz, 1H), 7.56 (br. s, 1H), 7.26 (dd, J = 8.5, 1.9 Hz, 1H), 7.20 (d, J = 8.8 Hz, 1H), 7.07 (d, J = 8.8 Hz, 2H), 6.73-6.80 (m, 2H), 6.42 (d, J = 6.0 Hz, 1H), 3.78 (s, 3H), 3.74 (s, 3H); MS m/z 433 [M + H]$^+$ |
| 24 | 2-[5-chloro-1-methyl-2-(trifluoromethyl)-1H-indol-3-yl]-N-[4-(difluoromethoxy)phenyl]pyrimidin-4-amine<br>$^1$H NMR (500 MHz, DMSO-$d_6$) δ ppm 10.47 (br. s, 1H), 8.47 (d, J = 6.6 Hz, 1H), 7.98 (d, J = 2.2 Hz, 1H), 7.84 (d, J = 9.1 Hz, 1H), 7.74 (d, J = 8.8 Hz, 2H), 7.50 (dd, J = 8.8, 1.9 Hz, 1H), 7.16 (d, J = 8.8 Hz, 2H), 7.18 (t, J = 74.4 Hz, 1H), 6.90 (d, J = 6.3 Hz, 1H), 4.00 (s, 3H); MS m/z 469 [M + H]$^+$ |
| 25 | N-(4-bromophenyl)-2-[5-chloro-1-methyl-2-(trifluoromethyl)-1H-indol-3-yl]pyrimidin-4-amine<br>$^1$H NMR (500 MHz, DMSO-$d_6$) δ ppm 10.24 (br. s, 1H), 8.49 (d, J = 6.0 Hz, 1H), 7.98 (d, J = 2.2 Hz, 1H), 7.83 (d, J = 8.8 Hz, 1H), 7.70 (d, J = 8.8 Hz, 2H), 7.43-7.52 (m, J = 8.5 Hz, 3H), 6.87 (d, J = 6.0 Hz, 1H), 4.00 (s, 3H); MS m/z 482 [M + H]$^+$ |
| 26 | N-(4-bromophenyl)-2-(6-fluoro-2-phenylimidazo[1,2-a]pyridin-3-yl)pyrimidin-4-amine<br>$^1$H NMR (500 MHz, DMSO-$d_6$) δ ppm 9.75 (br. s., 1H), 9.55 (d, J = 3.2 Hz, 1H), 8.49 (d, J = 5.4 Hz, 1H), 7.83 (dd, J = 8.8, 5.0 Hz, 1H), 7.67 (d, J = 7.9 Hz, 2H), 7.57 (td, J = 9.1, 1.6 Hz, 1H), 7.31-7.46 (m, J = 7.6 Hz, 3H), 7.01-7.21 (m, 4H), 6.72 (d, J = 5.7 Hz, 1H); MS m/z 461 [M + H]$^+$ |
| 27 | 2-(6-fluoro-2-phenylimidazo[1,2-a]pyridin-3-yl)-N-(4-methylphenyl)pyrimidin-4-amine<br>$^1$H NMR (500 MHz, DMSO-$d_6$) δ ppm 9.88 (br. s, 1H), 9.49-9.61 (m, 1H), 8.37 (d, J = 6.0 Hz, 1H), 7.90 (dd, J = 9.9, 5.2 Hz, 1H), 7.66-7.75 (m, 3H), 7.39-7.49 (m, 3H), 7.14 (d, J = 8.2 Hz, 2H), 6.94 (d, J = 8.2 Hz, 2H), 6.74 (d, J = 6.3 Hz, 1H), 2.23 (s, 3H); MS m/z 396 [M + H]$^+$ |
| 29 | N-(2,3-dihydro-1,4-benzodioxin-6-yl)-2-[2-(trifluoromethyl)imidazo[1,2-a]pyridin-3-yl]pyrimidin-4-amine<br>$^1$H NMR (500 MHz, DMSO-$d_6$) δ ppm 9.63 (s, 1H), 8.42 (d, J = 5.7 Hz, 1H), 7.84 (dt, J = 9.1, 0.9 Hz, 1H), 7.58 (ddd, J = 9.0, 6.8, 1.3 Hz, 1H), 7.22 (br. s., 1H), 7.15 (td, J = 6.9, 1.3 Hz, 0H), 7.01 (dd, J = 8.5, 2.2 Hz, 1H), 6.84 (d, J = 8.8 Hz, 1H), 6.71 (d, J = 6.0 Hz, 1H), 4.20-4.29 (m, 4H); MS m/z 410 [M + H]$^+$ |
| 30 | N-(6-methoxypyridin-3-yl)-2-[2-(trifluoromethyl)imidazo[1,2-a]pyridin-3-yl]pyrimidin-4-amine<br>$^1$H NMR (500 MHz, CHLOROFORM-d) δ ppm 9.53 (d, J = 6.9 Hz, 1H), 8.34 (d, J = 5.7 Hz, 1H), 8.10 (d, J = 2.5 Hz, 1H), 7.69 (dt, J = 9.1, 0.9 Hz, 1H), 7.65 (d, J = 7.6 Hz, 1H), 7.32 (ddd, J = 9.0, 6.8, 1.3 Hz, 1H), 6.91 (td, J = 7.0, 1.3 Hz, 2H), 6.75 (d, J = 8.5 Hz, 1H), 6.40 (d, J = 6.0 Hz, 1H), 3.90 (s, 3H); MS m/z 387 [M + H+ |
| 31 | N$^2$,N$^2$-dimethyl-N$^5$-{2-[2-(trifluoromethyl)imidazo [1,2-a]pyridin-3-yl]pyrimidin-4-yl}pyridine-2,5-diamine<br>$^1$H NMR (500 MHz, CHLOROFORM-d) δ ppm 9.55 (d, J = 6.9 Hz, 1H), 8.29 (d, J = 6.0 Hz, 1H), 8.10 (d, J = 2.5 Hz, 1H), 7.70 (d, J = 9.1 Hz, 1H), 7.51 (br. s, 1H), 7.32 (ddd, J = 9.1, 6.9, 1.1 Hz, 1H), 6.92 (td, J = 6.9, 0.9 Hz, 1H), 6.81 (br. s, 0H), 6.51 (d, J = 9.1 Hz, 1H), 6.35 (d, J = 5.4 Hz, 1H), 3.08 (s, 6H); MS m/z 400 [M + H]$^+$ |
| 32 | 2-[6-bromo-2-(trifluoromethyl)imidazo[1,2-a]pyridin-3-yl]-N-[4-(trifluoromethyl)phenyl]pyrimidin-4-amine<br>$^1$H NMR (500 MHz, DMSO-$d_6$) δ ppm 10.25 (br. s, 1H), 9.66 (dd, J = 1.9, 0.9 Hz, 1H), 8.60 (d, J = 6.0 Hz, 1H), 7.91 (d, J = 8.5 Hz, 2H), 7.87 (dd, J = 9.6, 0.8 Hz, 1H), 7.74 (dd, J = 9.5, 1.9 Hz, 1H), 7.69 (d, J = 8.8 Hz, 2H), 6.90 (d, J = 6.0 Hz, 1H); MS m/z 503 [M + H]$^+$ |
| 33 | 2-[6-bromo-2-(trifluoromethyl)imidazo[1,2-a]pyridin-3-yl]-N-(4-methoxyphenyl)pyrimidin-4-amine<br>$^1$H NMR (500 MHz, CHLOROFORM-d) δ ppm 9.70-9.86 (m, 1H), 8.32 (d, J = 4.7 Hz, 1H), 7.60 (d, J = 9.5 Hz, 1H), 7.40 (dd, J = 9.6, 1.7 Hz, 1H), 7.22 (d, J = 8.5 Hz, 2H), 6.89 (d, J = 8.8 Hz, 2H), 6.47 (br. s, 1H), 3.78 (s, 3H); MS m/z 465 [M + H]$^+$ |

| Cpd | Name & Data |
|---|---|
| 34 | N-(3-fluoro-4-methoxyphenyl)-2-[2-(trifluoromethyl)imidazo[1,2-a]pyridin-3-yl]pyrimidin-4-amine<br>$^1$H NMR (500 MHz, DMSO-$d_6$) δ ppm 9.77 (s, 1H), 9.35 (d, J = 6.9 Hz, 1H), 8.42 (d, J = 6.0 Hz, 1H), 7.80 (d, J = 9.1 Hz, 1H), 7.68 (d, J = 13.6 Hz, 1H), 7.53 (ddd, J = 9.1, 6.9, 1.3 Hz, 1H), 7.17-7.23 (m, 1H), 7.13 (td, J = 6.9, 1.1 Hz, 1H), 7.13 (td, J = 6.9, 0.9 Hz, 1H), 7.10 (t, J = 9.1 Hz, 1H), 6.70 (d, J = 6.0 Hz, 1H), 3.78 (s, 3H); MS m/z 404 [M + H]$^+$ |
| 35 | N-(3-chloro-4-methoxyphenyl)-2-[2-(trifluoromethyl)imidazo[1,2-a]pyridin-3-yl]pyrimidin-4-amine<br>$^1$H NMR (500 MHz, DMSO-$d_6$) δ ppm 9.80 (s, 1H), 9.40 (d, J = 6.9 Hz, 1H), 8.47 (d, J = 6.0 Hz, 1H), 7.88-7.92 (m, 1H), 7.85 (dt, J = 9.1, 1.0 Hz, 1H), 7.59 (ddd, J = 9.1, 6.6, 1.3 Hz, 1H), 7.43 (dd, J = 8.8, 2.8 Hz, 1H), 7.18 (td, J = 6.9, 1.3 Hz, 1H), 7.15 (d, J = 9.1 Hz, 1H), 6.74 (d, J = 6.0 Hz, 1H), 3.85 (s, 3H); MS m/z 420 [M + H]$^+$ |
| 36 | N-(3-chloro-4-methylphenyl)-2-[2-(trifluoromethyl)imidazo[1,2-a]pyridin-3-yl]pyrimidin-4-amine<br>$^1$H NMR (500 MHz, DMSO-$d_6$) δ ppm 9.92 (s, 1H), 9.38 (d, J = 7.3 Hz, 1H), 8.51 (d, J = 6.0 Hz, 1H), 7.94 (d, J = 1.9 Hz, 1H), 7.86 (dt, J = 9.1, 1.1 Hz, 1H), 7.59 (ddd, J = 9.1, 6.9, 1.3 Hz, 1H), 7.41 (dd, J = 8.2, 2.2 Hz, 1H), 7.31 (d, J = 8.5 Hz, 1H), 7.20 (td, J = 6.9, 1.3 Hz, 1H), 6.80 (d, J = 5.7 Hz, 1H), 2.30 (s, 3H); MS m/z 404 [M + H]$^+$ |
| 37 | N-(4-ethoxyphenyl)-2-[2-(trifluoromethyl)imidazo[1,2-a]pyridin-3-yl]pyrimidin-4-amine<br>$^1$H NMR (500 MHz, DMSO-$d_6$) δ ppm 9.64 (br. s, 1H), 9.43 (br. s, 1H), 8.41 (d, J = 6.0 Hz, 1H), 7.84 (dt, J = 9.1, 1.3 Hz, 1H), 7.57 (ddd, J = 9.1, 6.9, 1.1 Hz, 1H), 7.50 (d, J = 8.5 Hz, 1H), 7.16 (t, J = 6.5 Hz, 1H), 6.93 (d, J = 8.8 Hz, 2H), 6.69 (d, J = 6.0 Hz, 1H), 4.02 (q, J = 6.9 Hz, 2H), 1.34 (t, J = 6.9 Hz, 3H); MS m/z 400 [M + H]$^+$ |
| 38 | N-[4-(propan-2-yl)phenyl]-2-[2-(trifluoromethyl)imidazo[1,2-a]pyridin-3-yl]pyrimidin-4-amine<br>$^1$H NMR (500 MHz, DMSO-$d_6$) δ ppm 9.76 (s, 1H), 9.41 (d, J = 6.9 Hz, 1H), 8.45 (d, J = 6.0 Hz, 1H), 7.85 (dt, J = 9.1, 0.9 Hz, 1H), 7.58 (ddd, J = 8.8, 6.6, 1.3 Hz, 1H), 7.55 (d, J = 8.5 Hz, 2H), 7.23 (d, J = 8.5 Hz, 2H), 7.16 (td, J = 6.9, 0.9 Hz, 1H), 6.77 (d, J = 6.0 Hz, 1H), 2.89 (spt, J = 6.9 Hz, 1H), 1.21 (d, J = 6.9 Hz, 7H); MS m/z 398 [M + H]$^+$ |
| 39 | N-[4-(1H-pyrazol-1-yl)phenyl]-2-[2-(trifluoromethyl)imidazo[1,2-a]pyridin-3-yl]pyrimidin-4-amine<br>$^1$H NMR (500 MHz, DMSO-$d_6$) δ ppm 9.98 (s, 1H), 9.42 (d, J = 7.3 Hz, 1H), 8.51 (d, J = 5.7 Hz, 1H), 8.48 (d, J = 2.2 Hz, 1H), 7.86 (td, J = 9.1, 1.3 Hz, 1H), 7.76-7.84 (m, J = 3.5 Hz, 4H), 7.73 (d, J = 1.6 Hz, 1H), 7.59 (ddd, J = 9.0, 6.8, 1.3 Hz, 1H), 7.20 (td, J = 6.9, 1.3 Hz, 1H), 6.84 (d, J = 6.0 Hz, 1H), 6.54 (t, J = 1.9 Hz, 1H); MS m/z 422 [M + H]$^+$ |
| 45 | N-(4-methoxyphenyl)-2-[2-(trifluoromethyl)imidazo[1,2-a]pyrazin-3-yl]pyrimidin-4-amine<br>$^1$H NMR (500 MHz, Acetone-$d_6$) δ ppm 9.53 (br. s., 1H), 9.16 (d, J = 1.3 Hz, 1H), 8.81 (s, 1H), 8.38 (d, J = 6.0 Hz, 1H), 8.03 (d, J = 4.7 Hz, 1H), 7.46 (d, J = 8.5 Hz, 2H), 6.95 (d, J = 9.1 Hz, 2H), 6.70 (dd, J = 8.2, 2.5 Hz, 1H), 3.79 (s, 3H); MS m/z 387 [M + H]$^+$ |
| 46 | 2-[2-(trifluoromethyl)imidazo[1,2-a]pyrazin-3-yl]-N-[4-(trifluoromethyl)phenyl]pyrimidin-4-amine<br>$^1$H NMR (500 MHz, Acetone-$d_6$) δ ppm 9.41-9.49 (m, 1H), 9.20 (br. s, 1H), 8.49 (dd, J = 6.0, 2.2 Hz, 1H), 8.02-8.12 (m, 1H), 7.83-7.92 (m, 2H), 7.58 (d, J = 8.5 Hz, 2H), 6.93-7.32 (m, 2H); MS m/z 425 [M + H]$^+$ |
| 47 | N-(4-chlorophenyl)-2-[2-(trifluoromethyl)imidazo[1,2-a]pyrazin-3-yl]pyrimidin-4-amine<br>$^1$H NMR (500 MHz, Acetone-$d_6$) δ ppm 9.53 (dd, J = 4.9, 1.4 Hz, 1H), 9.25 (d, J = 1.3 Hz, 1H), 9.20 (br. s., 1H), 8.55 (d, J = 6.0 Hz, 1H), 8.15 (d, J = 4.7 Hz, 1H), 7.70-7.81 (m, 2H), 7.42 (d, J = 8.8 Hz, 2H), 6.91 (d, J = 6.0 Hz, 1H); MS m/z 391 [M + H]$^+$ |
| 48 | 2-[6-methoxy-2-(trifluoromethyl)imidazo[1,2-a]pyridin-3-yl]-N-[4-(trifluoromethyl)phenyl]pyrimidin-4-amine<br>$^1$H NMR (500 MHz, DMSO-$d_6$) δ ppm 10.31 (br. s, 1H), 9.02 (d, J = 2.5 Hz, 1H), 8.65 (d, J = 5.7 Hz, 1H), 7.96 (d, J = 8.5 Hz, 2H), 7.85 (d, J = 10.4 Hz, 1H), 7.74 (d, J = 8.5 Hz, 2H), 7.45 (dd, J = 9.8, 2.5 Hz, 1H), 6.95 (d, J = 6.0 Hz, 1H), 3.66 (s, 3H); MS m/z 454 [M + H]$^+$ |
| 49 | 2-[6-methoxy-2-(trifluoromethyl)imidazo[1,2-a]pyridin-3-yl]-N-[4-(trifluoromethoxy)phenyl]pyrimidin-4-amine<br>$^1$H NMR (500 MHz, DMSO-$d_6$) δ ppm 9.65 (br. s, 1H), 8.96-9.06 (m, 1H), 8.42 (d, J = 5.7 Hz, 1H), 7.76 (d, J = 9.8 Hz, 1H), 7.51 (d, J = 8.5 Hz, 2H), 7.36 (dd, J = 9.6, 2.4 Hz, 1H), 6.93 (d, J = 8.8 Hz, 2H), 6.69 (d, J = 6.0 Hz, 1H), 3.75 (s, 3H); MS m/z 470 [M + H]$^+$ |
| 50 | N-(4-methoxyphenyl)-2-[6-methoxy-2-(trifluoromethyl)imidazo[1,2-a]pyridin-3-yl]pyrimidin-4-amine<br>$^1$H NMR (500 MHz, DMSO-$d_6$) δ ppm 10.04 (br. s, 1H), 8.97 (d, J = 1.9 Hz, 1H), 8.54 (d, J = 5.7 Hz, 1H), 7.75-7.79 (m, 3H), 7.38 (dd, J = 9.1, 2.2 Hz, 1H), 7.34 (d, J = 8.5 Hz, 2H), 6.82 (d, J = 6.0 Hz, 1H), 3.59 (s, 3H), 3.33 (s, 3H); MS m/z 416 [M + H]$^+$ |
| 51 | N-[4-(difluoromethoxy)phenyl]-2-[6-methoxy-2-(trifluoromethyl)imidazo[1,2-a]pyridin-3-yl]pyrimidin-4-amine<br>$^1$H NMR (500 MHz, DMSO-$d_6$) δ ppm 9.90 (br. s, 1H), 8.98 (d, J = 1.9 Hz, 1H), 8.50 (d, J = 6.0 Hz, 1H), 7.78 (d, J = 9.5 Hz, 1H), 7.69 (d, J = 8.8 Hz, 2H), 7.37 (dd, J = 9.8, 2.5 Hz, 1H), 7.17 (d, J = 8.8 Hz, 2H), 7.19 (t, J = 74.4 Hz, 1H), 6.78 (d, J = 5.7 Hz, 1H), 3.61 (s, 3H); MS m/z 452 [M + H]$^+$ |
| 53 | N-[4-(difluoromethoxy)phenyl]-2-[2-(trifluoromethyl)imidazo[1,2-a]pyrazin-3-yl]pyrimidin-4-amine<br>$^1$H NMR (500 MHz, Acetone-$d_6$) δ ppm 9.74 (dd, J = 4.9, 1.4 Hz, 1H), 9.44 (d, J = 1.6 Hz, 1H), 9.30 (br. s., 1H), 8.72 (d, J = 6.0 Hz, 1H), 8.32 (d, J = 4.7 Hz, 1H), 7.89-8.00 (m, 2H), 7.42-7.52 (m, 2H), 7.07 (dd, J = 6.0, 1.6 Hz, 1H), 7.20 (t, J = 74.4 Hz, 1H); MS m/z 423 [M + H]$^+$ |

-continued

| Cpd | Name & Data |
|---|---|
| 54 | 2-[6-fluoro-2-(trifluoromethyl)imidazo[1,2-a]pyridin-3-yl]-N-[4-(trifluoromethyl)phenyl]pyrimidin-4-amine<br>$^1$H NMR (500 MHz, DMSO-$d_6$) δ ppm 10.25 (br. s, 1H), 9.58 (ddd, J = 5.7, 1.9, 0.9 Hz, 1H), 8.59 (d, J = 6.0 Hz, 1H), 7.97 (ddd, J = 9.8, 5.4, 0.9 Hz, 1H), 7.90 (d, J = 8.5 Hz, 2H), 7.73 (ddd, J = 9.9, 7.7, 2.5 Hz, 1H), 7.69 (d, J = 8.8 Hz, 2H), 6.90 (d, J = 6.0 Hz, 1H); MS m/z 442 [M + H]$^+$ |
| 55 | N-[4-(difluoromethoxy)phenyl]-2-[6-fluoro-2-(trifluoromethyl)imidazo[1,2-a]pyridin-3-yl]pyrimidin-4-amine<br>$^1$H NMR (500 MHz, Acetone-$d_6$) δ ppm 9.75 (dd, J = 5.5, 2.0 Hz, 1H), 9.10 (br. s, 1H), 8.51 (d, J = 5.7 Hz, 1H), 7.84 (ddd, J = 9.8, 5.4, 0.9 Hz, 1H), 7.71-7.76 (m, 2H), 7.60 (ddd, J = 10.0, 7.6, 2.5 Hz, 1H), 7.22-7.26 (m, 2H), 6.99 (t, J = 74.1 Hz, 1H), 6.83 (d, J = 6.0 Hz, 1H); MS m/z 440 [M + H]$^+$ |
| 56 | N-[4-(trifluoromethyl)phenyl]-2-[2-(trifluoromethyl)pyrazolo[1,5-a]pyridin-3-yl]pyrimidin-4-amine<br>$^1$H NMR (500 MHz, CHLOROFORM-d) δ ppm 10.03 (br. s, 1H), 8.48 (d, J = 6.9 Hz, 1H), 8.21-8.36 (m, 1H), 8.00-8.15 (m, 1H), 7.65-7.73 (m, 2H), 7.52 (d, J = 8.2 Hz, 2H), 7.39 (t, J = 7.7 Hz, 1H), 7.06-7.12 (m, 1H), 7.03 (t, J = 6.8 Hz, 1H); MS m/z 424 [M + H]$^+$ |
| 60 | N-(4-methoxyphenyl)-2-[2-(trifluoromethyl)pyrazolo[1,5-a]pyridin-3-yl]pyrimidin-4-amine<br>$^1$H NMR (500 MHz, CHLOROFORM-d) δ ppm 8.49 (d, J = 6.6 Hz, 1H), 8.03-8.31 (m, 2H), 7.30-7.55 (m, 3H), 7.00-7.12 (m, 2H), 6.79-6.87 (m, 3H), 3.76 (s, 3H); MS m/z 386 [M + H]$^+$ |
| 62 | N-(4-methylphenyl)-2-[2-(trifluoromethyl)imidazo[1,2-a]pyrazin-3-yl]pyrimidin-4-amine<br>$^1$H NMR (500 MHz, Acetone-$d_6$) δ ppm 9.58 (d, J = 3.8 Hz, 1H), 9.23 (d, J = 1.6 Hz, 1H), 8.95 (br. s., 1H), 8.48 (d, J = 6.0 Hz, 1H), 8.10 (d, J = 4.7 Hz, 1H), 7.53 (d, J = 8.5 Hz, 2H), 7.25 (d, J = 8.2 Hz, 2H), 6.83 (d, J = 6.0 Hz, 1H), 2.37 (s, 3H); MS m/z 371 [M + H]$^+$ |
| 118 | 2-(imidazo[1,2-a]pyridin-3-yl)-N-[4-(trifluoromethyl)phenyl]pyrimidin-4-amine<br>$^1$H NMR (500 MHz, DMSO-$d_6$) δ ppm 10.10 (s, 1H), 9.92 (d, J = 7.3 Hz, 1H), 8.51 (app. s, 1H), 8.48 (d, J = 5.7 Hz, 1H), 8.00 (d, J = 8.5 Hz, 2H), 7.75-7.86 (m, 3H), 7.46 (ddd, J = 9.1, 6.6, 0.9 Hz, 1H), 7.14 (td, J = 6.9, 1.1 Hz, 1H), 6.74 (d, J = 6.0 Hz, 1H); MS m/z 356 [M + H]$^+$ |

Example 2

N-(3-chloro-4-methoxyphenyl)-2-(2-methyl-1H-benzimidazol-1-yl)pyrimidin-4-amine (Cpd 40)

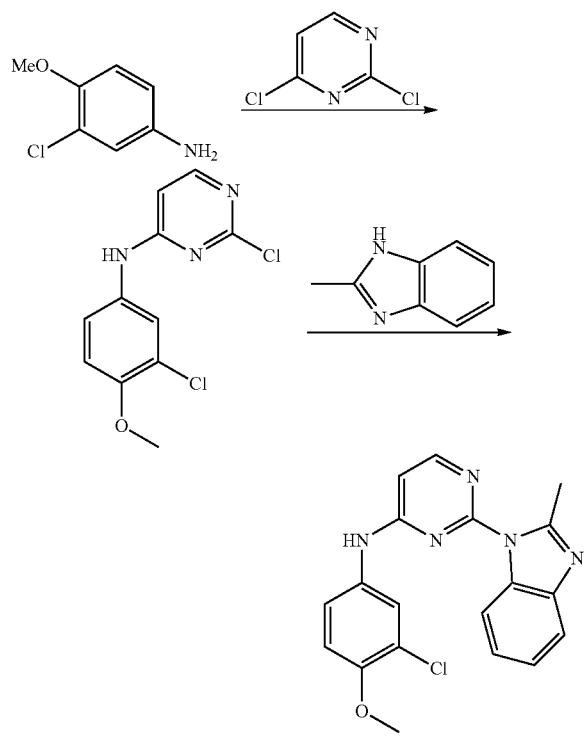

Step 1. 3-Chloro-4-methoxyaniline (2.07 g, 13.1 mmol), 2,4-dichloropyrimidine (1.95 g, 13.1 mmol) and triethylamine (2.1 mL, 15 mmol) were mixed in isopropanol (10 mL). The mixture was heated at 100° C. for 13 hours, then partially concentrated, diluted with water, and made basic with $K_2CO_3$. The precipitate was filtered, then washed with water, followed by hexane. The major isomer, 2-chloro-N-(3-chloro-4-methoxyphenyl)pyrimidin-4-amine (2.07 g, 59%) was recrystallized from methanol as a white solid.

$^1$H NMR (500 MHz, DMSO-$d_6$) δ ppm 9.99 (br. s, 1H), 8.15 (d, J=6.0 Hz, 1H), 7.73 (br. s., 1H), 7.47 (d, J=8.2 Hz, 1H), 7.19 (d, J=8.8 Hz, 1H), 6.69 (d, J=5.7 Hz, 1H), 3.85 (s, 3H).

Step 2. 2-Chloro-N-(3-chloro-4-methoxyphenyl)pyrimidin-4-amine (84 mg, 0.31 mmol), 2-methyl-1H-benzo[d]imidazole (82 mg, 0.62 mmol) and $K_2CO_3$ (86 mg, 0.62 mmol) were mixed in DMF (2 mL). The reaction mixture was heated at 120° C. for 3 days, then cooled, partitioned between water and EtOAc, and purified by silica gel chromatography to provide the title compound as a white solid (29 mg, 26%).

$^1$H NMR (500 MHz, DMSO-$d_6$) δ ppm 9.94 (s, 1H), 8.42 (d, J=5.7 Hz, 1H), 8.03-8.10 (m, 1H), 7.82-7.90 (m, 1H), 7.61 (d, J=7.3 Hz, 1H), 7.40-7.45 (m, 1H), 7.20-7.29 (m, 2H), 7.18 (d, J=8.8 Hz, 1H), 6.73 (d, J=5.7 Hz, 1H), 3.86 (s, 3H), 2.79 (s, 3H); MS m/z 366 [M+H]$^+$.

Additional compounds of Formula (I) or a form thereof described herein may be prepared according to the procedure of Example 2 by substituting the appropriate starting materials, reagents and reaction conditions.

| Cpd | Name & Data |
|---|---|
| 1 | N-(4-methoxyphenyl)-2-(2-methyl-1H-benzimidazol-1-yl)pyrimidin-4-amine<br>$^1$H NMR (500 MHz, DMSO-$d_6$) δ ppm 9.79 (br. s., 1H), 8.36 (d, J = 5.4 Hz, 1H), 7.95-8.17 (m, 1H), 7.59 (d, J = 7.9 Hz, 1H), 7.42-7.54 (m, 2H), 7.17-7.33 (m, 2H), 6.96 (d, J = 8.2 Hz, 2H), 6.68 (d, J = 5.0 Hz, 1H), 3.76 (s, 3H), 2.77 (s, 3H); MS m/z 332 [M + H]$^+$ |
| 41 | 2-(2-methyl-1H-benzimidazol-1-yl)-N-[4-(trifluoromethyl)phenyl]pyrimidin-4-amine<br>$^1$H NMR (500 MHz, DMSO-$d_6$) δ ppm 10.37 (s, 1H), 8.55 (d, J = 5.7 Hz, 1H), 8.01-8.06 (m, 1H), 7.90 (d, J = 8.5 Hz, 1H), 7.72 (d, J = 8.5 Hz, 2H), 7.61-7.65 (m, 1H), 7.26 (app. quind, J = 7.3, 1.4 Hz, 2H), 6.91 (d, J = 5.7 Hz, 1H), 2.81 (s, 3H); MS m/z 370 [M + H]$^+$ |
| 61 | N-[4-(difluoromethoxy)phenyl]-2-(2-methyl-1H-benzimidazol-1-yl)pyrimidin-4-amine<br>$^1$H NMR (500 MHz, Methanol-$d_4$) δ ppm 8.32 (1H, d, J = 5.5 Hz), 8.06 (1H, d, J = 8 Hz), 7.59 (3H, d, J = 8 Hz), 7.26 (2H, m), 7.14 (2H, d, J = 8 Hz), 7.0 (1H, t, J = 74 Hz), 6.69 (1H, d, J = 6 Hz), 2.82 (3H, s); MS m/z 368 [M + H]$^+$ |

Example 3

N-(3-chloro-4-methoxyphenyl)-2-[2-(trifluoromethyl)-1H-benzimidazol-1-yl]pyrimidin-4-amine (Cpd 42)

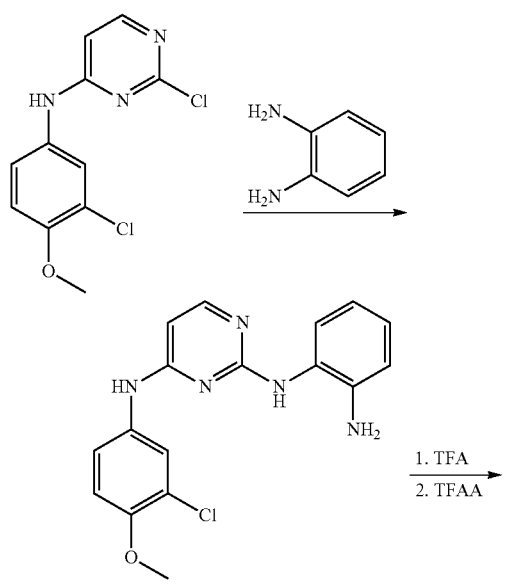

A mixture of 2-chloro-N-(3-chloro-4-methoxyphenyl)pyrimidin-4-amine (280 mg, 1.03 mmol) and benzene-1,2-diamine (540 mg, 5 mmol) in isopropanol (5 mL) was heated in a microwave oven at 160° C. for 10 minutes. The reaction mixture was diluted with water, extracted with EtOAc, then filtered through a short plug of silica gel, and concentrated to provide a first crude intermediate N$^2$-(2-aminophenyl)-N$^4$-(3-chloro-4-methoxyphenyl)pyrimidine-2,4-diamine.

The first crude intermediate was dissolved in dichloromethane (5 mL), then trifluoroacetic anhydride was added in two portions (0.5 mL each). The reaction mixture was washed with an aqueous NaHCO$_3$ solution, and purified by silica gel chromatography to provide a second crude intermediate N-(2-(4-(3-chloro-4-methoxyphenylamino)-pyrimidin-2-ylamino)phenyl)-2,2,2-trifluoroacetamide.

To a solution of the second crude intermediate (71 mg, 0.16 mmol) in acetonitrile (2 mL) was added trifluoroacetic acid (0.5 mL). The mixture was heated in a microwave oven at 180° C. for 1 hour and 45 minutes after which UPLC showed complete conversion. The final product was purified by silica gel chromatography to provide the title compound as a white solid (40 mg, 59%).

$^1$H NMR (500 MHz, DMSO-$d_6$) δ ppm 10.06-10.18 (m, 1H), 8.45 (d, J=5.7 Hz, 1H), 8.02 (d, J=8.2 Hz, 1H), 7.94 (d, J=7.3 Hz, 1H), 7.83-7.90 (m, 1H), 7.52-7.56 (m, J=8.2, 8.2, 1.3 Hz, 1H), 7.50 (td, J=7.9, 1.3 Hz, 1H), 7.43 (dd, J=9.0, 2.7 Hz, 1H), 7.15 (d, J=8.8 Hz, 1H), 6.86 (d, J=6.0 Hz, 1H), 3.84 (s, 3H); MS m/z 420 [M+H]$^+$.

Example 4

5-fluoro-N-(4-methylphenyl)-2-[2-(trifluoromethyl)imidazo[1,2-a]pyridin-3-yl]pyrimidin-4-amine (Cpd 43)

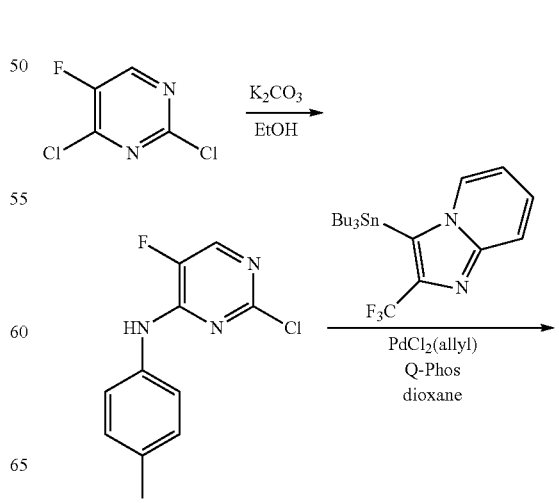

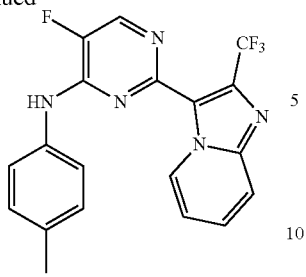

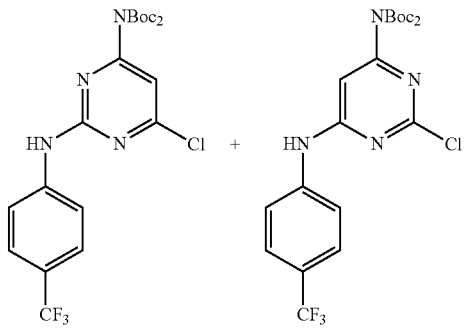

Step 1: A mixture of 2,4-dichloro-5-fluoropyrimidine (1.00 g, 5.99 mmol), 4-toluidine (642 mg, 5.99 mmol) and K$_2$CO$_3$ (1.66 g, 12.0 mmol) in EtOH (10 mL) was stirred for 18 hours at 50° C. The mixture was filtered through Celite and purified by column chromatography to yield 2-chloro-5-fluoro-N-p-tolylpyrimidin-4-amine (1.19 g, 84%).

Step 2: A mixture of 2-chloro-5-fluoro-N-p-tolylpyrimidin-4-amine (165 mg, 0.69 mmol), 3-(tributylstannyl)-2-(trifluoromethyl)imidazo[1,2-a]pyridine (300 mg, 0.63 mmol), Q-Phos (13.5 mg, 0.019 mmol) and PdCl$_2$(allyl) (6.9 mg, 0.019 mmol) in dioxane (1.5 mL) was stirred for 2 hours at 90° C. The mixture was purified by column chromatography to yield the title compound (213 mg, 80%).

$^1$H NMR (500 MHz, CHLOROFORM-d) δ ppm 9.24-9.29 (1H, m) 8.29 (1H, d, J=2.84 Hz) 7.66-7.71 (1H, m) 7.46 (2H, d, J=8.51 Hz) 7.31 (1H, ddd, J=9.14, 6.62, 1.26 Hz) 7.14 (2H, d, J=8.20 Hz) 6.82-6.89 (2H, m) 2.30 (3H, s); MS m/z 388.2 [M+H]$^+$.

Additional compounds of Formula (I) or a form thereof described herein may be prepared according to the procedure of Example 4 by substituting the appropriate starting materials, reagents and reaction conditions.

| Cpd | Name & Data |
|---|---|
| 44 | 5-chloro-N-(4-methylphenyl)-2-[2-(trifluoromethyl)imidazo[1,2-a]pyridin-3-yl]pyrimidin-4-amine<br>$^1$H NMR (500 MHz, CHLOROFORM-d) δ ppm 9.34-9.42 (1H, m) 8.51 (1H, s) 7.80 (1H, dd, J = 9.14, 0.95 Hz) 7.49 (2H, d, J = 8.51 Hz) 7.41 (1H, ddd, J = 8.99, 6.78, 1.26 Hz) 7.20-7.27 (3H, m) 6.91 (1H, td, J = 6.94, 1.26 Hz) 2.42 (3H, s); MS m/z 404.2 [M + H]$^+$ |

Example 5

2-(6-fluoro-2-methylimidazo[1,2-a]pyridin-3-yl)-N-[4-(trifluoromethyl)phenyl]pyrimidine-4,6-diamine (Cpd 68)

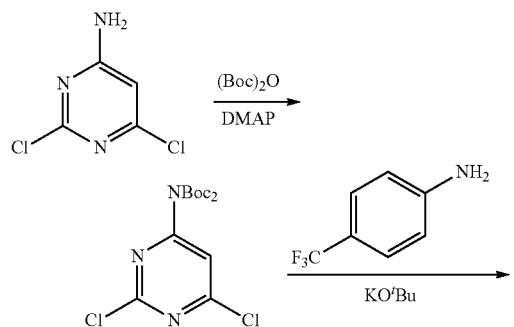

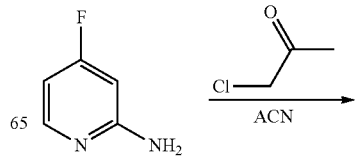

Step 1. A mixture of 2,6-dichloropyrimidine-4-amine (3.78 g, 23.05 mmol) and DMAP (cat.) in dichloromethane (20 mL) was treated with di-tert-butyldicarbonate (11.05 g, 50.71 mmol) at 0° C. After addition, the resulting mixture was stirred at ambient temperature overnight. The mixture was poured into ice-water (120 mL) and extracted with dichloromethane (150 mL). The organic phase was separated, washed with brine (100 mL), dried over MgSO$_4$, then filtered and evaporated. The residual material was separated by filtering through a pad of silica gel (100 g) to afford di-tert-butyl (2,6-dichloropyrimidin-4-yl)imidodicarbonate as an oil (7.55 g, 90%).

Step 2. A solution of di-tert-butyl (2,6-dichloropyrimidin-4-yl)imidodicarbonate (1.75 g, 4.81 mmol) and 4-trifluoromethylaniline (775.0 mg, 4.81 mmol) in THF (10 mL) was treated with potassium tert-butoxide solution (1M in THF, 9.62 mL, 9.62 mmol) at −78° C. The mixture was allowed to stir and warm to 0° C. over 20 minutes. The mixture was then poured into ice-water (120 mL) and extracted with dichloromethane (150 mL). The organic phase was separated, washed with brine (100 mL), dried over MgSO$_4$, then filtered and evaporated. The residual material was separated by silica gel column chromatography (by eluting with hexane then 2% ethyl acetate-hexane) to afford di-tert-butyl 6-chloro-2-(4-(trifluoromethyl)phenylamino)pyrimidin-4-yliminodicarbonate (750.0 mg, 32% yield), and (by eluting with 4% ethyl acetate-hexane) di-tert-butyl 2-chloro-6-(4-(trifluoromethyl)phenylamino)pyrimidin-4-yliminodicarbonate (1.08 g, 46%).

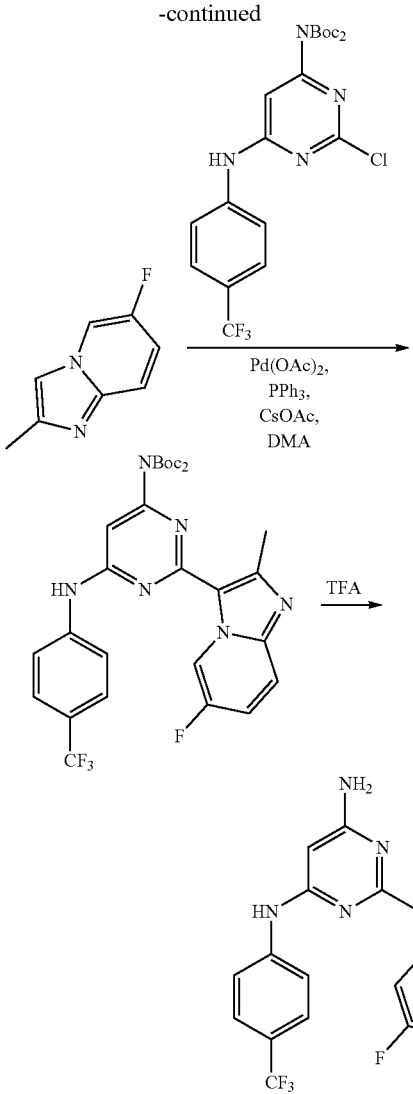

Step 3. 4-Fluoropyridin-2-amine (8.57 g, 76.44 mmol) and chloroacetone (12.99 g, 71.67 mmol) were pre-mixed and stirred in a 250 mL round bottom flask at 0° C. for 15 minutes. The resulting mixture was diluted with acetonitrile (50 mL) and refluxed for overnight. The acetonitrile was evaporated, and ethyl ether (200 mL) was added to produce a precipitate, which was collected by filtration. The solid was partitioned between dichloromethane (300 mL) and a saturated NaHCO$_3$ solution (250 mL). The organic layer was separated, dried over MgSO$_4$, then filtered and concentrated under the reduced pressure. The residual material was separated by silica gel column chromatography (1:1 ethyl acetate-hexane) to afford 6-fluoro-2-methylimidazo[1,2-a]pyridine (5.20 g, 46%) as a glassy solid.

$^1$H NMR (500 MHz, CHLOROFORM-d) δ ppm 7.95-7.99 (m, 1H), 7.46 (dd, J=5.04, 9.77 Hz, 1H), 7.34 (s, 1H), 6.99-7.06 (m, 1H), 2.44 (d, J=0.63 Hz, 3H); MS m/z 151.0 (100) [M+H]$^+$.

Step 4. A mixture of 6-fluoro-2-methylimidazo[1,2-a]pyridine (445.0 mg, 2.97 mmol), di-tert-butyl 2-chloro-6-(4-(trifluoromethyl)phenylamino)pyrimidin-4-yliminodicarbonate (1.0 g, 5.78 mmol), palladium (II) acetate (33.4 mg, 0.149 mmol), triphenylphosphine (46.7 mg, 0.178 mmol), cesium acetate (1.14 g, 5.94 mmol) and DMA (5 mL) was degassed by three cycles of vacuum pumping and N$_2$ purging, and then was heated to 100° C. for 1 hour. The solution was cooled and poured into water (50 mL), and this mixture was extracted with dichloromethane. The extract was dried over MgSO$_4$, then filtered and concentrated under the reduced pressure. The residual material was triturated with ethyl ether to afford di-tert-butyl 2-(6-fluoro-2-methylimidazo[1,2-a]pyridin-3-yl)-6-(4-(trifluoromethyl)phenylamino)pyrimidin-4-yliminodicarbonate (706.0 mg, 83%).

Step 5. A solution of di-tert-butyl 2-(6-fluoro-2-methylimidazo[1,2-a]pyridin-3-yl)-6-(4-(trifluoromethyl)phenylamino)pyrimidin-4-yliminodicarbonate (140 mg, 0.24 mmol) in dichloromethane (2 mL) was treated with TFA (0.4 mL) at 0° C. The resulting mixture was stirred at ambient temperature for 4 hours. The solvent was concentrated under reduced pressure, and the residual material was partitioned between ethyl acetate and a saturated NaHCO$_3$ solution. The organic layer was separated, dried over MgSO$_4$, then filtered and evaporated. The residual material was triturated with ethyl ether to afford the title compound as a white solid (87.0 mg, 87%). m.p. 209-211° C.

$^1$H NMR (500 MHz, Acetone-d$_6$) δ ppm 10.40 (dd, J=2.21, 5.36 Hz, 1H), 8.88 (s, 1H), 8.11-8.27 (m, 1H), 7.78-7.85 (m, 1H), 7.74 (d, J=8.83 Hz, 2H), 7.69 (d, J=8.83 Hz, 2H), 6.47 (br. s., 2H), 6.03 (s, 1H), 2.93 (s, 3H); MS m/z 403.5 (100) [M+H]$^+$, 404.4 (30).

Additional compounds of Formula (I) or a form thereof described herein may be prepared according to the procedure of Example 5 by substituting the appropriate starting materials, reagents and reaction conditions.

| Cpd | Name & Data |
|---|---|
| 65 | N-[4-(difluoromethoxy)phenyl]-2-[2-(trifluoromethyl)imidazo[1,2-a]pyridin-3-yl]pyrimidine-4,6-diamine<br>$^1$H NMR (500 MHz, Acetone-d$_6$) δ ppm 9.67 (ddd, J = 1.10, 1.26, 7.09 Hz, 1H), 8.40 (s, 1H), 7.73 (td, J = 1.10, 9.14 Hz, 1H), 7.59-7.66 (d, J = 9.1 Hz, 2H), 7.51 (ddd, J = 1.26, 6.94, 9.14 Hz, 1H), 7.15-7.23 (d, J = 9.1 Hz, 2H), 6.80-7.10 (t, J = 75.00 Hz, 1H), 7.05-7.12 (m, 1H), 6.11 (br. s., 2H), 5.96 (s, 1H); MS m/z 437.3 [M + H]$^+$ |
| 66 | 2-[2-(trifluoromethyl)imidazo[1,2-a]pyridin-3-yl]-N-[4-(trifluoromethyl)phenyl]pyrimidine-4,6-diamine<br>m.p. 203-205° C.; MS m/z 439.4 [M + H]$^+$ |
| 67 | N-[4-(trifluoromethoxy)phenyl]-2-[2-(trifluoromethyl)imidazo[1,2-a]pyridin-3-yl]pyrimidine-4,6-diamine<br>m.p. 199-202° C.; MS m/z 455.3 [M + H]$^+$ |
| 69 | N-[4-(difluoromethoxy)phenyl]-2-(6-fluoro-2-methylimidazo[1,2-a]pyridin-3-yl)pyrimidine-4,6-diamine<br>$^1$H NMR (500 MHz, Acetone-d$_6$) δ ppm 10.41 (dd, J = 2.21, 5.36 Hz, 1H), 8.57 (s, 1H), 8.19 (s, 1H), 7.71-7.89 (m, 1H), 7.53 (d, J = 9.77 Hz, 2H), 7.20-7.26 (d, J = 9.77 Hz, |

-continued

| Cpd | Name & Data |
|---|---|
| | 2H), 6.81-7.11 (t, J = 75.00 Hz, 1H), 6.36 (br, s., 2H), 5.91 (s, 1H), 2.91 (s, 3H); m.p. 136-138° C.; MS m/z 401.5 [M + H]+ |
| 75 | 2-(2-cyclopropyl-6-fluoroimidazo[1,2-a]pyridin-3-yl)-N-[4-(difluoromethoxy)-3-fluorophenyl]pyrimidine-4,6-diamine<br>1H NMR (500 MHz, DMSO-d6) δ ppm 10.06 (dd, J = 2.21, 5.99 Hz, 1H), 9.28 (s, 1H), 7.70-7.87 (m, 1H), 7.58 (dd, J = 5.52, 9.62 Hz, 1H), 7.41 (ddd, J = 2.68, 7.72, 9.77 Hz, 1H), 6.98-7.28 (t, J = 75.00 Hz, 1H), 7.24-7.32 (m, 1H), 7.18-7.24 (m, 1H), 6.73 (s, 2H), 5.72 (s, 1H), 3.42-3.56 (m, 1H), 0.89-1.11 (m, 4H); m.p. 198-200° C.; MS m/z 445.5 [M + H]+ |
| 84 | [3-(4-amino-6-{[4-(trifluoromethyl)phenyl]amino}pyrimidin-2-yl)-6-fluoroimidazo[1,2-a]pyridin-2-yl]methanol<br>1H NMR (500 MHz, METHANOL-d) δ ppm 9.36-9.77 (m, 1 H), 7.90-7.97 (m, 2 H), 7.59-7.69 (m, 1 H), 7.50-7.55 (m, 2 H), 7.-7.45 (m, 1 H), 6.55-6.58 (m, 1 H), 4.86 (s, 2 H); MS m/z 419.1 [M + H]+ |
| 100 | 2-(6-fluoro-2-methylimidazo[1,2-a]pyrimidin-3-yl)-N-[4-(trifluoromethyl)phenyl]pyrimidine-4,6-diamine<br>1H NMR (500 MHz, DMSO-d6) δ ppm 10.45 (dd, J = 2.84, 5.67 Hz, 1H), 9.46 (s, 1H), 8.76 (d, J = 2.84 Hz, 1H), 7.72 (d, J = 8.51 Hz, 2H), 7.64 (d, J = 8.51 Hz, 2H), 6.82 (s, 2H), 5.79 (s, 1H), 2.84 (s, 3H); m.p. 256-258° C.; MS m/z 404.3 [M + H]+ |

Example 6

2-(6-fluoro-2-methyl-1H-benzimidazol-1-yl)-N-[4-(trifluoromethyl)phenyl]pyrimidine-4,6-diamine (Cpd 71)

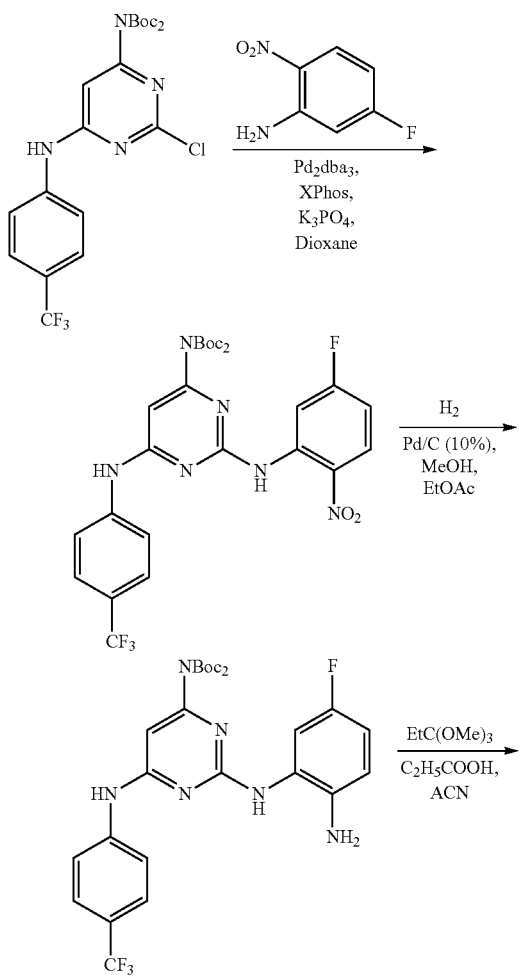

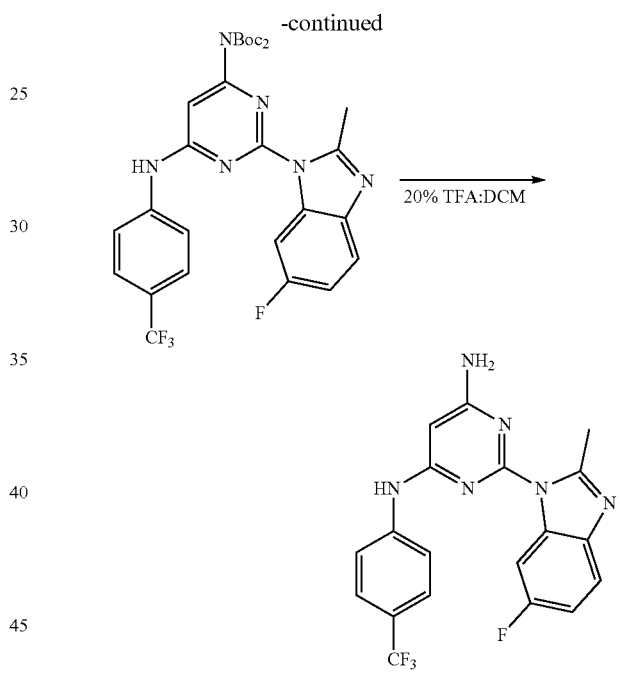

Step 1: A mixture of 5-fluoro-2-nitroaniline (156.2 mg, 1.00 mmol),), di-tert-butyl 2-chloro-6-(4-(trifluoromethyl)phenylamino)pyrimidin-4-yliminodicarbonate (480.0 mg, 0.98 mmol), 2-dicyclohexylphosphino-2',4',6'-triisopropylbiphenyl (Xphos) (56.1 mg, 0.1 mmol), tris(dibenzylideneacetone) dipalladium(0) (53.8 mg, 0.05 mmol) and potassium phosphate (625.0 mg, 2.95 mmol) in dioxane (2 mL) was degassed by three cycles of vacuum pumping and N2 purging, and then was heated to 100° C. for 2 hours. The solution was cooled and poured into water (10 mL), and this mixture was extracted with ethyl acetate (15 mL). The extract was dried over MgSO4, then filtered and evaporated. The residual material was separated by column chromatography (eluting with 1:1 dichloromethane:hexane, then 1:2 ethyl acetate:dichloromethane) to afford di-tert-butyl 2-(5-fluoro-2-nitrophenylamino)-6-(4-(trifluoromethyl)phenylamino)pyrimidin-4-yliminodicarbonate (483.0 mg, 81%).

Step 2: A pressure reaction vessel charged with di-tert-butyl 2-(5-fluoro-2-nitrophenylamino)-6-(4-(trifluoromethyl)phenylamino)pyrimidin-4-yliminodicarbonate (483.0 mg), Pd/C (10%, wet, 48.0 mg) and 1:1 ethyl acetate:methanol (5 mL) was placed on a Parr shaker. The mixture was degassed by three cycles of vacuum pumping and $N_2$ purging. The vessel was pressurized to 40 psi hydrogen and shaken for 2 hours. The charcoal was removed by filtration, and the solvent was evaporated to give di-tert-butyl 2-(2-amino-5-fluorophenylamino)-6-(4-(trifluoromethyl)phenylamino)-pyrimidin-4-yliminodicarbonate. The residual material was used in the next step without further purification. MS m/z 579.6 (100) [M+H]$^+$, 580.6 (40).

Step 3: A mixture of di-tert-butyl 2-(2-amino-5-fluorophenylamino)-6-(4-(trifluoromethyl)-phenylamino)pyrimidin-4-yliminodicarbonate (365.0 mg, 0.63 mmol), triethyl orthoacetate (306.0 mg, 1.89 mmol), p-toluenesulfonic acid (5.0 mg, 0.025 mmol) and ethanol (2.0 mL) was heated to reflux for 2 hours. After cooling, the mixture was partitioned between dichloromethane (20 mL) and a saturated $NaHCO_3$ solution (10 mL). The organic phase was washed with brine (10 mL), dried over $MgSO_4$, then filtered and evaporated. The residual oil was triturated with ethyl ether to afford di-tert-butyl 2-(6-fluoro-2-methyl-1H-benzo[d]imidazol-1-yl)-6-(4-(trifluoromethyl)phenylamino)pyrimidin-4-yliminodicarbonate (316.0 mg, 83%). MS m/z 603.6 (100) [M+H]$^+$, 604.6 (40).

Step 4: A solution of the product (316.0 mg, 0.52 mmol) in dichloromethane (3 mL) was treated with TFA (1 mL) at 0° C. The resulting mixture was stirred at ambient temperature for 4 hours. The solvent was evaporated, and the residual material was triturated with ethyl ether to afford the title compound as a white solid (152.0 mg, 73%). m.p. 253-255° C.

$^1$H NMR (500 MHz, DMSO-$d_6$) δ ppm 9.72 (s, 1H), 8.00 (d, J=8.51 Hz, 2H), 7.52-7.69 (m, 3H), 7.45 (dd, J=1.89, 9.14 Hz, 1H), 7.01-7.24 (m, 3H), 6.20 (s, 1H), 2.66 (s, 3H); MS m/z 403.3 (100) [M+H]$^+$.

Additional compounds of Formula (I) or a form thereof described herein may be prepared according to the procedure of Example 6 by substituting the appropriate starting materials, reagents and reaction conditions.

| Cpd | Name & Data |
|---|---|
| 93 | 2-(6-chloro-2-methyl-1H-benzimidazol-1-yl)-N-P-(trifluoromethyl)phenyl]pyrimidine-4,6-diamine<br>$^1$H NMR (500 MHz, DMSO-$d_6$) δ ppm 9.76 (s, 1H), 8.19 (d, J = 1.9 Hz, 1H), 7.74 (d, J = 8.5 Hz, 2H), 7.64 (d, J = 8.5 Hz, 2H), 7.60 (d, J = 8.5 Hz, 1H), 7.27 (dd, J = 8.5, 1.9 Hz, 1H), 7.02 (br. s., 2H), 5.90 (s, 1H), 2.83 (s, 3H); MS m/z 419.8 [M + H]$^+$ |
| 72 | N-[4-(difluoromethoxy)phenyl]-2-(6-fluoro-2-methyl-1H-benzimidazol-1-yl)pyrimidine-4,6-diamine<br>$^1$H NMR (500 MHz, DMSO-$d_6$) δ ppm 9.25 (s, 1H), 7.99 (dd, J = 2.21, 10.09 Hz, 1H), 7.56 (dd, J = 5.04, 8.83 Hz, 1H), 7.48 (d, J = 8.83 Hz, 2H), 7.00-7.30 (t, J = 75.00 Hz, 1H), 7.12-7.19 (m, 2H), 7.07 (dt, J = 2.36, 9.06 Hz, 1H), 6.84 (br. s., 2H), 5.74 (s, 1H), 2.80 (s, 3H); m.p. 168-170° C.; MS m/z 401.5 [M + H]$^+$ |
| 76 | N-[4-(difluoromethoxy)-3-fluorophenyl]-2-(6-fluoro-2-methyl-1H-benzimidazol-1-yl)pyrimidine-4,6-diamine<br>$^1$H NMR (500 MHz, DMSO-$d_6$) δ ppm 9.47 (s, 1H), 7.96 (d, J = 9.14 Hz, 1H), 7.66 (d, J = 12.93 Hz, 1H), 7.57 (dd, J = 5.04, 8.20 Hz, 1H), 7.00-7.28 (t, J = 70.00 Hz, 1H), 7.27-7.39 (m, 1H), 7.23 (d, J = 8.51 Hz, 1H), 7.08 (t, J = 8.20 Hz, 1H), 6.94 (br. s., 2H), 5.80 (s, 1H), 2.50 (br. s., 3H); m.p. 182-183° C.; MS m/z 419.4 [M + H]$^+$ |
| 77 | N-[4-(difluoromethoxy)-3-fluorophenyl]-2-(2-ethyl-6-fluoro-1H-benzimidazol-1-yl)pyrimidine-4,6-diamine<br>$^1$H NMR (500 MHz, DMSO-$d_6$) δ ppm 9.47 (br. s., 1H), 7.90 (d, J = 9.14 Hz, 1H), 7.50-7.74 (m, 2H), 7.29 (d, J = 5.04 Hz, 1H), 7.00-7.28 (t, J = 70.00 Hz, 1H), 7.22 (d, J = 8.20 Hz, 1H), 7.09 (d, J = 7.88 Hz, 1H), 6.93 (br. s., 2H), 5.80 (s, 1H), 3.27 (m,2H), 1.28 (t, J = 6.62 Hz, 3H); m.p. 156-158° C.; MS m/z 433.5 [M + H]$^+$ |
| 81 | 2-(2-ethyl-6-fluoro-1H-benzimidazol-1-yl)-N-[4-(trifluoromethyl)phenyl]pyrimidine-4,6-diamine<br>$^1$H NMR (500 MHz, DMSO-$d_6$) δ ppm 9.64 (s, 1H), 7.89 (dd, J = 2.52, 10.09 Hz, 1H), 7.70 (d, J = 8.20 Hz, 2H), 7.58-7.66 (m, 3H), 7.05-7.13 (m, 1H), 6.98 (br. s., 2H), 5.88 (s, 1H), 3.28 (q, J = 7.46 Hz, 2H), 1.28 (t, J = 7.57 Hz, 3H); m.p. 201-203° C.; MS m/z 417.2 [M + H]$^+$ |
| 96 | 2-(6-chloro-2-methyl-1H-benzimidazol-1-yl)-N-[3-fluoro-4-(trifluoromethyl)phenyl]pyrimidine-4,6-diamine<br>$^1$H NMR (500 MHz, Acetone-$d_6$) δ ppm 9.11 (br. s, 1H), 8.27 (d, J = 2.2 Hz, 1H), 7.78 (dd, J = 13.9, 1.6 Hz, 1H), 7.65 (t, J = 8.5 Hz, 1H), 7.56 (d, J = 8.5 Hz, 1H), 7.49 (d, J = 8.8 Hz, 1H), 7.25 (dd, J = 8.5, 1.9 Hz, 1H), 6.57 (br. s., 2H), 6.07 (s, 1H), 2.87 (s, 3H); MS m/z 437.8 [M + H]$^+$ |
| 97 | 2-(6-chloro-2-methyl-1H-benzimidazol-1-yl)-N-[4-(difluoromethoxy)phenyl]pyrimidine-4,6-diamine<br>$^1$H NMR (500 MHz, Acetone-$d_6$) δ ppm 8.56 (br. s, 1H), 8.32 (d, J = 2.2 Hz, 1H), 7.56 (dd, J = 6.6, 2.2 Hz, 2H), 7.53 (d, J = 8.8 Hz, 1H), 7.23 (dd, J = 8.5, 2.2 Hz, 1H), 7.20 (dd, J = 6.6, 2.2 Hz, 2H), 6.94 (t, J = 74.7 Hz, 1H), 6.35 (br. s., 2H), 5.91 (s, 1H), 2.85 (s, 3H); MS m/z 418.0 [M + H]$^+$ |
| 98 | 2-(5-chloro-2-methyl-1H-benzimidazol-1-yl)-N-[3-fluoro-4-(trifluoromethyl)phenyl]pyrimidine-4,6-diamine<br>$^1$H NMR (500 MHz, DMSO-$d_6$) δ ppm 9.94 (br. s, 1H), 8.10 (d, J = 8.7 Hz, 1H), 7.82 (dd, J = 14.3, 1.4 Hz, 1H), 7.67 (d, J = 2.0 Hz, 1H), 7.65 (d, J = 8.7 Hz, 1H), 7.42 (dd, J = 8.7, 1.1 Hz, 1H), 7.27 (dd, J = 8.7, 2.0 Hz, 1H), 7.10 (br. s, 2H), 5.93 (s, 1H), 2.83 (s, 3H); MS m/z 437.8 [M + H]$^+$ |
| 99 | 2-(5-chloro-2-methyl-1H-benzimidazol-1-yl)-N-[4-(difluoromethoxy)phenyl]pyrimidine-4,6-diamine<br>$^1$H NMR (500 MHz, DMSO-$d_6$) δ ppm 8.99 (br. s, 1H), 8.72 (d, J = 8.8 Hz, 1H), 8.03 (d, J = 2.5 Hz, 1H), 8.00-8.03 (m, 2H), 7.65-7.67 (m, 2H), 7.64 (dd, J = 8.8, 2.2 Hz, 1H), 7.42 (t, J = 75.0 Hz, 1H), 6.79 (br. s., 2H), 6.38 (s, 1H), 3.32 (s, 3H); MS m/z 417.8 [M + H]$^+$ |

| Cpd | Name & Data |
|---|---|
| 144 | N-[4-(difluoromethoxy)phenyl]-2-(2-ethyl-6-fluoro-1H-benzimidazol-1-yl)pyrimidine-4,6-diamine<br>$^1$H NMR (500 MHz, DMSO-d$_6$) δ ppm 9.25 (s, 1H), 7.84-8.12 (m, 1H), 7.60 (dd, J = 5.04, 8.51 Hz, 1H), 7.49 (d, J = 8.83 Hz, 2H), 7.01-7.31 (t, J = 75.00 Hz, 1H), 7.15 (d, J = 8.20 Hz, 2H), 7.04-7.13 (m, 1H), 6.84 (br. s., 2H), 5.76 (s, 1H), 3.28 (q, J = 7.25 Hz, 2H), 1.28 (t, J = 7.41 Hz, 3H); m.p. 166-168° C.; MS m/z 415.4 [M + H]$^+$ |

Example 7

2-(2-cyclopropyl-6-fluoro-1H-benzimidazol-1-yl)-N-[4-(trifluoromethyl)phenyl]pyrimidine-4,6-diamine (Cpd 82)

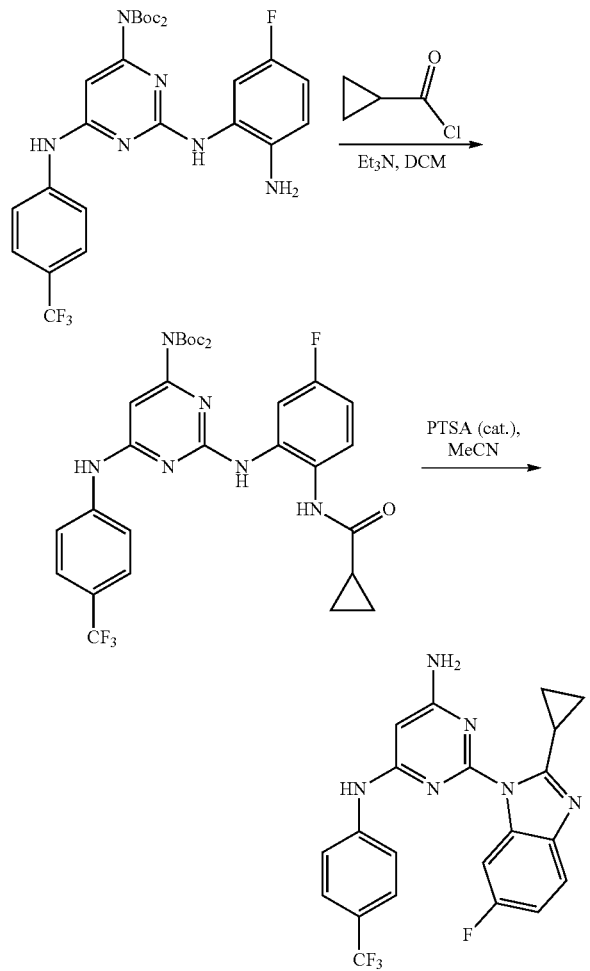

Step 1: To a solution of di-tert-butyl 2-(2-amino-5-fluorophenylamino)-6-(4-(trifluoromethyl)-phenylamino)pyrimidin-4-yliminodicarbonate (212.0 mg, 0.37 mmol), triethylamine (42.0 mg, 0.41 mmol) in dichloromethane (2 mL) was added cyclopropanecarbonyl chloride (38.3 mg, 0.37 mmol) at 0° C. The mixture was stirred at ambient temperature for 3 hours, then partitioned between dichloromethane and water. The organic phase was washed with brine, dried over MgSO$_4$, then filtered and evaporated to give di-tert-butyl 2-(2-(cyclopropanecarboxamido)-5-fluorophenylamino)-6-(4-(trifluoromethyl)phenylamino)-pyrimidin-4-yliminodicarbonate. The residual solid was used directly in the next step without further purification.

Step 2: A mixture of crude di-tert-butyl 2-(2-(cyclopropanecarboxamido)-5-fluorophenylamino)-6-(4-(trifluoromethyl)phenylamino)-pyrimidin-4-yliminodicarbonate, p-toluenesulfonic acid (7.0 mg, 0.037 mmol) and acetonitrile (3 mL) was heated in a microwave oven at 180° C. for 30 minutes. The mixture was partitioned between ethyl acetate and a saturated NaHCO$_3$ solution. The organic phase was washed with brine, dried over MgSO$_4$, then filtered and evaporated. The residual material was separated by silica gel column chromatography (eluting with 1:1 dichloromethane: hexane, then 1:5 MeOH:50% ethyl acetate in dichloromethane) to afford the title compound (103.0 mg, 65% for two steps). m.p. 203-206° C.

$^1$H NMR (500 MHz, DMSO-d$_6$) δ ppm 9.49-9.59 (m, 1H), 7.70 (td, J=1.00, 13.24 Hz, 1H), 7.64 (d, J=8.57 Hz, 2H), 7.49 (d, J=8.57 Hz, 2H), 7.36-7.42 (m, 1H), 6.91-6.97 (m, 1H), 6.88 (br. s, 2H), 5.77 (s, 1H), 2.88-3.01 (m, 1H), 0.97-1.05 (m, 2H), 0.86-0.95 (m, 2H); MS m/z 429.2 (100) [M+H]$^+$, 430.2 (20).

Additional compounds of Formula (I) or a form thereof described herein may be prepared according to the procedure of Example 7 by substituting the appropriate starting materials, reagents and reaction conditions.

| Cpd | Name & Data |
|---|---|
| 78 | 2-(2-cyclopropyl-6-fluoro-1H-benzimidazol-1-yl)-N-[4-(difluoromethoxy)-3-fluorophenyl]pyrimidine-4,6-diamine<br>$^1$H NMR (500 MHz, DMSO-d$_6$) δ ppm 9.53 (s, 1H), 7.70-7.95 (m, 2H), 7.52 (dd, J = 5.04, 8.83 Hz, 1H), 7.28 (d, J = 2.52 Hz, 1H), 6.98-7.26 (t, J = 70.00 Hz, 1H), 7.22 (m, 1H), 7.03-7.09 (m, 1H), 6.98 (br. s, 2H), 5.82 (s, 1H), 3.07 (m, 1H), 1.10-1.15 (m, 2H), 1.01-1.08 (m, 2H); m.p. 186-188° C.; MS m/z 445.5 [M + H]$^+$ |

-continued

| Cpd | Name & Data |
|---|---|
| 83 | 2-(2-cyclopropyl-5-fluoro-1H-benzimidazol-1-yl)-N-[4-(trifluoromethyl)phenyl]pyrimidine-4,6-diamine<br>$^1$H NMR (500 MHz, DMSO-$d_6$) δ ppm 9.69 (s, 1H), 7.96 (d, J = 5.04, 8.83 Hz, 1H), 7.79 (d, J = 8.51 Hz, 2H), 7.61 (d, J = 8.51 Hz, 2H), 7.34 (dd, J = 2.52, 9.46 Hz, 1H), 6.93-7.09 (m, 3H), 5.78-5.93 (m, 1H), 3.02 (s, 1H), 1.13-1.19 (m, 2H), 1.04-1.08 (m, 2H); MS m/z 429.2 [M + H]$^+$ |
| 143 | 2-(2-cyclopropyl-6-fluoro-1H-benzimidazol-1-yl)-N-[4-(difluoromethoxy)phenyl]pyrimidine-4,6-diamine<br>$^1$H NMR (500 MHz, DMSO-$d_6$) δ ppm 9.30 (s, 1H), 7.83-7.90 (m, 1H), 7.54 (d, J = 8.83 Hz, 3H), 7.00-7.30 (t, J = 75.00 Hz, 1H), 7.11-7.18 (m, 2H), 7.02-7.10 (m, 1H), 6.83-6.92 (m, 2H), 5.78 (s, 1H), 3.08-3.20 (m, 1H), 1.09-1.14 (m, 2H), 0.99-1.07 (m, 2H); m.p. 175-177° C.; MS m/z 427.2 [M + H]$^+$ |
| 145 | N-[4-(difluoromethoxy)phenyl]-2-[2-(difluoromethyl)-6-fluoro-1H-benzimidazol-1-yl]pyrimidine-4,6-diamine<br>$^1$H NMR (500 MHz, DMSO-$d_6$) δ ppm 9.32 (s, 1H), 8.36 (dd, J = 1.89, 10.09 Hz, 1H), 7.95-8.16 (t, J = 52.5 Hz, 1H), 7.85 (dd, J = 5.04, 8.83 Hz, 1H), 7.44 (d, J = 8.83 Hz, 2H), 7.04-7.34 (t, J = 75.00 Hz, 1H), 7.27 (dt, J = 2.36, 9.06 Hz, 1H), 7.20 (d, J = 8.83 Hz, 2H), 6.98 (br. s., 2H), 5.76 (s, 1H); m.p. 114-115° C.; MS m/z 437.4 [M + H]$^+$ |
| 149 | 2-(2-cyclopropyl-1H-benzimidazol-1-yl)-N-[4-(trifluoromethyl)phenyl]pyrimidine-4,6-diamine<br>$^1$H NMR (500 MHz, DMSO-$d_6$) δ ppm 9.70 (s, 1H), 7.92-7.97 (m, 1H), 7.81 (d, J = 8.51 Hz, 2H), 7.60 (d, J = 8.51 Hz, 2H), 7.50-7.55 (m, 1H), 7.19 (ddd, J = 1.58, 5.04, 7.25 Hz, 2H), 7.00 (br. s., 2H), 5.90 (s, 1H), 2.94-3.03 (m, 1H), 1.15 (m, 2H), 1.05 (m, 2H); m.p. 199-201° C.; MS m/z 411.3 [M + H]$^+$ |
| 150 | 2-[2-(methoxymethyl)-1H-benzimidazol-1-yl]-N-[4-(trifluoromethyl)phenyl]pyrimidine-4,6-diamine<br>$^1$H NMR (500 MHz, DMSO-$d_6$) δ ppm 9.66 (s, 1H), 8.09-8.20 (m, 1H), 7.73 (d, J = 8.51 Hz, 2H), 7.67-7.71 (m, 1H), 7.63 (d, J = 8.51 Hz, 2H), 7.26-7.31 (m, 2H), 6.97 (br. s., 2H), 5.87 (s, 1H), 5.04 (s, 2H), 3.25 (s, 3H); m.p. 212-213° C.; MS m/z 415.4 [M + H]$^+$ |
| 151 | 2-[2-(propan-2-yl)-1H-benzimidazol-1-yl]-N-[4-(trifluoromethyl)phenyl]pyrimidine-4,6-diamine<br>$^1$H NMR (500 MHz, DMSO-$d_6$) δ ppm 9.69 (s, 1H), 7.85-7.91 (m, 1H), 7.74 (d, J = 8.83 Hz, 2H), 7.61-7.65 (m, 1H), 7.59 (d, J = 8.83 Hz, 2H), 7.17-7.25 (m, 2H), 6.95 (s, 2H), 5.90 (s, 1H), 3.96-4.08 (m, 1H), 1.29 (d, J = 6.94 Hz, 6H); m.p. 216-218° C.; MS m/z 413.4 [M + H]$^+$ |
| 152 | 2-[2-(difluoromethyl)-1H-benzimidazol-1-yl]-N-[4-(trifluoromethyl)phenyl]pyrimidine-4,6-diamine<br>$^1$H NMR (500 MHz, DMSO-$d_6$) δ ppm 9.71 (s, 1H), 8.36-8.52 (m, 1H), 7.89-8.11 (t, J = 55.00 Hz, 1H), 7.80-7.87 (m, 1H), 7.68 (m. 4H), 7.35-7.48 (m, 2H), 6.92-7.20 (m, 2H), 5.91 (s, 1H); m.p. 187-188° C.; MS m/z 421.4 [M + H]$^+$ |

Example 8

2-(6-fluoro-2-methyl-1H-benzimidazol-1-yl)-N-(4-methoxyphenyl)pyrimidine-4,6-diamine (Cpd 265)

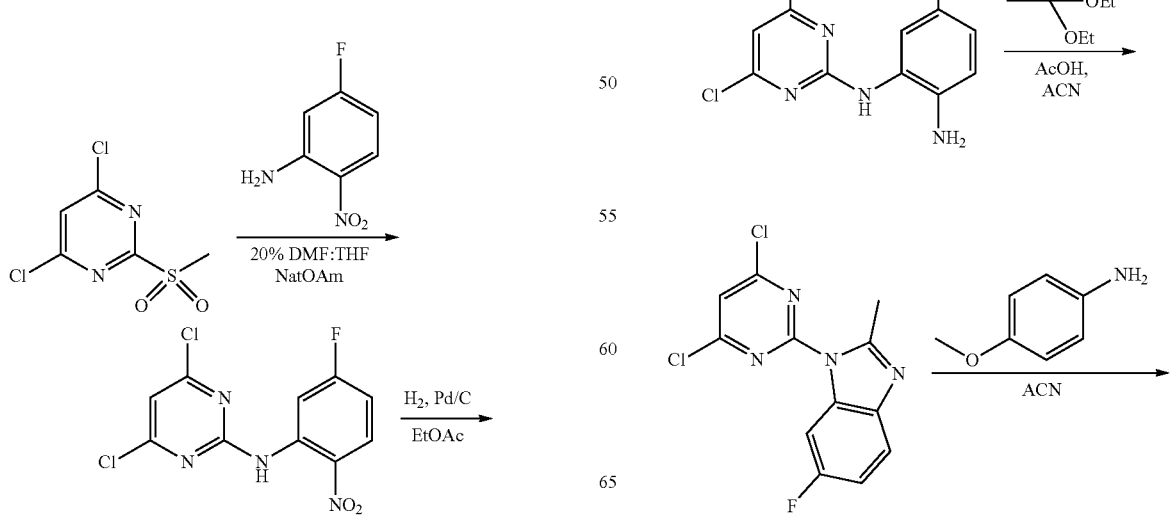

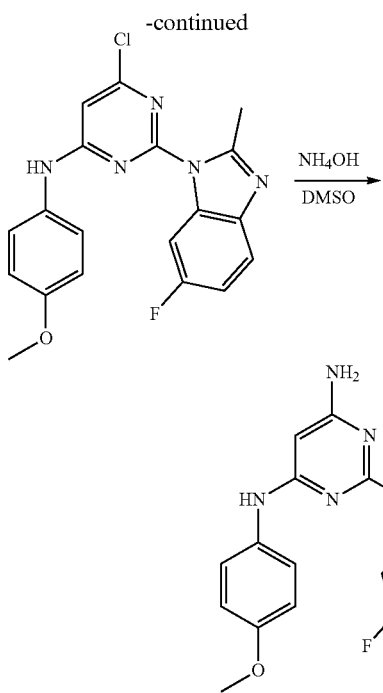

Step 1: To a mixture of 5-fluoro-2-nitroaniline (8.16 g, 35.93 mmol), 4,6-dichloro-2-(methylsulfonyl)pyrimidine (5.06 g, 32.67 mmol), THF (50 mL) and DMF (12 mL) was added sodium tert-pentoxide (2.5 M in THF, 28.6 mL, 71.5 mmol) dropwise at −78° C. The mixture was stirred at −78° C. for 30 minutes, then ice/water (300 mL) was added to form a precipitate. The solid was collected by filtration, then washed with water and hexane to afford 4,6-dichloro-N-(5-fluoro-2-nitrophenyl)pyrimidin-2-amine (9.32 g, 95%).

Step 2: A 250 mL flask charged with 4,6-dichloro-N-(5-fluoro-2-nitrophenyl)pyrimidin-2-amine (6.35 g, 21.03 mmol), Pd/C (10%, wet, 635.0 mg) and ethyl acetate (50 mL) was degassed by three cycles of vacuum pumping and $N_2$ purging, and then filled with hydrogen from a hydrogen balloon. The mixture was stirred at ambient temperature for 16 hours. The charcoal was removed by filtration, and the solvent was evaporated. The residual material was washed with hexane to afford $N^1$-(4,6-dichloropyrimidin-2-yl)-5-fluorobenzene-1,2-diamine as a white solid (5.55 g, 97%).

Step 3: A mixture of $N^1$-(4,6-dichloropyrimidin-2-yl)-5-fluorobenzene-1,2-diamine (2.57 g, 9.47 mmol), triethyl orthoacetate (6.06 g, 37.87 mmol), acetic acid (6 mL) and acetonitrile (30 mL) was stirred at ambient temperature for 18 hours. A saturated $NaHCO_3$ solution was added to the mixture portionwise at 0° C., with resultant bubbling of the mixture. The solution was added to the mixture until the bubbling ceased. The product was then extracted with ethyl acetate. The organic phase was washed with brine, dried over $MgSO_4$, then filtered and evaporated. The residual material was washed with hexane to afford 1-(4,6-dichloropyrimidin-2-yl)-6-fluoro-2-methyl-1H-benzo[d]imidazole as a brownish solid (2.41 g, 86%).

Step 4: A mixture of 1-(4,6-dichloropyrimidin-2-yl)-6-fluoro-2-methyl-1H-benzo[d]imidazole (150.0 mg, 0.51 mmol), 4-methoxyaniline (125.0 mg, 1.01 mmol) and acetonitrile (1 mL) was stirred at 80° C. for 18 hours. After cooling, ethyl ether was added to the mixture to form 6-chloro-2-(6-fluoro-2-methyl-1H-benzo[d]imidazol-1-yl)-N-(4-methoxyphenyl)pyrimidin-4-amine as a precipitate, which was isolated by filtration.

Step 5: To 6-chloro-2-(6-fluoro-2-methyl-1H-benzo[d]imidazol-1-yl)-N-(4-methoxyphenyl)-pyrimidin-4-amine was added DMSO (2 mL) and $NH_4OH$ (27%, 0.1 mL). The reaction mixture was sealed, placed in a microwave oven and heated at 170° C. for 1 hour. The reaction mixture was partitioned between ethyl acetate and water. The organic phase was washed with water (2×20 mL) and brine, then dried over $MgSO_4$ and filtered through a silica gel pad (10 g). The solvent was evaporated, and the residual material was triturated with dichloromethane to afford the title compound as a white solid (161.0 mg, 88%). m.p. 193-195° C.

$^1$H NMR (500 MHz, Acetone-$d_6$) □ δ ppm 8.74 (s, 1H), 8.11 (dd, J=2.52, 10.40 Hz, 1H), 7.52 (dd, J=5.20, 8.67 Hz, 1H), 7.34-7.43 (d, J=9.14 Hz, 2H), 7.01 (d, J=2.84 Hz, 1H), 6.94 (d, J=9.14 Hz, 2H), 6.49 (br. s., 2H), 5.76 (s, 1H), 3.79 (s, 3H), 2.84 (s, 3H); MS m/z 365.0 (100) [M+H]$^+$.

Additional compounds of Formula (I) or a form thereof described herein may be prepared according to the procedure of Example 8 by substituting the appropriate starting materials, reagents and reaction conditions.

| Cpd | Name & Data |
|---|---|
| 52 | 2-{[6-{[4-(difluoromethoxy)phenyl]amino}-2-(2-methyl-1H-benzimidazol-1-yl)pyrimidin-4-yl]amino}ethanol<br>$^1$H NMR (500 MHz, Methanol-$d_4$) δ ppm 8.17 (1H, dd, J = 7.2, 1.5 Hz), 7.59 (1H, dd, J = 7.2, 1.5 Hz), 7.51 (2H, d, J = 9 Hz), 7.28 (1H, m), 7.13 (2H, d, J = 9 Hz), 6.78 (1H, t, J = 75 Hz), 5.81 (1H, s), 3.75 (2H, t, J = 6 Hz), 3.53 (2H, br), 2.89 (3H, s); MS m/z 427.1 [M + H]$^+$ |
| 57 | 2-{[2-(2-methyl-1H-benzimidazol-1-yl)-6-{[4-(trifluoromethyl)phenyl]amino}pyrimidin-4-yl]amino}ethanol<br>$^1$H NMR (500 MHz, Methanol-$d_4$) δ ppm 8.13 (1H, d, J = 7.5 Hz), 7.71 (2H, d, J = 7.5 Hz), 7.6 (1H, dd, J = 9, 1 Hz), 7.56 (2H, d, J = 9 Hz), 7.27 (1H, m), 7.13 (2H, d, J = 9 Hz), 5.91 (1H, s), 3.76 (2H, t, J = 6 Hz), 3.55 (2H, br), 2.89 (3H, s); MS m/z 429.2 [M + H]$^+$ |
| 58 | $N^4$-(2-methoxyethyl)-2-(2-methyl-1H-benzimidazol-1-yl)-$N^6$-[4-(trifluoromethyl)phenyl]pyrimidine-4,6-diamine<br>$^1$H NMR (Methanol-$d_4$) δ ppm 8.15 (1H, d, J = 8 Hz), 7.67 (2H, d, J = 8.5 Hz), 7.59 (1H, d, J = 8 Hz), 7.53 (2H, d, J = 8.5 Hz), 7.26 (1H, m), 5.87 (1H, s), 3.58 (4H, br), 3.38 (3H, s).2.87 (3H, s); MS m/z 443.1 [M + H]$^+$ |
| 59 | $N^4$-[4-(difluoromethoxy)phenyl]-$N^6$-(2-methoxyethyl)-2-(2-methyl-1H-benzimidazol-1-yl)pyrimidine-4,6-diamine<br>$^1$H NMR (500 MHz, Methanol-$d_4$) δ ppm 8.06 (1H, d, J = 7 Hz), 7.47 (1H, m), 7.38 (2H, d, J = 9 Hz), 7.15 (1H, m), 7.00 (2H, d, J = 9 Hz), 5.68 (1H, s), 3.28 (3H, s), 2.76 (3H, s); MS m/z 441.1 [M + H]$^+$ |

-continued

| Cpd | Name & Data |
|---|---|
| 63 | 2-(2-methyl-1H-benzimidazol-1-yl)-N-[4-(trifluoromethyl)phenyl]pyrimidine-4,6-diamine<br>$^1$H NMR (500 MHz, Methanol-$d_4$) δ ppm 8.13 (1H, m), 7.73 (2H, d, J = 8.5 Hz), 7.61 (1H, m), 7.58 (2H, d, J = 8.5 Hz), 7.29 (2H, m), 5.95 (1H, s), 2.89 (3H, s); MS m/z 385.1 [M + H]$^+$ |
| 64 | 2-(5,6-difluoro-2-methyl-1H-benzimidazol-1-yl)-N-[4-(trifluoromethyl)phenyl]pyrimidine-4,6-diamine<br>$^1$H NMR (500 MHz, Methanol-$d_4$) δ ppm 8.19 (1H, dd, J = 11, 7.5 Hz), 7.67 (2H, d, J = 8.5 Hz), 7.6 (2H, d, J = 8.5 Hz), 7.43 (1H, dd, J = 11, 7.5 Hz), 5.93 (1H, s), 2.9 (3H, s); MS m/z 421.1 [M + H]$^+$ |
| 73 | 2-(2-methyl-1H-imidazo[4,5-b]pyridin-1-yl)-N-[4-(trifluoromethyl)phenyl]pyrimidine-4,6-diamine<br>$^1$H NMR (500 MHz, Methanol-$d_4$) δ ppm 8.61 (1H, dd, J = 8, 1.5 Hz), 8.39 (1H, d, J = 4 Hz), 7.65 (2H, d, J = 8.5 Hz), 7.57 (2H, d, J = 8.5 Hz), 7.28 (1H, dd, J = 8, 4 Hz), 5.91 (1H, s), 2.97 (3H, s); MS m/z 386.2 [M + H]$^+$ |
| 74 | 2-(5,6-difluoro-2-methyl-1H-benzimidazol-1-yl)-N-[3-fluoro-4-(trifluoromethyl)phenyl]pyrimidine-4,6-diamine<br>$^1$H NMR (500 MHz, Methanol-$d_4$) δ ppm 8.04 (1H, dd, J = 11, 7.5 Hz), 7.54 (1H, dd, J = 13.5, 1.5 Hz), 7.44 (1H, t, J = 8.5 Hz), 7.32 (1H, dd, J = 11, 7.5 Hz), 7.24 (1H, dd, J = 13.5, 1.5 Hz), 5.81 (1H, s), 2.78 (3H, s); MS m/z 439.1 [M + H]$^+$ |
| 79 | N-[4-(trifluoromethyl)phenyl]-2-(2,5,6-trimethyl-1H-benzimidazol-1-yl)pyrimidine-4,6-diamine<br>$^1$H NMR (500 MHz, DMSO-$d_6$) δ ppm 9.63 (s, 1H), 7.91 (s, 1H), 7.77 (d(AB), J = 8.8 Hz, 2H), 7.63 (d(AB), J = 7.9 Hz, 2H), 7.34 (s, 1H), 6.92 (br. s., 2H), 5.85 (s, 1H), 2.79 (s, 3H), 2.31 (s, 3H), 2.26 (s, 3H); MS m/z 413.0 [M + H]$^+$ |
| 80 | N-[3-fluoro-4-(trifluoromethyl)phenyl]-2-(2-methyl-1H-benzimidazol-1-yl)pyrimidine-4,6-diamine<br>$^1$H NMR (500 MHz, DMSO-$d_6$) δ ppm 9.90 (s, 1H), 8.05-8.10 (m, 1H), 7.89 (d, J = 14.2 Hz, 1H), 7.65 (t, J = 8.7 Hz, 1H), 7.57-7.62 (m, 1H), 7.41 (d, J = 8.5 Hz, 1H), 7.20-7.28 (m, 2H), 7.05 (br. s, 1H), 5.91 (s, 1H), 2.82 (s, 3H); MS m/z 403.1 [M + H]$^+$ |
| 85 | 2-(6-bromo-2-methyl-1H-benzimidazol-1-yl)-N-[4-(trifluoromethyl)phenyl]pyrimidine-4,6-diamine<br>$^1$H NMR (500 MHz, DMSO-$d_6$) δ ppm 9.68 (s, 1H), 8.31 (d, J = 1.6 Hz, 1H), 7.73 (d(AB), J = 8.2 Hz, 2H), 7.65 (d(AB), J = 8.5 Hz, 2H), 7.55 (d, J = 8.5 Hz, 1H), 7.39 (dd, J = 8.5, 1.9 Hz, 1H), 6.97-7.07 (m, 2H), 5.87 (s, 1H), 2.83 (s, 3H); MS m/z 463.0 [M + H]$^+$ |
| 86 | 2-(2,6-dimethyl-1H-benzimidazol-1-yl)-N-[4-(trifluoromethyl)phenyl]pyrimidine-4,6-diamine<br>$^1$H NMR (500 MHz, DMSO-$d_6$) δ ppm 9.63 (s, 1H), 7.88 (s, 1H), 7.74 (d(AB), J = 8.5 Hz, 2H), 7.61 (d(AB), J = 8.5 Hz, 2H), 7.44 (d, J = 8.2 Hz, 1H), 7.04 (dd, J = 8.2, 1.3 Hz, 1H), 6.93 (br. s., 2H), 5.84 (s, 1H), 2.77 (s, 3H), 2.34 (s, 3H); MS m/z 339.0 [M + H]$^+$ |
| 87 | 2-(6-ethyl-2-methyl-1H-benzimidazol-1-yl)-N-[4-(trifluoromethyl)phenyl]pyrimidine-4,6-diamine<br>$^1$H NMR (500 MHz, DMSO-$d_6$) δ ppm 9.68 (s, 1H), 7.89 (s, 1H), 7.77 (d(AB), J = 8.5 Hz, 2H), 7.61 (d(AB), J = 8.8 Hz, 2H), 7.52 (d, J = 8.2 Hz, 1H), 7.10 (dd, J = 8.2, 1.3 Hz, 1H), 6.95 (br. s., 2H), 5.86 (s, 1H), 2.81 (s, 3H), 2.64 (q, J = 7.6 Hz, 2H), 1.15 (t, J = 7.6 Hz, 3H); MS m/z 413.0 [M + H]$^+$ |
| 88 | 2-(4,6-difluoro-2-methyl-1H-benzimidazol-1-yl)-N-[4-(trifluoromethyl)phenyl]pyrimidine-4,6-diamine<br>$^1$H NMR (500 MHz, DMSO-$d_6$) δ ppm 9.68 (s, 1H), 7.85 (dd, J = 9.6, 2.0 Hz, 1H), 7.68-7.73 (d(AB), J = 8.5 Hz, 2H), 7.61-7.68 (d(AB), J = 8.8 Hz, 2H), 7.14 (td, J = 10.4, 2.2 Hz, 1H), 7.04 (br. s., 2H), 5.89 (s, 1H), 2.83 (s, 3H); MS m/z 421 [M + H]$^+$ |
| 89 | 2-(4,6-difluoro-2-methyl-1H-benzimidazol-1-yl)-N-[3-fluoro-4-(trifluoromethyl)phenyl]pyrimidine-4,6-diamine<br>$^1$H NMR (500 MHz, DMSO-$d_6$) δ ppm 9.92 (s, 1H), 7.80-7.84 (m, J = 9.5, 2.2 Hz, 1H), 7.80 (dd, J = 14.0, 1.1 Hz, 1H), 7.66 (t, J = 8.7 Hz, 1H), 7.38 (dd, J = 8.5, 1.3 Hz, 1H), 7.16 (dd, J = 10.4, 2.2 Hz, 1H), 7.11-7.16 (m, 2H), 5.91 (s, 1H); MS m/z 439 [M + H]$^+$ |
| 90 | 2-{[2-(4,6-difluoro-2-methyl-1H-benzimidazol-1-yl)-6-{[4-(trifluoromethyl)phenyl]amino}pyrimidin-4-yl]amino}ethanol<br>$^1$H NMR (500 MHz, DMSO-$d_6$) δ ppm 9.69 (br. s., 1H), 7.83 (d, J = 9.1 Hz, 1H), 7.70 (d(AB), J = 7.9 Hz, 2H), 7.64 (d(AB), J = 8.8 Hz, 2H), 7.15 (td, J = 10.3, 2.4 Hz, 1H), 5.96 (br. s, 1H), 4.83 (br. s, 1H), 3.59 (q, J = 5.7 Hz, 2H), 3.38-3.51 (m, 2H), 2.85 (s, 3H); MS m/z 465.0 [M + H]$^+$ |
| 91 | 2-(6-ethenyl-2-methyl-1H-benzimidazol-1-yl)-N-[4-(trifluoromethyl)phenyl]pyrimidine-4,6-diamine<br>$^1$H NMR (500 MHz, DMSO-$d_6$) δ ppm 9.68 (s, 1H), 8.17 (d, J = 1.6 Hz, 1H), 7.76 (d, J = 8.5 Hz, 1H), 7.61 (d, J = 8.8 Hz, 1H), 7.54 (d, J = 8.2 Hz, 1H), 7.39 (dd, J = 8.4, 1.4 Hz, 1H), 6.98 (br. s., 1H), 6.75 (dd, J = 17.7, 11.0 Hz, 1H), 5.87 (s, 1H), 5.64 (dd, J = 17.7, 0.6 Hz, 1H), 5.13 (dd, J = 11.0, 0.9 Hz, 1H), 2.82 (s, 1H); MS m/z 399 [M + H]$^+$ |
| 92 | 2-(2-cyclopropyl-6-fluoro-1H-imidazo[4,5-b]pyridin-1-yl)-N-[4-(trifluoromethyl)phenyl]pyrimidine-4,6-diamine<br>$^1$H NMR (500 MHz, Methanol-$d_4$) δ ppm 8.37 (1H, dd, J = 9, 3 Hz), 8.3 (1H, m), 7.72 (2H, d, J = 8.5 Hz), 7.6 (2H, d, J = 8.5 Hz), 5.96 (1H, s), 1.33 (2H, m), 1.19 (2H, m); MS m/z 430.1 [M + H]$^+$ |
| 94 | 2-(6-fluoro-2-methyl-1H-imidazo[4,5-b]pyridin-1-yl)-N-[4-(trifluoromethyl)phenyl]pyrimidine-4,6-diamine<br>$^1$H NMR (500 MHz, Methanol-$d_4$) δ ppm 8.52 (1H, dd, J = 9, 3 Hz), 8.33 (1H, dd, m), 7.65 (2H, d, J = 9 Hz), 7.60 (2H, d, J = 9 Hz), 5.95 (1H, s), 3.00 (3H, s); MS m/z 404.2 [M + H]$^+$ |

| Cpd | Name & Data |
|---|---|
| 101 | N-[4-(difluoromethoxy)-3-fluorophenyl]-2-(5,6-difluoro-2-methyl-1H-benzimidazol-1-yl)pyrimidine-4,6-diamine<br>$^1$H NMR (500 MHz, Methanol-d$_4$) δ ppm 8.19 (1H, dd, J = 11, 7.5 Hz), 7.53 (1H, dd, J = 13, 2.5 Hz), 7.44 (1H, dd, J = 10, 7.5 Hz), 7.23 (2H, m), 5.86 (1H, s), 2.89 (3H, s); MS m/z 437.1 [M + H]$^+$ |
| 102 | N-[4-(difluoromethoxy)phenyl]-2-(5,6-difluoro-2-methyl-1H-benzimidazol-1-yl)pyrimidine-4,6-diamine<br>$^1$H NMR (Methanol-d$_4$) δ ppm 8.18 (1H, dd, J = 11.5, 7.5 Hz), 7.44 (2H, d, J = 9 Hz), 7.40 (1H, dd, J = 11.5, 7.5 Hz), 7.14 (2H, d, 9 Hz), 6.77 (1H, t, J = 75 Hz), 5.79 (1H, s), 2.87 (1H, s); MS m/z 419.1 [M + H]$^+$ |
| 103 | 2-(2-cyclopropyl-6-fluoro-1H-imidazo[4,5-b]pyridin-1-yl)-N-[4-(difluoromethoxy)phenyl]pyrimidine-4,6-diamine<br>$^1$H NMR (500 MHz, Methanol-d$_4$) δ ppm 8.38 (1H, dd, J = 9, 3 Hz), 8.29 (1H, m), 7.5 (2H, d, J = 9 Hz), 7.14 (2H, d, J = 7 Hz), 6.78 (1H, t, J = 75 Hz), 3.4 (1H, m), 1.3 (2H, m), 1.17 (2H, m); MS m/z 428.1 [M + H]$^+$ |
| 104 | 2-(6-chloro-2-methyl-1H-imidazo[4,5-b]pyridin-1-yl)-N-[4-(trifluoromethyl)phenyl]pyrimidine-4,6-diamine<br>$^1$H NMR (500 MHz, METHANOL-d$_4$) δ ppm 8.77 (d, J = 2.21 Hz, 1H), 8.43 (d, J = 2.21 Hz, 1H), 7.60 (d, J = 6.94 Hz, 4H), 5.91 (s, 1H) 3.05 (s, 3H); MS m/z 420.1 [M + H]$^+$ |
| 105 | 2-(6-chloro-2-ethyl-1H-imidazo[4,5-b]pyridin-1-yl)-N-[4-(trifluoromethyl)phenyl]pyrimidine-4,6-diamine<br>$^1$H NMR (500 MHz, METHANOL-d$_4$) δ ppm 8.66 (d, J = 2.52 Hz, 1H), 8.38 (d, J = 2.21 Hz, 1H), 7.62 (dd, J = 19.50, 9.50 Hz, 4H), 5.92 (s, 1H), 3.48 (q, J = 7.60 Hz, 2H), 1.39 (t, J = 7.41 Hz, 3H); MS m/z 434.1 [M + H]$^+$ |
| 146 | 2-(2-methyl-1H-benzimidazol-1-yl)-N-[4-(methylsulfanyl)phenyl]pyrimidine-4,6-diamine<br>$^1$H NMR (500 MHz, Acetone-d$_6$) δ ppm 8.45-8.50 (1H, s) 8.25-8.30 (1H, m) 7.55-7.59 (1H, m) 7.50 (2H, s) 7.32 (2H, s) 7.17-7.25 (2H, m) 6.24-6.33 (2H, m) 5.92 (1H, s) 2.51 (3H, s) 2.07 (3H, s); MS m/z 363.2 [M + H]$^+$ |
| 147 | 2-[2-(1-methylcyclopropyl)-1H-benzimidazol-1-yl]-N-[4-(trifluoromethyl)phenyl]pyrimidine-4,6-diamine<br>$^1$H NMR (500 MHz, Acetone-d$_6$) δ ppm 8.72-8.80 (1H, s) 7.66-7.76 (3H, m) 7.46 (3H, d, J = 0.63 Hz) 7.08 (2 H, s) 6.18-6.28 (2H, m) 5.97 (1H, s) 1.30 (3H, s) 1.10 (2H, s) 0.61 (2H, d, J = 2.21 Hz); MS m/z 425.2 [M + H]$^+$ |
| 148 | N-[4-(difluoromethoxy)phenyl]-2-[2-(1-methylcyclopropyl)-1H-benzimidazol-1-yl]pyrimidine-4,6-diamine<br>$^1$H NMR (500 MHz, Acetone-d$_6$) δ ☐ppm 8.49 (1H, s) 8.16-8.20 (1H, m) 7.55-7.60 (3H, m) 7.15-7.23 (4H, m) 6.94 (1H, t, J = 75.00 Hz) 6.27 (2H, br. s.) 5.92 (1H, s) 3.32 (2H, q, J = 7.57 Hz) 1.34 (3H, t, J = 6.90 Hz); MS m/z 423.3 [M + H]$^+$ |
| 153 | 2-(2-ethyl-1H-benzimidazol-1-yl)-N-[4-(trifluoromethyl)phenyl]pyrimidine-4,6-diamine<br>$^1$H NMR (500 MHz, DMSO-d$_6$) δ ppm 9.66 (s, 1H), 7.96-8.10 (m, 1H), 7.73 (d, J = 8.83 Hz, 2H), 7.58-7.64 (m, 3H), 7.18-7.26 (m, 2H), 6.96 (br. s, 2H), 5.88 (s, 1H), 3.22-3.29 (m, 2H), 1.29 (t, J = 7.41 Hz, 3H); m.p. 183-185; MS m/z 415.4 (100) [M + H]$^+$, 416.4 (30) |
| 156 | N-[4-(difluoromethoxy)phenyl]-2-(2-ethyl-1H-benzimidazol-1-yl)pyrimidine-4,6-diamine<br>$^1$H NMR (500 MHz, Acetone-d$_6$) δ ppm 8.49 (1H, s) 8.16-8.20 (1H, m) 7.55-7.60 (3H, m) 7.15-7.23 (4H, m) 6.94 (1H, t, J = 75.00 Hz) 6.27 (2H, br. s.) 5.92 (1H, s) 3.32 (2H, q, J = 7.57 Hz) 1.34 (3H, t, J = 6.90 Hz); MS m/z 397.2 [M + H]$^+$ |
| 157 | N-[4-(difluoromethoxy)-3-fluorophenyl]-2-(2-ethyl-1H-benzimidazol-1-yl)pyrimidine-4,6-diamine<br>$^1$H NMR (500 MHz, Acetone-d$_6$) δ ppm 8.71 (1H, s) 8.13-8.18 (1H, m) 7.68-7.75 (1H, m) 7.57-7.62 (1H, m) 7.26-7.35 (2H, m) 7.16-7.25 (2H, m) 6.94 (1H, t, J = 73.80 Hz) 6.36 (2H, s) 5.98 (1H, s) 3.33 (2H, q, J = 7.60 Hz) 1.35 (3H, t, J = 7.90 Hz); MS m/z 415.2 [M + H]$^+$ |
| 182 | 2-[2-(methylsulfanyl)-1H-benzimidazol-1-yl]-N-[4-(trifluoromethyl)phenyl]pyrimidine-4,6-diamine<br>$^1$H NMR (500 MHz, Acetone-d$_6$) δ ppm 8.85 (br. s., 1H) 8.38 (d, J = 7.88 Hz, 1H), 7.83 (d, J = 8.51 Hz, 2H), 7.66 (d, J = 8.51 Hz, 2H), 7.56 (d, J = 7.57 Hz, 1H), 7.23 (td, J = 7.57, 1.26 Hz, 1H), 7.13-7.19 (m, 1H), 6.41 (br. s., 2H), 6.02 (s, 1H), 2.63 (s, 3H); MS m/z 418.3 [M + H]$^+$ |
| 196 | 2-(2-methyl-1H-benzimidazol-1-yl)-N-(4-methylphenyl)pyrimidine-4,6-diamine<br>$^1$H NMR (500 MHz, Methanol-d$_4$) δ ppm 8.13 (1H, m), 7.58 (1H, m), 7.3-7.25 (4H, m), 7.13 (1H, d, J = 8 Hz), 5.81 (1H, s), 2.86 (3H, s), 2.31 (3H, s); MS m/z 331.1 [M + H]$^+$ |
| 197 | N-(4-methoxyphenyl)-2-(2-methyl-1H-benzimidazol-1-yl)pyrimidine-4,6-diamine<br>$^1$H NMR (500 MHz, Methanol-d$_4$) δ ppm 8.13 (1H, m), 7.58 (1H, m), 7.33 (2H, d, J = 9 Hz), 7.27 (2H, m), 6.94 (2H, d, J = 9 Hz), 5.72 (1H, s), 3.81 (3H, s), 2.86 (3H, s); MS m/z 347.1 [M + H]$^+$ |
| 198 | N-[4-(dimethylamino)phenyl]-2-(2-methyl-1H-benzimidazol-1-yl)pyrimidine-4,6-diamine<br>$^1$H NMR (500 MHz, Methanol-d$_4$) δ ppm 8.12 (1H, m), 7.58 (1H, m), 7.27 (2H, m), 7.22 (2H, d, J = 9 Hz), 6.81 (2H, d, J = 9 Hz), 5.67 (1H, s), 2.92 (6H, s), 2.86 (3H, s); MS m/z 360.4 [M + H]$^+$ |
| 205 | N-(1,3-benzodioxol-5-yl)-2-(2-methyl-1H-benzimidazol-1-yl)pyrimidine-4,6-diamine<br>$^1$H NMR (500 MHz, DMSO-d$_6$): δ ppm 9.04 (1H, s), 8.20-8.17 (1H, m), 7.61-7.58 (1H, m), 7.27-7.21 (2H, m), 7.15 (1H, d, J = 1.8 Hz), 6.91 (1H, d, J = 8.2 Hz), 6.86 (1H, dd, J = 8.2, 1.8 Hz), 6.76 (2H, br s), 6.03 (2H, s), 5.72 (1H, s), 2.84 (3H, s); m.p. 166-167; MS m/z 359.1 [M + H]$^+$ |

-continued

| Cpd | Name & Data |
|---|---|
| 206 | N-(2,2-difluoro-1,3-benzodioxol-5-yl)-2-(2-methyl-1H-benzimidazol-1-yl)pyrimidine-4,6-diamine<br>$^1$H NMR (500 MHz, DMSO-d$_6$): δ ppm 9.40 (1H, s), 8.13 (1H, dd, J = 7.0, 1.2 Hz), 7.71 (1H, d, J = 2.1 Hz), 7.61 (1H, dd, J = 7.0, 1.2 Hz), 7.38 (1H, d, J = 8.6 Hz), 7.28-7.20 (3H, m), 6.88 (2H, br s), 5.79 (1H, s), 2.83 (3H, s); m.p.: 141-142; MS m/z 397.1 [M + H]$^+$ |
| 207 | N-(3-fluoro-4-methoxyphenyl)-2-(2-methyl-1H-benzimidazol-1-yl)pyrimidine-4,6-diamine<br>$^1$H NMR (500 MHz, DMSO-d$_6$): δ ppm 9.19 (1H, s), 8.18-8.15 (1H, m), 7.62-7.59 (1H, m), 7.50 (1H, dd, J = 13.6, 2.2 Hz), 7.28-7.13 (4H, m), 6.82 (2H, br s), 5.76 (1H, s), 3.85 (3H, s), 2.84 (3H, s); m.p.: 233-234; MS m/z 365.2 [M + H]$^+$ |
| 208 | N-(6-methoxypyridin-3-yl)-2-(2-methyl-1H-benzimidazol-1-yl)pyrimidine-4,6-diamine<br>$^1$H NMR (500 MHz, DMSO-d$_6$): δ ppm 9.10 (1H, s), 8.24 (1H, d, J = 2.6 Hz), 8.14 (1H, dd, J = 8.4, 1.2 Hz), 7.84 (1H, dd, J = 8.8, 2.7 Hz), 7.59 (1H, dd, J = 8.4, 1.5 Hz), 7.27-7.20 (2H, m), 6.85 (1H, d, J = 8.8 Hz), 6.80 (2H, br s), 5.69 (1H, s), 3.87 (3H, s), 2.80 (3H, s); m.p.: 118-119; MS m/z 348.2 [M + H]$^+$ |
| 209 | N-(4-chlorophenyl)-2-(2-methyl-1H-benzimidazol-1-yl)pyrimidine-4,6-diamine<br>$^1$H NMR (500 MHz, Methanol-d$_4$) δ ppm 8.11 (1H, m), 7.58 (1H, m), 7.45 (2H, d, J = 9 Hz), 7.28-7.23 (4H, m), 5.83 (1H, s), 2.85 (3H, s); MS m/z 351.6 [M + H]$^+$ |
| 210 | 4-{[6-amino-2-(2-methyl-1H-benzimidazol-1-yl)pyrimidin-4-yl]amino}benzonitrile<br>$^1$H NMR (500 MHz, Methanol-d$_4$) δ ppm 8.1 (1H, m), 7.75 (2H, d, J = 9 Hz), 7.61 (3H, m), 7.28 (2H, m), 5.95 (1H, s), 2.88 (3H, s); MS m/z 342.3 [M + H]$^+$ |
| 211 | 2-(2-methyl-1H-benzimidazol-1-yl)-N-(4-nitrophenyl)pyrimidine-4,6-diamine<br>$^1$H NMR (500 MHz, Methanol-d$_4$) δ ppm 8.16 (2H, m), 8.12 (1H, m), 7.79 (2H, m), 7.62 (1H, m), 7.29 (2H, m), 5.99 (1H, s), 2.90 (3H, s); MS m/z 362.3 [M + H]$^+$ |
| 212 | N-(4-bromophenyl)-2-(2-methyl-1H-benzimidazol-1-yl)pyrimidine-4,6-diamine<br>$^1$H NMR (500 MHz, Methanol-d$_4$) δ ppm 8.11 (1H, m), 7.59 (1H, m), 7.42 (4H, m), 7.27 (2H, m), 5.84 (1H, s), 2.86 (3H, s); MS m/z 397.0 [M + H]$^+$ |
| 221 | 2-(2-methyl-1H-benzimidazol-1-yl)-N-[4-(trifluoromethoxy)phenyl]pyrimidine-4,6-diamine<br>$^1$H NMR (500 MHz, Methanol-d$_4$) δ ppm 8.11 (1H, m), 7.57 (1H, m), 7.54 (2H, d, 9 Hz), 7.24 (2H, m), 7.19 (2H, d, J = 9 Hz), 5.84 (1H, S), 2.85 (3H, s); MS m/z 401.0 [M + H]$^+$ |
| 234 | N-[4-(difluoromethoxy)phenyl]-2-(2-methyl-1H-benzimidazol-1-yl)pyrimidine-4,6-diamine<br>$^1$H NMR (500 MHz, Methanol-d$_4$) δ ppm 8.11 (1H, m), 7.57 (1H, m), 7.45 (2H, d, 7 Hz), 7.25 (2H, m), 7.09 (2H, d, J = 9 Hz), 5.48 (1H, S), 2.85 (3H, s); MS m/z 383.1 [M + H]$^+$ |
| 235 | N-[4-(difluoromethoxy)-3-fluorophenyl]-2-(2-methyl-1H-benzimidazol-1-yl)pyrimidine-4,6-diamine<br>$^1$H NMR (500 MHz, Methanol-d$_4$) δ ppm 8.10 (1H, m), 7.58-7.54 (2H, m), 7.27-7.14 (4H, m), 5.47 (1H, s), 2.85 (3H, s); MS m/z 401.0 [M + H]$^+$ |
| 263 | N-(4-chlorophenyl)-2-(6-fluoro-2-methyl-1H-benzimidazol-1-yl)pyrimidine-4,6-diamine<br>$^1$H NMR (500 MHz, Acetone-d$_6$) δ ppm 8.59 (s, 1H), 8.05 (dd, J = 2.52, 10.40 Hz, 1H), 7.47-7.61 (m, 4H), 7.31-7.42 (m, 2H), 6.92-7.08 (m, 1H), 6.37 (br. s., 1H), 5.93 (s, 1H), 2.77-2.88 (m, 3H); m.p.: 183-185; MS m/z 369.0 [M + H]$^+$ |
| 264 | 2-(6-fluoro-2-methyl-1H-benzimidazol-1-yl)-N-(4-methylphenyl)pyrimidine-4,6-diamine<br>$^1$H NMR (500 MHz, Acetone-d$_6$) δ ppm 8.37 (br. s., 1H), 8.10 (dd, J = 2.52, 10.40 Hz, 1H), 7.52 (dd, J = 5.04, 8.83 Hz, 1H), 7.34 (d, J = 8.20 Hz, 2H), 7.18 (d, J = 8.20 Hz, 2H), 6.94-7.07 (m, 1H), 6.27 (br. s., 2H), 5.82-5.96 (m, 1H), 2.85 (s, 3H), 2.32 (s, 3H); m.p.: 210-212; MS m/z 349.0 [M + H]$^+$ |
| 266 | N-[4-(dimethylamino)phenyl]-2-(6-fluoro-2-methyl-1H-benzimidazol-1-yl)pyrimidine-4,6-diamine<br>$^1$H NMR (500 MHz, Acetone-d$_6$) δ ppm 8.11-8.16 (m, 1H), 8.07-8.10 (m, 1H), 7.47-7.56 (m, 1H), 7.23 (d, J = 9.77 Hz, 2H), 6.94-7.05 (m, 1H), 6.79 (d, J = 8.83 Hz, 2H), 6.09-6.25 (br, s, 2H), 5.67 (s, 1H), 2.94 (s, 6H), 2.85 (s, 3H); m.p.: 122-125; MS m/z 378.0 [M + H]$^+$ |
| 267 | N-(4-chloro-3-fluorophenyl)-2-(6-fluoro-2-methyl-1H-benzimidazol-1-yl)pyrimidine-4,6-diamine<br>$^1$H NMR (500 MHz, Acetone-d$_6$) δ ppm 8.80 (s, 1H), 8.03 (dd, J = 2.52, 10.09 Hz, 1H), 7.67 (dd, J = 2.36, 11.82 Hz, 1H), 7.54 (dd, J = 5.04, 8.51 Hz, 1H), 7.44 (t, J = 8.67 Hz, 1H), 7.27-7.37 (m, 1H), 6.95-7.09 (m, 1H), 6.46 (br. s., 2H), 5.99 (s, 1H), 2.85 (s, 3H); m.p.: 225-227; MS m/z 387.0 [M + H]$^+$ |
| 268 | 2-(6-fluoro-2-methyl-1H-benzimidazol-1-yl)-N-(3-methylphenyl)pyrimidine-4,6-diamine<br>$^1$H NMR (500 MHz, Acetone-d$_6$) δ ppm 8.37-8.52 (m, 1H), 8.14 (dd, J = 2.68, 10.25 Hz, 1H), 7.55 (dd, J = 5.20, 8.67 Hz, 1H), 7.40 (br. s., 1H), 7.22-7.30 (m, 2H), 7.00-7.11 (m, 1H), 6.94 (d, J = 6.62 Hz, 1H), 6.27-6.40 (s, 2H), 5.91-6.06 (s, 1H), 2.89 (s, 3H), 2.34 (s, 3H); m.p.: 203-205; MS m/z 349.0 [M + H]$^+$ |
| 269 | N-(2,2-difluoro-1,3-benzodioxol-5-yl)-2-(6-fluoro-2-methyl-1H-benzimidazol-1-yl)pyrimidine-4,6-diamine<br>$^1$H NMR (500 MHz, Acetone-d$_6$) δ ppm 8.62 (s, 1H), 8.04 (dd, J = 2.52, 10.40 Hz, 1H), 7.56 (d, J = 1.89 Hz, 1H), 7.53 (dd, J = 5.04, 8.83 Hz, 1H), 7.21-7.29 (m, 2H), 6.97-7.05 (m, 1H), 6.38 (br. s., 2H), 5.91 (s, 1H), 2.83 (s, 3H); m.p.: 212-215; MS m/z 415.0 [M + H]$^+$ |

Example 9

2-(2-methylpyrazolo[1,5-a]pyridin-3-yl)-N-[4-(trifluoromethyl)phenyl]pyrimidine-4,6-diamine (Cpd 154)

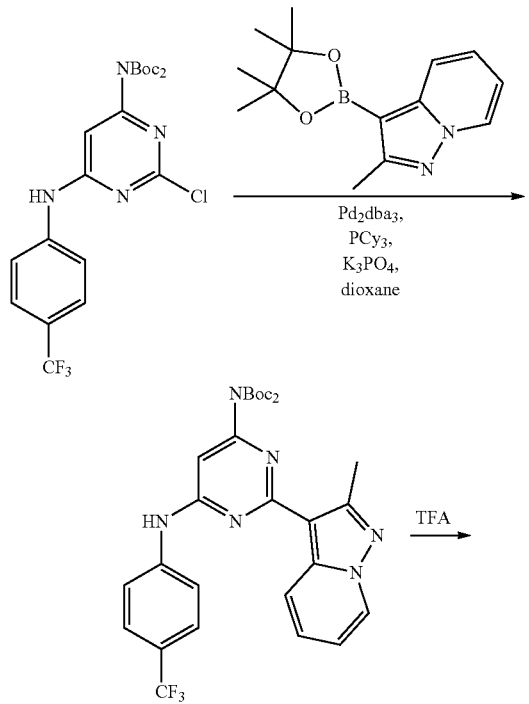

A mixture of 2-methyl-3-(4,4,5,5-tetramethyl-1,3,2-dioxaborolan-2-yl)pyrazolo[1,5-a]pyridine (53 mg, 0.205 mmol), di-tert-butyl 2-chloro-6-(4-(trifluoromethyl)phenylamino)pyrimidin-4-yliminodicarbonate (110 mg, 0.225 mmol), tris(dibenzylideneacetone) dipalladium(0) (18 mg, 0.02 mmol) tricyclohexylphosphine (14 mg, 0.051 mmol), and potassium phosphate (87.0 mg, 0.41 mmol) in dioxane (3.5 mL) and water (0.1 mL) was degassed by purging with argon, and then was heated at 85° C. for 3 hours. The solution was cooled and filtered via plug of Celite. The filtrate was concentrated and purified by silica gel column chromatography giving tert-butyl 3,3-dimethylbutanoyl(2-(2-methylpyrazolo[1,5-a]pyridin-3-yl)-6-(4-(trifluoromethyl)phenylamino)-pyrimidin-4-yl)carbamate (25 mg, 21%) as a clear oil, which was dissolved in dichloromethane (1 mL) and treated with TFA (0.1 mL) at 0° C. The resulting mixture was stirred at room temperature for 4 hours. The solvent was concentrated, and the residual material was partitioned between ethyl acetate and a saturated NaHCO₃ solution. The organic layer was separated, dried over Na₂SO₄, then filtered and evaporated. The residual material was triturated with ethyl ether to afford the title compound as a yellow solid (8 mg, 50%).

$^1$H NMR (500 MHz, Acetone-$d_6$) δ ppm 8.55 (d, J=8.8 Hz, 1H), 8.42 (br. s., 1H), 8.37 (d, J=6.6 Hz, 1H), 7.70 (d, J=8.8 Hz, 2H), 7.50 (d, J=8.5 Hz, 2H), 7.13 (ddd, J=8.4, 7.3, 0.8 Hz, 1H), 6.77 (td, J=6.6, 1.6 Hz, 1H), 5.82 (br. s., 2H), 5.77 (s, 1H), 2.66 (s, 3H); MS m/z 385.3 [M+H]⁺.

Additional compounds of Formula (I) or a form thereof described herein may be prepared according to the procedure of Example 9 by substituting the appropriate starting materials, reagents and reaction conditions.

| Cpd | Name & Data |
|---|---|
| 70 | N-[4-(trifluoromethyl)phenyl]-2-(1,3,5-trimethyl-1H-pyrazol-4-yl)pyrimidine-4,6-diamine<br>$^1$H NMR (500 MHz, CDCl₃) δ ppm 7.54 (2H, d, J = 8.7 Hz), 7.48 (2H, d, J = 8.7 Hz), 5.86 (1H, s), 5.60 (2H, v br), 3.73 (3H, s), 2.53 (3H, s), 2.50 (3H, s); m.p. 270-271° C.; MS m/z 363.0 [M + H]⁺ |

Example 10

5-fluoro-2-(6-fluoro-2-methyl-1H-benzimidazol-1-yl)-N-(4-methoxyphenyl)pyrimidine-4,6-diamine (Cpd 179)

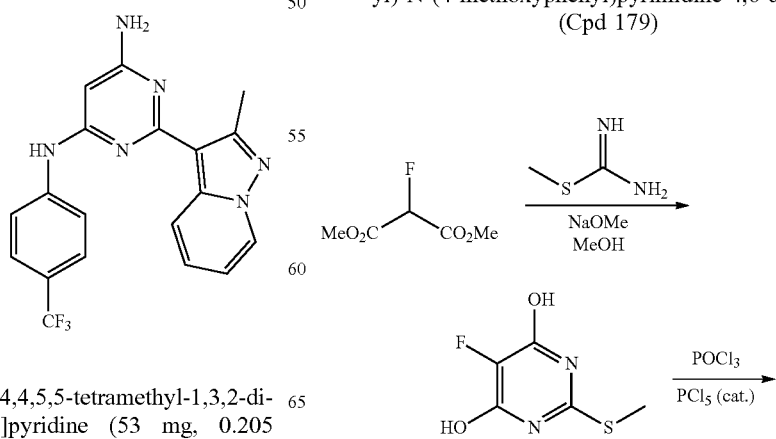

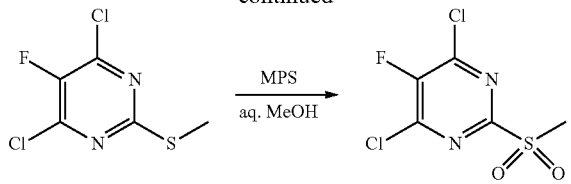

Step 1. To a solution of methyl carbamimidothioate-$(H_2SO_4)_{1/2}$ salt (45.90 g, 0.33 mol) and dimethyl 2-fluoromalonate (45.03 g, 0.30 mol) in MeOH (450 mL) at 0° C. was slowly added sodium methoxide (4.37 M in MeOH, 226 mL, 0.99 mol). The mixture was stirred for 16 hours at room temperature. The solution was concentrated under reduced pressure. The resulting slurry was diluted with water (50 mL) and acidified to about pH 2 by using a 6N HCl solution. The resulting precipitate was collected, washed with water and dried under vacuum to give 5-fluoro-2-(methylthio)pyrimidine-4,6-diol (46.85 g, 88%).

To a solution of 5-fluoro-2-(methylthio)pyrimidine-4,6-diol (13.2 g, 74.9 mmol) in $POCl_3$ (60 mL) was added a catalytic amount of $PCl_5$ (60 mg). The mixture was heated at 100° C. for 16 hours and then concentrated under reduced pressure. To the mixture was carefully added ice water (150 mL). The resulting precipitate was removed by filtration, washed with water, then dried under nitrogen to give 4,6-dichloro-5-fluoro-2-(methylthio)pyrimidine (13.5 g, 85%).

To a solution of 4,6-dichloro-5-fluoro-2-(methylthio)pyrimidine (12.4 g, 58.8 mmol) in MeOH (150 mL) was added potassium peroxymonosulfate ($2KHSO_5 \cdot KHSO_4 \cdot K_2SO_4$) (108.7 g, 176.4 mmol) and water (70 mL). The mixture was stirred for 6 hours at room temperature. The salt was removed by filtration, then washed with MeOH until no more product was observed. The combined organic mixture was concentrated then ice water was added to the mixture to provide a precipitate, which was filtered and washed by water. The solid was dried under nitrogen to yield 4,6-dichloro-5-fluoro-2-(methylsulfonyl)pyrimidine as a white solid (14.6 g, 99%).

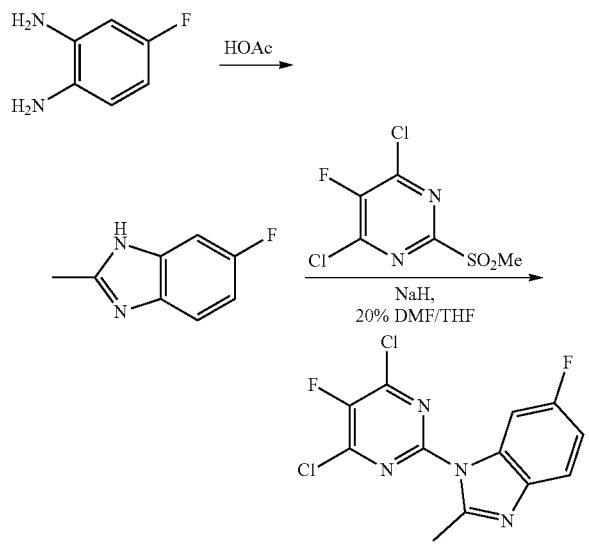

Step 2. A solution of 4-fluorobenzene-1,2-diamine (3.78 g, 30 mmol) in acetic acid (10.0 mL) was microwaved for 1 hour at 180° C. The mixture was concentrated under reduced pressure and triturated with ether to yield 6-fluoro-2-methyl-1H-benzo[d]imidazole as a brownish solid (4.31 g, 88%).

To a solution of 6-fluoro-2-methyl-1H-benzo[d]imidazole (2.31 g, 15.4 mmol) in THF (50 mL) and DMF (10 mL) at −78° C. was added 60% NaH (648 mg, 16.2 mmol). The mixture was stirred for about 10 minutes at room temperature. To the mixture at −78° C. was added 4,6-dichloro-5-fluoro-2-(methylsulfonyl)pyrimidine (3.74 g, 15.3 mmol) in one portion, then the mixture was stirred at −78° C. for 15 minutes. The reaction mixture was quenched with a 1M HCl solution (18 mL) and a crude mixture was extracted with EtOAc (200 mL). The organic layer was concentrated under reduced pressure, and purified by column chromatography (5-30% EtOAc/hexanes) to give 1-(4,6-dichloro-5-fluoropyrimidin-2-yl)-6-fluoro-2-methyl-1H-benzo[d]imidazole as a white solid (1.83 g, 38%).

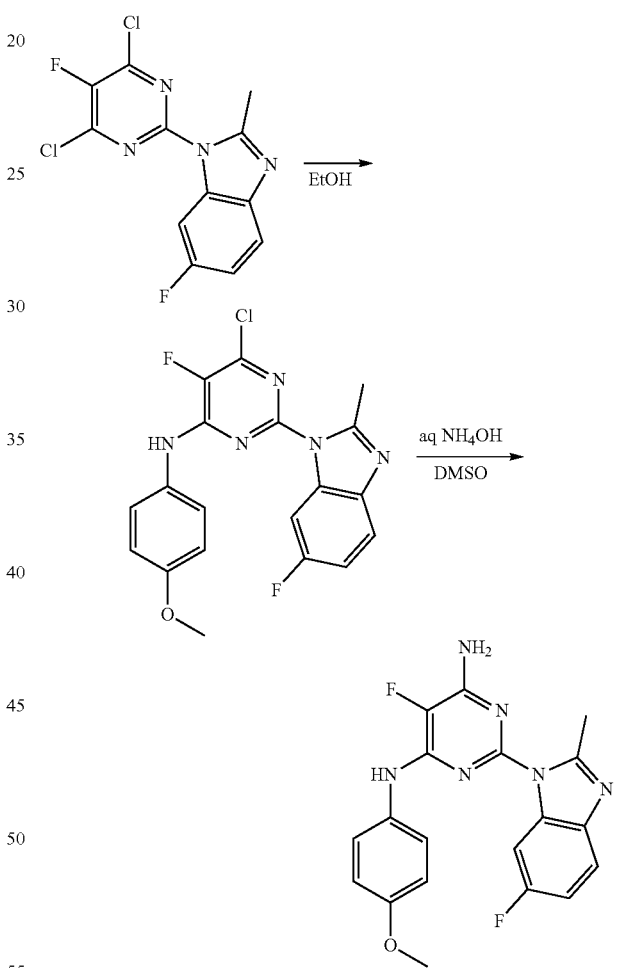

Step 3. The mixture of 1-(4,6-dichloro-5-fluoropyrimidin-2-yl)-6-fluoro-2-methyl-1H-benzo[d]-imidazole (63 mg, 0.2 mmol) and 4-methoxyaniline (49 mg, 0.4 mmol) in EtOH (1 mL) was stirred for 1 hour at 60° C. The precipitate was obtained by adding water (10 mL). The product (6-chloro-5-fluoro-2-(6-fluoro-2-methyl-1H-benzo[d]imidazol-1-yl)-N-(4-methoxyphenyl)-pyrimidin-4-amine) was removed by filtration and washed with water several times. The resulting crude 6-chloro-5-fluoro-2-(6-fluoro-2-methyl-1H-benzo[d]imidazol-1-yl)-N-(4-methoxyphenyl)pyrimidin-4-amine was used in the next step without further purification.

To the crude product in DMSO (5 mL) was added 14 M aqueous NH₄OH (3 mL). The suspended mixture was heated for 18 hours at 100° C. until all the starting material was consumed. After cooling to room temperature, water (10 mL) was added to the mixture to form a precipitate. The precipitate was isolated by filtration and washed with water several times. The resulting product was dried under nitrogen to give the title compound as an off-white solid (72 mg, 94%).

$^1$H NMR (500 MHz, Acetone-d$_6$) δ ppm 8.30 (1H, br. s.) 7.94 (1H, dd, J=9.93, 2.36 Hz) 7.48-7.56 (3H, m) 6.93-7.05 (3H, m) 6.48 (2H, br. s.) 3.83 (3H, s) 2.75 (3H, s); MS m/z 383.2 [M+H]$^+$.

Additional compounds of Formula (I) or a form thereof described herein may be prepared according to the procedure of Example 10 by substituting the appropriate starting materials, reagents and reaction conditions.

| Cpd | Name & Data |
|---|---|
| 95 | 5-fluoro-2-(2-methyl-1H-benzimidazol-1-yl)-N-[4-(trifluoromethyl)phenyl]pyrimidine-4,6-diamine<br>$^1$H NMR (500 MHz, DMSO-d$_6$) δ ppm 9.60 (1H, s) 8.02 (1H, dd, J = 7.25, 2.21 Hz) 7.86 (2H, d, J = 8.51 Hz) 7.65 (2H, d, J = 8.51 Hz) 7.56-7.60 (1H, m) 7.29 (2H, 2) 7.17-7.26 (2H, m) 2.75 (3H, s); MS m/z 403.2 [M + H]$^+$ |
| 106 | N-[4-(difluoromethoxy)phenyl]-5-fluoro-2-(2-methyl-1H-benzimidazol-1-yl)pyrimidine-4,6-diamine<br>$^1$H NMR (500 MHz, Acetone-d$_6$) δ ppm 8.39 (1H, s) 7.97 (1H, d, J = 7.88 Hz) 7.59-7.64 (2H, m) 7.42 (1H, d, J = 7.25 Hz) 7.01-7.11 (4H, m) 6.83 (1H, t, J = 74.56 Hz) 6.40 (2H, br. s.) 2.63 (3H, s); MS m/z 401.1 [M + H]$^+$ |
| 107 | 2-(2-ethyl-1H-benzimidazol-1-yl)-5-fluoro-N-[4-(trifluoromethyl)phenyl]pyrimidine-4,6-diamine<br>$^1$H NMR (500 MHz, Acetone-d$_6$) δ ppm 8.69 (1H, br. s.) 7.91 (1H, d, J = 7.88 Hz) 7.85 (2H, d, J = 8.51 Hz) 7.53 (2H, d, J = 8.51 Hz) 7.47 (1H, d, J = 6.94 Hz) 7.02-7.13 (2H, m) 6.54 (2H, br. s.) 3.14 (2H, q, J = 7.36 Hz) 1.20 (3H, t); MS m/z 417.1 [M + H]$^+$ |
| 108 | 5-fluoro-2-(5-fluoro-2-methyl-1H-benzimidazol-1-yl)-N-[4-(trifluoromethyl)phenyl]pyrimidine-4,6-diamine<br>$^1$H NMR (500 MHz, Acetone-d$_6$) δ ppm 8.85 (1H, br. s.) 8.13 (1H, dd, J = 9.46, 5.04 Hz) 7.98 (2H, d, J = 8.51 Hz) 7.71 (2H, d, J = 8.51 Hz) 7.31 (1H, dd, J = 9.62, 2.36 Hz) 6.96-7.04 (1H, m) 6.72 (2H, br. s.) 2.82 (3H, s); MS m/z 421.1 [M + H]$^+$ |
| 109 | 5-fluoro-2-(6-fluoro-2-methyl-1H-benzimidazol-1-yl)-N-[4-(trifluoromethyl)phenyl]pyrimidine-4,6-diamine<br>$^1$H NMR (500 MHz, Acetone-d$_6$) δ ppm 8.85 (1H, br. s.) 7.89-8.00 (3H, m) 7.71 (2H, d, J = 8.51 Hz) 7.56 (1H, dd, J = 8.83, 5.04 Hz) 7.02-7.08 (1H, m) 6.76 (2h, br. s.) 2.82 (3H, s); MS m/z 421.1 [M + H]$^+$ |
| 110 | N-[4-(difluoromethoxy)phenyl]-5-fluoro-2-(6-fluoro-2-methyl-1H-benzimidazol-1-yl)pyrimidine-4,6-diamine<br>$^1$H NMR (500 MHz, Acetone-d$_6$) δ ppm 8.01 (1H, dd, J = 10.40, 2.21 Hz) 7.81 (1H, br. s.) 7.68-7.72 (2H, m) 7.65 (1H, dd, J = 8.83, 5.04 Hz) 7.26-7.31 (2H, m) 7.12-7.18 (1H, m) 6.87 (1H, t, J = 74.56 Hz) 5.87 (2H, br. s.) 2.87 (3H, s); MS m/z 419.1 [M + H]$^+$ |
| 111 | N-[4-(difluoromethoxy)-3-fluorophenyl]-5-fluoro-2-(6-fluoro-2-methyl-1H-benzimidazol-1-yl)pyrimidine-4,6-diamine<br>$^1$H NMR (500 MHz, Acetone-d$_6$) δ ppm 8.73 (1H, s) 7.93 (1H, dd, J = 9.93, 2.36 Hz) 7.80 (1H, dd, J = 1 2.93, 2.52 Hz) 7.51-7.59 (2H, m) 7.36 (1H, t, J = (1H, t, J = 8.99 Hz) 7.01-7.08 (1H, m) 6.98 (1H, t, J = 73.77 Hz) 6.71 (2H, br. s.) 2.81 (3H, s); MS m/z 437.1 [M + H]$^+$ |
| 112 | N-[4-(difluoromethoxy)-3-fluorophenyl]-5-fluoro-2-(5-fluoro-2-methyl-1H-benzimidazol-1-yl)pyrimidine-4,6-diamine<br>$^1$H NMR (500 MHz, Acetone-d$_6$) δ ppm 8.19 (1H, dd, J = 9.46, 5.04 Hz) 7.94 (1H, br. s.) 7.79 (1H, dd, J = 12.93, 2.52 Hz) 7.35-7.50 (3H, m) 7.09-7.16 (1H, m) 6.87 (1H, t, J = 73.77 Hz) 5.91 (2H, s) 2.90 (3H, s); MS m/z 437.2 [M + H]$^+$ |
| 113 | N-[4-(difluoromethoxy)phenyl]-5-fluoro-2-(5-fluoro-2-methyl-1H-benzimidazol-1-yl)pyrimidine-4,6-diamine<br>$^1$H NMR (500 MHz, Acetone-d$_6$) δ ppm 8.19 (1H, dd, J = 9.46, 5.04 Hz) 7.81 (1H, br. s.) 7.67-7.74 (2H, m) 7.42 (1H, dd, J = 9.46, 2.84 Hz) 7.25-7.32 (2H, m) 7.07-7.16 (1H, m) 6.88 (1H, t, J = 74.56 Hz) 5.84 (2H, s) 2.88 (3H, s); MS m/z 419.1[M + H]$^+$ |
| 114 | 2-(6-chloro-2-methyl-1H-imidazo[4,5-b]pyridin-1-yl)-5-fluoro-N-[4-(trifluoromethyl)phenyl]pyrimidine-4,6-diamine<br>$^1$H NMR (500 MHz, Acetone-d$_6$) δ ppm 8.91 (1H, s) 8.57-8.58 (1H, m) 8.39 (1H, d, J = 2.21 Hz) 7.93 (2H, d, J = 8.51 Hz) 7.75 (2H, d, J = 8.51 Hz) 6.83 (2H, br. s.) 2.93 (3H, s); MS m/z 438.3 [M + H]$^+$ |
| 115 | 2-(6-chloro-2-methyl-1H-imidazo[4,5-b]pyridin-1-yl)-N-[4-(difluoromethoxy)phenyl]-5-fluoropyrimidine-4,6-diamine<br>$^1$H NMR (500 MHz, Acetone-d$_6$) δ ppm 8.47 (1H, br. s.) 8.41 (1H, d, J = 2.21 Hz) 8.23 (1H, d, J = 2.52 Hz) 7.55 (2H, d, J = 8.83 Hz) 7.11 (2H, d, J = 9.14 Hz) 6.85 (1H, t, J = 74.10 Hz) 6.55 (2H, br. s.) 2.74 (3H, s); MS m/z 436.2 [M + H]$^+$ |
| 116 | 2-(6-chloro-2-methyl-1H-imidazo[4,5-b]pyridin-1-yl)-N-[4-(difluoromethoxy)-3-fluorophenyl]-5-fluoropyrimidine-4,6-diamine<br>$^1$H NMR (500 MHz, Acetone-d$_6$) δ ppm 8.77 (1H, s) 8.56 (1H, d, J = 2.21 Hz) 7.73 (1H, dd, J = 12.61, 2.52 Hz) 7.50-7.56 (1H, m) 7.39 (1H, t, J = 8.99 Hz) 7.00 (1H, t, J = 73.61 Hz) 6.79 (2H, br. s.) 2.91 (3H, s); MS m/z 454.1 [M + H]$^+$ |
| 117 | 2-(2-cyclopropyl-6-fluoro-1H-imidazo[4,5-b]pyridin-1-yl)-5-fluoro-N-[4-(trifluoromethyl)phenyl]pyrimidine-4,6-diamine<br>$^1$H NMR (500 MHz, Acetone-d$_6$) δ ppm 8.90 (1H, s) 8.22-8.34 (2H, m) 7.99 (2H, d, J = 8.20 Hz) 7.71 (2H, d, J = 8.20 Hz) 6.84 (2H, br. s.) 3.20-3.29 (1H, m) 1.26-1.34 (2H, m) 1.06-1.12 (2H, m); MS m/z 448.1 [M + H]$^+$ |

-continued

| Cpd | Name & Data |
|---|---|
| 119 | N-[4-(difluoromethoxy)-3-fluorophenyl]-5-fluoro-2-(2-methyl-1H-benzimidazol-1-yl)pyrimidine-4,6-diamine<br>$^1$H NMR (500 MHz, Acetone-$d_6$) δ ppm 8.71 (1H, br. s.) 8.12 (1H, d, J = 8.51 Hz) 7.87 (1H, dd, J = 13.08, 2.68 Hz) 7.52-7.62 (2H, m) 7.34 (1H, t, J = 8.99 Hz) 7.17-7.27 (2H, m) 6.98 (1H, t, J = 73.93 Hz) 6.6 (2H, br. s.) 2.81 (3H, s); MS m/z 419.3 [M + H]$^+$ |
| 120 | 2-(2-cyclopropyl-1H-benzimidazol-1-yl)-5-fluoro-N-[4-(trifluoromethyl)phenyl]pyrimidine-4,6-diamine<br>$^1$H NMR (500 MHz, Acetone-$d_6$) δ ppm 8.85 (1H, br. s.) 8.06 (2H, d, J = 8.51 Hz) 8.00 (1H, dd, J = 7.25, 1.26 Hz) 7.67 (2H, d, J = 8.51 Hz) 7.50-7.56 (1H, m) 7.14-7.25 (2H, m) 6.70 (2H, br. s.) 2.96-3.05 (1H, m) 1.20-1.26 (2H, m) 1.00-1.06 (2H, m); MS m/z 429.2 [M + H]$^+$ |
| 121 | 2-(2-cyclopropyl-1H-benzimidazol-1-yl)-N-[4-(difluoromethoxy)phenyl]-5-fluoropyrimidine-4,6-diamine<br>$^1$H NMR (500 MHz, Acetone-$d_6$) δ ppm 8.40 (1H, s) 7.86 (1H, dd, J = 7.72, 1.73 Hz) 7.63-7.70 (2H, m) 7.36 (1H, d, J = 9.14 Hz) 6.98-7.08 (4H, m) 6.64-6.97 (1H, m) 6.41 (2H, s) 2.83-2.91 (1H, m) 1.01-1.07 (2H, m) 0.80-0.87 (2H, m); MS m/z 427.2 [M + H]$^+$ |
| 122 | 2-(2-cyclopropyl-1H-benzimidazol-1-yl)-N-[4-(difluoromethoxy)-3-fluorophenyl]-5-fluoropyrimidine-4,6-diamine<br>$^1$H NMR (500 MHz, Acetone-$d_6$) δ ppm 8.73 (1H, s) 7.96-8.03 (2H, m) 7.50-7.60 (2H, m) 7.32 (1H, t, J = 8.83 Hz) 7.20 (2H, dtd, J = 19.70, 7.33, 7.33, 1.26 Hz) 6.80-7.13 (2H, m) 6.66 (2H, s) 2.97-3.05 (1H, m) 1.23 (2H, dd, J = 5.04, 2.84 Hz) 1.01-1.08 (2H, m); MS m/z 445.2 [M + H]$^+$ |
| 123 | N-[4-(difluoromethoxy)phenyl]-2-(2-ethyl-1H-benzimidazol-1-yl)-5-fluoropyrimidine-4,6-diamine<br>$^1$H NMR (500 MHz, Acetone-$d_6$) δ ppm 8.52-8.56 (1H, s) 8.04-8.09 (1H, m) 7.76 (2H, d, J = 9.14 Hz) 7.57-7.61 (1H, m) 7.19 (4H, d, J = 8.83 Hz) 6.97 (1H, m) 6.49-6.58 (2H, s) 3.25 (2H, d, J = 7.57 Hz) 1.29-1.34 (3H, m); MS m/z 415.3[M + H]$^+$ |
| 124 | N-[4-(difluoromethoxy)-3-fluorophenyl]-2-(2-ethyl-1H-benzimidazol-1-yl)-5-fluoropyrimidine-4,6-diamine<br>$^1$H NMR (500 MHz, Acetone-$d_6$) δ ppm 8.72 (1H, s) 8.05-8.09 (1H, m) 7.87 (1H, dd, J = 12.93, 2.52 Hz) 7.59-7.63 (1H, m) 7.54 (1H, ddd, J = 8.91, 2.60, 1.42 Hz) 7.33 (1H, t, J = 8.83 Hz) 7.18-7.27 (2H, m) 6.98 (1H, t, J = 74.70 Hz) 6.64 (2H, 2) 3.28 (2H, q, J = 7.36 Hz) 1.35 (3H, t, J = 7.90 Hz); Ms m/z 433.3 [M + H]$^+$ |
| 125 | 2-(5,6-difluoro-2-methyl-1H-benzimidazol-1-yl)-5-fluoro-N-[4-(trifluoromethyl)-phenyl] pyrimidine4,6-diamine<br>$^1$H NMR (500 MHz, Acetone-$d_6$) δ ppm 8.69-8.75 (1H, m) 7.97-8.04 (1H, m) 7.76-7.83 (2H, m) 7.55-7.61 (2H, m) 7.30-7.37 (1H, m) 6.59-6.69 (2H, m) 2.68 (3H, s); MS m/z 439.2 [M + H]$^+$ |
| 126 | N-[4-(difluoromethoxy)-3-fluorophenyl]-2-(5,6-difluoro-2-methyl-1H-benzimidazol-1-yl)-5-fluoropyrimidine-4,6-diamine<br>$^1$H NMR (500 MHz, Acetone-$d_6$) δ ppm 8.72-8.76 (1H, m) 8.12-8.18 (1H, m) 7.74-7.80 (1H, m) 7.45-7.55 (2H, m) 7.34-7.40 (1H, m) 6.90-7.05 (1H, m) 6.69-6.78 (2H, m) 2.82 (3H, s); MS m/z 455.2 [M + H]$^+$ |
| 127 | 2-(4,6-difluoro-2-methyl-1H-benzimidazol-1-yl)-5-fluoro-N-[4-(trifluoromethyl)phenyl]pyrimidine-4,6-diamine<br>$^1$H NMR (500 MHz, Acetone-$d_6$) δ ppm 8.85-8.90 (1H, m) 7.93-7.99 (2H, m) 7.77-7.82 (1H, m) 7.72 (2H, s) 6.90-6.97 (1H, m) 6.73-6.84 (2H, m) 2.83 (3H, s); MS m/z 439.2 [M + H]$^+$ |
| 128 | N-[4-(difluoromethoxy)-3-fluorophenyl]-2-(4,6-difluoro-2-methyl-1H-benzimidazol-1-yl)-5-fluoropyrimidine-4,6-diamine<br>$^1$H NMR (500 MHz, Acetone-$d_6$) δ ppm 8.71-8.79 (1H, m) 7.74-7.82 (2H, m) 7.48-7.55 (1H, m) 7.33-7.40 (1H, m) 6.83-7.15 (3H, m) 6.70-6.79 (2H, m) 2.82 (3H, s); MS m/z 455.2 [M + H]$^+$ |
| 129 | 2-(2-ethyl-4,6-difluoro-1H-benzimidazol-1-yl)-5 -fluoro-N-[4-(trifluoromethyl)phenyl]pyrimidine-4,6-diamine<br>$^1$H NMR (500 MHz, Acetone-$d_6$) δ ppm 8.89 (1H, s) 7.95 (2H, d, J = 8.51 Hz) 7.66-7.77 (3H, m) 6.90-6.98 (1H, m) 6.79 (2H, br. s.) 3.30 (2H, q, J = 7.57 Hz) 1.34 (3H, t, J = 7.41 Hz); MS m/z 453.2 [M + H]$^+$ |
| 130 | N-[4-(difluoromethoxy)-3-fluorophenyl]-2-(2-ethyl-4,6-difluoro-1H-benzimidazol-1-yl)-5-fluoropyrimidine-4,6-diamine<br>$^1$H NMR (500 MHz, Acetone-$d_6$) δ ppm 8.75 (1H, s) 7.72-7.81 (2H, m) 7.51 (1H, ddd, J = 8.91, 2.60, 1.42 Hz) 7.35 (1H, t, J = 8.83 Hz) 6.81-7.14 (2H, m) 6.74 (2H, br. s.) 3.28 (2H, q, J = 7.25 Hz) 1.34 (3H, t, J = 7.41 Hz); MS m/z 469.2 [M + H]$^+$ |
| 131 | N-[4-(difluoromethoxy)phenyl]-2-(4,6-difluoro-2-methyl-1H-benzimidazol-1-yl)-5-fluoropyrimidine-4,6-diamine<br>$^1$H NMR (500 MHz, Acetone-$d_6$) δ ppm 8.59 (1H, s) 7.79 (1H, ddd, J = 9.85, 2.44, 0.95 Hz) 7.69-7.74 (2H, m) 7.20-7.24 (2H, m) 6.81-7.13 (2H, m) 6.65 (2H, br. s.) 2.78 (3H, s); MS m/z 437.2 [M + H]$^+$ |
| 132 | N-[4-(difluoromethoxy)phenyl]-2-(2-ethyl-4,6-difluoro-1H-benzimidazol-1-yl)-5-fluoropyrimidine-4,6-diamine<br>$^1$H NMR (500 MHz, Acetone-$d_6$) δ ppm 8.59 (1H, s) 7.75 (1H, ddd, J = 9.77, 2.21, 0.95 Hz) 7.68-7.72 (2H, m) 7.18-7.25 (2H, m) 6.81-7.13 (2H, m) 6.65 (2H, s) 3.25 (2H, q, J = 7.57 Hz) 1.28-1.33 (3H, m); MS m/z 451.2 [M + H]$^+$ |

-continued

| Cpd | Name & Data |
|---|---|
| 133 | N-[4-(difluoromethoxy)phenyl]-2-(5,6-difluoro-2-methyl-1H-benzimidazol-1-yl)-5-fluoropyrimidine-4,6-diamine<br>$^1$H NMR (500 MHz, Acetone-$d_6$) δ ppm 8.57 (1H, br. s.) 8.15 (1H, dd, J = 11.82, 7.72 Hz) 7.68-7.74 (2H, m) 7.46 (1H, dd, J = 10.72, 7.57 Hz) 7.21-7.26 (2H, m) 7.05 (2H, t, J = 76.30 Hz) 6.65 (2H, s) 2.78 (3H, s); MS m/z 437.3 [M + H]$^+$ |
| 134 | 5-fluoro-2-(4-fluoro-2-methyl-1H-benzimidazol-1-yl)-N-[4-(trifluoromethyl)phenyl]pyrimidine-4,6-diamine<br>$^1$H NMR (500 MHz, Acetone-$d_6$) δ ppm 8.87 (1H, br. s.) 7.99 (2H, d, J = 8.51 Hz) 7.92 (1H, d, J = 8.20 Hz) 7.69 (2H, d, J = 8.51 Hz) 7.19 (1H, td, J = 8.20, 5.04 Hz) 7.01 (1H, dd, J = 10.72, 7.25 Hz) 6.74 (2H, br. s.) 2.83 (3H, s); MS m/z 421.2 [M + H]$^+$ |
| 135 | N-[4-(difluoromethoxy)phenyl]-5-fluoro-2-(4-fluoro-2-methyl-1H-benzimidazol-1-yl)pyrimidine-4,6-diamine<br>$^1$H NMR (500 MHz, Acetone-$d_6$) δ ppm 8.57 (1H, s) 7.92 (1H, d, J = 9.14 Hz) 7.72-7.78 (2H, m) 6.80-7.24 (5H, m) 6.59 (2H, br. s.) 2.79 (3H, s); MS m/z 418.2 [M + H]$^+$ |
| 136 | N-[4-(difluoromethoxy)-3-fluorophenyl]-5-fluoro-2-(4-fluoro-2-methyl-1H-benzimidazol-1-yl)pyrimidine-4,6-diamine<br>$^1$H NMR (500 MHz, Acetone-$d_6$) δ ppm 8.74 (1H, s) 7.93 (1H, d, J = 7.57 Hz) 7.85 (1H, dd, J = 12.93, 2.52 Hz) 7.51-7.57 (1H, m) 7.34 (1H, t, J = 8.99 Hz) 6.82-7.23 (3H, m) 6.69 (2H, s) 2.86 (3H, s); MS m/z 437.2 [M + H]$^+$ |
| 137 | 5-fluoro-2-(2-methyl-1H-imidazo[4,5-b]pyridin-1-yl)-N-[4-(trifluoromethyl)phenyl]pyrimidine-4,6-diamine<br>$^1$H NMR (500 MHz, Acetone-$d_6$) δ ppm 8.88 (1H, br. s.) 8.47 (1H, dd, J = 8.04, 1.73 Hz) 8.40-8.44 (1H, m) 7.92-8.00 (2H, m) 7.72 (2H, d, J = 8.51 Hz) 7.18-7.23 (1H, m) 6.70-6.80 (2H, m) 2.90 (3H, s); MS m/z 404.2 [M + H]$^+$ |
| 138 | N-[4-(difluoromethoxy)phenyl]-5-fluoro-2-(2-methyl-1H-imidazo[4,5-b]pyridin-1-yl)pyrimidine-4,6-diamine<br>$^1$H NMR (500 MHz, Acetone-$d_6$) δ ppm 8.58 (1H, s) 8.46 (1H, dd, J = 8.20, 1.58 Hz) 8.40 (1H, dd, J = 4.73, 1.58 Hz) 7.70-7.76 (2H, m) 7.21-7.25 (2H, m) 7.15-7.19 (1H, m) 6.99 (2H, s) 6.56-6.66 (2H, m) 2.86 (3H, s); MS m/z 402.2 [M + H]$^+$ |
| 139 | N-[4-(difluoromethoxy)-3-fluorophenyl]-5-fluoro-2-(2-methyl-1H-imidazo[4,5-b]pyridin-1-yl)pyrimidine-4,6-diamine<br>$^1$H NMR (500 MHz, Acetone-$d_6$) δ ppm 8.75 (1H, br. s.) 8.45-8.50 (1H, m) 8.42 (1H, dd, J = 4.73, 1.58 Hz) 7.80 (1H, dd, J = 12.61, 2.52 Hz) 7.53 (1H, dt, J = 9.06, 1.93 Hz) 7.37 (1H, t, J = 8.83 Hz) 7.20 (1H, dd, J = 8.20, 4.73 Hz) 6.83-7.16 (2H, m) 6.72 (2H, br. s.) 2.89 (3H, s); MS m/z 420.2 [M + H]$^+$ |
| 140 | 2-(2-cyclopropyl-4-fluoro-1H-benzimidazol-1-yl)-5-fluoro-N-[4-(trifluoromethyl)-phenyl]pyrimidine4,6-diamine<br>$^1$H NMR (500 MHz, Acetone-$d_6$) δ ppm 8.88 (1H, s) 8.05 (2H, d, J = 8.51 Hz) 7.81 (1H, dd, J = 8.20, 0.63 Hz) 7.67 (2H, d, J = 8.51 Hz) 7.16 (1H, td, J = 8.12, 4.89 Hz) 6.95-7.02 (1H, m) 6.74 (2H, s) 2.96-3.03 (1H, m) 1.24-1.29 (2H, m) 1.03-1.08 (2H, m); MS m/z 447.2 [M + H]$^+$ |
| 141 | 2-(2-cyclopropyl-4-fluoro-1H-benzimidazol-1-yl)-N-[4-(difluoromethoxy)phenyl]-5-fluoropyrimidine-4,6-diamine<br>$^1$H NMR (500 MHz, Acetone-$d_6$) δ ppm 8.59 (1H, s) 7.77-7.84 (3H, m) 7.16-7.20 (2H, m) 7.12-7.16 (1H, m) 6.81-7.11 (2H, m) 6.61 (2H, s) 3.01 (1H, tt, J = 8.28, 4.97 Hz) 1.20-1.24 (2H, m) 1.03 (2H, dq, J = 8.32, 3.43 Hz); MS m/z 445.2 [M + H]$^+$ |
| 142 | 2-(2-cyclopropyl-4-fluoro-1H-benzimidazol-1-yl)-N-[4-(difluoromethoxy)-3-fluorophenyl]-5-fluoropyrimidine-4,6-diamine<br>$^1$H NMR (500 MHz, Acetone-$d_6$) δ ppm 8.77 (1H, s) 7.99 (1H, dd, J = 12.93, 2.52 Hz) 7.83 (1H, dd, J = 8.20, 0.95 Hz) 7.57 (1H, ddd, J = 9.06, 2.60, 1.58 Hz) 7.33 (1H, t, J = 8.99 Hz) 7.18 (1H, td, J = 8.12, 4.89 Hz) 6.83-7.13 (2H, m) 6.72 (2 H, s) 3.01 (1H, tt, J = 8.28, 4.97 Hz) 1.23-1.30 (2H, m) 1.08 (2H, dq, J = 8.32, 3.43 Hz); MS m/z 463.2 [M + H]$^+$ |
| 155 | 2-(2-cyclopropyl-6-fluoro-1H-imidazo[4,5-b]pyridin-1-yl)-N-[4-(difluoromethoxy)phenyl]-5-fluoropyrimidine-4,6-diamine<br>$^1$H NMR (500 MHz, Acetone-$d_6$) δ ppm 8.62 (1H, s) 8.23-8.32 (2H, m) 7.72-7.78 (2H, m) 7.18-7.24 (2H, m) 6.98 (1H, t, J = 75.30 Hz) 6.71 (2H, br. s.) 3.27 (1H, tt, J = 8.28, 4.97 Hz) 1.25 (2H, dd, J = 4.89, 3.00 Hz) 1.05 (2H, dd, J = 8.20, 3.15 Hz); MS m/z 446.2 [M + H]$^+$ |
| 158 | 2-(5-chloro-2-methyl-1H-benzimidazol-1-yl)-5-fluoro-N-[4-(trifluoromethyl)phenyl]pyrimidine-4,6-diamine<br>$^1$H NMR (500 MHz, Acetone-$d_6$) δ ppm 8.82 (1H, d, J = 1.58 Hz) 8.11 (1H, d, J = 8.20 Hz) 7.92-7.99 (2H, m) 7.69 (2H, d, J = 8.51 Hz) 7.58 (1H, d, J = 2.21 Hz) 7.19 (1H, dd, J = 8.83, 2.21 Hz) 6.70 (2H, br. s.) 2.82 (3H, s); MS m/z 437.2 [M + H]$^+$ |
| 159 | 2-(5-chloro-2-methyl-1H-benzimidazol-1-yl)-N-[4-(difluoromethoxy)phenyl]-5-fluoropyrimidine-4,6-diamine<br>$^1$H NMR (500 MHz, Acetone-$d_6$) δ ppm 8.42 (1H, s) 7.95-8.00 (1H, m) 7.55-7.62 (2H, m) 7.43 (1H, d, J = 1.58 Hz) 7.01-7.10 (3H, m) 6.84 (1H, t, J = 75.30 Hz) 6.44 (2H, br. s.) 2.64 (3H, s); MS m/z 435.2 [M + H]$^+$ |
| 160 | 2-(6-chloro-2-methyl-1H-benzimidazol-1-yl)-5-fluoro-N-[4-(trifluoromethyl)phenyl]pyrimidine-4,6-diamine<br>$^1$H NMR (500 MHz, Acetone-$d_6$) δ ppm 8.83 (1H, br. s.) 8.19 (1H, d, J = 1.58 Hz) 7.94 (2H, d, J = 8.20 Hz) 7.70 (3H, d, J = 8.51 Hz) 7.55 (1H, d, J = 8.51 Hz) 7.21-7.27 (1H, m) 6.72 (2H, br. s.) 2.82 (3H, s); MS m/z 437.2 [M + H]$^+$ |
| 161 | 2-(6-chloro-2-methyl-1H-benzimidazol-1-yl)-N-[4-(difluoromethoxy)phenyl]-5-fluoropyrimidine-4,6-diamine<br>$^1$H NMR (500 MHz, Acetone-$d_6$) δ ppm 8.57 (1H, s) 8.17-8.22 (1H, m) 7.70-7.77 (2H, m) 7.55 (1H, d, J = 8.20 Hz) 7.20-7.26 (3H, m) 6.97 (1H, t, J = 74.70 Hz) 6.62 (2H, br. s.) 2.80 (3H, s); MS m/z 435.2 [M + H]$^+$ |

-continued

| Cpd | Name & Data |
|---|---|
| 162 | 2-(2-ethyl-5-fluoro-1H-benzimidazol-1-yl)-5-fluoro-N-[4-(trifluoromethyl)phenyl]pyrimidine-4,6-diamine<br>$^1$H NMR (500 MHz, Acetone-$d_6$) δ ppm 8.85 (1H, br. s.) 8.08 (1H, dd, J = 8.67, 5.20 Hz) 7.97 (2H, d, J = 8.20 Hz) 7.64-7.73 (2H, m) 7.33 (1H, d, J = 6.62 Hz) 6.98-7.04 (1H, m) 6.72 (2H, br. s.) 3.29 (2H, q, J = 7.36 Hz) 1.34 (3H, t, J = 8.20 Hz); MS m/z 435.3 [M + H]$^+$ |
| 163 | N-[4-(difluoromethoxy)phenyl]-2-(2-ethyl-5-fluoro-1H-benzimidazol-1-yl)-5-fluoropyrimidine-4,6-diamine<br>$^1$H NMR (500 MHz, Acetone-$d_6$) δ ppm 8.56 (1H, s) 8.09 (1H, dd, J = 9.46, 5.04 Hz) 7.69-7.75 (2H, m) 7.31 (1H, dd, J = 9.30, 2.68 Hz) 7.18-7.24 (2H, m) 6.81-7.14 (2H, m) 6.57 (2H, br. s.) 3.22-3.29 (2H, m) 1.27-1.34 (3H, m); MS m/z 433.3 [M + H]$^+$ |
| 164 | 2-(2-ethyl-6-fluoro-1H-benzimidazol-1-yl)-5-fluoro-N-[4-(trifluoromethyl)phenyl]pyrimidine-4,6-diamine<br>$^1$H NMR (500 MHz, Acetone-$d_6$) δ ppm 8.85 (1H, s) 7.96 (2H, d, J = 8.51 Hz) 7.89 (1H, dd, J = 10.09, 2.52 Hz) 7.70 (2H, d, J = 8.51 Hz) 7.59 (1H, dd, J = 8.51, 5.04 Hz) 7.01-7.09 (1H, m) 6.75 (2H, br. s.) 3.29 (2H, q, J = 7.46 Hz) 1.33 (3H, t, J = 14.80 Hz); MS m/z 435.3 [M + H]$^+$ |
| 165 | N-[4-(difluoromethoxy)phenyl]-2-(2-ethyl-6-fluoro-1H-benzimidazol-1-yl)-5-fluoropyrimidine-4,6-diamine<br>$^1$H NMR (500 MHz, Acetone-$d_6$) δ ppm 8.56 (1H, s) 7.90 (1H, dd, J = 10.40, 2.52 Hz) 7.68-7.75 (2H, m) 7.56 (1H, dd, J = 8.83, 5.04 Hz) 7.18-7.26 (2H, m) 6.81-7.12 (2H, m) 6.61 (2H, br. s.) 3.25 (2H, q, J = 7.46 Hz) 1.26-1.34 (3H, m); MS m/z 433.3 [M + H]$^+$ |
| 172 | 5-methyl-2-(2-methyl-1H-benzimidazol-1-yl)-N-[4-(trifluoromethyl)phenyl]pyrimidine-4,6-diamine<br>$^1$H NMR (500 MHz, Acetone-$d_6$) δ ppm 8.19 (1H, s) 8.14 (1H, dt, J = 8.20, 0.95 Hz) 7.87 (2H, d, J = 8.51 Hz) 7.64 (2H, d, J = 8.51 Hz) 7.55-7.60 (1H, m) 7.22 (1H, ddd, J = 8.04, 7.09, 1.26 Hz) 7.15 (1H, ddd, J = 8.28, 7.17, 1.26 Hz) 6.31 (2H, br. s.) 2.80 (3H, s) 2.22 (3H, s); MS m/z 399.2 [M + H]$^+$ |
| 183 | 5-fluoro-2-(6-fluoro-2-methyl-1H-benzimidazol-1-yl)-N-[6-(trifluoromethyl)pyridin-3-yl]pyrimidine-4,6-diamine<br>$^1$H NMR (Methanol-$d_4$) δ ppm 8.92 (1H, d, J = 2.5 Hz), 8.34 (1H, dd, J = 8.5, 2.4 Hz), 7.81 (1H, dd, J = 9.8, 2.5 Hz), 7.75 (1H, d, J = 8.7 Hz), 7.54 (1H, dd, J = 8.7, 5 Hz), 7.06 (1H, td, J = 9.2, 2.5 Hz), 2.82 (3H, s); MS m/z 422.3 [M + H]$^+$ |
| 184 | 5-fluoro-2-(6-fluoro-2-methyl-1H-benzimidazol-1-yl)-N-(4-methylphenyl)pyrimidine-4,6-diamine<br>$^1$H NMR (500 MHz, Acetone-$d_6$) δ ppm 8.37 (br. s., 1H), 7.94 (dd, J = 10.4, 2.5 Hz, 1H), 7.50-7.58 (m, 3H), 7.20 (d, J = 8.2 Hz, 2H), 7.01 (ddd, J = 9.8, 8.8, 2.5 Hz, 1H), 6.52 (br. s., 2H), 2.78 (s, 3H), 2.34 (s, 3H); MS m/z 367.2 [M + H]$^+$ |
| 185 | N-(4-chlorophenyl)-5-fluoro-2-(6-fluoro-2-methyl-1H-benzimidazol-1-yl)pyrimidine-4,6-diamine<br>$^1$H NMR (500 MHz, Acetone-$d_6$) δ ppm 8.58 (br. s., 7H), 7.93 (dd, J = 10.2, 2.7 Hz, 1H), 7.70-7.76 (m, 2H), 7.54 (dd, J = 8.7, 5.2 Hz, 1H), 7.37-7.42 (m, 2H), 7.03 (ddd, J = 9.8, 8.8, 2.5 Hz, 1H), 6.63 (br. s., 2H), 2.79 (s, 3H); MS m/z 387.2 [M + H]$^+$ |
| 189 | 5-fluoro-2-(6-fluoro-2-methyl-1H-benzimidazol-1-yl)-N-(3-methoxyphenyl)pyrimidine-4,6-diamine<br>$^1$H NMR (500 MHz, Acetone-$d_6$) δ ppm 8.43 (br. s., 1H), 7.97 (dd, J = 10.1, 2.5 Hz, 1H), 7.54 (dd, J = 8.8, 5.0 Hz, 1H), 7.32-7.37 (m, 1H), 7.23-7.31 (m, 2H), 7.03 (ddd, J = 9.5, 8.7, 2.8 Hz, 1H), 6.68-6.75 (m, 1H), 6.57 (br. s., 2H), 3.77 (s, 3H), 2.81 (s, 3H); MS m/z 383.2 [M + H]$^+$ |
| 190 | N-(3-chlorophenyl)-5-fluoro-2-(6-fluoro-2-methyl-1H-benzimidazol-1-yl)pyrimidine-4,6-diamine<br>$^1$H NMR (500 MHz, Acetone-$d_6$) δ ppm 8.63 (br. s., 1H), 7.96 (dd, J = 10.1, 2.5 Hz, 1H), 7.91 (t, J = 2.0 Hz, 1H), 7.62 (ddd, J = 8.3, 2.0, 0.8 Hz, 1H), 7.55 (dd, J = 8.8, 5.0 Hz, 1H), 7.38 (t, J = 8.0 Hz, 1H), 7.14 (ddd, J = 8.2, 2.2, 0.9 Hz, 1H), 7.04 (ddd, J = 9.5, 8.5, 2.5 Hz, 1H), 6.68 (br. s., 2H), 2.82 (s, 3H); MS m/z 387.2 [M + H]$^+$ |
| 191 | 5-fluoro-2-(6-fluoro-2-methyl-1H-benzimidazol-1-yl)-N-[4-(trifluoromethoxy)phenyl]pyrimidine-4,6-diamine<br>$^1$H NMR (500 MHz, Acetone-$d_6$) δ ppm 9.21 (br. s., 1H), 8.49 (dd, J = 10.2, 2.7 Hz, 1H), 8.32-8.42 (m, 2H), 8.10 (dd, J = 8.7, 5.2 Hz, 1H), 7.91 (dd, J = 9.1, 0.9 Hz, 1H), 7.59 (ddd, J = 9.5, 8.5, 2.5 Hz, 1H), 7.21 (br. s., 2H), 3.34 (s, 3H); MS m/z 437.2 [M + H]$^+$ |
| 192 | 4-{[6-amino-5-fluoro-2-(6-fluoro-2-methyl-1H-benzimidazol-1-yl)pyrimidin-4-yl]amino}benzonitrile<br>$^1$H NMR (500 MHz, Acetone-$d_6$) δ ppm 8.79 (br. s., 1H), 7.80-7.86 (m, 2H), 7.78 (dd, J = 10.1, 2.5 Hz, 1H), 7.61 (dt, J = 8.8, 2.5 Hz, 2H), 7.42 (dd, J = 8.8, 5.0 Hz, 1H), 6.91 (ddd, J = 9.5, 8.5, 2.6 Hz, 1H), 6.65 (br. s., 2H), 2.67 (s, 3H); MS m/z 378.2 [M + H]$^+$ |
| 193 | methyl 4-{[6-amino-5-fluoro-2-(6-fluoro-2-methyl-1H-benzimidazol-1-yl)pyrimidin-4-yl]amino}benzoate<br>$^1$H NMR (500 MHz, Acetone-$d_6$) δ ppm 8.82 (br. s., 1H), 7.99-8.04 (m, 2H), 7.96 (dd, J = 10.1, 2.5 Hz, 1H), 7.85-7.90 (m, 2H), 7.56 (dd, J = 8.8, 5.0 Hz, 1H), 7.05 (ddd, J = 9.5, 8.5, 2.5 Hz, 1H), 6.73 (br. s., 2H), 3.88 (s, 3H), 2.83 (s, 3H); MS m/z 411.2 [M + H]$^+$ |
| 194 | 5-fluoro-2-(2-methyl-1H-benzimidazol-1-yl)-N-(3-methylphenyl)pyrimidine-4,6-diamine<br>$^1$H NMR (500 MHz, Acetone-$d_6$) δ ppm 8.36 (1H, br. s.) 8.19 (1H, d, J = 8.51 Hz) 7.64 (1H, s) 7.57 (1H, d, J = 7.57 Hz) 7.46 (1H, dd, J = 8.20, 2.21 Hz) 7.16-7.26 (3H, m) 6.94 (1H, d, J 6.49 (2H, br. s.) 2.81 (3H, s) 2.33 (3H, s); MS m/z 439.2 [M + H]$^+$ |

-continued

| Cpd | Name & Data |
|---|---|
| 195 | 5-fluoro-N-(3-methoxyphenyl)-2-(2-methyl-1H-benzimidazol-1-yl)pyrimidine-4,6-diamine<br>$^1$H NMR (500 MHz, Acetone-d$_6$) δ ppm 8.42 (1H, br. s.) 8.13-8.18 (1H, m) 7.58 (1H, d, J = 7.25 Hz) 7.40 (1H, t, J = 2.21 Hz) 7.16-7.32 (4H, m) 6.67-6.71 (1H, m) 6.52 (2H, br. s.) 3.75 (3H, s) 2.82 (3H, s); MS m/z 365.2 [M + H]$^+$ |
| 199 | 5-fluoro-2-(2-methyl-1H-benzimidazol-1-yl)-N-(4-methylphenyl)pyrimidine-4,6-diamine<br>$^1$H NMR (500 MHz, Acetone-d$_6$) δ ppm 8.35 (1H, br. s.) 8.13 (1H, d, J = 8.20 Hz) 7.54-7.61 (3H, m) 7.12-7.24 (4H, m) 6.45 (2H, br. s.) 2.78 (3H, s) 2.33 (3H, s); MS m/z 349.2 [M + H]$^+$ |
| 200 | 5-fluoro-N-(4-methoxyphenyl)-2-(2-methyl-1H-benzimidazol-1-yl)pyrimidine-4,6-diamine<br>$^1$H NMR (500 MHz, Acetone-d$_6$) δ ppm 8.28 (1H, br. s.) 8.12 (1H, d, J = 8.20 Hz) 7.52-7.60 (3H, m) 7.12-7.24 (2H, m) 6.93-6.98 (2H, m) 6.41 (2H, br. s.) 3.82 (3H, s) 2.76 (3H, s); MS m/z 365.2 [M + H]$^+$ |
| 201 | N-(4-chlorophenyl)-5-fluoro-2-(2-methyl-1H-benzimidazol-1-yl)pyrimidine-4,6-diamine<br>$^1$H NMR (500 MHz, Acetone-d$_6$) δ ppm 8.57 (1H, br. s.) 8.07-8.14 (1H, m) 7.73-7.80 (2H, m) 7.58 (1H, d, J = 6.94 Hz) 7.35-7.42 (2H, m) 7.15-7.26 (2H, m) 6.56 (2H, br. s.) 2.79 (3H, s); MS m/z 369.2 [M + H]$^+$ |
| 202 | 4-{[6-amino-5-fluoro-2-(2-methyl-1H-benzimidazol-1-yl)pyrimidin-4-yl]amino}benzonitrile<br>$^1$H NMR (500 MHz, Acetone-d$_6$) δ ppm 8.92 (1H, br. s.) 8.08-8.13 (1H, m) 7.97-8.03 (2H, m) 7.71-7.77 (2H, m) 7.56-7.62 (1H, m) 7.24 (2H, quind, J = 7.33, 7.33, 7.33, 7.33, 1.58 Hz) 6.73 (2H, br. s.) 2.80-2.83 (3H, m); MS m/z 360.2 [M + H]$^+$ |
| 203 | N-(1,3-benzodioxol-5-yl)-5-fluoro-2-(2-methyl-1H-benzimidazol-1-yl)pyrimidine-4,6-diamine<br>$^1$H NMR (500 MHz, Acetone-d$_6$) δ ppm 8.33 (1H, br. s.) 8.15 (1H, d, J = 6.62 Hz) 7.56 (1H, d, J = 7.25 Hz) 7.28 (1H, d, J = 2.21 Hz) 7.16-7.25 (2H, m) 7.09 (1H, dd, J = 8.51, 2.21 Hz) 6.85 (1H, d, J = 8.51 Hz) 6.45 (2H, br. s.) 6.02 (2H, s) 2.79 (3H, s); MS m/z [M + H]$^+$ |
| 204 | 5-fluoro-2-(2-methyl-1H-benzimidazol-1-yl)-N-[4-(trifluoromethoxy)phenyl]pyrimidine-4,6-diamine<br>$^1$H NMR (500 MHz, Acetone-d$_6$) δ ppm 8.63 (1H, br. s.) 8.11 (1H, d, J = 7.57 Hz) 7.80-7.89 (2H, m) 7.57 (1H, d, J = 7.88 Hz) 7.31-7.38 (2H, m) 7.15-7.26 (2H, m) 6.58 (2H, br. s.) 2.79 (3H, s); MS m/z 419.1 [M + H]$^+$ |
| 213 | 2-(5,6-difluoro-2-methyl-1H-benzimidazol-1-yl)-5-fluoro-N-(4-methylphenyl)pyrimidine-4,6-diamine<br>$^1$H NMR (500 MHz, Acetone-d$_6$) δ ppm 8.40 (1H, br. s.) 8.15 (1H, dd, J = 11.98, 7.88 Hz) 7.49-7.55 (2H, m) 7.44 (1H, dd, J = 10.72, 7.57 Hz) 7.21 (2H, d, J = 8.20 Hz) 6.55 (2H, br. s.) 2.79 (3H, s) 2.35 (3H, s); MS m/z 385.2 [M + H]$^+$ |
| 214 | 2-(5,6-difluoro-2-methyl-1H-benzimidazol-1-yl)-5-fluoro-N-(4-methoxyphenyl)pyrimidine-4,6-diamine<br>$^1$H NMR (500 MHz, Acetone-d$_6$) δ ppm 8.30 (1H, br. s.) 8.12 (1H, dd, J = 11.98, 7.88 Hz) 7.46-7.51 (2H, m) 7.41 (1H, dd, J = 10.72, 7.57 Hz) 6.93-6.98 (2H, m) 6.48 (2H, br. s.) 3.81 (3H, s) 2.75 (3H, s); MS m/z 401.3 [M + H]$^+$ |
| 215 | N-(4-chlorophenyl)-2-(5,6-difluoro-2-methyl-1H-benzimidazol-1-yl)-5-fluoropyrimidine-4,6-diamine<br>$^1$H NMR (500 MHz, Acetone-d$_6$) δ ppm 8.61 (1H, br. s.) 8.15 (1H, dd, J = 11.82, 7.72 Hz) 7.68-7.73 (2H, m) 7.38-7.50 (3H, m) 6.66 (2H, br. s.) 2.80 (3H, s); MS m/z 405.2 [M + H]$^+$ |
| 216 | N-[4-(difluoromethoxy)phenyl]-5-fluoro-2-[2-(methoxymethyl)-1H-benzimidazol-1-yl]pyrimidine-4,6-diamine<br>$^1$H NMR (500 MHz, Acetone-d$_6$) δ ppm 8.53 (1H, s) 8.13-8.17 (1H, m) 7.73-7.79 (2H, m) 7.64-7.69 (1H, m) 7.19-7.30 (4H, m) 6.82-7.13 (1H, m) 6.54 (2H, br. s.) 5.02 (2H, s) 3.28 (3H, s); MS m/z 431.3 [M + H]$^+$ |
| 217 | 5-fluoro-2-[2-(methoxymethyl)-1H-benzimidazol-1-yl]-N-(4-methylphenyl)pyrimidine-4,6-diamine<br>$^1$H NMR (500 MHz, Acetone-d$_6$) δ ppm 8.36 (1H, br. s.) 8.18 (1H, dd, J = 6.78, 1.73 Hz) 7.66 (1H, dd, J = 6.62, 1.89 Hz) 7.54-7.60 (2H, m) 7.17-7.30 (4H, m) 6.46 (2H, br. s.) 4.99-5.04 (2H, m) 3.28 (3H, s) 2.34 (3H, s); MS m/z 379.3 [M + H]$^+$ |
| 218 | 5-fluoro-2-[2-(methoxymethyl)-1H-benzimidazol-1-yl]-N-(4-methoxyphenyl)pyrimidine-4,6-diamine<br>$^1$H NMR (500 MHz, Acetone-d$_6$) δ ppm 8.31 (1H, br. s.) 8.14-8.19 (1H, m) 7.65 (1H, dd, J = 6.78, 1.73 Hz) 7.53-7.59 (2H, m) 7.25 (2H, quind, J = 7.41, 7.41, 7.41, 7.41, 1.58 Hz) 6.93-6.99 (2H, m) 6.43 (2H, br. s.) 4.97-5.02 (2H, m) 3.82 (3H, s); MS m/z 395.3 [M + H]$^+$ |
| 219 | N-(4-chlorophenyl)-5-fluoro-2-[2-(methoxymethyl)-1H-benzimidazol-1-yl]pyrimidine-4,6-diamine<br>$^1$H NMR (500 MHz, Acetone-d$_6$) δ ppm 8.58 (1H, br. s.) 8.12-8.17 (1H, m) 7.73-7.79 (2H, m) 7.65-7.70 (1H, m) 7.37-7.41 (2H, m) 7.24-7.32 (2H, m) 6.58 (2H, br. s.) 5.03 (2H, s) 3.29 (3H, s); MS m/z 399.2 [M + H]$^+$ |
| 220 | 5-fluoro-2-[2-(methoxymethyl)-1H-benzimidazol-1-yl]-N-[4-(trifluoromethyl)phenyl]pyrimidine-4,6-diamine<br>$^1$H NMR (500 MHz, Acetone-d$_6$) δ ppm 8.83 (1H, br. s.) 8.11-8.18 (1H, m) 7.96-8.03 (2H, m) 7.66-7.73 (3H, m) 7.25-7.33 (2H, m) 6.68 (2H, br. s.) 5.05 (2H, s) 3.29 (3H, s); MS m/z 433.2 [M + H]$^+$ |
| 222 | 1-(4-amino-5-fluoro-6-[4-(trifluoromethyl)phenyl]amino}pyrimidin-2-yl)-2-methyl-1H-benzimidazole-6-carbonitrile<br>$^1$H NMR (500 MHz, Acetone-d$_6$) δ ppm 8.91 (1H, s) 8.63 (1H, d, J = 1.58 Hz) 7.92-7.99 (2H, m) 7.74 (3H, t, J = 8.51 Hz) 7.61 (1H, dd, J = 8.20, 1.58 Hz) 6.84 (2H, br. s.) 2.90 (3H, s); MS m/z 428.3 [M + H]$^+$ |
| 223 | 1-(4-amino-6-[4-(difluoromethoxy)phenyl]amino}-5-fluoropyrimidin-2-yl)-2-methyl-1H-benzimidazole-6-carbonitrile<br>$^1$H NMR (500 MHz, Acetone-d$_6$) δ ppm 8.58-8.63 (2H, m) 7.68-7.75 (3H, m) |

| Cpd | Name & Data |
|---|---|
| | 7.57-7.62 (1H, m) 7.22-7.27 (2H, m) 6.84-7.16 (1H, m) 6.68 (2H, br. s.) 2.87 (3H, s); MS m/z 426.3 [M + H]$^+$ |
| 224 | 1-{4-amino-5-fluoro-6-[(4-methylphenyl)amino]pyrimidin-2- yl]-2-methyl-1H-benzimidazole-6-carbonitrile<br>$^1$H NMR (500 MHz, Acetone-d$_6$) δ ppm 8.61 (1H, s) 8.42 (1H, br. s.) 7.71 (1H, d, J = 8.20 Hz) 7.49-7.60 (3H, m) 7.24 (2H, d, J = 7.88 Hz) 6.58 (2H, br. s.) 2.87 (3H, s) 2.36 (3H, s); MS m/z 374.3 [M + H]$^+$ |
| 225 | 1-{4-amino-5-fluoro-6-[(4-methoxyphenyl)amino]pyrimidin-2-yl]-2-methyl-1H-benzimidazole-6-carbonitrile<br>$^1$H NMR (500 MHz, Acetone-d$_6$) δ ppm 8.62 (1H, s) 8.37 (1H, s) 7.71 (1H, d, J = 8.20 Hz) 7.49-7.60 (3H, m) 6.98-7.03 (2H, m) 6.57 (2H, br. s.) 3.84 (3H, s) 2.84 (3H, s); MS m/z 390.3 [M + H]$^+$ |
| 226 | 1-(4-amino-6-{[4-(difluoromethoxy)phenyl]amino}-5-fluoropyrimidin-2-yl)-2-methyl-1H-benzimidazole-5-carbonitrile<br>$^1$H NMR (500 MHz, Acetone-d$_6$) δ ppm 8.60 (1H, s) 8.28 (1H, dd, J = 8.51, 0.63 Hz) 8.00 (1H, dd, J = 1.58, 0.63 Hz) 7.70-7.77 (2H, m) 7.55 (1H, dd, J = 8.51, 1.58 Hz) 7.19-7.25 (2H, m) 6.98 (1H, t, J = 75.00 Hz) 6.63 (2H, br. s.) 2.83 (3H, s); MS m/z 426.3 [M + H]$^+$ |
| 227 | 1-{4-amino-5-fluoro-6-[(4-methylphenyl)amino]pyrimidin-2-yl}-2-methyl-1H-benzimidazole-5-carbonitrile<br>$^1$H NMR (500 MHz, Acetone-d$_6$) δ ppm 8.42 (1H, br. s.) 8.31 (1H, s) 7.99 (1H, s) 7.50-7.57 (3H, m) 7.20 (2H, d, J = 8.20 Hz) 6.55 (2H, br. s.) 2.83 (3H, s) 2.34 (3H, s); MS m/z 374.3 [M + H]$^+$ |
| 228 | 1-{4-amino-5-fluoro-6-[(4-methoxyphenyl)amino]pyrimidin-2-yl}-2-methyl-1H-benzimidazole-5-carbonitrile<br>$^1$H NMR (500 MHz, Acetone-d$_6$) δ ppm 8.33-8.39 (1H, m) 8.29 (1H, d, J = 8.51 Hz) 7.98 (1H, s) 7.49-7.56 (3H, m) 6.95-7.00 (2H, m) 6.51 (2H, br. s.) 3.83 (3H, s) 2.81 (3H, s); MS m/z 390.4 [M + H]$^+$ |
| 229 | 1-(4-amino-5-fluoro-6-{[4-(trifluoromethyl)phenyl]amino}pyrimidin-2-yl)-2-methyl-1H-benzimidazole-5-carbonitrile<br>$^1$H NMR (500 MHz, Acetone-d$_6$) δ ppm 8.90 (1H, s) 8.28 (1H, d, J = 8.51 Hz) 8.02 (1H, s) 7.97 (2H, d, J = 8.51 Hz) 7.71 (2H, d, J = 8.20 Hz) 7.58 (1H, dd, J = 8.51, 1.58 Hz) 6.78 (2H, br. s.) 2.87 (3H, s); MS m/z 428.3 [M + H]$^+$ |
| 230 | 1-{4-amino-6-[(4-chlorophenyl)amino]-5-fluoropyrimidin-2-yl}-2-methyl-1H-benzimidazole-5-carbonitrile<br>$^1$H NMR (500 MHz, Acetone-d$_6$) δ ppm 8.64 (1H, br. s.) 8.28 (1H, dd, J = 8.51, 0.63 Hz) 8.01 (1H, d, J = 1.58 Hz) 7.70-7.77 (3H, m) 6.94 (1H, t, J = 75.00 Hz) 6.68 (2H, s) 2.88 (2H, m) 6.67 (2H, br. s.) 2.84 (3H, s); MS m/z 394.2 [M + H]$^+$ |
| 231 | N-[4-(difluoromethoxy)phenyl]-5-fluoro-2-(2-methyl-6-nitro-1H-benzimidazol-1-yl)pyrimidine-4,6-diamine<br>$^1$H NMR (500 MHz, Acetone-d$_6$) δ ppm 9.02 (1H, d, J = 2.84 Hz) 8.62 (1H, br. s.) 8.19 (1H, dd, J = 8.83, 2.52 Hz) 7.71-7.77 (3H, m) 6.94 (1H, t, J = 75.00 Hz) 6.68 (2H, s) 2.88 (3H, s); MS m/z 446.2 [M + H]$^+$ |
| 232 | 5-fluoro-2-(2-methyl-6-nitro-1H-benzimidazol-1-yl)-N-(4-methylphenyl)pyrimidine-4,6-diamine<br>$^1$H NMR (500 MHz, Acetone-d$_6$) δ ppm 9.03 (1H, d, J = 2.84 Hz) 8.45 (1H, br. s.) 8.18 (1H, dd, J = 8.83, 2.21 Hz) 7.74 (1H, d, J = 8.83 Hz) 7.53-7.59 (2H, m) 7.18 (2H, d, J = 7.88 Hz) 6.61 (2H, br. s.) 2.87 (3H, s) 2.32 (3H, s); MS m/z 394.2 [M + H]$^+$ |
| 233 | 5-fluoro-N-(4-methoxyphenyl)-2-(2-methyl-6-nitro-1H-benzimidazol-1-yl)pyrimidine-4,6-diamine<br>$^1$H NMR (500 MHz, Acetone-d$_6$) δ ppm 9.03 (1H, d, J = 1.89 Hz) 8.38 (1H, br. s.) 8.17 (1H, dd, J = 8.83, 2.21 Hz) 7.73 (1H, d, J = 8.83 Hz) 7.52-7.60 (2H, m) 6.92-6.99 (2H, m) 6.57 (2H, br. s.) 3.80 (3H, s) 2.54 (3H, s); MS m/z 410.2 [M + H]$^+$ |
| 236 | 5-fluoro-2-(2-methyl-6-nitro-1H-benzimidazol-1-yl)-N-[4-(trifluoromethyl)phenyl]pyrimidine-4,6-diamine<br>$^1$H NMR (500 MHz, Acetone-d$_6$) δ ppm 9.04 (1H, d, J = 2.52 Hz) 8.90 (1H, br. s.) 8.21 (1H, dt, J = 8.83, 1.42 Hz) 7.99 (2H, d, J = 8.35, 3.31 Hz) 7.77 (1H, d, J = 8.83 Hz) 7.70 (2H, d, J = 8.51 Hz) 6.83 (2H, br. s.) 2.92 (3H, s); MS m/z 448.2 [M + H]$^+$ |
| 237 | N-(4-chlorophenyl)-2-(4,6-difluoro-2-methyl-1H-benzimidazol-1-yl)-5-fluoropyrimidine-4,6-diamine<br>$^1$H NMR (500 MHz, Acetone-d$_6$) δ ppm 8.62 (1H, br. s.) 7.79 (1H, dd, J = 10.25, 2.05 Hz) 7.69-7.74 (2H, m) 7.37-7.44 (2H, m) 6.92 (1H, td, J = 10.25, 2.21 Hz) 6.67 (2H, br. s.) 2.79-2.80 (3H, m); MS m/z 405.2 [M + H]$^+$ |
| 238 | 2-(4,6-difluoro-2-methyl-1H-benzimidazol-1-yl)-5-fluoro-N-[4-(trifluoromethoxy)phenyl]pyrimidine-4,6-diamine<br>$^1$H NMR (500 MHz, Acetone-d$_6$) δ ppm 8.69 (1H, s) 7.75-7.85 (3H, m) 7.36 (2H, d, J = 8.20 Hz) 6.92 (1H, td, J = 10.25, 2.52 Hz) 6.69 (2H, br. s.) 2.79 (3H, s); MS m/z 456.1 [M + H]$^+$ |
| 240 | N-(1,3-benzodioxol-5-yl)-2-(4,6-difluoro-2-methyl-1H-benzimidazol-1-yl)-5-fluoropyrimidine-4,6-diamine<br>$^1$H NMR (500 MHz, Acetone-d$_6$) δ ppm 8.37 (1H, br. s.) 7.80 (1H, dd, J = 9.46, 1.89 Hz) 7.20 (1H, d, J = 2.21 Hz) 7.05 (1H, dd, J = 8.35, 2.05 Hz) 6.84-6.92 (2H, m) 6.55 (2H, br. s.) 6.02 (2H, s) 2.79 (3H, s); MS m/z 416.2 [M + H]$^+$ |
| 241 | 2-(4,6-difluoro-2-methyl-1H-benzimidazol-1-yl)-5-fluoro-N-(4-methylphenyl)pyrimidine-4,6-diamine<br>$^1$H NMR (500 MHz, Acetone-d$_6$) δ ppm 8.41 (1H, br. s.) 7.80 (1H, dd, J = 9.93, 2.36 Hz) 7.50-7.56 (2H, m) 7.20 (2H, d, J = 8.20 Hz) 6.90 (1H, td, J = 10.25, 2.52 Hz) 6.56 (2H, br. s.) 2.79 (3H, s) 2.34 (3H, s); MS m/z 386.2 [M + H]$^+$ |

| Cpd | Name & Data |
|---|---|
| 242 | 2-(4,6-difluoro-2-methyl-1H-benzimidazol-1-yl)-5-fluoro-N-(4-methoxyphenyl)pyrimidine-4,6-diamine<br>$^1$H NMR (500 MHz, Acetone-$d_6$) δ ppm 8.34 (1H, br. s.) 7.76-7.83 (1H, m) 7.47-7.55 (2H, m) 6.94-7.00 (2H, m) 6.89 (1H, td, J = 10.25, 2.21 Hz) 6.52 (2H, br. s.) 3.82 (3H, s) 2.76 (3H, s); MS m/z 402.2 [M + H]$^+$ |
| 243 | 2-(5,7-difluoro-2-methyl-1H-benzimidazol-1-yl)-5-fluoro-N-[4-(trifluoromethyl)phenyl]pyrimidine-4,6-diamine<br>$^1$H NMR (500 MHz, Acetone-$d_6$) δ ppm 8.86 (1H, br. s.) 8.15 (1H, dd, J = 11.66, 7.88 Hz) 7.91-7.98 (2H, m) 7.72 (2H, d, J = 8.51 Hz) 7.48 (1H, dd, J = 10.72, 7.57 Hz) 6.78 (2H, br. s.) 2.83 (3H, s); MS m/z 439.3 [M + H]$^+$ |
| 244 | 5-fluoro-2-(6-methoxy-2-methyl-1H-benzimidazol-1-yl)-N-[4-(trifluoromethyl)phenyl]pyrimidine-4,6-diamine<br>$^1$H NMR (500 MHz, Acetone-$d_6$) δ ppm 8.82 (1H, br. s.) 8.00 (2H, d, J = 8.51 Hz) 7.65-7.73 (3H, m) 7.45 (1H, d, J = 8.51 Hz) 6.83-6.89 (1H, m) 6.67 (2H, br. s.) 3.64-3.69 (3H, m) 2.78 (3H, s); MS m/z 434.2 [M + H]$^+$ |
| 245 | N-(4-chlorophenyl)-5-fluoro-2-(6-methoxy-2-methyl-1H-benzimidazol-1-yl)pyrimidine-4,6-diamine<br>$^1$H NMR (500 MHz, Acetone-$d_6$) δ ppm 8.57 (1H, br. s.) 7.74-7.79 (2H, m) 7.68 (1H, d, J = 2.52 Hz) 7.44 (1H, d, J = 8.51 Hz) 7.35-7.41 (2H, m) 6.85 (1H, dd, J = 8.83, 2.52 Hz) 6.57 (2H, br. s.) 3.69 (3H, s) 2.75 (3H, s); MS m/z 399.2 [M + H]$^+$ |
| 246 | 5-fluoro-2-(6-methoxy-2-methyl-1H-benzimidazol-1-yl)-N-[4-(trifluoromethoxy)phenyl]pyrimidine-4,6-diamine<br>$^1$H NMR (500 MHz, Acetone-$d_6$) δ ppm 8.64 (1H, s) 7.84-7.89 (2H, m) 7.69 (1H, d, J = 2.21 Hz) 7.44 (1H, d, J = 8.83 Hz) 7.34 (2H, d, J = 8.20 Hz) 6.85 (1H, dd, J = 8.51, 2.52 Hz) 6.58 (2H, br. s.) 3.68 (3H, s) 2.75 (3H, s); MS m/z 449.2 [M + H]$^+$ |
| 247 | N-[4-(difluoromethoxy)phenyl]-5-fluoro-2-(6-methoxy-2-methyl-1H-benzimidazol-1-yl)pyrimidine-4,6-diamine<br>$^1$H NMR (500 MHz, Acetone-$d_6$) δ ppm 8.52 (1H, s) 7.74-7.79 (2H, m) 7.69 (1H, d, J = 2.51 Hz) 7.43 (1H, d, J = 8.51 Hz) 7.17-7.23 (2H, m) 6.81-7.12 (2H, m) 6.53 (2H, br. s.) 3.69 (3H, s) 2.74 (3H, s); MS m/z 432.2 [M + H]$^+$ |
| 248 | 5-fluoro-2-(6-methoxy-2-methyl-1H-benzimidazol-1-yl)-N-(4-methylphenyl)pyrimidine-4,6-diamine<br>$^1$H NMR (500 MHz, Acetone-$d_6$) δ ppm 8.34 (1H, br, s) 7.70 (1H, d, J = 2.52 Hz) 7.56-7.60 (2H, m) 7.42 (1H, d, J = 8.83 Hz) 7.17 (2H, d, J = 8.20 Hz) 6.83 (1H, dd, J = 8.83, 2.52 Hz) 6.45 (2H, br. s.) 3.65 (3H, s) 2.75 (3H, s) 2.33 (3H, s); MS m/z 380.2 [M + H]$^+$ |
| 249 | 5-fluoro-2-(6-methoxy-2-methyl-1H-benzimidazol-1-yl)-N-(4-methoxyphenyl)pyrimidine-4,6-diamine<br>$^1$H NMR (500 MHz, Acetone-$d_6$) δ ppm 8.27 (1H, br. s.) 7.70 (1H, d, J = 2.52 Hz) 7.54-7.60 (2H, m) 7.38-7.43 (1H, m) 6.92-6.97 (2H, m) 6.82 (1H, dd, J = 8.51, 2.52 Hz) 6.41 (2H, br. s.) 3.82 (3H, s) 3.67 (3H, s) 2.72 (3H, s); MS m/z 396.2 [M + H]$^+$ |
| 250 | N-(1,3-benzodioxol-5-yl)-5-fluoro-2-(6-methoxy-2-methyl-1H-benzimidazol-1-yl)pyrimidine-4,6-diamine<br>$^1$H NMR (500 MHz, Acetone-$d_6$) δ ppm 8.32 (1H, br. s.) 7.71 (1H, d, J = 2.52 Hz) 7.42 (1H, d, J = 8.51 Hz) 7.30-7.33 (1H, m) 7.09 (1H, dd, J = 8.35, 2.05 Hz) 6.81-6.87 (2H, m) 6.44 (2H, br. s.) 6.01 (2H, s) 3.72 (3H, s) 2.74 (3H, s); MS m/z 409.2 [M + H]$^+$ |
| 254 | 5-fluoro-2-(2-methyl-5-nitro-1H-benzimidazol-1-yl)-N-(4-methylphenyl)pyrimidine-4,6-diamine<br>$^1$H NMR (500 MHz, Acetone-$d_6$) δ ppm 8.45-8.49 (1H, m) 8.44 (1H, d, J = 1.89 Hz) 8.31 (1H, d, J = 9.14 Hz) 8.11 (1H, dd, J = 8.98, 2.36 Hz) 7.54-7.57 (2H, m) 7.21 (2H, d, J = 8.20 Hz) 6.59 (2H, br. s.) 2.85 (3H, s) 2.34 (3H, s); MS m/z 394.2 [M + H]$^+$ |
| 255 | 5-fluoro-N-(4-methoxyphenyl)-2-(2-methyl-5-nitro-1H-benzimidazol-1-yl)pyrimidine-4,6-diamine<br>$^1$H NMR (500 MHz, Acetone-$d_6$) δ ppm 8.43 (1H, d, J = 1.89 Hz) 8.40 (1H, br. s.) 8.30 (1H, d, J = 9.14 Hz) 8.10 (1H, dd, J = 8.99, 2.36 Hz) 7.52-7.57 (2H, m) 6.96-7.01 (2H, m) 6.55 (2H, br. s.) 3.83 (3H, s) 2.83 (3H, s); MS m/z 410.2 [M + H]$^+$ |
| 256 | 2-(6-amino-2-methyl-1H-benzimidazol-1-yl)-5-fluoro-N-(4-methoxyphenyl)pyrimidine-4,6-diamine<br>$^1$H NMR (500 MHz, Acetone-$d_6$) δ ppm 8.25 (1H, s) 7.53-7.59 (2H, m) 7.42 (1H, d, J = 1.58 Hz) 7.24 (1H, d, J = 8.83 Hz) 6.93-6.99 (2H, m) 6.61 (1H, dd, J = 8.20, 2.21 Hz) 6.33 (2H, s) 4.30 (2H, br. s.) 3.81 (3H, s) 2.67 (3H, s); MS m/z 380.3 [M + H]$^+$ |
| 257 | 2-(6-amino-2-methyl-1H-benzimidazol-1-yl)-N-[4-(difluoromethoxy)phenyl]-5-fluoropyrimidine-4,6-diamine<br>$^1$H NMR (500 MHz, Acetone-$d_6$) δ ppm 8.48 (1H, br. s.) 7.75-7.82 (2H, m) 7.42 (1H, d, J = 2.21 Hz) 7.25 (1H, d, J = 8.20 Hz) 7.04 (2H, d, J = 8.20 Hz) 6.47 (1H, dd, J = 75.00 Hz) 6.64 (1H, dd, J = 8.51, 2.21 Hz) 6.44 (2H, br. s.) 4.36 (2H, s) 2.68 (3H, s); MS m/z 416.2 [M + H]$^+$ |
| 258 | 2-(6-amino-2-methyl-1H-benzimidazol-1-yl)-5-fluoro-N-(4-methylphenyl)pyrimidine-4,6-diamine<br>$^1$H NMR (500 MHz, Acetone-$d_6$) δ ppm 8.15 (1H, br. s.) 7.39-7.46 (2H, m) 7.28 (1H, d, J = 2.21 Hz) 7.09 (1H, d, J = 8.20 Hz) 7.04 (2H, d, J = 8.20 Hz) 6.47 (1H, dd, J = 8.51, 2.21 Hz) 6.22 (2H, s) 4.16 (2H, s) 2.54 (3H, s) 2.18 (3H, s); MS m/z 364.3 [M + H]$^+$ |
| 259 | N-(4-chlorophenyl)-5-fluoro-2-(5-fluoro-2-methyl-1H-benzimidazol-1-yl)pyrimidine-4,6-diamine<br>$^1$H NMR (500 MHz, Acetone-$d_6$) δ ppm 8.60 (1H, br. s.) 8.13 (1H, dd, J = 9.46, 5.04 Hz) 7.71-7.78 (2H, m) 7.36-7.43 (2H, m) 7.29 (1H, dd, J = 9.30, 2.36 Hz) 6.99 (1H, td, J = 9.30, 2.52 Hz) 6.60 (2H, br. s.) 2.80 (3H, s); MS m/z 387.2 [M + H]$^+$ |

-continued

| Cpd | Name & Data |
|---|---|
| 260 | N-(4-chloro-3-fluorophenyl)-5-fluoro-2-(5-fluoro-2-methyl-1H-benzimidazol-1-yl)pyrimidine-4,6-diamine<br>$^1$H NMR (500 MHz, Acetone-$d_6$) δ ppm 8.76 (1H, br. s.) 8.13 (1H, dd, J = 8.83, 5.04 Hz) 7.86 (1H, dd, J = 11.98, 2.52 Hz) 7.54-7.59 (1H, m) 7.45-7.51 (1H, m) 7.30 (1H, dd, J = 9.30, 2.36 Hz) 7.02 (1H, td, J = 9.22, 2.68 Hz) 6.69 (2H, br. s.) 2.84 (3H, s); MS m/z 405.2 [M + H]$^+$ |
| 261 | N-(4-chloro-3-fluorophenyl)-5-fluoro-2-(2-methyl-1H-benzimidazol-1-yl)pyrimidine-4,6-diamine<br>$^1$H NMR (500 MHz, Acetone-$d_6$) δ ppm 8.74 (1H, br. s.) 8.11 (1H, dd, J = 7.57, 1.89 Hz) 7.90 (1H, dd, J = 11.98, 2.52 Hz) 7.58 (2H, td, J = 7.88, 2.21 Hz) 7.47 (1H, t, J = 7.57, 1.89 Hz) 7.18-7.28 (2H, m) 6.65 (2H, br. s.) 2.82 (3H, s); MS m/z 387.2 [M + H]$^+$ |
| 262 | N-(4-chloro-3-fluorophenyl)-5-fluoro-2-(6-fluoro-2-methyl-1H-benzimidazol-1-yl)pyrimidine-4,6-diamine<br>$^1$H NMR (500 MHz, Acetone-$d_6$) δ ppm 8.77 (1H, br. s.) 7.93 (1H, dd, J = 10.09, 2.21 Hz) 7.83 (1H, dd, J = 11.82, 2.36 Hz) 7.53-7.59 (2H, m) 7.46-7.51 (1H, m) 7.05 (1H, td, J = 9.14, 2.52 Hz) 6.72 (2H, br. s.) 2.82 (3H, s); MS m/z 405.2 [M + H]$^+$ |
| 270 | 2-(2-ethyl-1H-benzimidazol-1-yl)-5-fluoro-N-(4-methylphenyl)pyrimidine-4,6-diamine<br>$^1$H NMR (500 MHz, Acetone-$d_6$) δ ppm 8.36 (1H, br. s.) 8.07-8.11 (1H, m) 7.54-7.62 (3H, m) 7.15-7.24 (4H, m) 6.46 (2H, br. s.) 3.26 (2H, q, J = 7.46 Hz) 2.33 (3H, s) 1.30-1.33 (3H, m); MS m/z 363.3 [M + H]$^+$ |
| 271 | 2-(2-ethyl-1H-benzimidazol-1-yl)-5-fluoro-N-(4-methoxyphenyl)pyrimidine-4,6-diamine<br>$^1$H NMR (500 MHz, Acetone-$d_6$) δ ppm 8.15 (1H, br. s.) 7.93-7.97 (1H, m) 7.39-7.46 (3H, m) 6.99-7.10 (2H, m) 6.78-6.83 (2H, m) 6.28 (2H, s) 3.68 (3H, s) 3.10 (2H, q, J = 7.36 Hz) 1.14-1.17 (3H, m); MS m/z 379.3 [M + H]$^+$ |
| 272 | 2-(2-ethyl-1H-benzimidazol-1-yl)-5-fluoro-N-[4-(trifluoromethoxy)phenyl]pyrimidine-4,6-diamine<br>$^1$H NMR (500 MHz, Acetone-$d_6$) δ ppm 8.67 (1H, s) 8.04-8.10 (1H, m) 7.80-7.87 (2H, m) 7.58-7.64 (1H, m) 7.33 (2H, d, J = 8.20 Hz) 7.14-7.26 (2H, m) 6.60 (2H, 2) 3.26 (2H, q, J = 7.36 Hz) 1.31-1.34 (3H, m); MS m/z 433.2 [M + H]$^+$ |
| 273 | N-(1,3-benzodioxo1-5-yl)-2-(2-ethyl-1H-benzimidazol-1-yl)-5-fluoropyrimidine-4,6-diamine<br>$^1$H NMR (500 MHz, Acetone-$d_6$) δ ppm 8.32 (1H, br. s.) 8.08-8.13 (1H, m) 7.58 (1H, d, J = 7.57 Hz) 7.28 (1H, d, J = 1.89 Hz) 7.15-7.24 (2H, m) 7.07 (1H, dd, J = 8.67, 2.05 Hz) 6.85 (1H, d, J = 8.51 Hz) 6.40-6.48 (2H, m) 6.01 (2H, s) 3.25 (2H, q, J = 7.57 Hz) 1.30-1.33 (3H, m); MS m/z 393.2 [M + H]$^+$ |
| 274 | N-(4-chlorophenyl)-2-(2-ethyl-1H-benzimidazol-1-yl)-5-fluoropyrimidine-4,6-diamine<br>$^1$H NMR (500 MHz, Acetone-$d_6$) δ ppm 8.57 (1H, br. s.) 8.03-8.09 (1H, m) 7.72-7.79 (2H, m) 7.60 (1H, d, J = 7.57 Hz) 7.34-7.40 (2H, m) 7.16-7.26 (2H, m) 6.56 (2H, br. s.) 3.26 (2H, q, J = 7.57 Hz) 1.33 (3H, t, J = 7.57 Hz); MS m/z 383.4 [M + H]$^+$ |
| 275 | N-(4-chloro-3-fluorophenyl)-2-(2-ethyl-1H-benzimidazol-1-yl)-5-fluoropyrimidine-4,6-diamine<br>$^1$H NMR (500 MHz, Acetone-$d_6$) δ ppm 8.75 (1H, br. s.) 8.06 (1H, d, J = 6.94 Hz) 7.90 (1H, dd, J = 11.98, 2.52 Hz) 7.62 (1H, dd, J = 6.94, 1.58 Hz) 7.54-7.58 (1H, m) 7.42-7.49 (1H, m) 7.18-7.29 (2H, m) 6.65 (2H, br. s.) 3.29 (2H, q, J = 7.36 Hz) 1.36 (3H, t, J = 7.41 Hz); MS m/z 401.4 [M + H]$^+$ |
| 276 | 2-(2-cyclopropyl-1H-benzimidazol-1-yl)-5-fluoro-N-(4-methylphenyl)pyrimidine-4,6-diamine<br>$^1$H NMR (500 MHz, Acetone-$d_6$) δ ppm 8.36 (1H, br. s.) 8.02-8.06 (1H, m) 7.61-7.67 (2H, m) 7.46-7.53 (1H, m) 7.12-7.23 (4H, m) 6.47 (2H, br. s.) 3.01-3.10 (1H, m) 2.32 (3H, s) 1.16-1.21 (2H, m) 0.98 (2H, dq, J = 8.47, 3.38 Hz); MS m/z 375.4 [M + H]$^+$ |
| 277 | 2-(2-cyclopropyl-1H-benzimidazol-1-yl)-5-fluoro-N-(4-methoxyphenyl)pyrimidine-4,6-diamine<br>$^1$H NMR (500 MHz, Acetone-$d_6$) δ ppm 8.29 (1H, br. s.) 8.04 (1H, d, J = 8.83 Hz) 7.58-7.65 (2H, m) 7.46-7.51 (1H, m) 7.10-7.21 (2H, m) 6.89-6.96 (2H, m) 6.43 (2H, br. s.) 3.81 (3H, s) 3.02-3.10 (1H, m) 1.13-1.18 (2H, m) 0.96 (2H, dq, J = 8.35, 3.42 Hz); MS m/z 391.3 [M + H]$^+$ |
| 278 | 2-(2-cyclopropyl-1H-benzimidazol-1-yl)-5-fluoro-N-[4-(trifluoromethoxy)phenyl]pyrimidine-4,6-diamine<br>$^1$H NMR (500 MHz, Acetone-$d_6$) δ ppm 8.65 (1H, s) 7.98-8.03 (1H, m) 7.87-7.93 (2H, m) 7.49-7.54 (1H, m) 7.31 (2H, d, J = 8.20 Hz) 7.12-7.24 (2H, m) 6.60 (2H, br. s.) 2.98-3.05 (1H, m) 1.17-1.23 (2H, m) 0.95-1.02 (2H, m); MS m/z 445.3 [M + H]$^+$ |
| 279 | N-(4-chlorophenyl)-2-(2-cyclopropyl-1H-benzimidazol-1-yl)-5-fluoropyrimidine-4,6-diamine<br>$^1$H NMR (500 MHz, Acetone-$d_6$) δ ppm 8.59 (1H, br. s.) 7.97-8.04 (1H, m) 7.80-7.86 (2H, m) 7.47-7.55 (1H, m) 7.32-7.38 (2H, m) 7.12-7.23 (2H, m) 6.58 (2H, br. s.) 2.96-3.05 (1H, m) 1.17-1.25 (2H, m) 0.97-1.04 (2H, m); MS m/z 395.3 [M + H]$^+$ |
| 280 | N-(4-chloro-3-fluorophenyl)-2-(2-cyclopropyl-1H-benzimidazol-1-yl)-5-fluoropyrimidine-4,6-diamine<br>$^1$H NMR (500 MHz, Acetone-$d_6$) δ ppm 8.77 (1H, br. s.) 7.96-8.06 (2H, m) 7.60 (1H, dd, J = 7.88, 2.52 Hz) 7.53 (1H, d, J = 6.94 Hz) 7.45 (1H, t, J = 8.67 Hz) 7.16-7.25 (2H, m) 6.68 (2H, br. s.) 2.96-3.03 (1H, m) 1.21-1.26 (2H, m) 1.02-1.07 (2H, m); MS m/z 413.3 [M + H]$^+$ |
| 281 | 5-fluoro-2-(5-fluoro-2-methyl-1H-benzimidazol-1-yl)-N-(4-methylphenyl)pyrimidine-4,6-diamine<br>$^1$H NMR (500 MHz, Acetone-$d_6$) δ ppm 8.39 (1H, br. s.) 8.15 (1H, dd, J = 8.51, 5.04 Hz) 7.53-7.58 (2H, m) 7.27 (1H, dd, J = 9.62, 2.36 Hz) 7.19 (2H, d, J = 8.51, 5.04 Hz) (1H, m) 6.51 (2H, br. s.) 2.79 (3H, s) 2.34 (3H, s); MS m/z 367.3 [M + H]$^+$ |
| 282 | 5-fluoro-2-(5-fluoro-2-methyl-1H-benzimidazol-1-yl)-N-(4-methoxyphenyl)pyrimidine-4,6-diamine<br>$^1$H NMR (500 MHz, Acetone-$d_6$) δ ppm 8.30 (1H, br. s.) 8.14 (1H, dd, J = 9.30, 4.89 Hz) 7.51-7.58 (2H, m) 7.26 (1H, dd, J = 9.46, 2.52 Hz) 6.91-7.00 (3H, m) 6.44 (2H, br. s.) 3.83 (3H, s) 2.76 (3H, s); MS m/z 383.3 [M + H]$^+$ |

-continued

| Cpd | Name & Data |
|---|---|
| 283 | 5-fluoro-2-(5-fluoro-2-methyl-1H-benzimidazol-1-yl)-N-[4-(trifluoromethoxy)phenyl]pyrimidine-4,6-diamine<br>$^1$H NMR (500 MHz, Acetone-$d_6$) δ ppm 8.66 (1H, s) 8.12 (1H, dd, J = 8.67, 4.89 Hz) 7.80-7.86 (2H, m) 7.35 (2H, d, J = 8.20 Hz) 7.29 (1H, dd, J = 8.83, 2.52 Hz) 6.97 (1H, td, J = 9.30, 2.52 Hz) 6.62 (2H, s) 2.79 (3H, s); MS m/z 437.3 [M + H]$^+$ |
| 284 | 2-(6-amino-2-methyl-1H-benzimidazol-1-yl)-5-fluoro-N-[4-(trifluoromethyl)phenyl]pyrimidine-4,6-diamine<br>$^1$H NMR (500 MHz, Acetone-$d_6$) δ ppm 7.86 (2H, d, J = 8.51 Hz) 7.53 (2H, d, J = 8.51 Hz) 7.28 (1H, d, J = 2.21 Hz) 7.13 (1H, d, J = 8.51 Hz) 6.50 (1H, dd, J = 8.51, 2.21 Hz) 6.42 (2H, br. s.) 4.26 (2H, s) 2.56 (3H, s) MS m/z 418.3 [M + H]$^+$ |

Example 11

5-fluoro-N-(4-methoxyphenyl)-2-(2-methylpyrazolo[1,5-a]pyridin-3-yl)pyrimidine-4,6-diamine (Cpd 239)

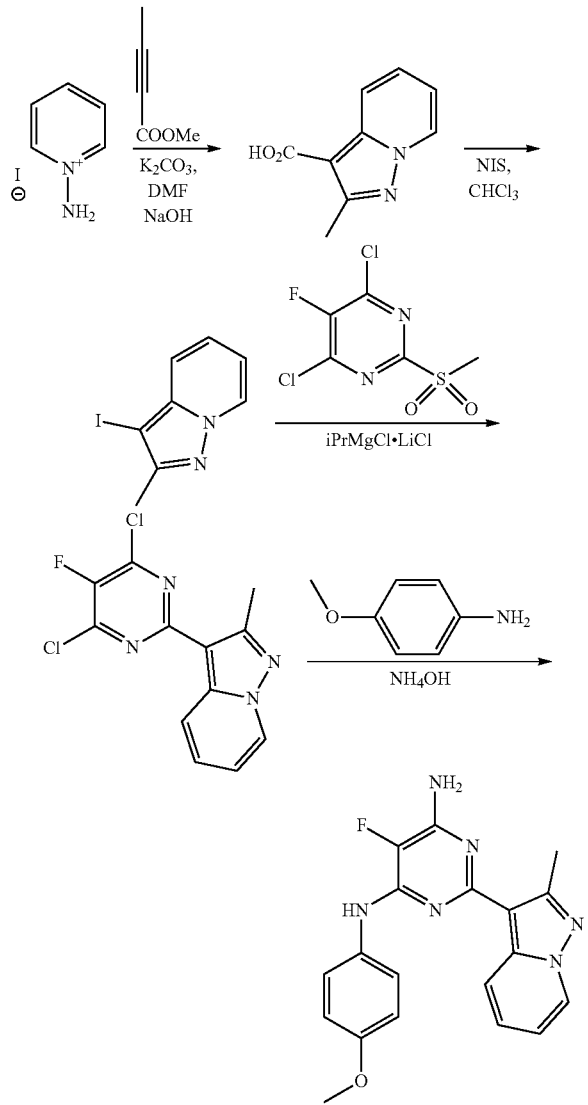

Step 1. To a mixture of 1-aminopyridinium iodide (9.59 g, 43.2 mmol) and methyl but-2-ynoate (5.2 mL, 51.83 mmol) in DMF (50 mL) at 0° C. was added $K_2CO_3$ (11.94 g, 86.4 mmol). The reaction mixture was warmed to room temperature and stirred for 3 days until UPLC showed complete conversion to product. The reaction mixture was partitioned between water and EtOAc. The organic phase was concentrated, then MeOH (50 mL) and NaOH (6 mL, 50% in $H_2O$) were added and the reaction mixture was heated at 70° C. for 1 hour. The MeOH was evaporated and the remaining mixture was acidified with 1N HCl to about pH 4. A crude 2-methylpyrazolo[1,5-a]pyridine-3-carboxylic acid was isolated on a filter and dried under vacuum, then dissolved in MeOH (50 mL) and $CHCl_3$ (100 mL) and N-iodosuccinimide (7.3 g, 32.4 mmol) were added in one portion. The reaction mixture was stirred for 20 minutes at room temperature. The MeOH was evaporated and the remainder was washed three times with an aqueous $NaHCO_3$ solution. The organic phase was dried over $Na_2SO_4$, the solvent was removed under reduced pressure, and the crude product was purified by silica gel chromatography to give 3-iodo-2-methylpyrazolo[1,5-a]pyridine (4.2 g, 38% for 3 steps) as an off-white solid.

$^1$H NMR (500 MHz, Acetone-$d_6$) δ ppm 8.51 (dt, J=6.8, 1.3 Hz, 1H), 7.41 (dt, J=8.8, 1.3 Hz, 1H), 7.31 (ddd, J=8.8, 6.8, 1.3 Hz, 1H), 6.90 (td, J=6.8, 1.3 Hz, 1H), 2.42 (s, 3H); MS m/z 298.1 [M+H]$^+$.

Step 2. To a solution of 3-iodo-2-methylpyrazolo[1,5-a]pyridine (340 mg, 1.32 mmol) in dry THF (10 mL) at 0° C. was added an isopropylmagnesium chloride lithium chloride complex solution (iPrMgCl.LiCl) (1.5 mL, 1.97 mL). The reaction mixture was stirred at 0° C. for 30 minutes and 4,6-dichloro-5-fluoro-2-(methylsulfonyl)pyrimidine (484 mg, 1.97 mmol) in dry THF (20 mL) was added. The reaction mixture was stirred at 0° C. for 1 hour, and the reaction was quenched with water. The crude product was extracted with $CH_2Cl_2$ three times. The combined organic extracts were washed with brine, then dried over $Na_2SO_4$, concentrated, and triturated in $CH_3CN$ (10 mL). The resulting precipitate was filtered and dried providing 3-(4,6-dichloro-5-fluoropyrimidin-2-yl)-2-methylpyrazolo[1,5-a]pyridine (270 mg, 68%) isolated as a tan solid.

$^1$H NMR (500 MHz, DMSO-$d_6$) δ ppm 8.79 (d, J=6.9 Hz, 1H), 8.34 (d, J=8.8 Hz, 1H), 7.61 (ddd, J=8.8, 6.9, 0.9 Hz, 1H), 7.13 (td, J=6.9, 1.1 Hz, 1H), 2.70 (s, 3H). MS m/z 298.1 [M+H]$^+$.

Step 3. 3-(4,6-Dichloro-5-fluoropyrimidin-2-yl)-2-methylpyrazolo[1,5-a]pyridine (65 mg, 0.21 mmol) and 4-methoxyaniline (52 mg, 0.42 mmol) were mixed in EtOH (1 mL) and heated in a sealed tube at 100° C. until UPLC showed complete conversion (3 hours). After the starting materials were consumed, the reaction was cooled to room temperature and diluted with water (5 mL) to precipitate the product. The product was collected by filtration, washed with water and subsequently washed with hexanes. The crude product, without drying, was dissolved in iPrOAc (2 mL), then saturated ammonia in water (150 µL) was added.

The reaction mixture was heated at 100° C. in a sealed tube for 24 hours until UPLC showed complete consumption of starting material. A crude product was precipitated by addition of water (10 mL), then filtered and purified by chromatography on silica gel to provide the title compound (26 mg, 34% in two steps).

$^1$H NMR (500 MHz, Acetone-$d_6$) δ ppm 8.54 (dt, J=8.9, 1.2 Hz, 1H), 8.47 (dt, J=6.9, 1.1 Hz, 1H), 7.93 (br. s., 1H), 7.59 (dd, J=6.6, 2.2 Hz, 2H), 7.21 (ddd, J=9.0, 6.8, 0.9 Hz, 1H), 6.98 (dd, J=6.6, 2.2 Hz, 2H), 6.87 (td, J=6.8, 1.3 Hz, 1H), 5.96 (br. s., 2H), 2.84 (s, 3H), 2.70 (s, 3H); MS m/z 383.2 [M+H]$^+$.

Additional compounds of Formula (I) or a form thereof described herein may be prepared according to the procedure of Example 11 by substituting the appropriate starting materials, reagents and reaction conditions.

| Cpd | Name & Data |
|---|---|
| 173 | N-[4-(difluoromethoxy)phenyl]-5-fluoro-2-(2-methylpyrazolo[1,5-a]pyridin-3-yl)pyrimidine-4,6-diamine<br>$^1$H NMR (500 MHz, Acetone-$d_6$) δ ppm 8.55 (dt, J = 8.9, 1.2 Hz, 1H), 8.49 (dt, J = 6.9, 1.0 Hz, 1H), 8.20 (br. s., 1H), 7.76-7.81 (m, 2H), 7.20-7.27 (m, 3H), 6.98 (t, J = 75 Hz, 1H) 6.89 (td, J = 6.9, 1.4 Hz, 1H), 6.08 (br. s, 2H), 2.72 (s, 3H); MS m/z 401.2 [M + H]$^+$ |
| 177 | 5-fluoro-2-(2-methylpyrazolo[1,5-a]pyridin-3-yl)-N-[4-(trifluoromethyl)phenyl]pyrimidine-4,6-diamine<br>$^1$H NMR (500 MHz, Acetone-$d_6$) δ ppm 8.44 (dt, J = 9.1, 1.1 Hz, 1H), 8.37 (dt, J = 6.9, 0.9 Hz, 1H), 8.39 (br. s., 1H), 7.87 (d, J = 8.5 Hz, 2H), 7.55 (d, J = 8.5 Hz, 2H), 7.13 (ddd, J = 9.1, 6.7, 1.3 Hz, 1H), 6.77 (td, J = 6.8, 1.6 Hz, 1H), 6.09 (br. s., 2H), 2.62 (s, 3H); MS m/z 403.4 [M + H]$^+$ |
| 178 | 5-fluoro-2-[6-fluoro-2-(trifluoromethyl)imidazo[1,2-a]pyridin-3-yl]-N-[4-(trifluoromethyl)phenyl]pyrimidine-4,6-diamine<br>$^1$H NMR (500 MHz, Acetone-$d_6$) δ ppm 8.76-8.81 (m, 1H), 8.70 (br. s., 1H), 7.91 (d, J = 8.5 Hz, 2H), 7.68 (dd, J = 10.1, 4.7 Hz, 1H), 7.47 (d, J = 8.5 Hz, 2H), 7.45 (t, J = 9.8 Hz, 1H), 6.52 (br. s., 2H); MS m/z 475.3 [M + H]$^+$ |

Example 12

2-(2-cyclopropylpyrazolo[1,5-a]pyridin-3-yl)-N-[4-(difluoromethoxy)phenyl]-5-fluoropyrimidine-4,6-diamine (Cpd 180)

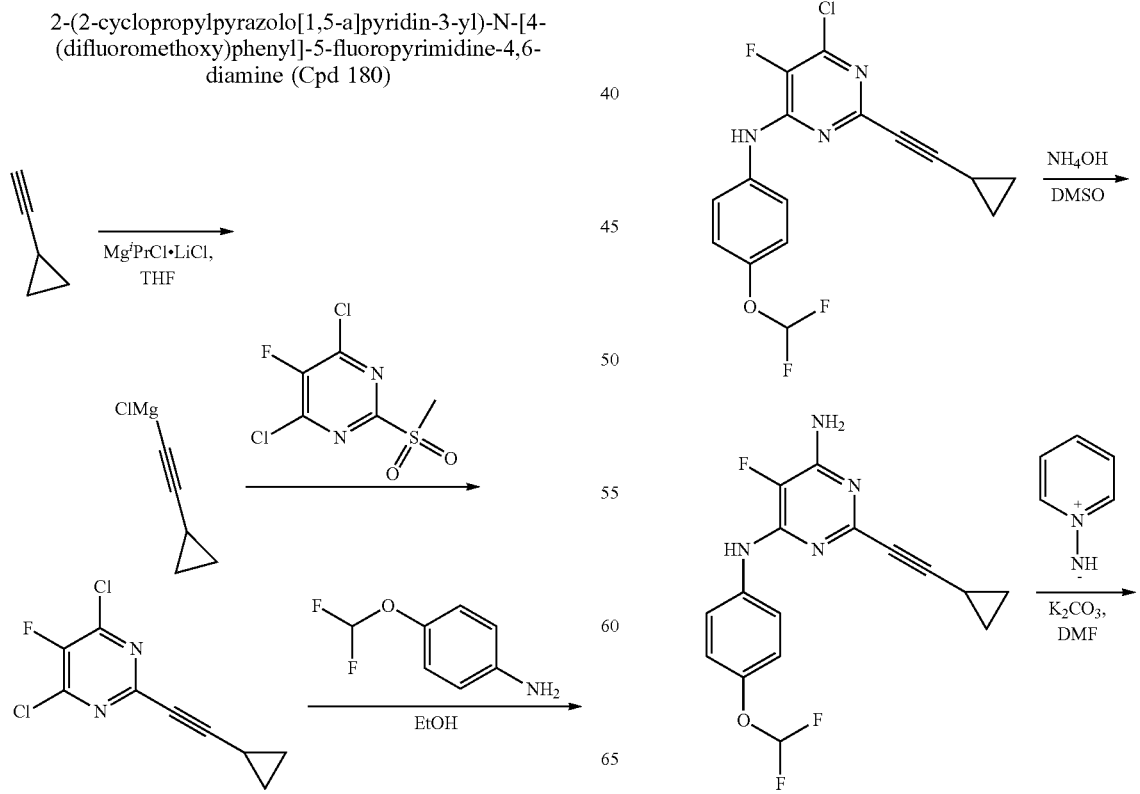

193
-continued

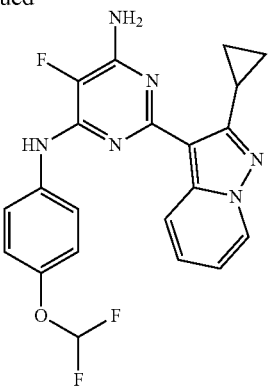

Step 1. To a solution of cyclopropylacetylene (777.0 mg, 9.82 mmol) in THF (5 mL) at −78° C. was added an isopropylmagnesium chloride lithium chloride complex solution (9.0 mL, 1.3 M in THF) dropwise. The mixture was warmed to 0° C. and stirred for 30 minutes. To the mixture at −78° C. was added 4,6-dichloro-5-fluoro-2-(methylsulfonyl)pyrimidine (4.80 g, 19.6 mmol), then the mixture was warmed to 0° C. and stirred for 1 hour. The mixture was partitioned between ethyl acetate and water. The organic phase was washed with brine, dried over MgSO$_4$, then filtered and evaporated. The residual material was separated by silica gel column chromatography (eluting with 1:9 ethyl acetate-hexane) to afford 4,6-dichloro-2-(cyclopropylethynyl)-5-fluoropyrimidine (1.17 g, 45%).

$^1$H NMR (500 MHz, Acetone-d$_6$) δ ppm 1.53-1.67 (m, 1H), 0.98-1.10 (m, 2H), 0.83-0.94 (m, 2H); MS m/z 231.1 (100) [M+H]$^+$.

Step 2. A mixture of 4,6-dichloro-2-(cyclopropylethynyl)-5-fluoropyrimidine (241.0 mg, 1.04 mmol) and 4-difluoromethoxy aniline (707.0 mg, 4.45 mmol) in EtOH (2 mL) was stirred at reflux for 1 hour. After cooling, the mixture was partitioned between ethyl acetate and water. The organic phase was washed with brine, dried over MgSO$_4$, then filtered and evaporated. The residual material was separated by silica gel column chromatography (eluting with 1:20 and 1:10 ethyl acetate-hexane) to afford 6-chloro-2-(cyclopropylethynyl)-N-(4-(difluoromethoxy)phenyl)-5-fluoropyrimidin-4-amine (258.0 mg, 70%); MS m/z 354.2 (100) [M+H]$^+$, 356.2 (40).

Step 3. To 6-chloro-2-(cyclopropylethynyl)-N-(4(difluoromethoxy)phenyl)-5-fluoropyrimidin-4-amine was added DMSO (2 mL) and NH$_4$OH (27%, 0.1 mL). The reaction mixture was sealed and stirred at 100° C. for 2 days. The reaction mixture was partitioned between ethyl acetate and water. The organic phase was washed with water (2×20 mL) and brine, dried over MgSO$_4$, then filtered and evaporated. The residual material was separated by silica gel column chromatography (eluting with 1:4 ethyl acetate-hexane) to afford 2-(2-cyclopropylpyrazolo[1,5-a]pyridin-3-yl)-N-[4-(difluoromethoxy)phenyl]-5-fluoropyrimidine-4,6-diamine (149.0 mg, 64%). MS m/z 335.5 (80) [M+H]$^+$, 336.2 (100).

Step 4. A mixture of 2-(2-cyclopropylpyrazolo[1,5-a]pyridin-3-yl)-N-[4-(difluoromethoxy)phenyl]-5-fluoropyrimidine-4,6-diamine (100.0 mg, 0.30 mmol), pyridinium-1-ylazanide (74.0 mg, 0.30 mmol), K$_2$CO$_3$ (43.0 mg, 0.31 mmol) and DMF (2 mL) was stirred at room temperature for 1 day, and then at 80° C. for 1 day. The reaction mixture was partitioned between ethyl acetate and water. The organic phase was washed with water and brine, dried over MgSO$_4$, then filtered and evaporated. The residual material was

194 separated by silica gel column chromatography (eluting with 1:1 dichloromethane:hexane, then 1:3 ethyl acetate:dichloromethane) to afford the title compound (32.0 mg, 28% yield): m.p. 53-55° C.

$^1$H NMR (500 MHz, Acetone-d$_6$) δ ppm 8.55 (d, J=8.83 Hz, 1H), 8.41 (d, J=6.94 Hz, 1H). 8.20 (br. s., 1H), 7.63-7.91 (m, 2H), 7.21 (ddd, J=0.95, 6.78, 8.98 Hz, 1H), 7.17 (d, J=8.83 Hz, 2H), 6.80-7.10 (t, J=75.00 Hz, 1H), 6.86 (dt, J=1.26, 6.78 Hz, 1H), 6.10 (br. s., 2H), 3.44 (m, 1H), 0.53-1.13 (m, 4H); MS m/z 427.3 (100) [M+H]$^+$, 428.3 (50).

Example 13

[3-(4-amino-6-{[4-(difluoromethoxy)phenyl]amino}-5-fluoropyrimidin-2-yl)-5-fluoropyrazolo[1,5-a]pyridin-2-yl]methanol (Cpd 181)

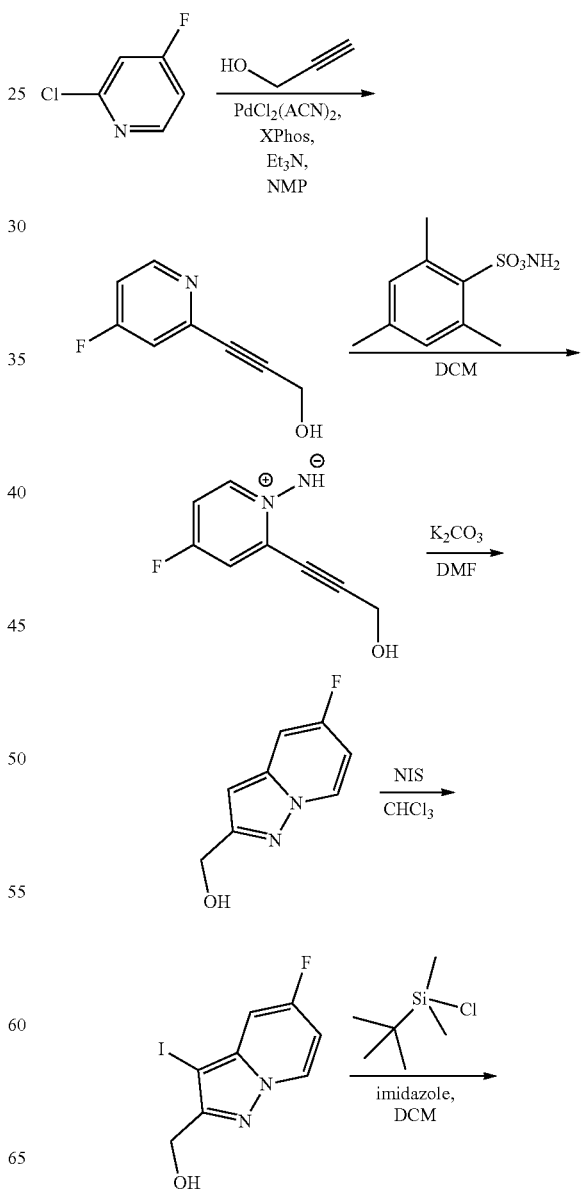

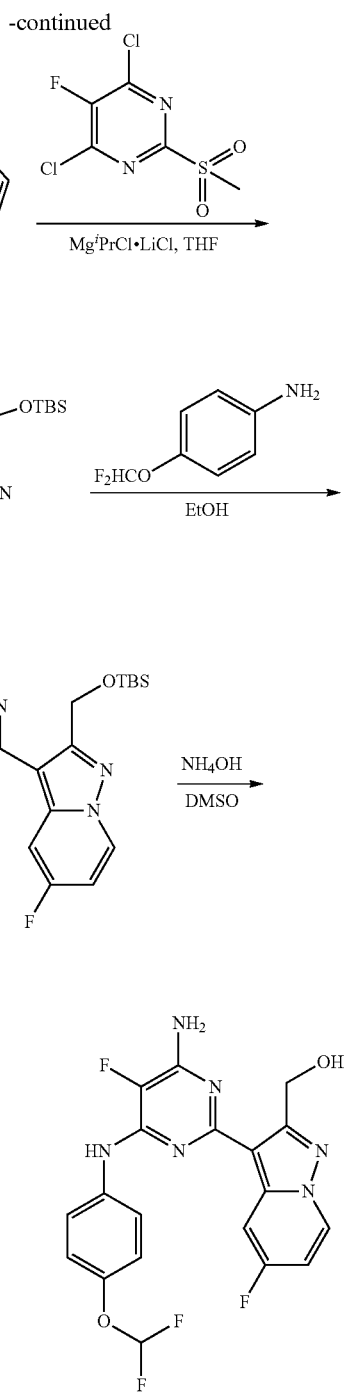

Step 1. A mixture of 2-chloro-4-fluoropyridine (2.19 g, 16.65 mmol), prop-2-yn-1-ol (1.86 g, 33.29 mmol), bis(acetonitrile)dichloropalladium(II) (215.6 mg, 0.83 mmol) and 2-dicyclohexylphosphino-2',4',6'-triisopropylbiphenyl (Xphos) (794.3 mg, 0.17 mmol) in NMP (15 mL) was degassed by three cycles of vacuum pumping and N₂ purging, and then triethylamine (4.7 mL, 33.3 mmol) was added. The mixture was degassed and purged with N₂, then heated at 60° C. overnight. The solution was cooled and poured into water (100 mL), and the product was extracted with ethyl acetate (150 mL). The extract was dried over MgSO₄, then filtered and concentrated under the reduced pressure. The residual material was separated by column chromatography (eluting with 0 to 10% dichloromethane-hexane) to yield 3-(4-fluoropyridin-2-yl)prop-2-yn-1-ol as an oil (2.40 g, 96%).

Step 2-4. To a solution of 3-(4-fluoropyridin-2-yl)prop-2-yn-1-ol (820.0 mg, 5.43 mmol) in dichloromethane (10 mL) was added 2-[(aminooxy)sulfonyl]-1,3,5-trimethylbenzene (1.5 g, 6.98 mmol) portion wise at 0° C. The resulting mixture was stirred at ambient temperature for 2 days. The solvent removed under a blowing N₂ stream to give a crude mixture. To the crude mixture in DMF (3 mL) was added K₂CO₃ (825.0 mg, 5.97 mmol) at 0° C. The resulting mixture was stirred at room temperature for 24 hours, and then partitioned between ethyl acetate and water. The organic phase was washed with water and brine, dried over MgSO₄, then filtered and evaporated. The residual material was used in the next step without further purification.

A mixture of crude material, N-iodosuccinimide (1.2 g, 5.33 mmol) in chloroform (10 mL) was stirred at ambient temperature for 2 hours, and then partitioned between ethyl acetate and water. The organic phase was washed with water and brine, dried over MgSO₄, then filtered and evaporated. The residual material was separated by silica gel column chromatography (eluting with 1:1 dichloromethane:hexane, then 1% methanol in 1:4 ethyl acetate:dichloromethane to afford (5-fluoro-3-iodopyrazolo[1,5-a]pyridin-2-yl)methanol as an oil (1.4 g, 50%).

Step 5. To a solution of (5-fluoro-3-iodopyrazolo[1,5-a]pyridin-2-yl)methanol (500.0 mg, 1.71 mmol) in dichloromethane (3 mL) was added imidazole (139.5 mg, 2.05 mmol), followed by tert-butyldimethylsilyl chloride (384.0 mg, 2.55 mmol) in dichloromethane (5 mL) added dropwise at 0° C. The resulting mixture was stirred at ambient temperature for 30 minutes, then filtered through a pad of silica gel/selite, washing with dichloromethane to provide 2-[(tert-butyldimethylsilyloxy)methyl]-5-fluoro-3-iodopyrazolo[1,5-a]pyridine (470.0 mg, 72%).

Step 6. To a solution of 2-[(tert-butyldimethylsilyloxy)methyl]-5-fluoro-3-iodopyrazolo[1,5-a]pyridine (470.0 mg, 1.15 mmol) in THF (5 mL) was added an isopropylmagnesium chloride lithium chloride complex solution (1.07 mL, 1.3 M in THF) at –78° C. dropwise. The mixture was warmed to 0° C. and stirred for 30 minutes, and then 4,6-dichloro-5-fluoro-2-(methylsulfonyl)pyrimidine (4.80 g, 19.6 mmol) was added in one portion at –78° C. The mixture was stirred at 0° C. for 1 hour and then partitioned between ethyl acetate and water. The organic phase was washed with brine, dried over MgSO₄, then filtered and evaporated. The residual material was separated by silica gel column chromatography (eluting with 1:9 ethyl acetate:hexane) to afford 2-[(tert-butyldimethylsilyloxy)methyl]-3-(4,6-dichloro-5-fluoropyrimidin-2-yl)-5-fluoropyrazolo[1,5-a]pyridine (205.0 mg, 40%).

Steps 7-8. A mixture of 2-[(tert-butyldimethylsilyloxy)methyl]-3-(4,6-dichloro-5-fluoropyrimidin-2-yl)-5-fluoropyrazolo[1,5-a]pyridine (102.0 mg, 0.23 mmol), 4-difluoromethoxy aniline (145.0 mg, 0.92 mmol) and ethanol (1 mL) was heated at 90° C. overnight. After cooling, the mixture was poured into ice-water to afford a solid. The solid was collected by filtration, followed by washing with water and hexane. The solid was dried under the vacuum to provide 2-[2-[(tert-butyldimethylsilyloxy)methyl]-5-fluoropyrazolo[1,5-a]pyridin-3-yl]-6-chloro-N-(4-difluoromethoxy)phenyl]-5-fluoropyrimidin-4-amine (a mixture of TBS protected and unprotected product).

To the dried solid was added DMSO (3 mL) and NH₄OH (0.3 mL). The reaction mixture was sealed and stirred at 100° C. for 2 days. The mixture was partitioned between ethyl acetate and water and the organic phase was washed with water (2×10 mL) and brine, dried over MgSO$_4$, then filtered and evaporated. The residual material was separated by silica gel column chromatography (eluting with 1-5% methanol in dichloromethane) to provide the title compound as a white solid (25.0 mg, 25% for two steps); m.p. 198-200° C.

$^1$H NMR (500 MHz, Acetone-d$_6$) δ ppm 8.50-8.64 (m, 1H), 8.35 (s, 1H), 8.06-8.21 (m, 1H), 7.64 (d, J=8.83 Hz, 2H), 7.24 (d, J=8.83 Hz, 2H), 6.80-7.10 (t, J=75.00 Hz, 1H), 6.86-6.93 (m, 1H), 6.23-6.41 (m, 2H), 5.46-5.66 (m, 1H), 4.68-4.83 (m, 2H); MS m/z 435.2 (100) [M+H]$^+$, 436.2 (20).

Additional compounds of Formula (I) or a form thereof described herein may be prepared according to the procedure of Example 13 by substituting the appropriate starting materials, reagents and reaction conditions.

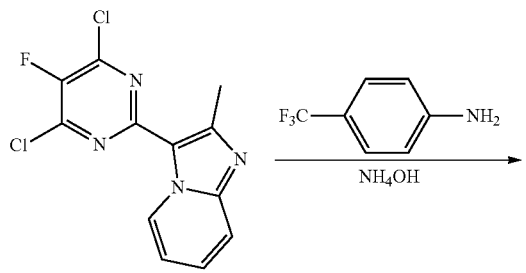

| Cpd | Name & Data |
|---|---|
| 186 | N-[4-(difluoromethoxy)phenyl]-2-(2-ethyl-5-fluoropyrazolo[1,5-a]pyridin-3-yl)-5-fluoropyrimidine-4,6-diamine<br>$^1$H NMR (500 MHz, Acetone-d$_6$) δ ppm 8.54 (dd, J = 5.20, 7.41 Hz, 1H), 8.25 (dd, J = 2.68, 10.88 Hz, 1H), 8.18 (br. s., 1H), 7.71 (d, J = 9.14 Hz, 2H), 7.21 (d, J = 9.14 Hz, 2H), 6.80-7.10 (t, J = 75.00 Hz, 1H), 6.76-6.88 (m, 1H), 6.14 (br. s., 2H), 3.24 (q, J = 7.57 Hz, 2H), 1.20-1.35 (m, 3H); m.p. 103-105° C.; MS m/z 433.6 [M + H]$^+$ |
| 187 | 2-(2-ethyl-5-fluoropyrazolo[1,5-a]pyridin-3-yl)-5-fluoro-N-[4-(trifluoromethyl)phenyl]pyrimidine-4,6-diamine<br>$^1$H NMR (500 MHz, Acetone-d$_6$) δ ppm 8.53-8.59 (m, 1H), 8.50 (br. s., 1H), 8.28 (dd, J = 2.68, 10.25 Hz, 1H), 7.93 (d, J = 8.51 Hz, 2H), 7.69 (d, J = 8.51 Hz, 2H), 6.83 (dt, J = 2.99, 7.33 Hz, 1H), 6.28 (br. s., 2H), 3.28 (q, J = 7.46 Hz, 2H), 1.28 (t, J = 7.57 Hz, 3H); m.p. 164-166° C.; MS m/z 435.2 [M + H]$^+$ |
| 188 | N-[4-(difluoromethoxy)-3-fluorophenyl]-2-(2-ethyl-5-fluoropyrazolo[1,5-a]pyridin-3-yl)-5-fluoropyrimidine-4,6-diamine<br>$^1$H NMR (500 MHz, Acetone-d$_6$) δ ppm 8.49-8.64 (m, 1H), 8.33-8.40 (m, 1H), 8.24-8.32 (m, 1H), 7.77-7.85 (m, 1H), 7.44-7.50 (m, 1H), 7.29-7.38 (m, 1H), 6.80-7.10 (t, J = 75.00 Hz, 1H), 6.81-6.87 (m, 1H), 6.17-6.34 (m, 2H), 3.27 (d, J = 7.57 Hz, 2H), 1.28 (t, J = 7.57 Hz, 3H); m.p. 150-152° C.; MS m/z 452. [M + H]$^+$ |

Example 14

5-fluoro-2-(2-methylimidazo[1,2-a]pyridin-3-yl)-N-[4-(trifluoromethyl)phenyl]pyrimidine-4,6-diamine
(Cpd 169)

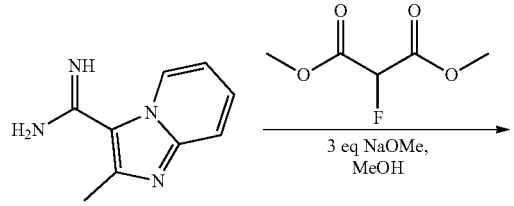

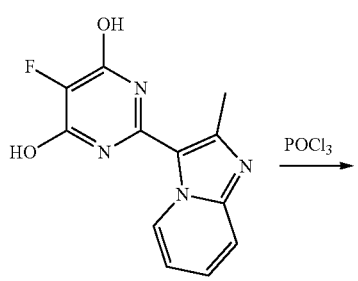

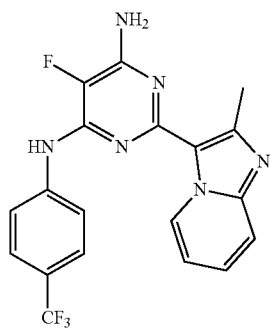

Step 1. To a solution of 2-methylimidazo[1,2-a]pyridine-3-carboximidamide pivaloate (250 mg, 0.905 mmol) and dimethyl 2-fluoromalonate (272 mg, 1.81 mmol) in MeOH (5 mL) was added 30% NaOMe in MeOH (0.2 mL). The mixture was heated at 85° C. in a sealed tube for 72 hours until UPLC showed complete consumption of the starting material. The reaction mixture was concentrated under reduced pressure, then diluted with water (5 mL), and acidified with 1N HCl to about pH 7. A tan precipitate was collected by filtration giving 5-fluoro-2-(2-methylimidazo[1,2-a]pyridin-3-yl)pyrimidine-4,6-diol. 5-fluoro-2-(2-methylimidazo[1,2-a]pyridin-3-yl)pyrimidine-4,6-diol (180 mg, 76%). The product (180 mg, 0.69 mmol) was mixed with phosphorus oxychloride (3 mL) in a microwave vial, then the vial was sealed and microwaved for 15 minutes at 150° C. The reaction mixture was transferred into a 25 mL round-bottom flask and concentrated under reduced pressure. The remainder was redissolved in EtOAc (10 mL) and washed with an aqueous NaHCO$_3$ solution three times. The organic phase was dried over Na$_2$SO$_4$, then filtered and evaporated to afford 3-(4,6-dichloro-5-fluoropyrimidin-2-yl)-2-methylimidazo[1,2-a]pyridine (164 mg, 80%) as a yellow solid.

$^1$H NMR (500 MHz, DMSO-d$_6$) δ ppm 9.59 (dt, J=6.9, 0.9 Hz, 1H), 7.77 (d, J=8.8 Hz, 1H), 7.62 (t, J=7.9 Hz, 1H), 7.32 (t, J=6.9 Hz, 1H), 2.77 (s, 3H); MS m/z 298.1 [M+H]$^+$.

Step 2. 3-(4,6-Dichloro-5-fluoropyrimidin-2-yl)-2-methylimidazo[1,2-a]pyridine (50 mg, 0.168 mmol) and 4-trifluoromethyl aniline (54 mg, 0.336 mmol) were mixed in EtOH (2 mL) and heated in a sealed tube at 100° C. until UPLC showed complete consumption of the starting material (48 hours). The reaction mixture was cooled to room temperature and diluted with water (5 mL) to form a precipitate. The product was collected by filtration, then washed with hexanes. The crude product, without drying, was dissolved in CH$_3$CN (2 mL), then saturated ammonia (4 mL) in water was added. The reaction mixture was heated at 100° C. in a sealed tube for 16 hours until UPLC showed complete consumption of starting material. A crude product was precipitated by addition of water (10 mL). The precipitate was filtered, then washed with hexanes and dried to yield the title compound (32 mg, 47% over two steps) as a light tan solid.

$^1$H NMR (500 MHz, Acetone-d$_6$) δ ppm 9.76 (dt, J=7.1, 1.0 Hz, 1H), 8.50 (br. s., 1H), 7.85 (d, J=8.5 Hz, 2H), 7.57 (d, J=8.5 Hz, 2H), 7.40 (d, J=8.8 Hz, 1H), 7.19 (ddd, J=8.5, 6.5, 1.8 Hz, 1H), 6.74 (td, J=6.9, 1.3 Hz, 1H), 6.27 (br. s., 2H), 2.64 (s, 3H); MS m/z 403.3 [M+H]$^+$.

Additional compounds of Formula (I) or a form thereof described herein may be prepared according to the procedure of Example 14 by substituting the appropriate starting materials, reagents and reaction conditions.

| Cpd | Name & Data |
|---|---|
| 170 | N-[4-(difluoromethoxy)phenyl]-5-fluoro-2-(2-methylimidazo[1,2-a]pyridin-3-yl)pyrimidine-4,6-diamine<br>MS m/z 401.3 [M + H]$^+$ |
| 171 | N-[4-(difluoromethoxy)-3-fluorophenyl]-5-fluoro-2-(2-methylimidazo[1,2-a]pyridin-3-yl)pyrimidine-4,6-diamine<br>$^1$H NMR (500 MHz, DMSO-d$_6$) δ ppm 9.83 (d, J = 6.9 Hz, 1H), 9.25 (br. s, 1H), 7.80 (dd, J = 13.4, 2.0 Hz, 1H), 7.57 (d, J = 8.8 Hz, 1H), 7.44 (d, J = 8.5 Hz, 1H), 7.31-7.39 (m, 2H), 7.18 (t, J = 73.1 Hz, 1H), 6.88-6.97 (m, 3H), 3.31 (s, 3H); MS m/z 419.3 [M + H]$^+$ |
| 174 | 5-fluoro-N-[4-(trifluoromethyl)phenyl]-2-(2,6,8-trimethylimidazo[1,2-a]pyrazin-3-yl)pyrimidine-4,6-diamine<br>$^1$H NMR (500 MHz, DMSO-d$_6$) δ ppm 9.48 (s, 1H), 9.39 (s, 1H), 7.83 (d, J = 8.51 Hz, 2H), 7.68 (d, J = 8.83 Hz, 2H), 7.11 (s, 2H), 2.75 (s, 3H), 2.72 (s, 3H), 2.55 (s, 3H); m.p. 166-168° C.; MS m/z 432.3 [M + H]$^+$ |
| 175 | N-[4-(difluoromethoxy)phenyl]-5-fluoro-2-(2,6,8-trimethylimidazo[1,2-a]pyrazin-3-yl)pyrimidine-4,6-diamine<br>m.p. 141-143° C.; MS m/z 430.4 [M + H]$^+$ |
| 176 | N-[4-(difluoromethoxy)-3-fluorophenyl]-5-fluoro-2-(2,6,8-trimethylimidazo[1,2-a]pyrazin-3-yl)pyrimidine-4,6-diamine<br>$^1$H NMR (500 MHz, DMSO-d$_6$) δ ppm 9.40 (s, 1H), 9.32 (s, 1H), 7.71-7.83 (m, 1H), 7.40-7.45 (m, 1H), 7.31-7.37 (m, 1H), 7.04-7.32 (t, J = 70.00 Hz, 1H), 7.07 (s, 2H), 2.74 (s, 3H), 2.72 (s, 3H), 2.38 (s, 3H); m.p. 140-141° C.; MS m/z 448.4 [M + H]$^+$ |
| 251 | N-(4-chlorophenyl)-5-fluoro-2-(6-fluoro-2-methylimidazo[1,2-a]pyridin-3-yl)pyrimidine-4,6-diamine<br>$^1$H NMR (500 MHz, Acetone-d$_6$) δ □ ppm 9.88-10.04 (m, 1H), 8.33-8.46 (m, 1H), 7.72 (d, J = 8.83 Hz, 2H), 7.48-7.59 (m, 1H), 7.39 (d, J = 8.83 Hz, 2H), 7.27-7.34 (m, 1H), 6.34-6.45 (br., s, 2H), 2.73 (s, 3H); m.p. 226-229° C.; MS m/z 388.2 [M + H]$^+$ |
| 252 | 5-fluoro-2-(6-fluoro-2-methylimidazo[1,2-a]pyridin-3-yl)-N-(4-methoxyphenyl)pyrimidine-4,6-diamine<br>$^1$H NMR (500 MHz, Acetone-d$_6$) δ ppm 9.91 (dd, J = 2.52, 5.99 Hz, 1H), 8.10 (br. s., 1H), 7.45-7.58 ( d, J = 8.83 Hz, 2H), 7.26 (d, J = 1.89 Hz, 1H), 6.96 (d, J = 8.83 Hz, 2H), 6.23 (br. s., 2H), 3.81 (s, 3H), 2.70 (s, 3H); m.p. 204-206° C.; MS m/z 384.2 [M + H]$^+$ |
| 253 | 5-fluoro-2-(6-fluoro-2-methylimidazo[1,2-a]pyridin-3-yl)-N-(4-methylphenyl)pyrimidine-4,6-diamine<br>m.p. 210-212° C.; MS m/z 368.2 [M + H]$^+$ |

Example 15

5-chloro-2-(2-methyl-1H-benzimidazol-1-yl)-N-[4-(trifluoromethyl)phenyl]pyrimidine-4,6-diamine (Cpd 166)

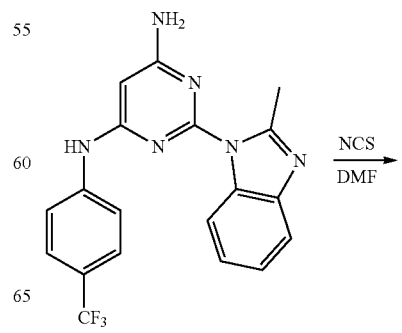

-continued

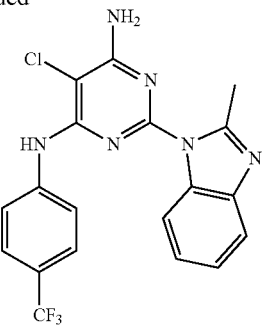

To a solution of 2-(2-methyl-1H-benzo[d]imidazol-1-yl)-N4-(4-(trifluoromethyl)-phenyl)pyrimidine-4,6-diamine (76 mg, 0.20 mmol) in DMF (1.5 mL) was added N-chlorosuccinimide (29 mg, 0.22 mmol). The mixture was stirred for 2 hours at room temperature. Ice water (5 mL) and a saturated NaHCO$_3$ solution (2 mL) was added to the mixture. The resulting precipitate was filtered, washed by water, and dried under nitrogen to yield the title compound (77 mg, 92%) as an off-white solid.

$^1$H NMR (500 MHz, Acetone-d$_6$) δ ppm 8.40 (1H, s) 7.95-8.00 (1H, m) 7.76-7.83 (2H, m) 7.57 (2H, d, J=8.51 Hz) 7.40-7.45 (1H, m) 7.06-7.11 (1H, m) 6.98-7.04 (1H, m) 6.52-6.75 (2H, m) 2.68 (3H, s); MS m/z 419.1 [M+H]$^+$.

Additional compounds of Formula (I) or a form thereof described herein may be prepared according to the procedure of Example 15 by substituting the appropriate starting materials, reagents and reaction conditions.

| Cpd | Name & Data |
|---|---|
| 167 | 5-chloro-2-(2-ethyl-1H-benzimidazol-1-yl)-N-[4-(trifluoromethyl)phenyl]pyrimidine-4,6-diamine<br>$^1$H NMR (500 MHz, Acetone-d$_6$) δ ppm 8.55 (1H, s) 8.07-8.12 (1H, m) 7.91-7.96 (2H, m) 7.71 (2H, d, J = 8.51 Hz) 7.58-7.63 (1H, m) 7.13-7.26 (2H, m) 6.80 (2H, br. s.) 3.23-3.30 (2H, m) 1.31 (3H, t, J = 7.41 Hz); MS m/z 433.2 [M + H]$^+$ |
| 168 | 5-chloro-N-[4-(difluoromethoxy)phenyl]-2-(2-ethyl-1H-benzimidazol-1-yl)pyrimidine-4,6-diamine<br>$^1$H NMR (500 MHz, Acetone-d$_6$) δ ppm 8.31 (1H, s) 8.09-8.13 (1H, m) 7.65-7.71 (2H, m) 7.55-7.60 (1H, m) 7.13-7.25 (4H, m) 6.99 (1H, t, J = 74.40 Hz) 6.68 (2H, br. s.) 3.19-3.25 (2H, m) 1.28 (3H, t, J = 7.41 Hz); MS m/z 431.2 [M + H]$^+$ |

BIOLOGICAL EXAMPLES

The following biological examples demonstrate the usefulness of the compounds described herein to inhibit Bmi-1 function and reduce the level of Bmi-1 protein.

Example 1

Sandwich ELISA Assay
Cell Seeding and Compound Treatment (Day 1):
HT-1080 cells were seeded at 8000 cells/well (50 μL) in 96-well tissue culture plates. After the cells became adherent (3-4 hours), 2× diluted stocks of test compounds in 50 μL DMEM containing 1% DMSO (final DMSO concentration was 0.5%) were added and the plates were incubated at 37° C. under 5% CO$_2$ for 40-48 hours.
ELISA Plate First Antibody Preparation (Day 2):
The First Antibody (Millipore Mouse, monoclonal to mouse Bmi-1, clone F6, catalog #05-637) diluted to 2 μg/mL in PBS was added (100 μL) to each well of a Nunc MaxiSorp 96-well ELISA plate. The plate was covered with a plate seal and allowed to stand overnight.

Cell Lysate Preparation (Day 3):
Fresh 1× Lysis buffer was prepared on the day of the assay as follows: 1 mM EDTA, 150 mM NaCl, 0.5% Triton-X 100, 10 mM NaF, 20 mM B-Glycerophosphate, 1 mM DTT (in PBS, pH 7.2-7.4) and 1× HALT protease inhibitor cocktail (Pierce #78410).
The 1× Lysis Buffer (40 μL) was added to each well and the plate was shaken for 5-10 minutes on an orbital shaker to allow cell lysis, then diluent (1% BSA in PBS in 0.5% NP40) (100 μL) was added to each well.
A standard curve was prepared at the following Bmi-1 concentrations: 8000, 4000, 2000, 1000, 500, 250, 125, 0 pg/mL The Bmi-1 Recombinant Protein Standard (Novus Biologicals PCGF4 Recombinant Protein (P01), catalog #H00000648-P01) used to prepare the standard curve was stored at −80° C. On first thaw, the Bmi-1 Recombinant Protein Standard was diluted to 10 μg/μL in Blocking Buffer (1% BSA in PBS; BSA: Fisher Scientific Catalog #1600-100). Aliquots were taken and refrozen at −80° C. The aliquots may be kept at 4° C. and reused after first thaw, but only within 1-2 weeks. The Bmi-1 Recombinant Protein Standard contains a GST-fusion tag that appears around 70 Kda on Western Blot.
ELISA Assay (Day 3):
The prepared ELISA plate was washed 3× with Wash Buffer (0.05% Tween-20 in PBS). The final wash was removed from the plate and the plate was blotted dry. Blocking Buffer (300 μL) (1% BSA in PBS) was added to each well. The plate was covered with a plate seal and incubated at room temperature for 1 hour. The blocked plate was washed 3× with Wash Buffer, then the final wash was removed and the plate was blotted dry. The previously prepared samples and standards were added (100 μL/well) and the plate was covered with a plate seal and incubated at 4° C. overnight.
ELISA Assay (Day 4):
The prepared ELISA plate was removed from 4° C., incubated at room temperature for 30 minutes, then washed and blotted dry as previously described for Day 3. The Second Antibody (Cell Signaling Rabbit anti-Bmi-1, Cat #2830) diluted to 1:600 in Blocking Buffer was added (100 μL) to each well, except as needed for background control wells. The plate was covered with a plate seal and incubated for 1.5 hrs at room temperature.
The ELISA plate was washed and blotted dry as previously described. The Third Antibody (Cell Signaling HRP conjugated anti-rabbit IgG (CellSignaling, Cat #:7074) diluted to 1:300 in Blocking Buffer was added (100 μL) to each well, except as needed for background control wells. The plate was incubated for 1 hr at room temperature.
The plate was washed and blotted dry as previously described, then prepared TMB substrate (TMB substrate kit, Pierce catalog #34021) (prepared by mixing kit reagents 1:1) (100 µL) was added per well. The plate was incubated for 20-30 minutes at room temperature in the dark, then Stop Solution (2 M sulfuric acid in water) (50 µL) was added per well. The plates were read at OD450 (experimental) and OD570 (reference).

As shown in Table 1, test compounds described herein had Bmi-1 ELISA $EC_{50}$ values between >0.1 µM to ≤3 µM (one star), an $EC_{50}$ between >0.01 µM to ≤0.1 µM (two stars), an $EC_{50}$ value between <0.001 µM to ≤0.01 µM (three stars) or an $EC_{50}$ value of ≤0.001 µM (four stars).

TABLE 1

| Cpd | $EC_{50}$ |
|---|---|
| 1 | ** |
| 2 | * |
| 3 | ** |
| 4 | ** |
| 5 | * |
| 6 | ** |
| 7 | * |
| 8 | * |
| 9 | *** |
| 10 | ** |
| 11 | * |
| 12 | ** |
| 13 | * |
| 14 | * |
| 15 | ** |
| 16 | ** |
| 17 | * |
| 18 | * |
| 19 | * |
| 20 | * |
| 21 | *** |
| 22 | ** |
| 23 | * |
| 24 | * |
| 25 | * |
| 26 | * |
| 27 | * |
| 28 | * |
| 29 | ** |
| 30 | * |
| 31 | ** |
| 32 | * |
| 33 | ** |
| 34 | *** |
| 35 | * |
| 36 | ** |
| 37 | ** |
| 38 | * |
| 39 | * |
| 40 | * |
| 41 | * |
| 42 | ** |
| 43 | ** |
| 44 | * |
| 45 | * |
| 46 | * |
| 47 | * |
| 48 | * |
| 49 | * |
| 50 | ** |
| 51 | * |
| 52 | * |
| 53 | * |
| 54 | * |
| 55 | * |
| 56 | * |
| 57 | * |
| 58 | * |
| 59 | * |
| 60 | ** |
| 61 | * |
| 62 | ** |
| 63 | ** |
| 64 | ** |
| 65 | ** |
| 66 | ** |
| 67 | * |
| 68 | ** |
| 69 | ** |
| 70 | * |
| 71 | ** |
| 72 | ** |
| 73 | ** |
| 74 | * |
| 75 | * |
| 76 | ** |
| 77 | ** |
| 78 | ** |
| 79 | * |
| 80 | ** |
| 81 | ** |
| 82 | ** |
| 83 | ** |
| 84 | * |
| 85 | * |
| 86 | ** |
| 87 | * |
| 88 | ** |
| 89 | * |
| 90 | * |
| 91 | * |
| 92 | ** |
| 93 | ** |
| 94 | ** |
| 95 | ** |
| 96 | * |
| 97 | ** |
| 98 | * |
| 99 | * |
| 100 | * |
| 101 | ** |
| 102 | ** |
| 103 | ** |
| 104 | ** |
| 105 | ** |
| 106 | ** |
| 107 | ** |
| 108 | * |
| 109 | ** |
| 110 | ** |
| 111 | ** |
| 112 | ** |
| 113 | ** |
| 114 | ** |
| 115 | ** |
| 116 | ** |
| 117 | ** |
| 118 | * |
| 119 | ** |
| 120 | ** |
| 121 | *** |
| 122 | ** |
| 123 | *** |
| 124 | ** |
| 125 | * |
| 126 | ** |
| 127 | ** |
| 128 | ** |
| 129 | ** |
| 130 | ** |
| 131 | ** |
| 132 | ** |
| 133 | ** |
| 134 | ** |
| 135 | ** |
| 136 | ** |
| 137 | ** |
| 138 | ** |
| 139 | * |
| 140 | ** |
| 141 | ** |

TABLE 1-continued

| Cpd | EC$_{50}$ |
|---|---|
| 142 | ** |
| 143 | *** |
| 144 | ** |
| 145 | *** |
| 146 | ** |
| 147 | * |
| 148 | * |
| 149 | ** |
| 150 | ** |
| 151 | ** |
| 152 | ** |
| 153 | ** |
| 154 | * |
| 155 | ** |
| 156 | *** |
| 157 | ** |
| 158 | * |
| 159 | * |
| 160 | ** |
| 161 | ** |
| 162 | ** |
| 163 | ** |
| 164 | ** |
| 165 | *** |
| 166 | * |
| 167 | ** |
| 168 | * |
| 169 | * |
| 170 | * |
| 171 | * |
| 172 | * |
| 173 | * |
| 174 | * |
| 175 | * |
| 176 | * |
| 177 | * |
| 178 | * |
| 179 | *** |
| 180 | * |
| 181 | ** |
| 182 | * |
| 183 | ** |
| 184 | *** |
| 185 | ** |
| 186 | * |
| 187 | * |
| 188 | * |
| 189 | * |
| 190 | * |
| 191 | ** |
| 192 | * |
| 193 | ** |
| 194 | * |
| 195 | * |
| 196 | *** |
| 197 | *** |
| 198 | *** |
| 199 | *** |
| 200 | *** |
| 201 | ** |
| 202 | * |
| 203 | *** |
| 204 | ** |
| 205 | *** |
| 206 | ** |
| 207 | *** |
| 208 | *** |
| 209 | ** |
| 210 | * |
| 211 | * |
| 212 | ** |
| 213 | *** |
| 214 | ** |
| 215 | * |
| 216 | ** |
| 217 | ** |
| 218 | *** |
| 219 | * |
| 220 | ** |
| 221 | * |
| 222 | * |
| 223 | * |
| 224 | ** |
| 225 | ** |
| 226 | * |
| 227 | ** |
| 228 | ** |
| 229 | * |
| 230 | * |
| 231 | * |
| 232 | ** |
| 233 | ** |
| 234 | ** |
| 235 | ** |
| 236 | * |
| 237 | ** |
| 238 | * |
| 239 | ** |
| 240 | *** |
| 241 | ** |
| 242 | *** |
| 243 | ** |
| 244 | ** |
| 245 | ** |
| 246 | ** |
| 247 | ** |
| 248 | ** |
| 249 | ** |
| 250 | ** |
| 251 | * |
| 252 | ** |
| 253 | *** |
| 254 | ** |
| 255 | * |
| 256 | ** |
| 257 | ** |
| 258 | *** |
| 259 | * |
| 260 | * |
| 261 | ** |
| 262 | ** |
| 263 | ** |
| 264 | *** |
| 265 | *** |
| 266 | ** |
| 267 | * |
| 268 | * |
| 269 | * |
| 270 | *** |
| 271 | *** |
| 272 | ** |
| 273 | *** |
| 274 | ** |
| 275 | ** |
| 276 | *** |
| 277 | **** |
| 278 | * |
| 279 | ** |
| 280 | ** |
| 281 | *** |
| 282 | *** |
| 283 | * |
| 284 | ** |

Example 2

In Vitro Cancer Stem Cell Assay

The effect on inhibition of Bmi-1 function and reduction in the level of Bmi-1 protein by a compound of Formula (I) or a form thereof was tested in the in vitro pediatric Baylor Xenograft Derived (BXD) brain tumor model and in cells from primary patient cultures (PPC).

Cells were grown under conditions to measure either general cell growth (such as in fetal bovine serum (FBS) containing media in conventional tissue culture plates) or in conditions specifically for cancer stem cell (CSC) growth (low serum, nonadherent plates) to assess the effect of Bmi-1 inhibition and reduction in the level of Bmi-1 protein by a compound of Formula (I) on these populations. The cells were treated with a predetermined dose range of Compound 109 at fixed time points over a time period of from 24 hours to 13 days. The effect of inhibition on cell growth viability was quantitated using conventional 2D growth and neurosphere growth using a cell-counting kit (CCK) (supplied by Dojindo Molecular Technologies, Inc.).

FIG. 1 demonstrates the effect of Compound 109 in a BXD GBM model where the CSC population (as measured by number of neurospheres) was dose dependently reduced over a period of 13 days in the presence of the stated concentrations of Compound 109.

Figure 2:
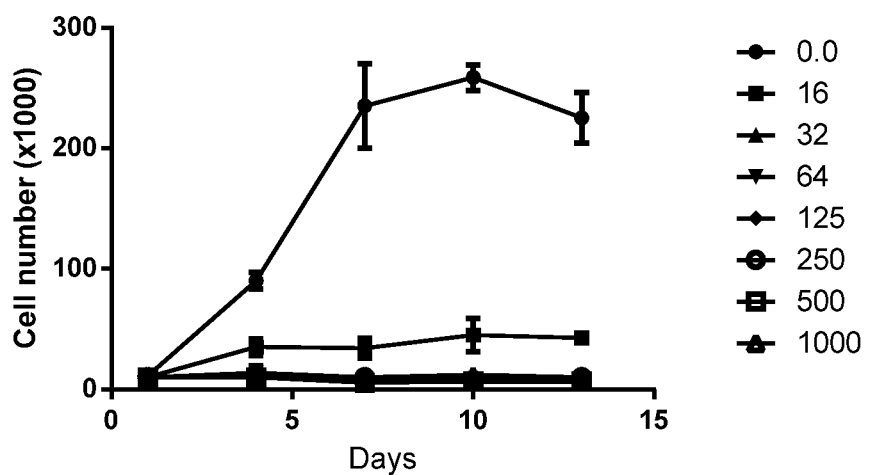
FIG. 2 demonstrates the reduction of a CSC population in a BXD GBM model as the result of treatment with a compound of Formula (I), or a form thereof.

FIG. 2 demonstrates the effect of Compound 109 in a BXD GBM model where the CSC population (as measured by number of neurospheres) was universally reduced over a period of 13 days in the presence of the stated concentrations of Compound 109.

Figure 3:
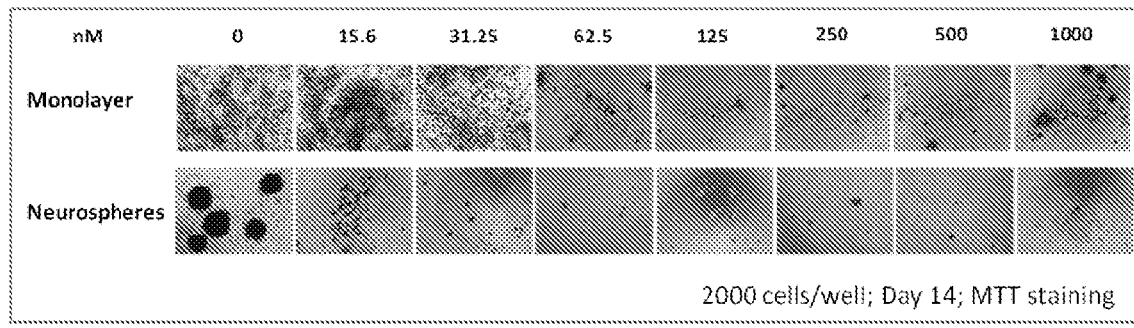
FIG. 3 demonstrates the reduction of monolayer and neurosphere CSC populations in a tumorosphere assay as the result of contacting the cells with a compound of Formula (I), or a form thereof.

FIG. 3 demonstrates the effect of Compound 109 in a tumorosphere assay where 2000 PPC CSCs per well were cultured either under standard 2D tissue culture conditions (with FBS) or conditions selective for CSC growth (attachment-free, serum-free) for 13 days in the presence of the stated concentrations of Compound 109. Both the monolayer and neurosphere CSC populations were reduced as the result of contacting the PPC CSCs with Compound 109, representative of a compound of Formula (I) or a form thereof, at concentrations of 62.5 nm and 15.6 nm, respectively.

Taken together, the data from FIGS. 1-3 demonstrate the preferential reduction of cancer stem cell populations compared to general cell populations as a result of inhibition of Bmi-1 function and reduction in the level of Bmi-1 protein by a compound of Formula (I) or a form thereof.

Example 3

In Vivo Survival Assay

A glioblastoma animal model was developed in which U87-MG tumor cells were injected intracranially into nu/nu mice and a tumor was allowed to become established over a 10 day period. The mice were dosed daily with vehicle, Compound 109 or temozolomide (a standard-of-care agent), as indicated. The comparative results for survival for each treatment group (n=10) from administration of vehicle, Compound 109 and temozolomide are shown in FIG. 4.

Figure 4:
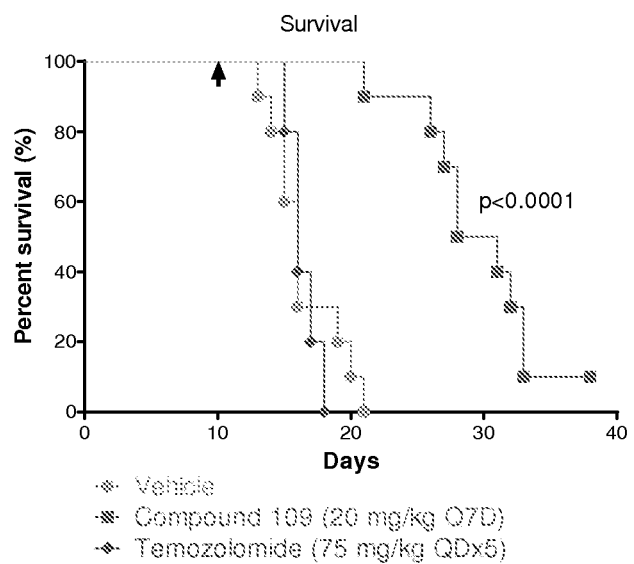
FIG. 4 demonstrates the comparative effect on survival of mice treated with vehicle, temozolomide or a compound of Formula (I), or a form thereof, in an orthotopic model of glioblastoma.

FIG. 4 demonstrates the effect of daily dosing of Compound 109 compared to temozolomide, at the indicated dose levels, on survival over a 40 day time period in an orthotopic model of glioblastoma. Cells were implanted intracranially into nude mice and dosing was begun 10 days later with either vehicle, Compound 109 or temozolomide. Compound 109 demonstrated extended survival of these tumor bearing mice over both vehicle and temozolomide (p<0.0001).

The following publications are incorporated by reference into the present application for any and all purposes to the same extent as if each individual publication was fully set forth herein:

1. M. J. Alkema, J. Wiegant, A. K. Raap, A. Berns, L. M. van, *Hum. Mol. Genet.* 2, 1597 (1993).
2. Y. Haupt, M. L. Bath, A. W. Harris, J. M. Adams, *Oncogene* 8, 3161-3164 (1993).
3. J. M. Adams, S. Cory, *Cancer Surv.* 15, 119 (1992).
4. Y. Haupt, G. Bath, J. M. Adams, *Mol. Biol. Rep.* 17, 17 (1992).
5. L. M. van, M. Frasch, E. Wientjens, A. Berns, *Nature* 353, 353 (1991).
6. L. M. van et al., *Cell* 65, 737 (1991).
7. J. J. Jacobs et al., *Genes Dev.* 13, 2678 (1999).
8. B. Scheijen, J. Jonkers, D. Acton, A. Berns, *J. Virol.* 71, 9 (1997).
9. J. J. Jacobs, K. Kieboom, S. Marino, R. A. DePinho, L. M. van, *Nature* 397, 164 (1999).
10. P. R. Solomon et al., *Indian J. Med. Res.* 127, 52 (2008).
11. B. Quesnel, C. Preudhomme, P. Fenaux, *Leuk. Lymphoma* 22, 11 (1996).
12. S. Faderl et al., *Cytokines Cell Mol. Ther.* 5, 159 (1999).
13. S. Faderl et al., *Clin. Cancer Res.* 5, 1855 (1999).
14. S. W. Bruggeman et al., *Cancer Cell* 12, 328 (2007).
15. S. J. Kuerbitz, J. Malandro, N. Compitello, S. B. Baylin, J. R. Graff, *Cell Growth Differ.* 10, 27 (1999).
16. S. Liu et al., *Cancer Res.* 66, 6063 (2006).
17. J. Wei, L. Zhai, J. Xu, H. Wang, *J. Biol. Chem.* 281, 22537 (2006).
18. M. Courel, L. Friesenhahn, J. A. Lees, *Dev. Dyn.* 237, 1232 (2008).
21. D. F. Dukers et al., *Am. J. Pathol.* 164, 873 (2004).
22. F. M. Raaphorst et al., *Am. J. Pathol.* 157, 709 (2000).
23. M. Sanchez-Beato et al., *J. Pathol.* 204, 528 (2004).
24. S. Bea et al., *Blood* 93, 4365 (1999).
25. M. S. Lindstrom, U. Klangby, K. G. Wiman, *Oncogene* 20, 2171 (2001).
26. F. J. van Kemenade et al., *Blood* 97, 3896 (2001).
27. F. M. Raaphorst, C. J. Meijer, A. P. Otte, *Cancer Res.* 62, 618 (2002).
28. F. M. Raaphorst et al., *Am. J. Pathol.* 164, 533 (2004).
29. V. Fernandez, E. Hartmann, G. Ott, E. Campo, A. Rosenwald, *J. Clin. Oncol.* 23, 6364 (2005).
30. B. T. Spike, K. F. Macleod, *Cell Cycle* 4, 42 (2005).
31. A. Dutton et al., *Blood* 109, 2597 (2007).
32. M. Chowdhury et al., *Leukemia* 21, 1116 (2007).
33. W. A. Dik et al., *Leukemia* 19, 1948 (2005).
34. M. Sawa et al., *Int. J. Hematol.* 82, 42-47 (2005).
35. J. Yang et al., *Proc. Natl. Acad. Sci. U. S. A* 104, 10494 (2007).
36. G. D. van et al., *Exp. Hematol.* 35, 1538 (2007).
37. J. C. van Galen et al., *J. Clin. Pathol.* 60, 167 (2007).
38. R. Kuppers, U. Klein, M. L. Hansmann, K. Rajewsky, *N. Engl. J. Med.* 341, 1520 (1999).
39. A. A. Alizadeh et al., *Nature* 403, 503 (2000).
40. C. P. Hans et al., *Blood* 103, 275 (2004).
41. W. P. de Boer, J. J. Oudejans, C. J. Meijer, J. Lankelma, *Bioinformatics.* 19, 2000 (2003).
42. S. Bea et al., *Cancer Res.* 61, 2409 (2001).
43. G. V. Glinsky, O. Berezovska, A. B. Glinskii, *J. Clin. Invest* 115, 1503-1521 (2005).
44. K. Mihara et al., *Rinsho Ketsueki* 48, 659 (2007).
45. J. B. Ames, K. Collett, L. A. Akslen, *Histopathology* 52, 370 (2008).
46. I. B. Engelsen et al., *Br. J. Cancer* 98, 1662 (2008).
47. V. Hayry et al., *Acta Neuropathol.* (2008).
48. V. Hayry et al., *Neuropathol. Appl. Neurobiol.* (2008).
49. K. H. Huang, J. H. Liu, X. X. Li, L. B. Song, M. S. Zeng, *Nan. Fang Yi. Ke. Da. Xue. Xue. Bao.* 27, 973 (2007).
50. E. M. Hurt, B. T. Kawasaki, G. J. Klarmann, S. B. Thomas, W. L. Farrar, *Br. J. Cancer* 98, 756 (2008).
51. J. H. Liu et al., *J. Surg. Oncol.* 97, 267 (2008).
52. K. Mihara et al., *Blood* 107, 305 (2006).
53. L. B. Song et al., *Cancer Res.* 66, 6225 (2006).

54. H. Vekony et al., *J. Clin. Pathol.* 61, 744 (2008).
55. H. Wang et al., *J. Cancer Res. Clin. Oncol.* 134, 535 (2008).
56. R. H. Breuer et al., *Neoplasia.* 6, 736 (2004).
57. S. Vonlanthen et al., *Br. J. Cancer* 84, 1372 (2001).
58. S. K. Li et al., *J. Biol. Chem.* (2008).
59. W. J. Guo, S. Datta, V. Band, G. P. Dimri, *Mol. Biol. Cell* 18, 536 (2007).
60. K. Nowak et al., *Nucleic Acids Res.* 34, 1745 (2006).
61. H. Cui et al., *Am. J. Pathol.* 170, 1370-1378 (2007).
62. G. P. Dimri et al., *Cancer Res.* 62, 4736 (2002).
63. M. K. Kang et al., *Br. J. Cancer* 96, 126 (2007).
64. J. H. Kim et al., *Cancer Lett.* 203, 217 (2004).
65. J. H. Kim et al., *Breast* 13, 383-388 (2004).
66. H. Koga et al., *Oncogene* 18, 3799 (1999).
67. N. Kozakowski, A. Soleiman, J. Pammer, *Pathol. Oncol. Res.* 14, 9 (2008).
68. F. Zhang, L. Sui, T. Xin, *Exp. Oncol.* 30, 70 (2008).
69. L. Liu, L. G. Andrews, T. O. Tollefsbol, *Oncogene* 25, 4370-4375 (2006).
76. Park et al., 2003, *Nature.* 423:302-305.
77. Lessard et al., 2003, *Nature* 423:255-260.
78. Wiederschain et al., 2007, *Mol Cell Biol.* 27(13):4968-4967.
79. Reinisch et al., 2006, *Histol Histopathol.* 21:1143-1149.
80. Breuer et al., 2005, *Lung Cancer.* 48:299-306.

Without regard to whether a document cited herein was specifically and individually indicated as being incorporated by reference, all documents referred to herein are incorporated by reference into the present application for any and all purposes to the same extent as if each individual reference was fully set forth herein.

Although certain embodiments have been described in detail above, those having ordinary skill in the art will clearly understand that many modifications are possible in the embodiments without departing from the teachings thereof. All such modifications are intended to be encompassed within the scope of the claims presented herein.

What is claimed is:

1. A method of treating a cancer mediated by Bmi-1 in a subject in need thereof, wherein the cancer is selected from the group consisting of acute myeloid leukemia, brain tumor, breast cancer, Burkitt's lymphoma, colorectal cancer, diffuse large B cell lymphomas (DLBCL), fibrosarcoma, gastric cancer, glioblastoma, hepatocellular carcinoma, Hodgkin's lymphoma, liver carcinoma, lung cancer, mantle cell lymphoma (MCL), medulloblastoma, neuroblastoma, non-Hodgkin's lymphoma, non-small cell lung cancer, prostate cancer, salivary gland cancer, T cell lymphoma, and T-cell acute lymphoblastic leukaemia (T-ALL), the method comprising administering to the subject an effective amount of a compound or salt form thereof, selected from the group consisting of:

2-(2-methyl-1H-benzimidazol-1-yl)-N-[4-(trifluoromethyl)phenyl]pyrimidine-4,6-diamine,
2-(5,6-difluoro-2-methyl-1H-benzimidazol-1-yl)-N-[4-(trifluoromethyl)phenyl]pyrimidine-4,6-diamine,
N-[4-(difluoromethoxy)phenyl]-2-[2-(trifluoromethyl)imidazo[1,2-a]pyridin-3-yl]pyrimidine-4,6-diamine,
2-[2-(trifluoromethyl)imidazo[1,2-a]pyridin-3-yl]-N-[4-(trifluoromethyl)phenyl]pyrimidine-4,6-diamine,
N-[4-(trifluoromethoxy)phenyl]-2-[2-(trifluoromethyl)imidazo[1,2-a]pyridin-3-yl]pyrimidine-4,6-diamine,
2-(6-fluoro-2-methylimidazo[1,2-a]pyridin-3-yl)-N-[4-(trifluoromethyl)phenyl]pyrimidine-4,6-diamine,
N-[4-(difluoromethoxy)phenyl]-2-(6-fluoro-2-methyl-imidazo[1,2-a]pyridin-3-yl)pyrimidine-4,6-diamine,
N-[4-(trifluoromethyl)phenyl]-2-(1,3,5-trimethyl-1H-pyrazol-4-yl)pyrimidine-4,6-diamine,
2-(6-fluoro-2-methyl-1H-benzimidazol-1-yl)-N-[4-(trifluoromethyl)phenyl]pyrimidine-4,6-diamine,
N-[4-(difluoromethoxy)phenyl]-2-(6-fluoro-2-methyl-1H-benzimidazol-1-yl)pyrimidine-4,6-diamine,
2-(2-methyl-1H-imidazo[4,5-b]pyridin-1-yl)-N-[4-(trifluoromethyl)phenyl]pyrimidine-4,6-diamine,
2-(5,6-difluoro-2-methyl-1H-benzimidazol-1-yl)-N-[3-fluoro-4-(trifluoromethyl)phenyl]pyrimidine-4,6-diamine,
2-(2-cyclopropyl-6-fluoroimidazo[1,2-a]pyridin-3-yl)-N-[4-(difluoromethoxy)-3-fluorophenyl]pyrimidine-4,6-diamine,
N-[4-(difluoromethoxy)-3-fluorophenyl]-2-(6-fluoro-2-methyl-1H-benzimidazol-1-yl)pyrimidine-4,6-diamine,
N-[4-(difluoromethoxy)-3-fluorophenyl]-2-(2-ethyl-6-fluoro-1H-benzimidazol-1-yl)pyrimidine-4,6-diamine,
2-(2-cyclopropyl-6-fluoro-1H-benzimidazol-1-yl)-N-[4-(difluoromethoxy)-3-fluorophenyl]pyrimidine-4,6-diamine,
N-[4-(trifluoromethyl)phenyl]-2-(2,5,6-trimethyl-1H-benzimidazol-1-yl)pyrimidine-4,6-diamine,
N-[3-fluoro-4-(trifluoromethyl)phenyl]-2-(2-methyl-1H-benzimidazol-1-yl)pyrimidine-4,6-diamine,
2-(2-ethyl-6-fluoro-1H-benzimidazol-1-yl)-N-[4-(trifluoromethyl)phenyl]pyrimidine-4,6-diamine,
2-(2-cyclopropyl-6-fluoro-1H-benzimidazol-1-yl)-N-[4-(trifluoromethyl)phenyl]pyrimidine-4,6-diamine,
2-(2-cyclopropyl-5-fluoro-1H-benzimidazol-1-yl)-N-[4-(trifluoromethyl)phenyl]pyrimidine-4,6-diamine,
[3-(4-amino-6-{[4-(trifluoromethyl)phenyl]amino}pyrimidin-2-yl)-6-fluoroimidazo[1,2-a]pyridin-2-yl]methanol,
2-(6-bromo-2-methyl-1H-benzimidazol-1-yl)-N-[4-(trifluoromethyl)phenyl]pyrimidine-4,6-diamine,
2-(2,6-dimethyl-1H-benzimidazol-1-yl)-N-[4-(trifluoromethyl)phenyl]pyrimidine-4,6-diamine,
2-(6-ethyl-2-methyl-1H-benzimidazol-1-yl)-N-[4-(trifluoromethyl)phenyl]pyrimidine-4,6-diamine,
2-(4,6-difluoro-2-methyl-1H-benzimidazol-1-yl)-N-[4-(trifluoromethyl)phenyl]pyrimidine-4,6-diamine,
2-(4,6-difluoro-2-methyl-1H-benzimidazol-1-yl)-N-[3-fluoro-4-(trifluoromethyl)phenyl]pyrimidine-4,6-diamine,
2-(6-ethenyl-2-methyl-1H-benzimidazol-1-yl)-N-[4-(trifluoromethyl)phenyl]pyrimidine-4,6-diamine,
2-(2-cyclopropyl-6-fluoro-1H-imidazo[4,5-b]pyridin-1-yl)-N-[4-(trifluoromethyl)phenyl]pyrimidine-4,6-diamine,
2-(6-chloro-2-methyl-1H-benzimidazol-1-yl)-N-[4-(trifluoromethyl)phenyl]pyrimidine-4,6-diamine,
2-(6-fluoro-2-methyl-1H-imidazo[4,5-b]pyridin-1-yl)-N-[4-(trifluoromethyl)phenyl]pyrimidine-4,6-diamine,
5-fluoro-2-(2-methyl-1H-benzimidazol-1-yl)-N-[4-(trifluoromethyl)phenyl]pyrimidine-4,6-diamine,
2-(6-chloro-2-methyl-1H-benzimidazol-1-yl)-N-[3-fluoro-4-(trifluoromethyl)phenyl]pyrimidine-4,6-diamine,
2-(6-chloro-2-methyl-1H-benzimidazol-1-yl)-N-[4-(difluoromethoxy)phenyl]pyrimidine-4,6-diamine,
2-(5-chloro-2-methyl-1H-benzimidazol-1-yl)-N-[3-fluoro-4-(trifluoromethyl)phenyl]pyrimidine-4,6-diamine,
2-(5-chloro-2-methyl-1H-benzimidazol-1-yl)-N-[4-(difluoromethoxy)phenyl]pyrimidine-4,6-diamine, 2-(6-fluoro-2-methylimidazo[1,2-a]pyrimidin-3-yl)-N-[4-(trifluoromethyl)phenyl]pyrimidine-4,6-diamine,
N-[4-(difluoromethoxy)-3-fluorophenyl]-2-(5,6-difluoro-2-methyl-1H-benzimidazol-1-yl)pyrimidine-4,6-diamine,
N-[4-(difluoromethoxy)phenyl]-2-(5,6-difluoro-2-methyl-1H-benzimidazol-1-yl)pyrimidine-4,6-diamine,
2-(2-cyclopropyl-6-fluoro-1H-imidazo[4,5-b]pyridin-1-yl)-N-[4-(difluoromethoxy)phenyl]pyrimidine-4,6-diamine,
2-(6-chloro-2-methyl-1H-imidazo[4,5-b]pyridin-1-yl)-N-[4-(trifluoromethyl)phenyl]pyrimidine-4,6-diamine,
2-(6-chloro-2-ethyl-1H-imidazo[4,5-b]pyridin-1-yl)-N-[4-(trifluoromethyl)phenyl]pyrimidine-4,6-diamine,
N-[4-(difluoromethoxy)phenyl]-5-fluoro-2-(2-methyl-1H-benzimidazol-1-yl)pyrimidine-4,6-diamine,
2-(2-ethyl-1H-benzimidazol-1-yl)-5-fluoro-N-[4-(trifluoromethyl)phenyl]pyrimidine-4,6-diamine,
5-fluoro-2-(5-fluoro-2-methyl-1H-benzimidazol-1-yl)-N-[4-(trifluoromethyl)phenyl]pyrimidine-4,6-diamine,
5-fluoro-2-(6-fluoro-2-methyl-1H-benzimidazol-1-yl)-N-[4-(trifluoromethyl)phenyl]pyrimidine-4,6-diamine,
N-[4-(difluoromethoxy)phenyl]-5-fluoro-2-(6-fluoro-2-methyl-1H-benzimidazol-1-yl)pyrimidine-4,6-diamine,
N-[4-(difluoromethoxy)-3-fluorophenyl]-5-fluoro-2-(6-fluoro-2-methyl-1H-benzimidazol-1-yl)pyrimidine-4,6-diamine,
N-[4-(difluoromethoxy)-3-fluorophenyl]-5-fluoro-2-(5-fluoro-2-methyl-1H-benzimidazol-1-yl)pyrimidine-4,6-diamine,
N-[4-(difluoromethoxy)phenyl]-5-fluoro-2-(5-fluoro-2-methyl-1H-benzimidazol-1-yl)pyrimidine-4,6-diamine,
2-(6-chloro-2-methyl-1H-imidazo [4,5-b]pyridin-1-yl)-5-fluoro-N-[4-(trifluoromethyl)phenyl]pyrimidine-4,6-diamine,
2-(6-chloro-2-methyl-1H-imidazo [4,5-b]pyridin-1-yl)-N-[4-(difluoromethoxy)phenyl]-5-fluoropyrimidine-4,6-diamine,
2-(6-chloro-2-methyl-1H-imidazo [4,5-b]pyridin-1-yl)-N-[4-(difluoromethoxy)-3-fluorophenyl]-5-fluoropyrimidine-4,6-diamine,
2-(2-cyclopropyl-6-fluoro-1H-imidazo[4,5-b]pyridin-1-yl)-5-fluoro-N-[4-(trifluoromethyl)phenyl]pyrimidine-4,6-diamine,
N-[4-(difluoromethoxy)-3-fluorophenyl]-5-fluoro-2-(2-methyl-1H-benzimidazol-1-yl)pyrimidine-4,6-diamine,
2-(2-cyclopropyl-1H-benzimidazol-1-yl)-5-fluoro-N-[4-(trifluoromethyl)phenyl]pyrimidine-4,6-diamine,
2-(2-cyclopropyl-1H-benzimidazol-1-yl)-N-[4-(difluoromethoxy)phenyl]-5-fluoropyrimidine-4,6-diamine,
2-(2-cyclopropyl-1H-benzimidazol-1-yl)-N-[4-(difluoromethoxy)-3-fluorophenyl]-5-fluoropyrimidine-4,6-diamine,
N-[4-(difluoromethoxy)phenyl]-2-(2-ethyl-1H-benzimidazol-1-yl)-5-fluoropyrimidine-4,6-diamine,
N-[4-(difluoromethoxy)-3-fluorophenyl]-2-(2-ethyl-1H-benzimidazol-1-yl)-5-fluoropyrimidine-4,6-diamine,
2-(5,6-difluoro-2-methyl-1H-benzimidazol-1-yl)-5-fluoro-N-[4-(trifluoromethyl)phenyl]pyrimidine-4,6-diamine,
N-[4-(difluoromethoxy)-3-fluorophenyl]-2-(5,6-difluoro-2-methyl-1H-benzimidazol-1-yl)-5-fluoropyrimidine-4,6-diamine,
2-(4,6-difluoro-2-methyl-1H-benzimidazol-1-yl)-5-fluoro-N-[4-(trifluoromethyl)phenyl]pyrimidine-4,6-diamine,
N-[4-(difluoromethoxy)-3-fluorophenyl]-2-(4,6-difluoro-2-methyl-1H-benzimidazol-1-yl)-5-fluoropyrimidine-4,6-diamine,
2-(2-ethyl-4,6-difluoro-1H-benzimidazol-1-yl)-5-fluoro-N-[4-(trifluoromethyl)phenyl]pyrimidine-4,6-diamine,
N-[4-(difluoromethoxy)-3-fluorophenyl]-2-(2-ethyl-4,6-difluoro-1H-benzimidazol-1-yl)-5-fluoropyrimidine-4,6-diamine,
N-[4-(difluoromethoxy)phenyl]-2-(4,6-difluoro-2-methyl-1H-benzimidazol-1-yl)-5-fluoropyrimidine-4,6-diamine,
N-[4-(difluoromethoxy)phenyl]-2-(2-ethyl-4,6-difluoro-1H-benzimidazol-1-yl)-5-fluoropyrimidine-4,6-diamine,
N-[4-(difluoromethoxy)phenyl]-2-(5,6-difluoro-2-methyl-1H-benzimidazol-1-yl)-5-fluoropyrimidine-4,6-diamine,
5-fluoro-2-(4-fluoro-2-methyl-1H-benzimidazol-1-yl)-N-[4-(trifluoromethyl)phenyl]pyrimidine-4,6-diamine,
N-[4-(difluoromethoxy)phenyl]-5-fluoro-2-(4-fluoro-2-methyl-1H-benzimidazol-1-yl)pyrimidine-4,6-diamine,
N-[4-(difluoromethoxy)-3-fluorophenyl]-5-fluoro-2-(4-fluoro-2-methyl-1H-benzimidazol-1-yl)pyrimidine-4,6-diamine,
5-fluoro-2-(2-methyl-1H-imidazo [4,5-b]pyridin-1-yl)-N-[4-(trifluoromethyl)phenyl]pyrimidine-4,6-diamine,
N-[4-(difluoromethoxy)phenyl]-5-fluoro-2-(2-methyl-1H-imidazo[4,5-b]pyridin-1-yl)pyrimidine-4,6-diamine,
N-[4-(difluoromethoxy)-3-fluorophenyl]-5-fluoro-2-(2-methyl-1H-imidazo [4,5-b]pyridin-1-yl)pyrimidine-4,6-diamine,
2-(2-cyclopropyl-4-fluoro-1H-benzimidazol-1-yl)-5-fluoro-N-[4-(trifluoromethyl)phenyl]pyrimidine-4,6-diamine,
2-(2-cyclopropyl-4-fluoro-1H-benzimidazol-1-yl)-N-[4-(difluoromethoxy)phenyl]-5-fluoropyrimidine-4,6-diamine,
2-(2-cyclopropyl-4-fluoro-1H-benzimidazol-1-yl)-N-[4-(difluoromethoxy)-3-fluorophenyl]-5-fluoropyrimidine-4,6-diamine,
2-(2-cyclopropyl-6-fluoro-1H-benzimidazol-1-yl)-N-[4-(difluoromethoxy)phenyl]pyrimidine-4,6-diamine,
N-[4-(difluoromethoxy)phenyl]-2-(2-ethyl-6-fluoro-1H-benzimidazol-1-yl)pyrimidine-4,6-diamine,
N-[4-(difluoromethoxy)phenyl]-2-[2-(difluoromethyl)-6-fluoro-1H-benzimidazol-1-yl]pyrimidine-4,6-diamine,
2-(2-methyl-1H-benzimidazol-1-yl)-N-[4-(methylsulfanyl)phenyl]pyrimidine-4,6-diamine,
2-[2-(1-methylcyclopropyl)-1H-benzimidazol-1-yl]-N-[4-(trifluoromethyl)phenyl]pyrimidine-4,6-diamine,
N-[4-(difluoromethoxy)phenyl]-2-[2-(1-methylcyclopropyl)-1H-benzimidazol-1-yl]pyrimidine-4,6-diamine,
2-(2-cyclopropyl-1H-benzimidazol-1-yl)-N-[4-(trifluoromethyl)phenyl]pyrimidine-4,6-diamine,
2-[2-(methoxymethyl)-1H-benzimidazol-1-yl]-N-[4-(trifluoromethyl)phenyl]pyrimidine-4,6-diamine,
2-[2-(propan-2-yl)-1H-benzimidazol-1-yl]-N-[4-(trifluoromethyl)phenyl]pyrimidine-4,6-diamine,
2-[2-(difluoromethyl)-1H-benzimidazol-1-yl]-N-[4-(trifluoromethyl)phenyl]pyrimidine-4,6-diamine,
2-(2-ethyl-1H-benzimidazol-1-yl)-N-[4-(trifluoromethyl)phenyl]pyrimidine-4,6-diamine, 2-(2-methylpyrazolo[1,5-a]pyridin-3-yl)-N-[4-(trifluoromethyl)phenyl]pyrimidine-4,6-diamine,
2-(2-cyclopropyl-6-fluoro-1H-imidazo[4,5-b]pyridin-1-yl)-N-[4-(difluoromethoxy)phenyl]-5-fluoropyrimidine-4,6-diamine,
N-[4-(difluoromethoxy)phenyl]-2-(2-ethyl-1H-benzimidazol-1-yl)pyrimidine-4,6-diamine,
N-[4-(difluoromethoxy)-3-fluorophenyl]-2-(2-ethyl-1H-benzimidazol-1-yl)pyrimidine-4,6-diamine,
2-(5-chloro-2-methyl-1H-benzimidazol-1-yl)-5-fluoro-N-[4-(trifluoromethyl)phenyl]pyrimidine-4,6-diamine,
2-(5-chloro-2-methyl-1H-benzimidazol-1-yl)-N-[4-(difluoromethoxy)phenyl]-5-fluoropyrimidine-4,6-diamine,
2-(6-chloro-2-methyl-1H-benzimidazol-1-yl)-5-fluoro-N-[4-(trifluoromethyl)phenyl]pyrimidine-4,6-diamine,
2-(6-chloro-2-methyl-1H-benzimidazol-1-yl)-N-[4-(difluoromethoxy)phenyl]-5-fluoropyrimidine-4,6-diamine,
2-(2-ethyl-5-fluoro-1H-benzimidazol-1-yl)-5-fluoro-N-[4-(trifluoromethyl)phenyl]pyrimidine-4,6-diamine,
N-[4-(difluoromethoxy)phenyl]-2-(2-ethyl-5-fluoro-1H-benzimidazol-1-yl)-5-fluoropyrimidine-4,6-diamine,
2-(2-ethyl-6-fluoro-1H-benzimidazol-1-yl)-5-fluoro-N-[4-(trifluoromethyl)phenyl]pyrimidine-4,6-diamine,
N-[4-(difluoromethoxy)phenyl]-2-(2-ethyl-6-fluoro-1H-benzimidazol-1-yl)-5-fluoropyrimidine-4,6-diamine,
5-chloro-2-(2-methyl-1H-benzimidazol-1-yl)-N-[4-(trifluoromethyl)phenyl]pyrimidine-4,6-diamine,
5-chloro-2-(2-ethyl-1H-benzimidazol-1-yl)-N-[4-(trifluoromethyl)phenyl]pyrimidine-4,6-diamine,
5-chloro-N-[4-(difluoromethoxy)phenyl]-2-(2-ethyl-1H-benzimidazol-1-yl)pyrimidine-4,6-diamine,
5-fluoro-2-(2-methylimidazo[1,2-a]pyridin-3-yl)-N-[4-(trifluoromethyl)phenyl]pyrimidine-4,6-diamine,
N-[4-(difluoromethoxy)phenyl]-5-fluoro-2-(2-methylimidazo[1,2-a]pyridin-3-yl)pyrimidine-4,6-diamine,
N-[4-(difluoromethoxy)-3-fluorophenyl]-5-fluoro-2-(2-methylimidazo[1,2-a]pyridin-3-yl)pyrimidine-4,6-diamine,
5-methyl-2-(2-methyl-1H-benzimidazol-1-yl)-N-[4-(trifluoromethyl)phenyl]pyrimidine-4,6-diamine,
N-[4-(difluoromethoxy)phenyl]-5-fluoro-2-(2-methylpyrazolo[1,5-a]pyridin-3-yl)pyrimidine-4,6-diamine,
5-fluoro-N-[4-(trifluoromethyl)phenyl]-2-(2,6,8-trimethylimidazo[1,2-a]pyrazin-3-yl)pyrimidine-4,6-diamine,
N-[4-(difluoromethoxy)phenyl]-5-fluoro-2-(2,6,8-trimethylimidazo[1,2-a]pyrazin-3-yl)pyrimidine-4,6-diamine,
N-[4-(difluoromethoxy)-3-fluorophenyl]-5-fluoro-2-(2,6,8-trimethylimidazo[1,2-a]pyrazin-3-yl)pyrimidine-4,6-diamine,
5-fluoro-2-(2-methylpyrazolo[1,5-a]pyridin-3-yl)-N-[4-(trifluoromethyl)phenyl]pyrimidine-4,6-diamine,
5-fluoro-2-{6-fluoro-2-(trifluoromethyl)imidazo[1,2-a]pyridin-3-yl}-N-[4-(trifluoromethyl)phenyl]pyrimidine-4,6-diamine,
5-fluoro-2-(6-fluoro-2-methyl-1H-benzimidazol-1-yl)-N-(4-methoxyphenyl)pyrimidine-4,6-diamine,
2-(2-cyclopropylpyrazolo[1,5-a]pyridin-3-yl)-N-[4-(difluoromethoxy)phenyl]-5-fluoropyrimidine-4,6-diamine,
[3-(4-amino-6-{[4-(difluoromethoxy)phenyl]amino}-5-fluoropyrimidin-2-yl)-5-fluoropyrazolo[1,5-a]pyridin-2-yl]methanol,
2-[2-(methylsulfanyl)-1H-benzimidazol-1-yl]-N-[4-(trifluoromethyl)phenyl]pyrimidine-4,6-diamine,
5-fluoro-2-(6-fluoro-2-methyl-1H-benzimidazol-1-yl)-N-(4-methylphenyl)pyrimidine-4,6-diamine,
N-(4-chlorophenyl)-5-fluoro-2-(6-fluoro-2-methyl-1H-benzimidazol-1-yl)pyrimidine-4,6-diamine,
N-[4-(difluoromethoxy)phenyl]-2-(2-ethyl-5-fluoropyrazolo[1,5-a]pyridin-3-yl)-5-fluoropyrimidine-4,6-diamine,
2-(2-ethyl-5-fluoropyrazolo[1,5-a]pyridin-3-yl)-5-fluoro-N-[4-(trifluoromethyl)phenyl]pyrimidine-4,6-diamine,
N-[4-(difluoromethoxy)-3-fluorophenyl]-2-(2-ethyl-5-fluoropyrazolo[1,5-a]pyridin-3-yl)-5-fluoropyrimidine-4,6-diamine,
5-fluoro-2-(6-fluoro-2-methyl-1H-benzimidazol-1-yl)-N-(3-methoxyphenyl)pyrimidine-4,6-diamine,
N-(3-chlorophenyl)-5-fluoro-2-(6-fluoro-2-methyl-1H-benzimidazol-1-yl)pyrimidine-4,6-diamine,
5-fluoro-2-(6-fluoro-2-methyl-1H-benzimidazol-1-yl)-N-[4-(trifluoromethoxy)phenyl]pyrimidine-4,6-diamine,
4-{[6-amino-5-fluoro-2-(6-fluoro-2-methyl-1H-benzimidazol-1-yl)pyrimidin-4-yl]amino}benzonitrile,
methyl 4-{[6-amino-5-fluoro-2-(6-fluoro-2-methyl-1H-benzimidazol-1-yl)pyrimidin-4-yl]amino}benzoate,
5-fluoro-2-(2-methyl-1H-benzimidazol-1-yl)-N-(3-methylphenyl)pyrimidine-4,6-diamine,
5-fluoro-N-(3-methoxyphenyl)-2-(2-methyl-1H-benzimidazol-1-yl)pyrimidine-4,6-diamine,
2-(2-methyl-1H-benzimidazol-1-yl)-N-(4-methylphenyl)pyrimidine-4,6-diamine,
N-(4-methoxyphenyl)-2-(2-methyl-1H-benzimidazol-1-yl)pyrimidine-4,6-diamine,
N-[4-(dimethylamino)phenyl]-2-(2-methyl-1H-benzimidazol-1-yl)pyrimidine-4,6-diamine,
5-fluoro-2-(2-methyl-1H-benzimidazol-1-yl)-N-(4-methylphenyl)pyrimidine-4,6-diamine,
5-fluoro-N-(4-methoxyphenyl)-2-(2-methyl-1H-benzimidazol-1-yl)pyrimidine-4,6-diamine,
N-(4-chlorophenyl)-5-fluoro-2-(2-methyl-1H-benzimidazol-1-yl)pyrimidine-4,6-diamine,
4{-1 [6-amino-5-fluoro-2-(2-methyl-1H-benzimidazol-1-yl)pyrimidin-4-yl]amino}benzonitrile,
5-fluoro-2-(2-methyl-1H-benzimidazol-1-yl)-N-[4-(trifluoromethoxy)phenyl]pyrimidine-4,6-diamine,
N-(3-fluoro-4-methoxyphenyl)-2-(2-methyl-1H-benzimidazol-1-yl)pyrimidine-4,6-diamine,
N-(4-chlorophenyl)-2-(2-methyl-1H-benzimidazol-1-yl)pyrimidine-4,6-diamine,
4-{[6-amino-2-(2-methyl-1H-benzimidazol-1-yl)pyrimidin-4-yl]amino}benzonitrile,
2-(2-methyl-1H-benzimidazol-1-yl)-N-(4-nitrophenyl)pyrimidine-4,6-diamine,
N-(4-bromophenyl)-2-(2-methyl-1H-benzimidazol-1-yl)pyrimidine-4,6-diamine,
2-(5,6-difluoro-2-methyl-1H-benzimidazol-1-yl)-5-fluoro-N-(4-methylphenyl)pyrimidine-4,6-diamine,
2-(5,6-difluoro-2-methyl-1H-benzimidazol-1-yl)-5-fluoro-N-(4-methoxyphenyl)pyrimidine-4,6-diamine,
N-(4-chlorophenyl)-2-(5,6-difluoro-2-methyl-1H-benzimidazol-1-yl)-5-fluoropyrimidine-4,6-diamine,
N-[4-(difluoromethoxy)phenyl]-5-fluoro-2-[2-(methoxymethyl)-1H-benzimidazol-1-yl]pyrimidine-4,6-diamine,
5-fluoro-2-[2-(methoxymethyl)-1H-benzimidazol-1-yl]-N-(4-methylphenyl)pyrimidine-4,6-diamine,
5-fluoro-2-[2-(methoxymethyl)-1H-benzimidazol-1-yl]-N-(4-methoxyphenyl)pyrimidine-4,6-diamine,
N-(4-chlorophenyl)-5-fluoro-2-[2-(methoxymethyl)-1H-benzimidazol-1-yl]pyrimidine-4,6-diamine, 5-fluoro-2-[2-(methoxymethyl)-1H-benzimidazol-1-yl]-N-[4-(trifluoromethyl)phenyl]pyrimidine-4,6-diamine,
2-(2-methyl-1H-benzimidazol-1-yl)-N-[4-(trifluoromethoxy)phenyl[pyrimidine-4,6-diamine,
1-(4-amino-5-fluoro-6-1 [4-(trifluoromethyl)phenyl]amino}pyrimidin-2-yl)-2-methyl-1H-benzimidazole-6-carbonitrile,
1-(4-amino-6-{[4-(difluoromethoxy)phenyl]amino}-5-fluoropyrimidin-2-yl)-2-methyl-1H-benzimidazole-6-carbonitrile,
1-{4-amino-5-fluoro-6-[(4-methylphenyl)amino[pyrimidin-2-yl}-2-methyl-1H-benzimidazole-6-carbonitrile,
1{-4-amino-5-fluoro-6-[(4-methoxyphenyl)amino[pyrimidin-2-yl}1-2-methyl-1H-benzimidazole-6-carbonitrile,
1-(4-amino-6-{[4-(difluoromethoxy)phenyl]amino}-5-fluoropyrimidin-2-yl)-2-methyl-1H-benzimidazole-5-carbonitrile,
1-{4-amino-5-fluoro-6-[(4-methylphenyl)amino]pyrimidin-2-yl}-2-methyl-1H-benzimidazole-5-carbonitrile,
1-{4-amino-5-fluoro-6-[(4-methoxyphenyl)amino]pyrimidin-2-yl}1-2-methyl-1H-benzimidazole-5-carbonitrile,
1-(4-amino-5-fluoro-6-[4-(trifluoromethyl)phenyl]amino}pyrimidin-2-yl)-2-methyl-1H-benzimidazole-5-carbonitrile,
1-{4-amino-6-[(4-chlorophenyl)amino]-5-fluoropyrimidin-2-yl}1-2-methyl-1H-benzimidazole-5-carbonitrile,
N-[4-(difluoromethoxy)phenyl]-5-fluoro-2-(2-methyl-6-nitro-1H-benzimidazol-1-yl)pyrimidine-4,6-diamine,
5-fluoro-2-(2-methyl-6-nitro-1H-benzimidazol-1-yl)-N-(4-methylphenyl)pyrimidine-4,6-diamine,
5-fluoro-N-(4-methoxyphenyl)-2-(2-methyl-6-nitro-1H-benzimidazol-1-yl)pyrimidine-4,6-diamine,
N-[4-(difluoromethoxy)phenyl]-2-(2-methyl-1H-benzimidazol-1-yl)pyrimidine-4,6-diamine,
N-[4-(difluoromethoxy)-3-fluorophenyl]-2-(2-methyl-1H-benzimidazol-1-yl)pyrimidine-4,6-diamine,
5-fluoro-2-(2-methyl-6-nitro-1H-benzimidazol-1-yl)-N-[4-(trifluoromethyl)phenyl]pyrimidine-4,6-diamine,
N-(4-chlorophenyl)-2-(4,6-difluoro-2-methyl-1H-benzimidazol-1-yl)-5-fluoropyrimidine-4,6-diamine,
2-(4,6-difluoro-2-methyl-1H-benzimidazol-1-yl)-5-fluoro-N-[4-(trifluoromethoxy)phenyl]pyrimidine-4,6-diamine,
5-fluoro-N-(4-methoxyphenyl)-2-(2-methylpyrazolo[1,5-a]pyridin-3-yl)pyrimidine-4,6-diamine,
2-(4,6-difluoro-2-methyl-1H-benzimidazol-1-yl)-5-fluoro-N-(4-methylphenyl)pyrimidine-4,6-diamine,
2-(4,6-difluoro-2-methyl-1H-benzimidazol-1-yl)-5-fluoro-N-(4-methoxyphenyl)pyrimidine-4,6-diamine,
2-(5,7-difluoro-2-methyl-1H-benzimidazol-1-yl)-5-fluoro-N-[4-(trifluoromethyl)phenyl]pyrimidine-4,6-diamine,
5-fluoro-2-(6-methoxy-2-methyl-1H-benzimidazol-1-yl)-N-[4-(trifluoromethyl)phenyl]pyrimidine-4,6-diamine,
N-(4-chlorophenyl)-5-fluoro-2-(6-methoxy-2-methyl-1H-benzimidazol-1-yl)pyrimidine-4,6-diamine,
5-fluoro-2-(6-methoxy-2-methyl-1H-benzimidazol-1-yl)-N-[4-(trifluoromethoxy)phenyl]pyrimidine-4,6-diamine,
N-[4-(difluoromethoxy)phenyl]-5-fluoro-2-(6-methoxy-2-methyl-1H-benzimidazol-1-yl)pyrimidine-4,6-diamine,
5-fluoro-2-(6-methoxy-2-methyl-1H-benzimidazol-1-yl)-N-(4-methylphenyl)pyrimidine-4,6-diamine,
5-fluoro-2-(6-methoxy-2-methyl-1H-benzimidazol-1-yl)-N-(4-methoxyphenyl)pyrimidine-4,6-diamine,
N-(4-chlorophenyl)-5-fluoro-2-(6-fluoro-2-methylimidazo[1,2-a]pyridin-3-yl)pyrimidine-4,6-diamine,
5-fluoro-2-(6-fluoro-2-methylimidazo[1,2-a]pyridin-3-yl)-N-(4-methoxyphenyl)pyrimidine-4,6-diamine,
5-fluoro-2-(6-fluoro-2-methylimidazo[1,2-a]pyridin-3-yl)-N-(4-methylphenyl)pyrimidine-4,6-diamine,
5-fluoro-2-(2-methyl-5-nitro-1H-benzimidazol-1-yl)-N-(4-methylphenyl)pyrimidine-4,6-diamine,
5-fluoro-N-(4-methoxyphenyl)-2-(2-methyl-5-nitro-1H-benzimidazol-1-yl)pyrimidine-4,6-diamine,
2-(6-amino-2-methyl-1H-benzimidazol-1-yl)-5-fluoro-N-(4-methoxyphenyl)pyrimidine-4,6-diamine,
2-(6-amino-2-methyl-1H-benzimidazol-1-yl)-N-[4-(difluoromethoxy)phenyl]-5-fluoropyrimidine-4,6-diamine,
2-(6-amino-2-methyl-1H-benzimidazol-1-yl)-5-fluoro-N-(4-methylphenyl)pyrimidine-4,6-diamine,
N-(4-chlorophenyl)-5-fluoro-2-(5-fluoro-2-methyl-1H-benzimidazol-1-yl)pyrimidine-4,6-diamine,
N-(4-chloro-3-fluorophenyl)-5-fluoro-2-(5-fluoro-2-methyl-1H-benzimidazol-1-yl)pyrimidine-4,6-diamine,
N-(4-chloro-3-fluorophenyl)-5-fluoro-2-(2-methyl-1H-benzimidazol-1-yl)pyrimidine-4,6-diamine,
N-(4-chloro-3-fluorophenyl)-5-fluoro-2-(6-fluoro-2-methyl-1H-benzimidazol-1-yl)pyrimidine-4,6-diamine,
N-(4-chlorophenyl)-2-(6-fluoro-2-methyl-1H-benzimidazol-1-yl)pyrimidine-4,6-diamine,
2-(6-fluoro-2-methyl-1H-benzimidazol-1-yl)-N-(4-methylphenyl)pyrimidine-4,6-diamine,
2-(6-fluoro-2-methyl-1H-benzimidazol-1-yl)-N-(4-methoxyphenyl)pyrimidine-4,6-diamine,
N-[4-(dimethylamino)phenyl]-2-(6-fluoro-2-methyl-1H-benzimidazol-1-yl)pyrimidine-4,6-diamine,
N-(4-chloro-3-fluorophenyl)-2-(6-fluoro-2-methyl-1H-benzimidazol-1-yl)pyrimidine-4,6-diamine,
2-(6-fluoro-2-methyl-1H-benzimidazol-1-yl)-N-(3-methylphenyl)pyrimidine-4,6-diamine,
2-(2-ethyl-1H-benzimidazol-1-yl)-5-fluoro-N-(4-methylphenyl)pyrimidine-4,6-diamine,
2-(2-ethyl-1H-benzimidazol-1-yl)-5-fluoro-N-(4-methoxyphenyl)pyrimidine-4,6-diamine,
2-(2-ethyl-1H-benzimidazol-1-yl)-5-fluoro-N-[4-(trifluoromethoxy)phenyl]pyrimidine-4,6-diamine,
N-(4-chlorophenyl)-2-(2-ethyl-1H-benzimidazol-1-yl)-5-fluoropyrimidine-4,6-diamine,
N-(4-chloro-3-fluorophenyl)-2-(2-ethyl-1H-benzimidazol-1-yl)-5-fluoropyrimidine-4,6-diamine,
2-(2-cyclopropyl-1H-benzimidazol-1-yl)-5-fluoro-N-(4-methylphenyl)pyrimidine-4,6-diamine,
2-(2-cyclopropyl-1H-benzimidazol-1-yl)-5-fluoro-N-(4-methoxyphenyl)pyrimidine-4,6-diamine,
2-(2-cyclopropyl-1H-benzimidazol-1-yl)-5-fluoro-N-[4-(trifluoromethoxy)phenyl]pyrimidine-4,6-diamine,
N-(4-chlorophenyl)-2-(2-cyclopropyl-1H-benzimidazol-1-yl)-5-fluoropyrimidine-4,6-diamine,
N-(4-chloro-3-fluorophenyl)-2-(2-cyclopropyl-1H-benzimidazol-1-yl)-5-fluoropyrimidine-4,6-diamine,
5-fluoro-2-(5-fluoro-2-methyl-1H-benzimidazol-1-yl)-N-(4-methylphenyl)pyrimidine-4,6-diamine,
5-fluoro-2-(5-fluoro-2-methyl-1H-benzimidazol-1-yl)-N-(4-methoxyphenyl)pyrimidine-4,6-diamine, 5-fluoro-2-(5-fluoro-2-methyl-1H-benzimidazol-1-yl)-N-[4-(trifluoromethoxy)phenyl]pyrimidine-4,6-diamine, and 2-(6-amino-2-methyl-1H-benzimidazol-1-yl)-5-fluoro-N-[4-(trifluoromethyl)phenyl]pyrimidine-4,6-diamine.

2. The method of claim 1, comprising administering the compound, or salt form thereof, in combination with one or more additional agents selected from the group consisting of anti-cancer agents, anti-proliferative agents, chemotherapeutic agents, immunomodulatory agents, anti-angiogenic agents, anti-inflammatory agents, alkylating agents, steroidal and non-steroidal anti-inflammatory agents, pain relievers, leukotriene antagonists, β2-agonists, anticholinergic agents, hormonal agents, biological agents, tubulin binding agents, glucocorticoids, corticosteroid agents, antibacterial agents, antihistamines, anti-malarial agents, anti-viral agents, and antibiotics; and, optionally with radiation therapy.

3. The method of claim 1, wherein the compound or salt form thereof is selected from the group consisting of:

2-(2-methyl-1H-benzimidazol-1-yl)-N-[4-(trifluoromethyl)phenyl]pyrimidine-4,6-diamine, 2-(5,6-difluoro-2-methyl-1H-benzimidazol-1-yl)-N-[4-(trifluoromethyl)phenyl]pyrimidine-4,6-diamine, N-[4-(difluoromethoxy)phenyl]-2-[2-(trifluoromethyl)imidazo[1,2-a]pyridin-3-yl]pyrimidine-4,6-diamine, 2-[2-(trifluoromethyl)imidazo[1,2-a]pyridin-3-yl]-N-[4-(trifluoromethyl)phenyl]pyrimidine-4,6-diamine, N-[4-(trifluoromethoxy)phenyl]-2-[2-(trifluoromethyl)imidazo[1,2-a]pyridin-3-yl]pyrimidine-4,6-diamine, 2-(6-fluoro-2-methylimidazo[1,2-a]pyridin-3-yl)-N-[4-(trifluoromethyl)phenyl]pyrimidine-4,6-diamine, N-[4-(difluoromethoxy)phenyl]-2-(6-fluoro-2-methylimidazo[1,2-a]pyridin-3-yl)pyrimidine-4,6-diamine, N-[4-(trifluoromethyl)phenyl]-2-(1,3,5-trimethyl-1H-pyrazol-4-yl)pyrimidine-4,6-diamine, 2-(6-fluoro-2-methyl-1H-benzimidazol-1-yl)-N-[4-(trifluoromethyl)phenyl]pyrimidine-4,6-diamine, N-[4-(difluoromethoxy)phenyl]-2-(6-fluoro-2-methyl-1H-benzimidazol-1-yl)pyrimidine-4,6-diamine, 2-(2-methyl-1H-imidazo[4,5-b]pyridin-1-yl)-N-[4-(trifluoromethyl)phenyl]pyrimidine-4,6-diamine, 2-(5,6-difluoro-2-methyl-1H-benzimidazol-1-yl)-N-[3-fluoro-4-(trifluoromethyl)phenyl]pyrimidine-4,6-diamine, 2-(2-cyclopropyl-6-fluoroimidazo[1,2-a]pyridin-3-yl)-N-[4-(difluoromethoxy)-3-fluorophenyl]pyrimidine-4,6-diamine, N-[4-(difluoromethoxy)-3-fluorophenyl]-2-(6-fluoro-2-methyl-1H-benzimidazol-1-yl)pyrimidine-4,6-diamine, N-[4-(difluoromethoxy)-3-fluorophenyl]-2-(2-ethyl-6-fluoro-1H-benzimidazol-1-yl)pyrimidine-4,6-diamine, 2-(2-cyclopropyl-6-fluoro-1H-benzimidazol-1-yl)-N-[4-(difluoromethoxy)-3-fluorophenyl]pyrimidine-4,6-diamine, N-[4-(trifluoromethyl)phenyl]-2-(2,5,6-trimethyl-1H-benzimidazol-1-yl)pyrimidine-4,6-diamine, N-[3-fluoro-4-(trifluoromethyl)phenyl]-2-(2-methyl-1H-benzimidazol-1-yl)pyrimidine-4,6-diamine, 2-(2-ethyl-6-fluoro-1H-benzimidazol-1-yl)-N-[4-(trifluoromethyl)phenyl]pyrimidine-4,6-diamine, 2-(2-cyclopropyl-6-fluoro-1H-benzimidazol-1-yl)-N-[4-(trifluoromethyl)phenyl]pyrimidine-4,6-diamine, 2-(2-cyclopropyl-5-fluoro-1H-benzimidazol-1-yl)-N-[4-(trifluoromethyl)phenyl]pyrimidine-4,6-diamine,

[3-(4-amino-6-{[4-(trifluoromethyl)phenyl]amino}pyrimidin-2-yl)-6-fluoroimidazo[1,2-a]pyridin-2-yl]methanol, 2-(6-bromo-2-methyl-1H-benzimidazol-1-yl)-N-[4-(trifluoromethyl)phenyl]pyrimidine-4,6-diamine, 2-(2,6-dimethyl-1H-benzimidazol-1-yl)-N-[4-(trifluoromethyl)phenyl]pyrimidine-4,6-diamine, 2-(6-ethyl-2-methyl-1H-benzimidazol-1-yl)-N-[4-(trifluoromethyl)phenyl]pyrimidine-4,6-diamine, 2-(4,6-difluoro-2-methyl-1H-benzimidazol-1-yl)-N-[4-(trifluoromethyl)phenyl]pyrimidine-4,6-diamine, 2-(4,6-difluoro-2-methyl-1H-benzimidazol-1-yl)-N-[3-fluoro-4-(trifluoromethyl)phenyl]pyrimidine-4,6-diamine, 2-(6-ethenyl-2-methyl-1H-benzimidazol-1-yl)-N-[4-(trifluoromethyl)phenyl]pyrimidine-4,6-diamine, 2-(2-cyclopropyl-6-fluoro-1H-imidazo[4,5-b]pyridin-1-yl)-N-[4-(trifluoromethyl)phenyl]pyrimidine-4,6-diamine, 2-(6-chloro-2-methyl-1H-benzimidazol-1-yl)-N-[4-(trifluoromethyl)phenyl]pyrimidine-4,6-diamine, 2-(6-fluoro-2-methyl-1H-imidazo[4,5-b]pyridin-1-yl)-N-[4-(trifluoromethyl)phenyl]pyrimidine-4,6-diamine, 5-fluoro-2-(2-methyl-1H-benzimidazol-1-yl)-N-[4-(trifluoromethyl)phenyl]pyrimidine-4,6-diamine, 2-(6-chloro-2-methyl-1H-benzimidazol-1-yl)-N-[3-fluoro-4-(trifluoromethyl)phenyl]pyrimidine-4,6-diamine, 2-(6-chloro-2-methyl-1H-benzimidazol-1-yl)-N-[4-(difluoromethoxy)phenyl]pyrimidine-4,6-diamine, 2-(5-chloro-2-methyl-1H-benzimidazol-1-yl)-N-[3-fluoro-4-(trifluoromethyl)phenyl]pyrimidine-4,6-diamine, 2-(5-chloro-2-methyl-1H-benzimidazol-1-yl)-N-[4-(difluoromethoxy)phenyl]pyrimidine-4,6-diamine, 2-(6-fluoro-2-methylimidazo[1,2-a]pyrimidin-3-yl)-N-[4-(trifluoromethyl)phenyl]pyrimidine-4,6-diamine, N-[4-(difluoromethoxy)-3-fluorophenyl]-2-(5,6-difluoro-2-methyl-1H-benzimidazol-1-yl)pyrimidine-4,6-diamine, N-[4-(difluoromethoxy)phenyl]-2-(5,6-difluoro-2-methyl-1H-benzimidazol-1-yl)pyrimidine-4,6-diamine, 2-(2-cyclopropyl-6-fluoro-1H-imidazo[4,5-b]pyridin-1-yl)-N-[4-(difluoromethoxy)phenyl]pyrimidine-4,6-diamine, 2-(6-chloro-2-methyl-1H-imidazo [4,5-b]pyridin-1-yl)-N-[4-(trifluoromethyl)phenyl]pyrimidine-4,6-diamine, 2-(6-chloro-2-ethyl-1H-imidazo[4,5-b]pyridin-1-yl)-N-[4-(trifluoromethyl)phenyl]pyrimidine-4,6-diamine, N-[4-(difluoromethoxy)phenyl]-5-fluoro-2-(2-methyl-1H-benzimidazol-1-yl)pyrimidine-4,6-diamine, 2-(2-ethyl-1H-benzimidazol-1-yl)-5-fluoro-N-[4-(trifluoromethyl)phenyl]pyrimidine-4,6-diamine, 5-fluoro-2-(5-fluoro-2-methyl-1H-benzimidazol-1-yl)-N-[4-(trifluoromethyl)phenyl]pyrimidine-4,6-diamine, 5-fluoro-2-(6-fluoro-2-methyl-1H-benzimidazol-1-yl)-N-[4-(trifluoromethyl)phenyl]pyrimidine-4,6-diamine, N-[4-(difluoromethoxy)phenyl]-5-fluoro-2-(6-fluoro-2-methyl-1H-benzimidazol-1-yl)pyrimidine-4,6-diamine, N-[4-(difluoromethoxy)-3-fluorophenyl]-5-fluoro-2-(6-fluoro-2-methyl-1H-benzimidazol-1-yl)pyrimidine-4,6-diamine, N-[4-(difluoromethoxy)-3-fluorophenyl]-5-fluoro-2-(5-fluoro-2-methyl-1H-benzimidazol-1-yl)pyrimidine-4,6-diamine, N-[4-(difluoromethoxy)phenyl]-5-fluoro-2-(5-fluoro-2-methyl-1H-benzimidazol-1-yl)pyrimidine-4,6-diamine,
2-(6-chloro-2-methyl-1H-imidazo[4,5-b]pyridin-1-yl)-5-fluoro-N-[4-(trifluoromethyl)phenyl]pyrimidine-4,6-diamine,
2-(6-chloro-2-methyl-1H-imidazo[4,5-b]pyridin-1-yl)-N-[4-(difluoromethoxy)phenyl]-5-fluoropyrimidine-4,6-diamine,
2-(6-chloro-2-methyl-1H-imidazo[4,5-b]pyridin-1-yl)-N-[4-(difluoromethoxy)-3-fluorophenyl]-5-fluoropyrimidine-4,6-diamine,
2-(2-cyclopropyl-6-fluoro-1H-imidazo[4,5-b]pyridin-1-yl)-5-fluoro-N-[4-(trifluoromethyl)phenyl]pyrimidine-4,6-diamine,
N-[4-(difluoromethoxy)-3-fluorophenyl]-5-fluoro-2-(2-methyl-1H-benzimidazol-1-yl)pyrimidine-4,6-diamine,
2-(2-cyclopropyl-1H-benzimidazol-1-yl)-5-fluoro-N-[4-(trifluoromethyl)phenyl]pyrimidine-4,6-diamine,
2-(2-cyclopropyl-1H-benzimidazol-1-yl)-N-[4-(difluoromethoxy)phenyl]-5-fluoropyrimidine-4,6-diamine,
2-(2-cyclopropyl-1H-benzimidazol-1-yl)-N-[4-(difluoromethoxy)-3-fluorophenyl]-5-fluoropyrimidine-4,6-diamine,
N-[4-(difluoromethoxy)phenyl]-2-(2-ethyl-1H-benzimidazol-1-yl)-5-fluoropyrimidine-4,6-diamine,
N-[4-(difluoromethoxy)-3-fluorophenyl]-2-(2-ethyl-1H-benzimidazol-1-yl)-5-fluoropyrimidine-4,6-diamine,
2-(5,6-difluoro-2-methyl-1H-benzimidazol-1-yl)-5-fluoro-N-[4-(trifluoromethyl)phenyl]pyrimidine-4,6-diamine,
N-[4-(difluoromethoxy)-3-fluorophenyl]-2-(5,6-difluoro-2-methyl-1H-benzimidazol-1-yl)-5-fluoropyrimidine-4,6-diamine,
2-(4,6-difluoro-2-methyl-1H-benzimidazol-1-yl)-5-fluoro-N-[4-(trifluoromethyl)phenyl]pyrimidine-4,6-diamine,
N-[4-(difluoromethoxy)-3-fluorophenyl]-2-(4,6-difluoro-2-methyl-1H-benzimidazol-1-yl)-5-fluoropyrimidine-4,6-diamine,
2-(2-ethyl-4,6-difluoro-1H-benzimidazol-1-yl)-5-fluoro-N-[4-(trifluoromethyl)phenyl]pyrimidine-4,6-diamine,
N-[4-(difluoromethoxy)-3-fluorophenyl]-2-(2-ethyl-4,6-difluoro-1H-benzimidazol-1-yl)-5-fluoropyrimidine-4,6-diamine,
N-[4-(difluoromethoxy)phenyl]-2-(4,6-difluoro-2-methyl-1H-benzimidazol-1-yl)-5-fluoropyrimidine-4,6-diamine,
N-[4-(difluoromethoxy)phenyl]-2-(2-ethyl-4,6-difluoro-1H-benzimidazol-1-yl)-5-fluoropyrimidine-4,6-diamine,
N-[4-(difluoromethoxy)phenyl]-2-(5,6-difluoro-2-methyl-1H-benzimidazol-1-yl)-5-fluoropyrimidine-4,6-diamine,
5-fluoro-2-(4-fluoro-2-methyl-1H-benzimidazol-1-yl)-N-[4-(trifluoromethyl)phenyl]pyrimidine-4,6-diamine,
N-[4-(difluoromethoxy)phenyl]-5-fluoro-2-(4-fluoro-2-methyl-1H-benzimidazol-1-yl)pyrimidine-4,6-diamine,
N-[4-(difluoromethoxy)-3-fluorophenyl]-5-fluoro-2-(4-fluoro-2-methyl-1H-benzimidazol-1-yl)pyrimidine-4,6-diamine,
5-fluoro-2-(2-methyl-1H-imidazo[4,5-b]pyridin-1-yl)-N-[4-(trifluoromethyl)phenyl]pyrimidine-4,6-diamine,
N-[4-(difluoromethoxy)phenyl]-5-fluoro-2-(2-methyl-1H-imidazo[4,5-b]pyridin-1-yl)pyrimidine-4,6-diamine,
N-[4-(difluoromethoxy)-3-fluorophenyl]-5-fluoro-2-(2-methyl-1H-imidazo[4,5-b]pyridin-1-yl)pyrimidine-4,6-diamine,
2-(2-cyclopropyl-4-fluoro-1H-benzimidazol-1-yl)-5-fluoro-N-[4-(trifluoromethyl)phenyl]pyrimidine-4,6-diamine,
2-(2-cyclopropyl-4-fluoro-1H-benzimidazol-1-yl)-N-[4-(difluoromethoxy)phenyl]-5-fluoropyrimidine-4,6-diamine,
2-(2-cyclopropyl-4-fluoro-1H-benzimidazol-1-yl)-N-[4-(difluoromethoxy)-3-fluorophenyl]-5-fluoropyrimidine-4,6-diamine,
2-(2-cyclopropyl-6-fluoro-1H-benzimidazol-1-yl)-N-[4-(difluoromethoxy)phenyl]pyrimidine-4,6-diamine,
N-[4-(difluoromethoxy)phenyl]-2-(2-ethyl-6-fluoro-1H-benzimidazol-1-yl)pyrimidine-4,6-diamine,
N-[4-(difluoromethoxy)phenyl]-2-[2-(difluoromethyl)-6-fluoro-1H-benzimidazol-1-yl]pyrimidine-4,6-diamine,
2-(2-methyl-1H-benzimidazol-1-yl)-N-[4-(methylsulfanyl)phenyl]pyrimidine-4,6-diamine,
2-[2-(1-methylcyclopropyl)-1H-benzimidazol-1-yl]-N-[4-(trifluoromethyl)phenyl]pyrimidine-4,6-diamine,
N-[4-(difluoromethoxy)phenyl]-2-[2-(1-methylcyclopropyl)-1H-benzimidazol-1-yl]pyrimidine-4,6-diamine,
2-(2-cyclopropyl-1H-benzimidazol-1-yl)-N-[4-(trifluoromethyl)phenyl]pyrimidine-4,6-diamine,
2-[2-(methoxymethyl)-1H-benzimidazol-1-yl]-N-[4-(trifluoromethyl)phenyl]pyrimidine-4,6-diamine,
2-[2-(propan-2-yl)-1H-benzimidazol-1-yl]-N-[4-(trifluoromethyl)phenyl]pyrimidine-4,6-diamine,
2-[2-(difluoromethyl)-1H-benzimidazol-1-yl]-N-[4-(trifluoromethyl)phenyl]pyrimidine-4,6-diamine,
2-(2-ethyl-1H-benzimidazol-1-yl)-N-[4-(trifluoromethyl)phenyl]pyrimidine-4,6-diamine,
2-(2-methylpyrazolo[1,5-a]pyridin-3-yl)-N-[4-(trifluoromethyl)phenyl]pyrimidine-4,6-diamine,
2-(2-cyclopropyl-6-fluoro-1H-imidazo[4,5-b]pyridin-1-yl)-N-[4-(difluoromethoxy)phenyl]-5-fluoropyrimidine-4,6-diamine,
5-fluoro-2-(2-methyl-6-nitro-1H-benzimidazol-1-yl)-N-[4-(trifluoromethyl)phenyl]pyrimidine-4,6-diamine,
N-(4-chlorophenyl)-2-(4,6-difluoro-2-methyl-1H-benzimidazol-1-yl)-5-fluoropyrimidine-4,6-diamine,
2-(4,6-difluoro-2-methyl-1H-benzimidazol-1-yl)-5-fluoro-N-[4-(trifluoromethoxy)phenyl]pyrimidine-4,6-diamine,
5-fluoro-N-(4-methoxyphenyl)-2-(2-methylpyrazolo[1,5-a]pyridin-3-yl)pyrimidine-4,6-diamine,
2-(4,6-difluoro-2-methyl-1H-benzimidazol-1-yl)-5-fluoro-N-(4-methylphenyl)pyrimidine-4,6-diamine,
2-(4,6-difluoro-2-methyl-1H-benzimidazol-1-yl)-5-fluoro-N-(4-methoxyphenyl)pyrimidine-4,6-diamine,
2-(5,7-difluoro-2-methyl-1H-benzimidazol-1-yl)-5-fluoro-N-[4-(trifluoromethyl)phenyl]pyrimidine-4,6-diamine,
5-fluoro-2-(6-methoxy-2-methyl-1H-benzimidazol-1-yl)-N-[4-(trifluoromethyl)phenyl[pyrimidine-4,6-diamine,
N-(4-chlorophenyl)-5-fluoro-2-(6-methoxy-2-methyl-1H-benzimidazol-1-yl)pyrimidine-4,6-diamine,
5-fluoro-2-(6-methoxy-2-methyl-1H-benzimidazol-1-yl)-N-[4-(trifluoromethoxy)phenyl[pyrimidine-4,6-diamine, N-[4-(difluoromethoxy)phenyl]-5-fluoro-2-(6-methoxy-2-methyl-1H-benzimidazol-1-yl)pyrimidine-4,6-diamine,
5-fluoro-2-(6-methoxy-2-methyl-1H-benzimidazol-1-yl)-N-(4-methylphenyl)pyrimidine-4,6-diamine,
5-fluoro-2-(6-methoxy-2-methyl-1H-benzimidazol-1-yl)-N-(4-methoxyphenyl)pyrimidine-4,6-diamine,
N-(4-chlorophenyl)-5-fluoro-2-(6-fluoro-2-methylimidazo[1,2-a[pyridin-3-yl)pyrimidine-4,6-diamine,
5-fluoro-2-(6-fluoro-2-methylimidazo[1,2-a[pyridin-3-yl)-N-(4-methoxyphenyl)pyrimidine-4,6-diamine,
5-fluoro-2-(6-fluoro-2-methylimidazo[1,2-a[pyridin-3-yl)-N-(4-methylphenyl)pyrimidine-4,6-diamine,
5-fluoro-2-(2-methyl-5-nitro-1H-benzimidazol-1-yl)-N-(4-methylphenyl)pyrimidine-4,6-diamine,
5-fluoro-N-(4-methoxyphenyl)-2-(2-methyl-5-nitro-1H-benzimidazol-1-yl)pyrimidine-4,6-diamine,
2-(6-amino-2-methyl-1H-benzimidazol-1-yl)-5-fluoro-N-(4-methoxyphenyl)pyrimidine-4,6-diamine,
2-(6-amino-2-methyl-1H-benzimidazol-1-yl)-N-[4-(difluoromethoxy)phenyl]-5-fluoropyrimidine-4,6-diamine,
2-(6-amino-2-methyl-1H-benzimidazol-1-yl)-5-fluoro-N-(4-methylphenyl)pyrimidine-4,6-diamine,
N-(4-chlorophenyl)-5-fluoro-2-(5-fluoro-2-methyl-1H-benzimidazol-1-yl)pyrimidine-4,6-diamine,
N-(4-chloro-3-fluorophenyl)-5-fluoro-2-(5-fluoro-2-methyl-1H-benzimidazol-1-yl)pyrimidine-4,6-diamine,
N-(4-chloro-3-fluorophenyl)-5-fluoro-2-(2-methyl-1H-benzimidazol-1-yl)pyrimidine-4,6-diamine,
N-(4-chloro-3-fluorophenyl)-5-fluoro-2-(6-fluoro-2-methyl-1H-benzimidazol-1-yl)pyrimidine-4,6-diamine,
N-(4-chlorophenyl)-2-(6-fluoro-2-methyl-1H-benzimidazol-1-yl)pyrimidine-4,6-diamine,
2-(6-fluoro-2-methyl-1H-benzimidazol-1-yl)-N-(4-methylphenyl)pyrimidine-4,6-diamine,
2-(6-fluoro-2-methyl-1H-benzimidazol-1-yl)-N-(4-methoxyphenyl)pyrimidine-4,6-diamine,
N-[4-(dimethylamino)phenyl]-2-(6-fluoro-2-methyl-1H-benzimidazol-1-yl)pyrimidine-4,6-diamine,
N-(4-chloro-3-fluorophenyl)-2-(6-fluoro-2-methyl-1H-benzimidazol-1-yl)pyrimidine-4,6-diamine,
2-(6-fluoro-2-methyl-1H-benzimidazol-1-yl)-N-(3-methylphenyl)pyrimidine-4,6-diamine,
2-(2-ethyl-1H-benzimidazol-1-yl)-5-fluoro-N-(4-methylphenyl)pyrimidine-4,6-diamine,
2-(2-ethyl-1H-benzimidazol-1-yl)-5-fluoro-N-(4-methoxyphenyl)pyrimidine-4,6-diamine,
2-(2-ethyl-1H-benzimidazol-1-yl)-5-fluoro-N-[4-(trifluoromethoxy)phenyl]pyrimidine-4,6-diamine,
N-(4-chlorophenyl)-2-(2-ethyl-1H-benzimidazol-1-yl)-5-fluoropyrimidine-4,6-diamine,
N-(4-chloro-3-fluorophenyl)-2-(2-ethyl-1H-benzimidazol-1-yl)-5-fluoropyrimidine-4,6-diamine,
2-(2-cyclopropyl-1H-benzimidazol-1-yl)-5-fluoro-N-(4-methylphenyl)pyrimidine-4,6-diamine,
2-(2-cyclopropyl-1H-benzimidazol-1-yl)-5-fluoro-N-(4-methoxyphenyl)pyrimidine-4,6-diamine,
2-(2-cyclopropyl-1H-benzimidazol-1-yl)-5-fluoro-N-[4-(trifluoromethoxy)phenyl]pyrimidine-4,6-diamine,
N-(4-chlorophenyl)-2-(2-cyclopropyl-1H-benzimidazol-1-yl)-5-fluoropyrimidine-4,6-diamine,
N-(4-chloro-3-fluorophenyl)-2-(2-cyclopropyl-1H-benzimidazol-1-yl)-5-fluoropyrimidine-4,6-diamine, and
5-fluoro-2-(5-fluoro-2-methyl-1H-benzimidazol-1-yl)-N-(4-methylphenyl)pyrimidine-4,6-diamine.

4. A method of treating a cancer mediated by Bmi-1 in a subject in need thereof, wherein the cancer is selected from the group consisting of acute myeloid leukemia, brain tumor, breast cancer, Burkitt's lymphoma, colorectal cancer, diffuse large B cell lymphomas (DLBCL), fibrosarcoma, gastric cancer, glioblastoma, hepatocellular carcinoma, Hodgkin's lymphoma, liver carcinoma, lung cancer, mantle cell lymphoma (MCL), medulloblastoma, neuroblastoma, non-Hodgkin's lymphoma, non-small cell lung cancer, prostate cancer, salivary gland cancer, T cell lymphoma, and T-cell acute lymphoblastic leukaemia (T-ALL), the method comprising administering to the subject an effective amount of 5-fluoro-2-(6-fluoro-2-methyl-1H-benzimidazol-1-yl)-N-[4-(trifluoromethyl)phenyl]pyrimidine-4,6-diamine, or a salt form thereof.

5. The method of claim 1, wherein the cancer is selected from the group consisting of acute myeloid leukemia and fibrosarcoma.

6. The method of claim 5, wherein the cancer is acute myeloid leukemia.

7. The method of claim 4, wherein the cancer is selected from the group consisting of acute myeloid leukemia and fibrosarcoma.

8. The method of claim 7, wherein the cancer is acute myeloid leukemia.

9. A method of treating a cancer mediated by BMI-1 in a subject in need thereof, wherein the cancer is selected from the group consisting of sarcomas, brain tumors, and glioblastomas, the method comprising administering to the subject an effective amount of 5-fluoro-2-(6-fluoro-2-methyl-1H-benzimidazol-1-yl)-N-[4-(trifluoromethyl)phenyl]pyrimidine-4,6-diamine, or salt form thereof.

10. The method of claim 9, wherein the compound is a salt form of 5-fluoro-2-(6-fluoro-2-methyl-1H-benzimidazol-1-yl)-N-[4-(trifluoromethyl)phenyl]pyrimidine-4,6-diamine.

11. The method of claim 9, wherein the compound is 5-fluoro-2-(6-fluoro-2-methyl-1H-benzimidazol-1-yl)-N-[4-(trifluoromethyl)phenyl]pyrimidine-4,6-diamine.

12. The method of claim 1, wherein the cancer is selected from the group consisting of fibro sarcoma, brain tumors, and glioblastomas.

13. The method of claim 12, wherein the cancer is fibro sarcoma.

14. The method of claim 12, wherein the cancer is a brain tumor.

15. The method of claim 14, wherein the cancer is a pediatric brain tumor.

16. The method of claim 12, wherein the cancer is a glioblastoma.

* * * * *